US011207310B2

(12) United States Patent
Hayden et al.

(10) Patent No.: US 11,207,310 B2
(45) Date of Patent: *Dec. 28, 2021

(54) USE OF PRIDOPIDINE FOR TREATING FUNCTIONAL DECLINE

(71) Applicant: PRILENIA NEUROTHERAPEUTICS LTD., Herzliya (IL)

(72) Inventors: Michael Hayden, Herzliya (IL); Spyridon Papapetropoulos, Wellesley Hills, MA (US); Juha-Matti Savola, Reinach (CH); Eli Eyal, Petah-Tikva (IL); Beth Borowsky, Flemington, NJ (US); Igor Grachev, Millstone Township, NJ (US)

(73) Assignee: PRILENIA NEUROTHERAPEUTICS LTD., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/685,993

(22) Filed: Aug. 24, 2017

(65) Prior Publication Data

US 2018/0055832 A1 Mar. 1, 2018

Related U.S. Application Data

(60) Provisional application No. 62/416,685, filed on Nov. 2, 2016, provisional application No. 62/411,511, filed on Oct. 21, 2016, provisional application No. 62/395,263, filed on Sep. 15, 2016, provisional application No. 62/379,175, filed on Aug. 24, 2016.

(51) Int. Cl.
*A61K 31/451* (2006.01)
*A61K 9/00* (2006.01)

(52) U.S. Cl.
CPC .......... *A61K 31/451* (2013.01); *A61K 9/0053* (2013.01)

(58) Field of Classification Search
CPC .................................................. A61K 31/451
See application file for complete search history.

(56) References Cited

U.S. PATENT DOCUMENTS

| | | | |
|---|---|---|---|
| 6,903,120 B2 | 6/2005 | Svan | |
| 7,417,043 B2 | 8/2008 | Sonesson et al. | |
| 7,923,459 B2 | 4/2011 | Gauthier et al. | |
| 8,703,763 B2 | 4/2014 | Sheldon | |
| 8,703,764 B2 | 4/2014 | Sheldon | |
| 8,669,048 B2 | 11/2014 | Pera et al. | |
| 9,006,445 B2 | 4/2015 | Sonesson et al. | |
| 9,012,476 B2 | 4/2015 | Zimmermann et al. | |
| 9,139,525 B2 | 9/2015 | Wikström | |
| 9,187,567 B2 | 11/2015 | Nichols et al. | |
| RE46,117 E | 8/2016 | Sonesson et al. | |
| 9,602,765 B2 | 3/2017 | Wang et al. | |
| 9,744,155 B2 | 8/2017 | Matson | |
| 9,814,706 B2 | 11/2017 | Zimmermann et al. | |
| 2006/0287299 A1 | 12/2006 | Sheldon | |
| 2007/0286902 A1 | 12/2007 | Xie et al. | |
| 2010/0048509 A1 | 2/2010 | Kovacic et al. | |
| 2010/0167286 A1 | 7/2010 | Pera et al. | |
| 2011/0206782 A1 | 8/2011 | Zhang | |
| 2012/0288562 A1 | 11/2012 | Cade et al. | |
| 2013/0197031 A1 | 8/2013 | Sonesson | |
| 2013/0267469 A1* | 10/2013 | Matson ............... | A61K 31/405 514/16.4 |
| 2013/0267552 A1 | 10/2013 | Waters et al. | |
| 2014/0088140 A1 | 3/2014 | Hayden et al. | |
| 2014/0088145 A1 | 3/2014 | Hayden et al. | |
| 2014/0378508 A1* | 12/2014 | Bassan ................ | A61K 31/451 514/315 |
| 2015/0202302 A1 | 7/2015 | Licht et al. | |
| 2015/0209346 A1 | 7/2015 | Hayden | |
| 2015/0216850 A1 | 8/2015 | Hayden et al. | |
| 2015/0374671 A1 | 12/2015 | Schmidt et al. | |
| 2016/0095847 A1 | 4/2016 | Sonesson et al. | |
| 2016/0166559 A1 | 6/2016 | Sonesson | |
| 2016/0176821 A1 | 6/2016 | Wu et al. | |
| 2016/0243098 A1 | 8/2016 | Geva et al. | |
| 2017/0020854 A1 | 1/2017 | Licht et al. | |
| 2017/0022158 A1 | 1/2017 | Barel et al. | |

(Continued)

FOREIGN PATENT DOCUMENTS

WO 1999/003470 1/1999
WO WO 2001/046145 6/2001

(Continued)

OTHER PUBLICATIONS

HD study group HART investigators (Movement Disorders (2013) 28-1407-1415) (Year: 2013).*
Yebenes et al. (The Lancet, Neurology (2012) 10:1049-1057). (Year: 2012).*
International Preliminary Report of Patentability dated Dec. 22, 2015 in connection with PCT International Application No. PCT/US2014/043204, filed Jun. 19, 2014, including Written Opinion of the International Searching Authority.
Notification of Transmittal of the International Search Report and the Written Opinion of the International Searching Authority, or the Declaration, including an International Search Report and Written Opinion of the International Searching Authority, dated Apr. 23, 2015 in connection with PCT International Application No. PCT/US2015/012248, filed Jan. 21, 2015.
Apr. 6, 2015 Office Action (Restriction Requirement) in connection with U.S. Appl. No. 14/309,111.

(Continued)

*Primary Examiner* — Marcos L Sznaidman
(74) *Attorney, Agent, or Firm* — Mark S. Cohen; Pearl Cohen Zedek Latzer Baratz LLP

(57) ABSTRACT

This invention provides a method of maintaining functional capacity, improving functional capacity, or lessening the decline of functional capacity in a human patient comprising periodically orally administering to the patient a pharmaceutical composition comprising pridopidine such that a dose of 90-225 mg of pridopidine is administered to the patient per day, so as to thereby maintain functional capacity, improve functional capacity, or lessen the decline of functional capacity in the human patient.

16 Claims, 63 Drawing Sheets

(56) References Cited

U.S. PATENT DOCUMENTS

| | | |
|---|---|---|
| 2017/0266170 A1 | 9/2017 | Waters |
| 2018/0235950 A1 | 8/2018 | Sonesson et al. |
| 2019/0015401 A1 | 1/2019 | Sonesson |
| 2019/0030016 A1 | 1/2019 | Schmidt et al. |
| 2019/0046516 A1 | 2/2019 | Russ et al. |
| 2019/0192496 A1 | 6/2019 | Hayden et al. |
| 2019/0209542 A1 | 7/2019 | Licht et al. |
| 2019/0336488 A1 | 11/2019 | Hayden et al. |
| 2019/0350915 A1 | 11/2019 | Bassan et al. |

FOREIGN PATENT DOCUMENTS

| | | |
|---|---|---|
| WO | WO 2005/097122 | 10/2005 |
| WO | WO 2006/040155 | 4/2006 |
| WO | WO 2007/067617 | 6/2007 |
| WO | WO 2008/127188 | 10/2008 |
| WO | WO 2011/107583 | 9/2011 |
| WO | WO 2011/107583 A1 | 9/2011 |
| WO | WO 2012/002863 | 3/2012 |
| WO | WO 2012/028635 | 3/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138130 | 9/2016 |
| WO | WO 2016/138135 | 9/2016 |
| WO | WO 2017/015609 | 1/2017 |
| WO | WO 2017/015615 | 1/2017 |
| WO | 2017/048457 | 3/2017 |
| WO | 2017/147366 | 8/2017 |
| WO | WO 2017/147366 | 8/2017 |
| WO | WO 2018/039475 | 3/2018 |
| WO | WO 2018/039477 | 3/2018 |
| WO | WO/2018/053275 | 3/2018 |
| WO | WO/2018/053280 | 3/2018 |
| WO | WO/2018/053287 | 3/2018 |
| WO | WO 2018/136600 | 7/2018 |
| WO | WO 2019/036358 | 2/2019 |
| WO | WO 2019/046568 | 3/2019 |

OTHER PUBLICATIONS

Jul. 22, 2015 Office Action in connection with U.S. Appl. No. 14/309,111.
Oct. 22, 2015 Response to dated Jul. 22, 2015 Office Action in connection with U.S. Appl. No. 14/309,111.
Jan. 11, 2016 Office Action in connection with U.S. Appl. No. 14/309,111.
May 6, 2016 Response to dated Jan. 11, 2016 Office Action in connection with U.S. Appl. No. 14/309,111.
May 25, 2016 Advisory Action in connection with U.S. Appl. No. 14/309,111 .
Jun. 13, 2016 Response to dated May 25, 2016 Advisory Action in connection with U.S. Appl. No. 14/309,111.
Mar. 9, 2017 Office Action in connection with U.S. Appl. No. 14/309,111.
Jul. 10, 2017 response to dated Mar. 9, 2017 Office Action in connection with U.S. Appl. No. 14/309,111.
Sep. 15, 2017 Office Action in connection with U.S. Appl. No. 14/309,111.
Feb. 15, 2018 Response to dated Sep. 15, 2017 Office Action in connection with U.S. Appl. No. 14/309,111.
Jul. 1, 2016 Office Action issued in connection with U.S. Appl. No. 15/052,368.
Sep. 1, 2017 response to dated Jul. 1, 2016 Office Action issued in connection with U.S. Appl. No. 15/052,368.
Nov. 15, 2016 Office Action issued in connection with U.S. Appl. No. 15/052,368.
Feb. 15, 2017 response to dated Nov. 15, 2016 Office Action issued in connection with U.S. Appl. No. 15/052,368.
May 9, 2017 Office Action issued in connection with U.S. Appl. No. 15/052,368.
Jul. 10, 2017 Response to dated May 9, 2017 Office Action issued in connection with U.S. Appl. No. 15/052,368.
Jul. 19, 2017 Advisory Action issued in connection with U.S. Appl. No. 15/052,368.
Sep. 11, 2017 Response to dated Jul. 19, 2017 Advisory Action issued in connection with U.S. Appl. No. 15/052,368.
Oct. 4, 2017 Advisory Action issued in connection with U.S. Appl. No. 15/052,368.
Nov. 9, 2017 Response to Advisory Actions and dated May 9, 2017 Office Action issued in connection with U.S. Appl. No. 15/052,368.
Office Action issued in 2017 in connection with Chilean Patent Application No. 201503690 (including English Language Translation).
Jan. 25, 2018 Office Action issued in connection with U.S. Appl. No. 15/052,368.
Apr. 6, 2017 First Office Action issued by the Chinese Patent Office in connection with Chinese Patent Application No. 201480035525.7 (including English Language Translation).
Nov. 29, 2016 Office Action issued by Eurasian Patent Office in connection with Eurasian Patent Application No. 201690069.
Jan. 11, 2017 European Search Report issued in connection with European Patent Application No. 14813621.1.
Aug. 3, 2017 Response to dated Jan. 11, 2017 European Search Report issued in connection with European Patent Application No. 14813621.1.
Aug. 31, 2017 Office Action issued by Ukrainian Patent Office in connection with Ukrainian Patent Application No. a 2016 00462.
Apr. 29, 2016 Notice issued by Vietnamese Patent Office in connection with Vietnamese Patent Application No. 1-2016-00207.
Response to dated Apr. 29, 2016 Notice issued by Vietnamese Patent Office in connection with Vietnamese Patent Application No. 1-2016-00207 (and response later filed).
Sep. 30, 2016 Office Action issued by New Zealand Patent Office in connection with New Zealand Patent Application No. 630726.
Barendse, Evelien M et al. "Working Memory Deficits in High-Functioning Adolescents with Autism Spectrum Disorders: Neuropsychological and Neuroimaging Correlates." Journal of Neurodevelopmental Disorders 5.1 (2013): 14. PMC. Web. Nov. 6, 2017.
Carlsson Research, "Carlsson Research Reports Positive Effects of ACR16 in Huntington Disease Phase II Study" Press Release, May 8, 2006.
Chemical Abstract CA 132:35590. "Synthesis of piperidine analogos of 1-(3-cholrophenyl)piperazine, a well known serotonin ligand." Radl et al., Journal of Heterocyclic Chemistry (1999), 36(4), pp. 1017-1022.
Clinical Trials Summary for NCT00665223, Feb. 3, 2010 Update, https://clinicaltrials.gov/archive/NCT00665223/2010_02_03.
Dahlen, Patrik. NeuroSearch provides update on the Huntexil® development programme and plans a comprehensive restructuring of the company's operations. Sep. 27, 2011.
NeuroSearch and Patrik Dahlen, NeuroSearch provides update on the Huntexil® development programme and plans a comprehensive restructuring of the company's operations. Sep. 27, 2011.
NeuroSearch, "NeuroSearch A/S reports conclusions from the Multiple Ascending Dose study (MAD) with Huntexil®", May 28, 2012.
Darpo et al. ""Cardiac Safety of Pridopidine, a Treatment for Huntington's Disease as evaluated by Healthy Volunteers and Patients"" Poster, Presented at the World Congress on Huntington's Disease, Rio De Janeiro Brazil Sep. 15-18, 2013.
Dyhring T, Nielsen EØ, Sonesson C, Pettersson F, Karlsson J, Svensson P, Christophersen P, Waters N., The dopaminergic stabilizers pridopidine (ACR16) and (−)-OSU6162 display dopamine D(2) receptor antagonism and fast receptor dissociation properties. Eur J Pharmacol. Feb. 25, 2010;628(1-3):19-26.
Goodman, LaVonne, Huntington's Disease Drug Works—ACR-16 (Huntexil) Trial Results: Good News from Europe, posted Feb. 16, 2010.

(56) References Cited

OTHER PUBLICATIONS

Grunblatt et al (PubMed Abstract 10335493) J Neural Transm Suppl. 1999; 55:57-70. "Potent neuroprotective and antioxidant activity of apomorphine in MPTP and 6-hydroxydopamine induced neurotoxicity."

Huang, Yen-Chu et al. "Increased Prothrombin, Apolipoprotein A-IV, and Haptoglobin in the Cerebrospinal Fluid of Patients with Huntington's Disease." Ed. Mark Smith. PLoS ONE 6.1 (2011): e15809. PMC. Web. Sep. 17, 2015.

"Huntington Study Group, Program of the Third Annual Huntington Disease Clinical Research Symposium, Neurotherapeutics, vol. 7, No. 1, 2010. Notes: Poster 18 Lack of Awareness of Motor and Cognitive Phenoconversion in Huntington's Disease. Poster 19: Validation of the Modified Motor Score (mMS): A Subscale of the Unified Huntington's Disease Rating Scale (UHDRS) Motor Score. Poster 20: Pridopidine (ACR16) in Huntington's Disease: An Update on the MermaiHD and HART Studies. Poster 23: Pharmacology of the Dopaminergic Stabilizer Pridopidine (ACR16)".

Huntington Study Group HART Investigators, "A Randomized, Double-Blind, Placebo-Controlled Trial of Pridopidine in Huntington's Disease" Movement Disorders, vol. 28, No. 10, 2013.

Johansson, Birgitta et al., Placebo-controlled cross-over study of the monoaminergic stabiliser (−)-OSU6162 in mental fatigue following stroke or traumatic brain injury, Acta Neuropsychiatrica/ vol. 24 / Issue 05 / Oct. 2012, pp. 266-274.

Kieburtz, KD and The Huntington Study Group HART Investigators, A Randomized, Double Blind Placebo-Controlled Trial of Pridopidine in Huntington's Disease. Movement Disorders (2013), 28 (10):1407-1415.

Lanctot, KL et al. "GABAergic Function in Alzheimer's Disease: Evidence for Dysfunction and Potential as a Therapeutic Target for the Treatment of Behavioural and Psychological Symptoms of Dementia" 2004 Canadian Journal of Psychiatry; vol. 49. p. 439-53; abstract; p. 447 para 1,2.

Landwehrmeyer, B. et al. Effects of Dopaminergic Stabilizer pridopidine on motor symptoms in Huntington's Disease: a meta-analysis. Aug. 31, 2011. Presented Sep. 11-14, 2011. (Poster).

Ludin et al., "Efficacy and Safety of the Dopaminergic Stabilizer Pridopidine (ACR16) in Patients With Huntington's Disease" Clinical Neuropharmacology, Sep./Oct. 2010—vol. 33—Issue 5—pp. 260-264, abstract.

McGarry et al., "Effect of Pridopidine on Total Functional Capacity (TFC) in Huntington Disease (HD): A Comparison of Open-HART Subjects with Historical Placebo Controls," poster presented at Movement Disorders: Huntington's Disease, Chorea & Tardive Dyskinesia, also published Neurology, Apr. 18, 2017, vol. 88 No. 16 Supplement P2.011, http://www.neurology.org/content/88/16_Supplement/P2.011.

Michl, Martin et al. "Pridopidine in the pharmacological treatment of Huntington's disease", Clin. Invest. (2013) 3(7), 691-699.

Millter, Marsha, "Swedish Company Announces Results of Phase II study of Dopamine Stabilizing Compound" Huntington's Disease Advocacy Center, 2006, http://www.hdac.org/features/article.php?p_articleNumber=254.

NeuroSearch and Fleming Pederson, "NeuroSearch announces positive top-line results from Phase III Huntexil® study in Huntington's disease (the MermaiHD study)", Feb. 3, 2010.

Neurosearch webite. The MermaiHD study. Apr. 2010.

"Trial watch: NeuroSearch's dopaminergic stabilizer improves movement disorders in Huntington's disease" Nature Reviews Drug Discovery 9, 260 (Apr. 2010).

Nilsson, M et al. "The dopaminergic stabiliser ACR16 counteracts the behavioural primitivization induced by the NMDA receptor antagonist MK-801 in mice" 2004 Progress in Neuropsychopharmacol Biol Psychiatry; vol. 28 p. 677-85.

Østerberg, Ole et al. A single center, randomized, placebo-controlled, double-blind study to evaluate the safety. Presented at sixth Annual Huntington Disease Clinical Research Symposium, Nov. 2012, Seattle, Washington, USA. Neurotherapeutics (2012) 9:1-17).

Østerberg, O et al. "A single-center, randomized, placebo-controlled, doubleblind study to evaluate the safety, tolerability, and pharmacokinetics of multiple-ascending doses of pridopidine in healthy volunteers", Abstract of Sixth Annual Huntington Disease Clinical Research Symposium, published in Neurotherapeutics, 10(1), p. 175, ISSN 1933-7213, Symposium held on Nov. 10, 2012.

Diana Raffelsbauer, EHDN News, Article of the Month, Jan. 2012, Issue 15 (cites to Yebenes et al., Lancet Neurology 2011 below).

Rung, Johan P., et al. The dopaminergic stabilizers (−)-OSU6162 and ACR16 reverse (+)-MK-801-induced social withdrawal in rats.Prog Neuropsychopharmacol Biol Psychiatry. Jun. 2005; 29(5):833-9.

Rung et al. "Effects of the dopamine stabilizers (S)-(−)-OSU6162 and ACR16 on prolactin secretion in drug-naive and monoamine-depleted rats." Naunyn Schmiedebergs Arch Pharmacol. Jul. 2011;384(1):39-45 (abstract).

Sahlholm K, Århem P, Fuxe K, Marcellino D., The dopamine stabilizers ACR16 and (−)-OSU6162 display nanomolar affinities at the σ-1 receptor. Mol Psychiatry. Jan. 2013;18(1):12-4.

Squitieri et al. "One-year safety and tolerability profile of pridopidine in patients with Huntington disease" Neurology 80, Mar. 19, 2013.

Tedroff J, Ekesbo A, Sonesson C, Waters N, Carlsson A., Long-lasting improvement following (−)-OSU6162 in a patient with Huntington's disease. Neurology. Oct. 22, 1999;53(7):1605-6.

Yebenes et al. "Pridopidine for the treatment of motor function in patients with Huntington's disease (MermaiHD): a phase 3, randomised, double-blind, placebo-controlled trial" Lancet Neurol. Dec. 2011; 10 (12):1049-57.

International Preliminary Report on Patentability for PCT International Application No. PCT/US2017/048461 dated Nov. 9, 2017.

Written Opinion of the International Search Authority for PCT International Application No. PCT/US2017/048461 dated Nov. 9, 2017.

Apr. 25, 2018 Response to dated Jan. 25, 2018 Office Action issued in connection with U.S. Appl. No. 15/052,368.

Jul. 3, 2018 Office Action issued in connection with U.S. Appl. No. 15/052,368.

May 25, 2018 Office Action issued in connection with European Patent Application No. 14813621.1.

International Preliminary Report on Patentability dated Mar. 7, 2019 for PCT Application No. PCT/US2017/048461.

Kalia, L. V., Kalia, S. K., & Salter, M. W. (2008). NMDA receptors in clinicai neurology: excitatory times ahead. The Lancet Neurology, 7(8), 742-755.

Constantinescu et al. (2009)—Levels of the light subunit of neurofilament triplet protein in cerebrospinal fluid in Huntington's disease, Parkinsonism & Related Disorders, pp. 245-248.

De Yebenes, J. G. et al. (2011)—Pridopidine for the treatment of motor function in patients with Huntington's disease (MermaiHD): a phase 3, randomized, double-blind, placebo-controlled trial. The Lancet Neurolog, vol. 10, not 12, p. 1049-1057.

Dubinsky, R. et al. (2010)—Third Annual Huntington Disease Clinical Research Symposium. Neurotherapeutics, vol. 7, not 1, pp. 135-147.

HS Group, et al. (1996)—Unified Huntington's disease rating scale: reliability and consistency. Mov Disord, vol. 11, No. 2, pp. 136-142.

Huntington Study Group Hart Investigators (2013)—A randomized, double-blind, placebo-controlled trial of pridopidine in Huntington's disease. Movement Disorders, vol. 28, not 10, pp. 1407-1415. First published Feb. 28, 2013.

Paulsen, J. S. et al. (2010)—Challenges assessing clinical endpoints in early Huntington disease. Movement Disorders, vol. 25, not 15, pp. 2595-2603.

Posakony J. et al. (2004)—Inhibitors of Sir2: Evaluation of Splitomicin Analogues. J.Med.Chem, 47, pp. 2635-2644.

Zhang, M. et al. (2008)—Studies on the structure—activity relationship of bicifadine analogs as monoamine transporter inhibitors. Bioorganic & medicinal chemistry letters, 18(13), pp. 3682-3686.

Alexander, G. E. et al. (1986)—Parallel organization of functionally segregated circuits linking basal ganglia and cortex. Annual review of neuroscience, 9(1), pp. 357-381.

(56) References Cited

OTHER PUBLICATIONS

Bezdicek, O. et al. (2013)—Validity of the Montreal Cognitive Assessment in the detection of cognitive dysfunction in Huntington's disease. Applied Neuropsychology: Adult, 20(1), pp. 33-40.
Bowie, C. R. et al.—(2006)—Administration and interpretation of the Trail Making Test. Nature protocols, 1(5), p. 2277.
Briefs, B., 2010, NeuroSearch's dopaminergic stabilizer improves movement disorders in Huntington's disease. Nature Reviews Drug Discovery 9, 260.
Brown, M. et al.—(2000)—Physical and performance measures for the identification of mild to moderate frailty. The Journals of Gerontology Series A: Biological Sciences and Medical Sciences, 55(6), pp. M350-M355.
Carlsson Research; May 8, 2006; "Carlsson Research Reports Positive Effects of ACR16 in Huntington Disease Phase II Study" Press Release.
Carlsson, A. et al.—(1963)—Effect of chlorpromazine or haloperidol on formation of 3-methoxytyramine and normetanephrine in mouse brain. Acta pharmacologica et toxicologica, 20(2), pp. 140-144.
Cepeda, C. et al.—(2010)—Genetic mouse models of Huntington's disease: focus on electrophysiological mechanisms. ASN neuro, 2(2), AN20090058.
Clinical Trial EudraCT No. 2004-000394-60, "A randomised phase II multicentre, double blind, parallel group, placebo controlled study of ACR16 50 mg once daily for the symptomatic treatment of Huntington disease" EU Clinical Trials Register, Sponsor: A. Carlsson Research AB, Sponsor Protocol No. ACR16C007 Start Date: Jun. 30, 2004 https://www.clinicaltrialsregister.eu/ctr-search/search?query=ACR16C007.
Clinical Trial, NCT00665223, "A Study of Treatment With Pridopidine (ACR16) in Patients With Huntington's Disease (MermaiHD)", ClinicalTrials.gov, Sponsor Teva Pharmaceutical Industries, First Posted: Apr. 23, 2008 https://clinicaltrials.gov/ct2/show/NCT00665223?term=Pridopidine&cond=Huntington+Disease&rank=6.
Clinical Trial, NCT00724048, "A Study of Pridopidine (ACR16) for the Treatment of Patients With Huntington's Disease (HART)", ClinicalTrials.gov, Sponsor Teva Pharmaceutical Industries, First Posted: Jul. 29, 2008 https://clinicaltrials.gov/ct2/show/record?term=Pridopidine&cond=Huntington+Disease&rank=5.
Craufurd, D. et al.—(2001)—Behavioral changes in Huntington disease. Cognitive and Behavioral Neurology, 14(4), pp. 219-226.
Dahlen, Patrik; NeuroSearch A/S reports conclusions from the Multiple Ascending Dose study (MAD) with Huntexil®, May 28, 2012.
Dunlop, B. W. et al.—(2007)—The role of dopamine in the pathophysiology of depression. Archives of general psychiatry, 64(3), pp. 327-337.
Dyhring, T. et al. (2010)—The dopaminergic stabilizers pridopidine (ACR16) and (−)-OSU6162 display dopamine D2 receptor antagonism and fast receptor dissociation properties. European journal of pharmacology, 628(1-3), pp. 19-26.
Exploratory Population Pharmacokinetic Modeling and Simulations With Pridopidine (Report No. CP-13-013), Jul. 10, 2013, Pharsight Consulting Services.
Extended European Search Report for EP Application No. 1481362.1 dated Jan. 11, 2017.
Group, T. E. (1990)—EuroQol—a new facility for the measurement of health-related quality of life. Health policy, 16(3), pp. 199-208.
Guy, W. E.—(1976)—ECDEU assessment manual for psychopharmacology-revised (DHEW Publ No. ADM 76-338). Rockville, MD, US Department of Health, Education, and Welfare. Public Health Service, Alcohol, Drug Abuse, and Mental Health Administration, NIMH Psychopharmacology Research Branch, Division of Extramural Research Programs, 1076, pp. 534-537.
Hobart, J. C. et al.—(2003)—Measuring the impact of MS on walking ability: the 12-Item MS Walking Scale (MSWS-12). Neurology, 60(1), pp. 31-36.

Hocaoglu, M. B. et al.—(2012)—The Huntington's Disease health-related Quality of Life questionnaire (HDQoL): a disease-specific measure of health-related quality of life. Clinical genetics, 81(2), pp. 117-122.
Huang, Y. C. et al. (2011)—Increased prothrombin, apolipoprotein A-IV, and haptoglobin in the cerebrospinal fluid of patients with Huntington's disease. PLoS One, 6(1), p. 1-9.
Huntington Study Group TREND-HD Investigators. (2008). Randomized controlled trial of ethyl-eicosapentaenoic acid in Huntington disease. Archives of neurology, 65(12), pp. 1582-1589.
Huntington Study Group. (2003). Dosage effects of riluzole in Huntington's disease: a multicenter placebo-controlled study. Neurology, 61(11), pp. 1551-1556.
Huntington Study Group. (2006). Tetrabenazine as antichorea therapy in Huntington disease: a randomized controlled trial. Neurology, 66(3), pp. 366-372.
Huot, P. et al.—(2006)—The fate of striatal dopaminergic neurons in Parkinson's disease and Huntington's chorea. Brain, 130(1), pp. 222-232.
Joffres, C. et al.—(2000)—Qualitative analysis of the clinician interview-based impression of change (Plus): methodological issues and implications for clinical research. International psychogeriatrics, 12(3), pp. 403-413.
Kingma, E. M. et al.—(2008)—Behavioural problems in Huntington's disease using the Problem Behaviours Assessment. General hospital psychiatry, 30(2), pp. 155-161.
Kung, V. W. S. et al.—(2007)—Dopamine-dependent long term potentiation in the dorsal striatum is reduced in the R6/2 mouse model of Huntington's disease. Neuroscience, 146(4), pp. 1571-1580.
Landwehrmeyer, B. et al.—(2011)—Effects of the Dopaminergic Stabilizer Pridopidine on Motor Symptoms in Huntington'S Disease: A Meta-Analysis: 211. Clinical Genetics, 80, pp. 48-49.
Mahant, N. et al. & Huntington Study Group—(2003)—Huntington's disease: clinical correlates of disability and progression. Neurology, 61(8), pp. 1085-1092.
McGarry, A. et al.—(2017)—Effect of Pridopidine on Total Functional Capacity (TFC) in Huntington Disease (HD): A Comparison of Open-HART Subjects with Historical Placebo Controls (P2. 011).
Mestre, T. et al.—(2009)—Therapeutic interventions for disease progression in Huntington's disease. Cochrane database of systematic reviews, (3).
Michl, M. et al.—(2013)—Pridopidine in the pharmacological treatment of Huntington's disease. Clinical Investigation, 3(7), pp. 691-699.
Millter, Marsha, (2006)—"Swedish Company Announces Results of Phase II study of Dopamine Stabilizing Compound" Huntington's Disease Advocacy Center, http://www.hdac.org/features/article.php?p articleNumber=254.
Myers, R. H., et al. (1991)—Factors associated with slow progression in Huntington's disease. Archives of neurology, 48(8), pp. 800-804.
Natesan, S. et al. (2006)—The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. Journal of Pharmacology and Experimental Therapeutics, 318(2), pp. 810-818.
NeuroSearch and Fleming Pederson, Feb. 3, 2010, "NeuroSearch announces positive top-line results from Phase III Huntexil® study in Huntington's disease (the MermaiHD study)".
NeuroSearch and Patrik Dahlen, Sep. 27, 2011, "NeuroSearch provides update on the Huntexil® development programme and plans a comprehensive restructuring of the company's operations".
NeuroSearch, May 28, 2012, "NeuroSearch A/S reports conclusions from the Multiple Ascending Dose study (MAD) with Huntexil®".
NewsHD, "Sorry folks, the PRIDE-HD trial did NOT show that Pridopidine slows the progression of Huntington's disease," Oct. 1, 2016, http://www.newshd.net/hdbuzz/9617/sorry-folks-the-pride-hd-trial-did-not-show-that-pridopidine-slows-the-progression-of-huntingtons-disease/.
NewsHD, "Teva Announces Results from Exploratory 52-Week Phase 2 PRIDE-HD Study of Pridopidine in Huntington Disease,"Sep.

(56) References Cited

OTHER PUBLICATIONS 19, 2016, http://www.newshd.net/important/9571/teva-announces-results-from-exploratory-52-week-phase-2-pride-hd-study-of-pridopidine-huntington-disease/.
Nieoullon, A. et al.—(2003)—Dopamine: a key regulator to adapt action, emotion, motivation and cognition. Current Opinion in Neurology, 16, pp. S3-S9.
Osterberg, O. et al.—(2012)—"A single-center, randomized, placebo-controlled, doubleblind study to evaluate the safety" Presented at the Sixth Annual Huntington Disease Clinical Research Symposium, Neurotherapeutics, 9(1-17).
Osterberg, O. et al.—(2013)—"A single-center, randomized, placebo-controlled, doubleblind study to evaluate the safety, tolerability, and pharmacokinetics of multiple-ascending doses of pridopidine in healthy volunteers", Abstract of Sixth Annual Huntington Disease Clinical Research Symposium, published in Neurotherapeutics, 10(1).
Podsiadlo, D. et al.—(1991)—The timed "Up & Go": a test of basic functional mobility for frail elderly persons. Journal of the American geriatrics Society, 39(2), pp. 142-148.
Ponten, H. et al.—(2010)—In vivo pharmacology of the dopaminergic stabilizer pridopidine. European journal of pharmacology, 644(1-3), pp. 88-95.
Posner, K. et al.—(2011)—The Columbia-Suicide Severity Rating Scale: initial validity and internal consistency findings from three multisite studies with adolescents and adults. American journal of psychiatry, 168(12), pp. 1266-1277.
Raffelsbauer, Diane, EHDN News, Article of the Month, Jan. 2012, Issue 15.
Rao, A. K. et al.—(2009)—Clinical measurement of mobility and balance impairments in Huntington's disease: validity and responsiveness. Gait & posture, 29(3), pp. 433-436.
Reuben, D. B. et al.—(1990)—An objective measure of physical function of elderly outpatients: the Physical Performance Test. Journal of the American Geriatrics Society, 38(10), pp. 1105-1112.
Stroop, J. R.—(1935)—Studies of interference in serial verbal reactions. Journal of experimental psychology, 18(6), p. 643.
Waters, S. et al.—(2009)—Medical Treatments. Pharmacology of the dopaminergic stabilizer pridopidine (ACR16). Clinical Genetics—76(S1):74. (Abstract D10).
Zhan, L. et al.—(2011)—Altered expression and coregulation of dopamine signalling genes in schizophrenia and bipolar disorder. Neuropathology and applied neurobiology, 37(2), pp. 206-219.
Craufurd, et al. (2001)—Behavioral changes in Huntington disease. Cognitive and Behavioral Neurology, 14.4: 219-226.
Dorsey, E. R., et al. (2013). Natural history of Huntington disease. JAMA neurology, 70(12), 1520-1530.
Dorsey, R. et al. (2011)—Use of tetrabenazine in Huntington disease patients on antidepressants or with advanced disease: results from the TETRA-HD study. PLoS currents, 3.
Epping, E. A. et al. (2011)—Depression in the early stages of Huntington disease—Neurodegenerative disease management, 1(5), 407-414.
Geva, M. et al. (2016)—Pridopidine activates neuroprotective pathways impaired in Huntington Disease—Human molecular genetics, 25(18), 3975-3987.
Hedlin, M.(2011)—Pridopidine—Huntexil—ACR-16—Hopes—Huntington's Disease Information—XP055707622—Retrieved from the Internet—URL:https://hopes.stanford.edu/pridopidine-huntexil-acr-16/.
Ho, A. K. et al. (2009)—Health-related quality of life in Huntington's disease: Which factors matter most?—Movement Disorders, 24(4), 574-578.
Huntington, H. (1996). Unified Huntington's disease rating scale: reliability and consistency. Movement Disorders, 11, 136-142.
Kieburtz, K. et al. (2017)—Efficacy, safety, and tolerability of pridopidine in Huntington disease (HD): Results from the phase II, double-blind, placebo-controlled, dose-ranging study, Pride-HD (P2. 005)—American Academy of Neurology.
Kingma, E. M., et al. (2008). Behavioural problems in Huntington's disease using the Problem Behaviours Assessment. General hospital psychiatry, 30(2), 155-161.
Kirkwood, S. C., et al. (2001)—Progression of symptoms in the early and middle stages of Huntington disease. Archives of neurology, 58(2), 273-278.
Pagan, F., et al. (2017). The diagnosis and natural history of Huntington disease. In Handbook of Clinical Neurology (vol. 144, pp. 63-67). Elsevier.
Papapetropoulos S. (Globes, Sep. 19, 2016)—Trial finds Teva drug could slow Huntington's disease.
Paulsen, J. S. et al. (2005)—Critical periods of suicide risk in Huntington's disease—American Journal of Psychiatry, 162(4), 725-731.
Paulsen, J. S. et al. (2005)—Depression and stages of Huntington's disease—The Journal of neuropsychiatry and clinical neurosciences, 17(4), 496-502.
Rabinovich-Guilatt et al. (2016)—The effect of mild and moderate renal impairment on the pharmacokinetics of pridopidine, a new drug for Huntington's disease—British journal of clinical pharmacology, 81(2), 246-255.
Ryskamp, D. et al.(2017)—The sigma-1 receptor mediates the beneficial effects of pridopidine in a mouse model of Huntington disease—Neurobiology of disease, 97, 46-59.
Squitieri, F. et al. (2015)—Profile of pridopidine and its potential in the treatment of Huntington disease: the evidence to date—Drug design, development and therapy, 9, 5827.
Supplementary European Search Report for EP Application No. 17 84 4433 dated Mar. 25, 2020.
Teva, T. (2016)—Announces results from exploratory 52-week phase 2 PRIDE-HD study of pridopidine in huntington disease—ChemDiv.
Van Walsem, Marleen R., et al. Health-related quality of life and unmet healthcare needs in Huntington's disease. Health and quality of life outcomes, 2017, 15.1: 6.
Zielonka, D. et al. (2015)—Update on Huntington's disease: advances in care and emerging therapeutic options—Parkinsonism & related disorders, 21(3), 169-178.
Bemelmans, Alexis-Pierre, et al. Brain-derived neurotrophic factor-mediated protection of striatal neurons in an excitotoxic rat model of Huntington's disease, as demonstrated by adenoviral gene transfer. *Human gene therapy*, 1999, 10.18: 2987-2997.
Canals, Josep M., et al. Brain-derived neurotrophic factor regulates the onset and severity of motor dysfunction associated with enkephalinergic neuronal degeneration in Huntington's disease. *Journal of Neuroscience*, 2004, 24.35: 7727-7739.
Cho, Sung-Rae, et al. Induction of neostriatal neurogenesis slows disease progression in a transgenic murine model of Huntington disease. *The Journal of ciinical investigation*, 2007, 117.10: 2889-2902.
Ciammola, A., et al. Low brain-derived neurotrophic factor (BDNF) levels in serum of Huntington's disease patients. *American Journal of Medical Genetics Part B: Neuropsychiatric Genetics*, 2007, 144.4: 574-577.
De Tommaso, Marina, et al. Effects of rivastigmine on motor and cognitive impairment in Huntington's disease. Movement disorders, 2004, 19.12: 1516-1518.
Dragatsis, Ioannis; Levine, Michael S.; Zeitlin, Scott. Inactivation of Hdh in the brain and testis results in progressive neurodegeneration and sterility in mice. *Nature genetics*, 2000, 26.3: 300-306.
Ferrara, J. M. et al.(2012)—Effect of tetrabenazine on motor function in patients with Huntington disease—Neurology and therapy, 1(1), 5.
Ferrer, I., et al. Brain-derived neurotrophic factor in Huntington disease. *Brain research*, 2000, 866.1-2: 257-261.
Fisher et al., "Results of phase 2 SIGNAL trial of the SEMA4D blocking antibody suggest pepinemab is a novel potential treatment for neurodegenerative disease", 2021 in 16th Annual CHDI HD Therapeutics Conference.
Folstein, Marshal F.; Robins, Lee N.; Helzer, John E. The mini-mental state examination. Archives of general psychiatry, 1983, 40.7: 812-812.

(56) References Cited

OTHER PUBLICATIONS

Francardo, Veronica, et al. Pridopidine induces functional neurorestoration via the sigma-1 receptor in a mouse model of parkinson's disease. *Neurotherapeutics*, 2019, 16.2: 465-479.

Gauthier, Laurent R., et al. Huntingtin controls neurotrophic support and survival of neurons by enhancing BDNF vesicular transport along microtubules. *Cell*, 2004, 118.1: 127-138.

Geva, M., et al. Pridopidine for the Treatment of Early Huntington's Disease: 250. *Movement Disorders*, 2020, 35.

Gharami, Kusumika, et al. Brain-derived neurotrophic factor over-expression in the forebrain ameliorates Huntington's disease phenotypes in mice. *Journal of neurochemistry*, 2008, 105.2: 369-379.

Giralt, A., et al. Brain-derived neurotrophic factor modulates the severity of cognitive alterations induced by mutant huntingtin: involvement of phospholipaseCγ activity and glutamate receptor expression. *Neuroscience*, 2009, 158.4: 1234-1250.

International Search Report for PCT Application No. PCT/IL2020/050654 dated Aug. 4, 2020.

Mangiarini, Laura, et al. Exon 1 of the HD gene with an expanded CAG repeat is sufficient to cause a progressive neurological phenotype in transgenic mice. *Cell*, 1996, 87.3: 493-506.

Paulsen, Jane S., et al. Cognitive and behavioral changes in Huntington disease before diagnosis. Handbook of clinical neurology, 2017, 144: 69-91.

Peng, Qi, et al. The antidepressant sertraline improves the phenotype, promotes neurogenesis and increases BDNF levels in the R6/2 Huntington's disease mouse model. *Experimental neurology*, 2008, 210.1: 154-163.

Pérez-Navarro, Esther, et al. Brain-derived neurotrophic factor, neurotrophin-3, and neurotrophin-4/5 prevent the death of striatal projection neurons in a rodent model of Huntington's disease. *Journal of neurochemistry*, 2000, 75.5: 2190-2199.

Pineda, José R., et al. Brain-derived neurotrophic factor modulates dopaminergic deficits in a transgenic mouse model of Huntington's disease. *Journal of neurochemistry*, 2005, 93.5: 1057-1068.

Reading, Paul J.; Luce, Anna K.; Mckeith, Ian G. Rivastigmine in the treatment of parkinsonian psychosis and cognitive impairment: preliminary findings from an open trial. Movement disorders: official journal of the Movement Disorder Society, 2001, 16.6: 1171-1174.

Rösler, Michael, et al. Efficacy and safety of rivastigmine in patients with Alzheimer's disease: international randomised controlled trialCommentary: Another piece of the Alzheimer's jigsaw. Bmj, 1999, 318.7184: 633-640.

Šešok, Sanja, et al. Cognitive function in early dinical phase huntington disease after rivastigmine treatment. Psychiatria Danubina, 2014, 26.3: 239-248.

Simmons, Danielle A., et al. Up-regulating BDNF with an ampakine rescues synaptic plasticity and memory in Huntington's disease knockin mice. *Proceedings of the National Academy of Sciences*, 2009, 106.12: 4906-4911.

Slow, Elizabeth J., et al. Selective striatal neuronal loss in a YAC128 mouse model of Huntington disease. *Human molecular genetics*, 2003, 12.13: 1555-1567.

Spires, Tara L., et al. Environmental enrichment rescues protein deficits in a mouse model of Huntington's disease, indicating a possible disease mechanism. *Journal of Neuroscience*, 2004, 24.9: 2270-2276.

Squitieri, Ferdinando, et al. Pridopidine, a dopamine stabilizer, improves motor performance and shows neuroprotective effects in Huntington disease R6/2 mouse model. *Journal of cellular and molecular medicine*, 2015, 19.11: 2540-2548.

Squitieri, Ferdinando, et al. Short-term effects of olanzapine in Huntington disease. Cognitive and Behaviorsl Neurology, 2001, 14.1: 69-72. Abstract.

Stout, Julie C., et al. HD-CAB: A cognitive assessment battery for clinical trials in Huntington's disease1, 2, 3. Movement Disorders, 2014, 29.10: 1281-1288.

Strand, Andrew D., et al. Expression profiling of Huntington's disease models suggests that brain-derived neurotrophic factor depletion plays a major role in striatal degeneration. *Journal of Neuroscience*, 2007, 27.43: 11758-11768.

Xie, Yuxiang; Hayden, Michael R.; Xu, Baoji. BDNF overexpression in the forebrain rescues Huntington's disease phenotypes in YAC128 mice. *Journal of Neuroscience*, 2010, 30.44: 14708-14718.

Yung-Chi, Cheng; Prusoff, William H. Relationship between the inhibition constant (KI) and the concentration of inhibitor which causes 50 per cent inhibition (I50) of an enzymatic reaction. *Biochemical pharmacology*, 1973, 22.23: 3099-3108.

Zuccato, Chiara, et al. Loss of huntingtin-mediated BDNF gene transcription in Huntington's disease. *Science*, 2001, 293.5529: 493-498.

Zuccato, Chiara; Cattaneo, Elena. Brain-derived neurotrophic factor in neurodegenerative diseases. *Nature Reviews Neurology*, 2009, 5.6: 311.

Zuccato, Chiara; Cattaneo, Elena. Role of brain-derived neurotrophic factor in Huntington's disease. *Progress in neurobiology*, 2007, 81.5-6: 294-330.

* cited by examiner

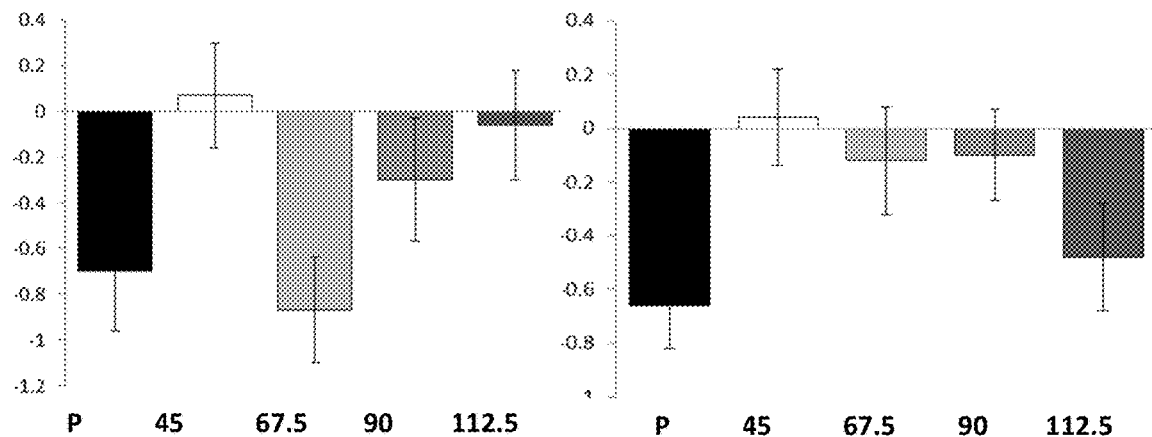
Fig. 11e
Fig. 11f
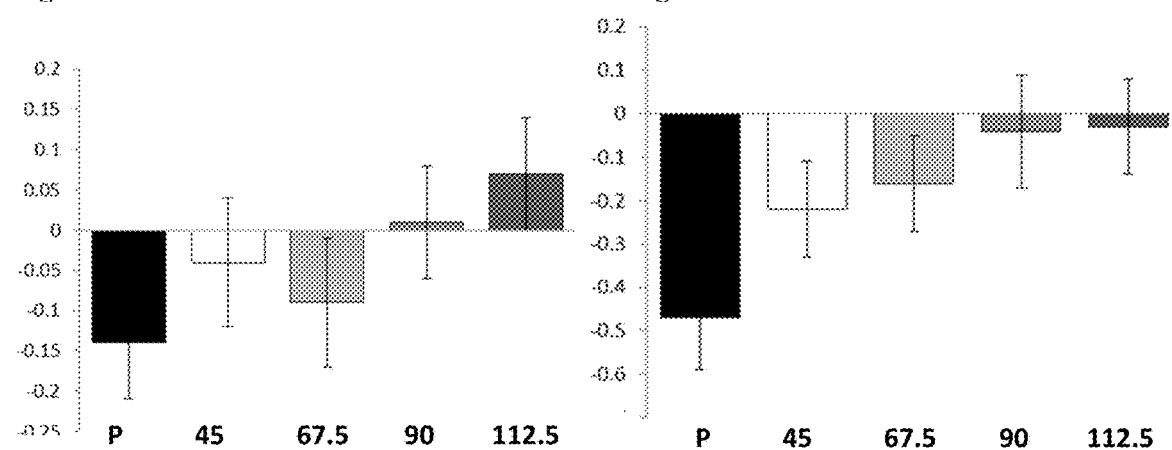
Fig. 12a
Fig. 12b
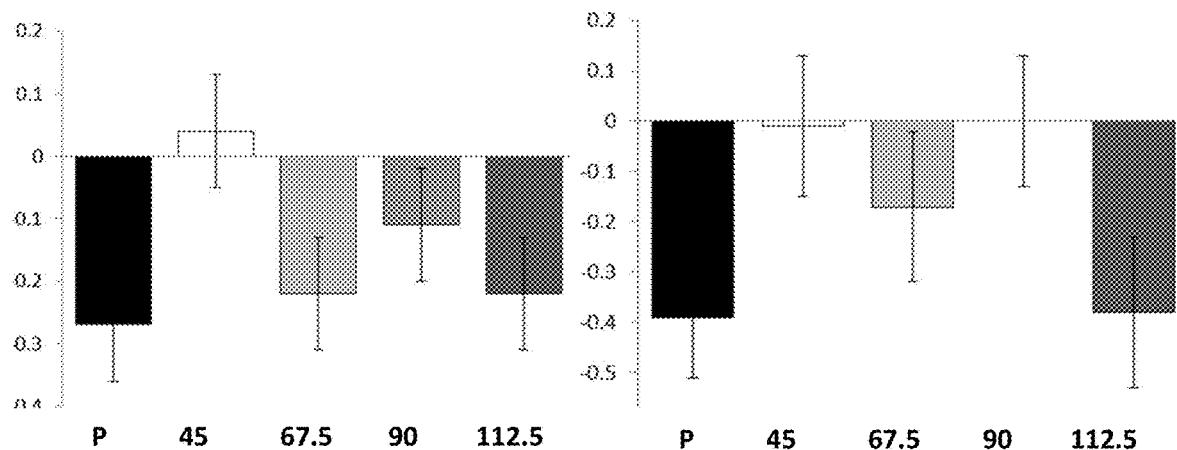
Fig. 12c
Fig. 12d Fig. 17e
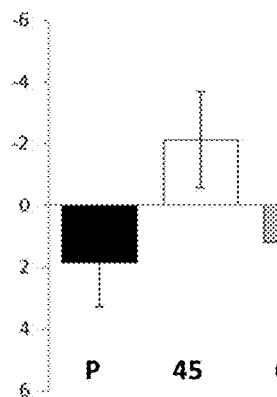
Fig. 17f
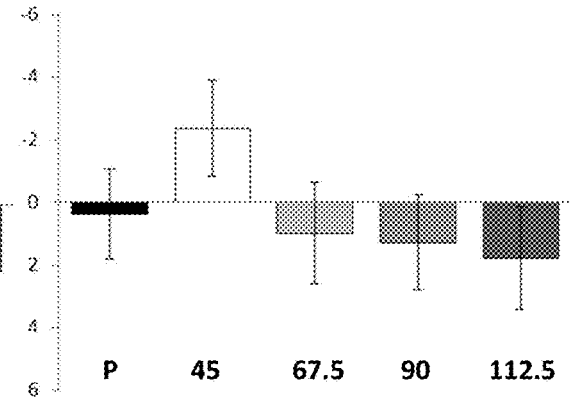
Fig. 17g
Fig. 17h
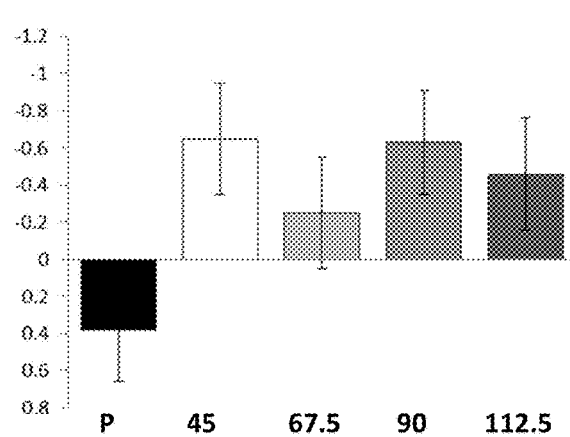
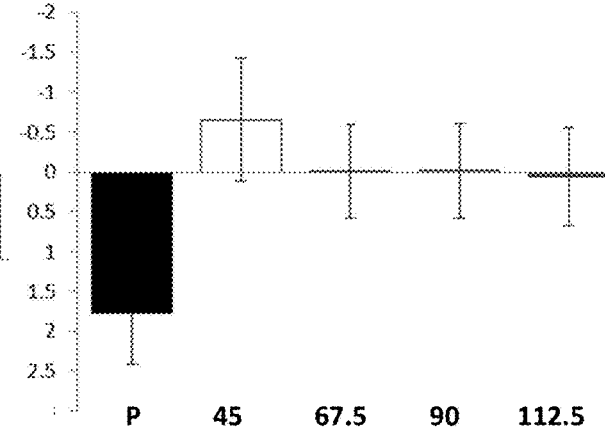
Fig. 17i
Fig. 17j
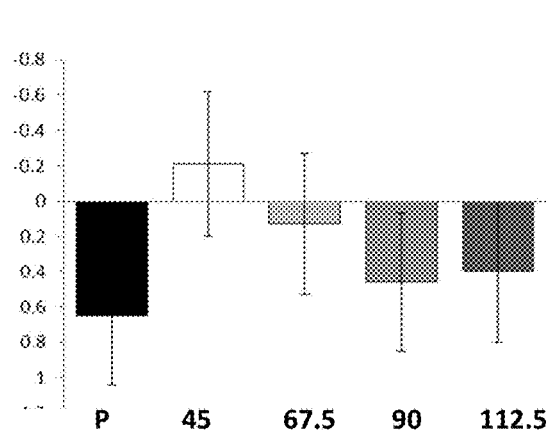
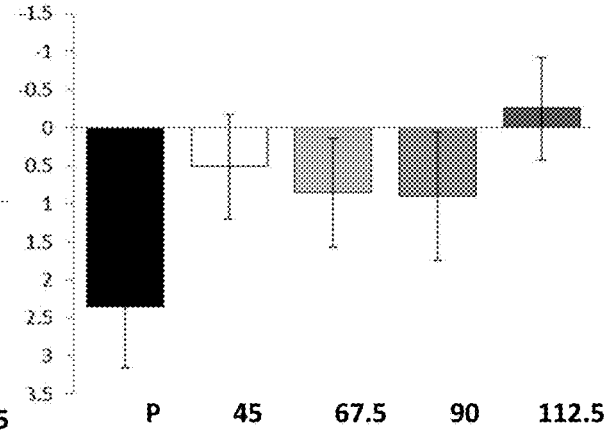

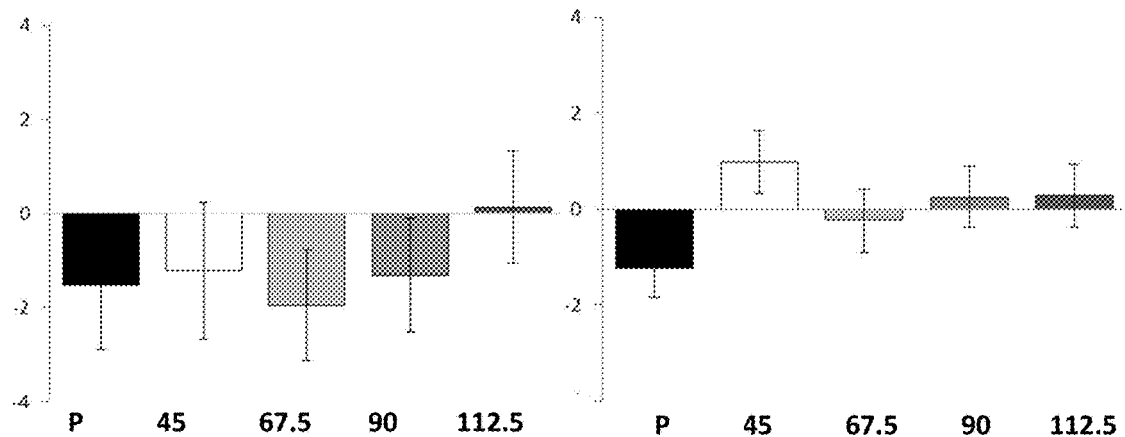
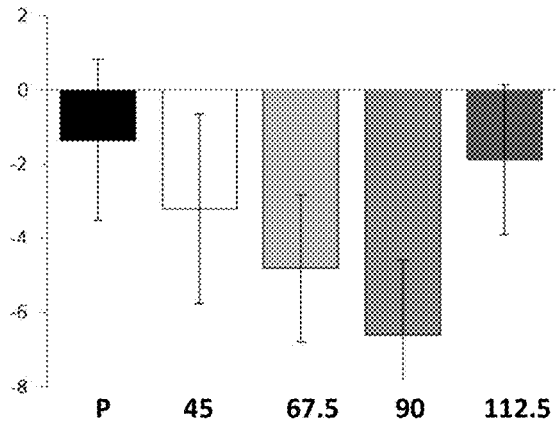
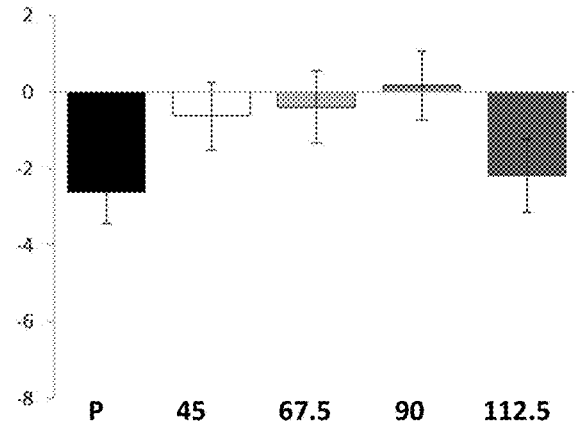

Fig. 34c
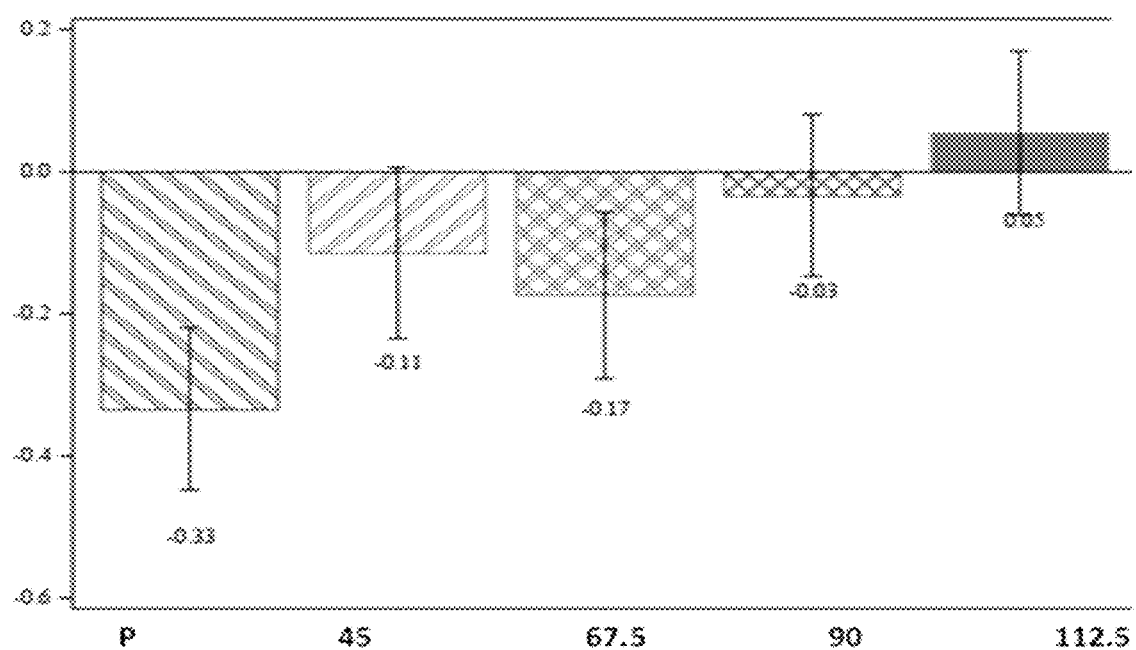
Fig. 35a                    Fig. 35b
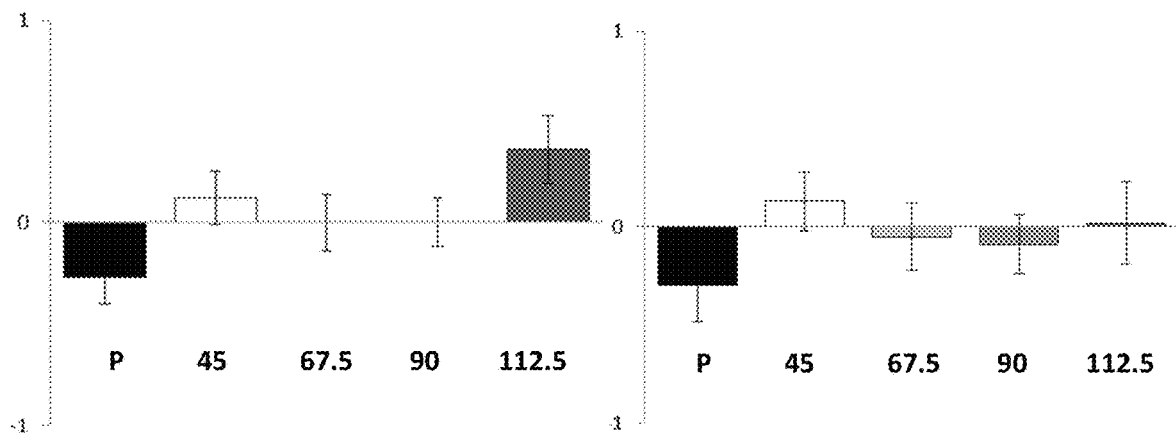

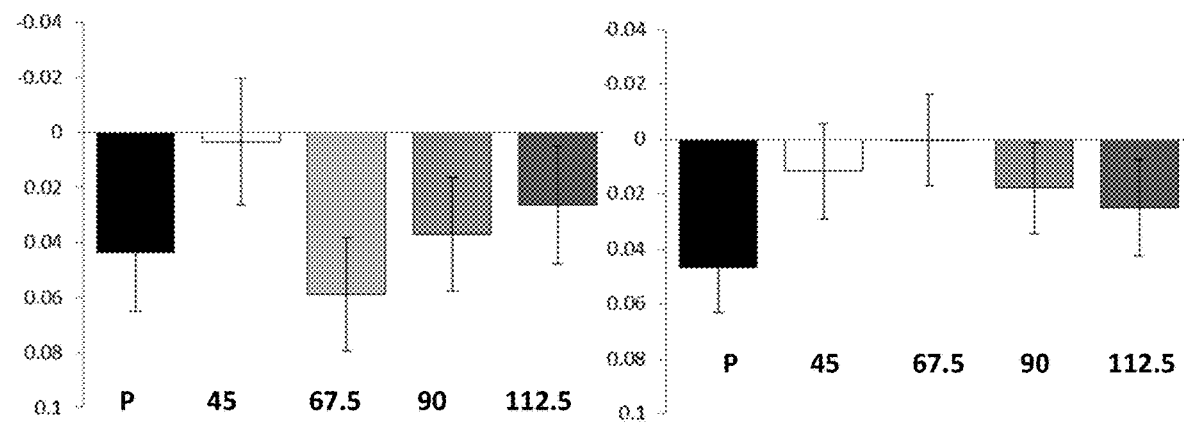
Fig. 39c
Fig. 39d
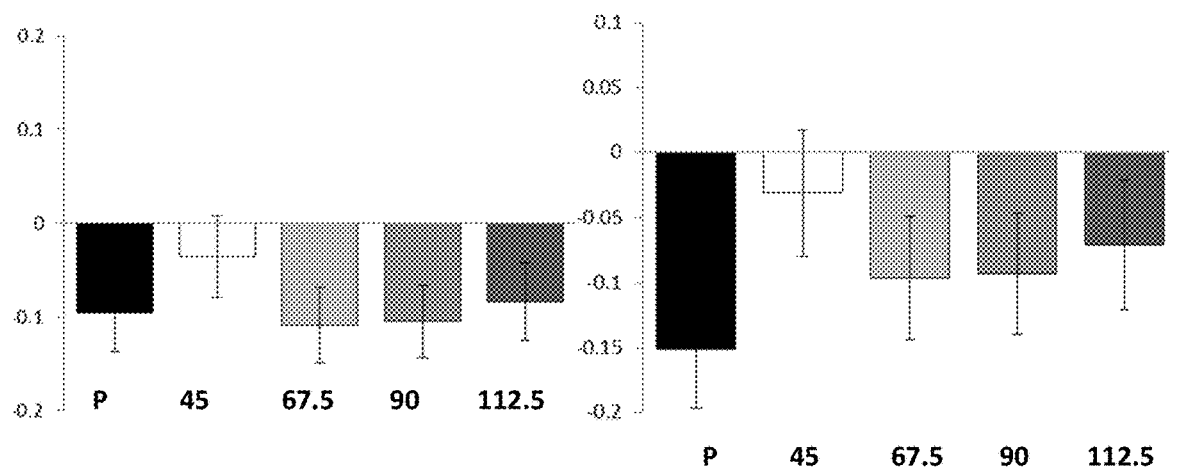
Fig. 39e
Fig. 39f

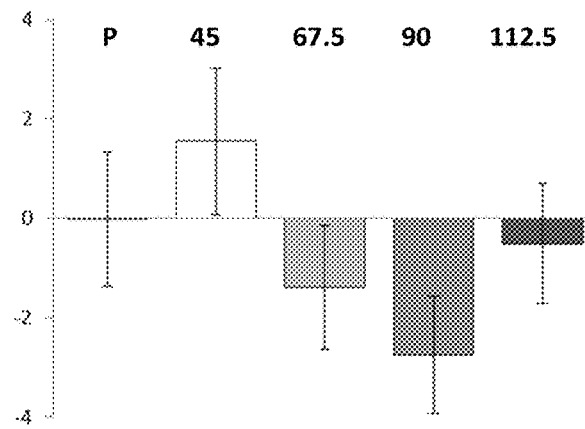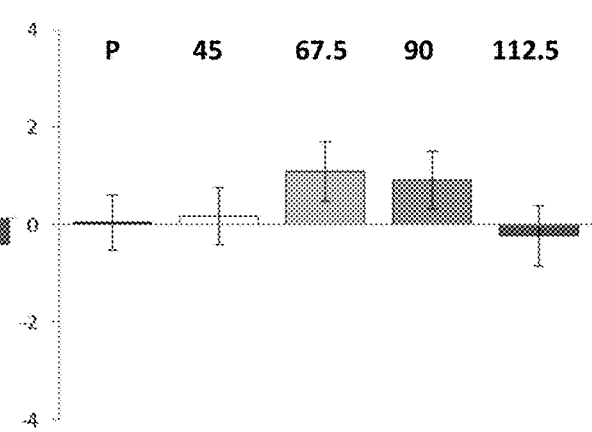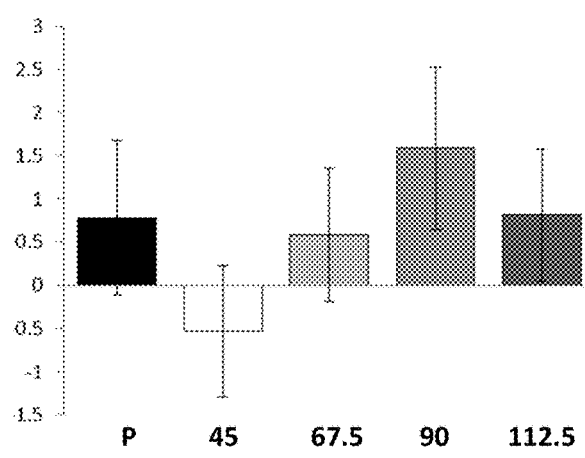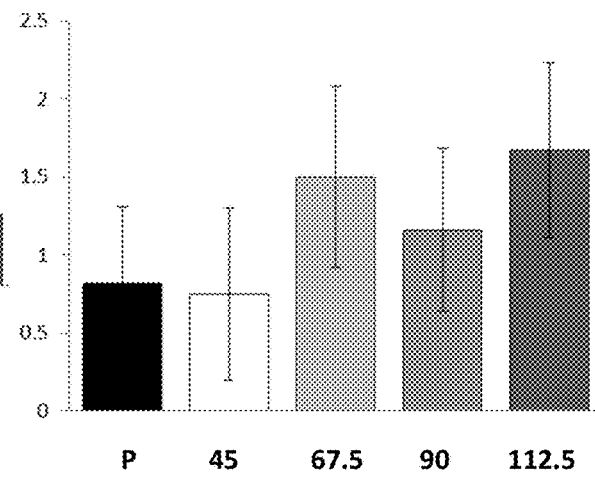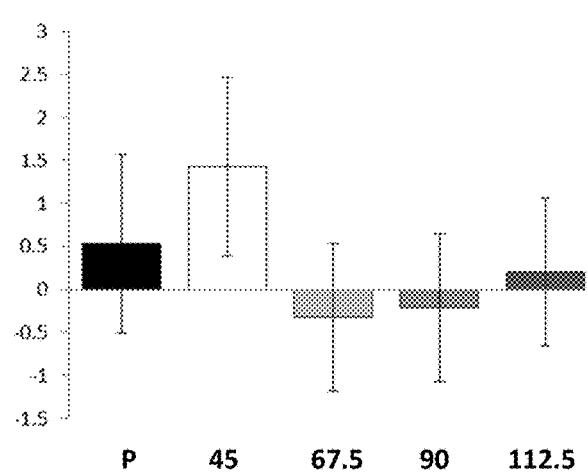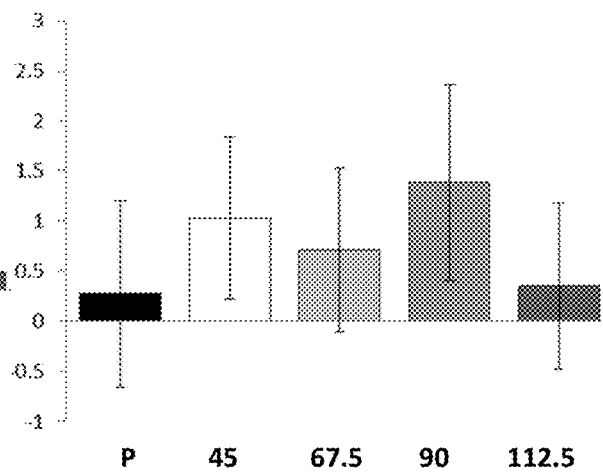

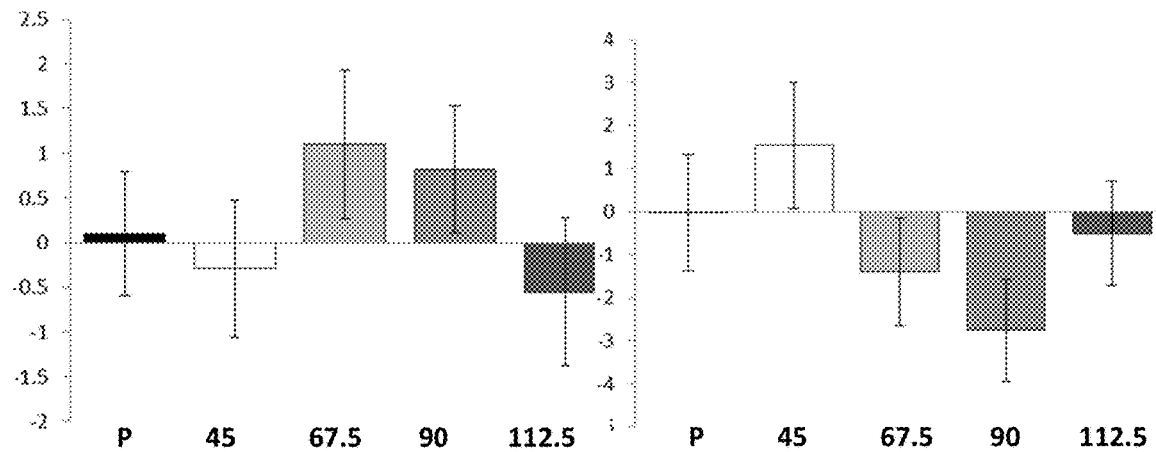
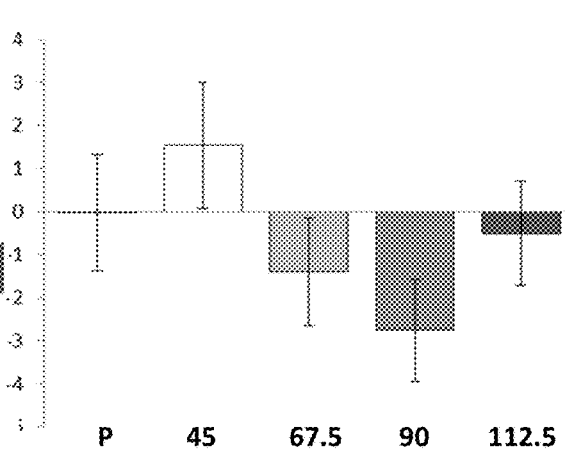
Fig. 46l
Fig. 46m
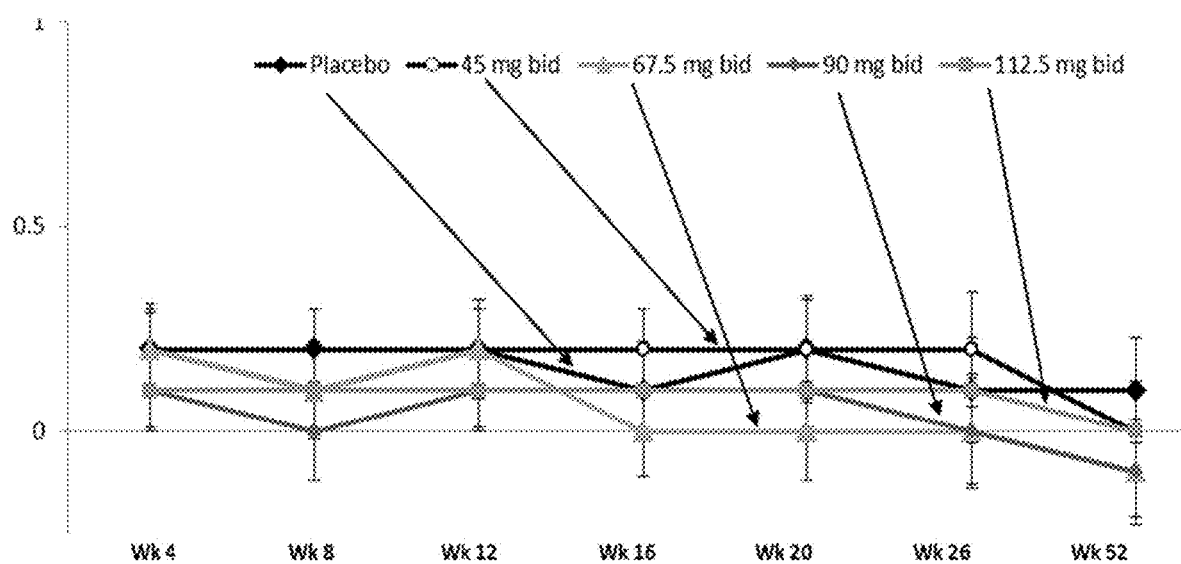
Fig. 46n
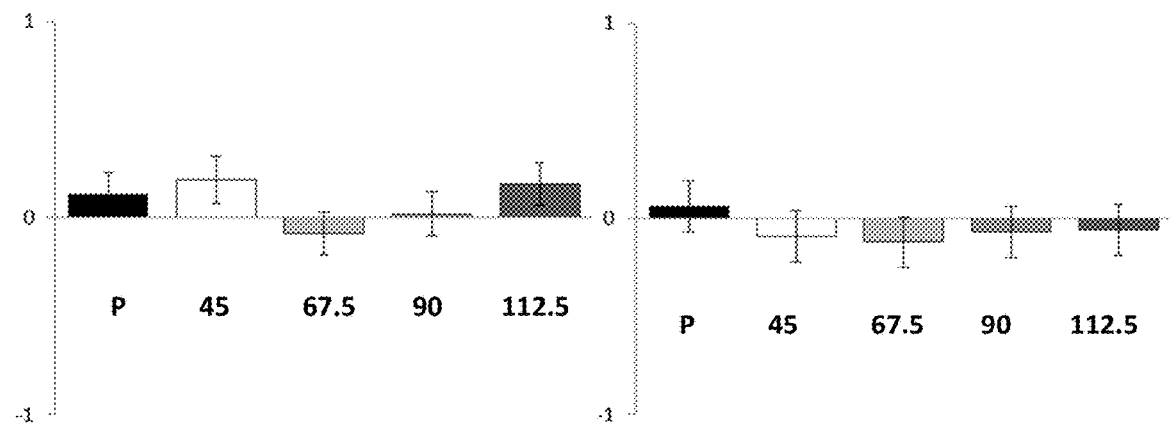
Fig. 46o
Fig. 46p

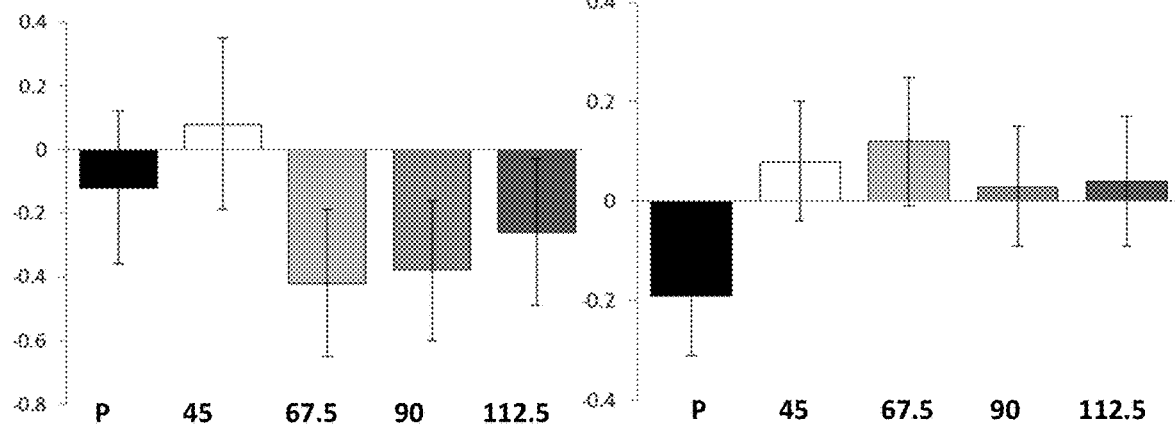
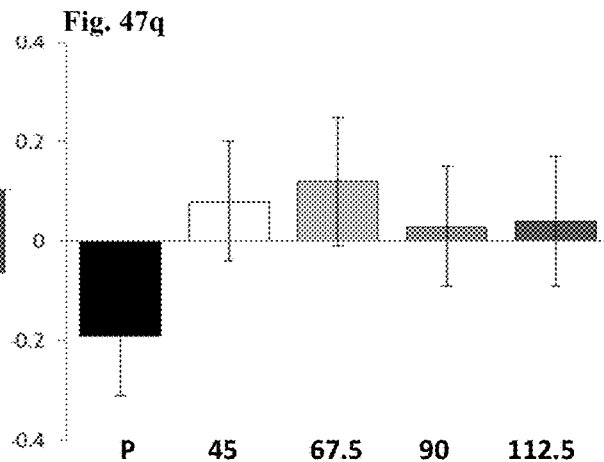
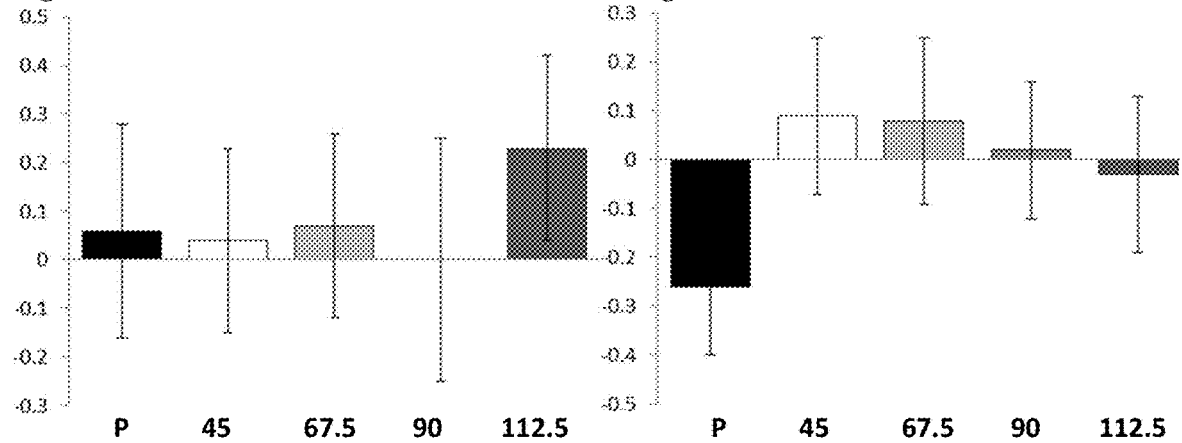
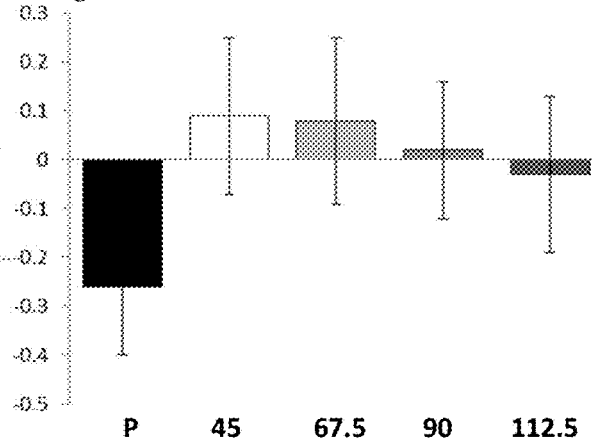
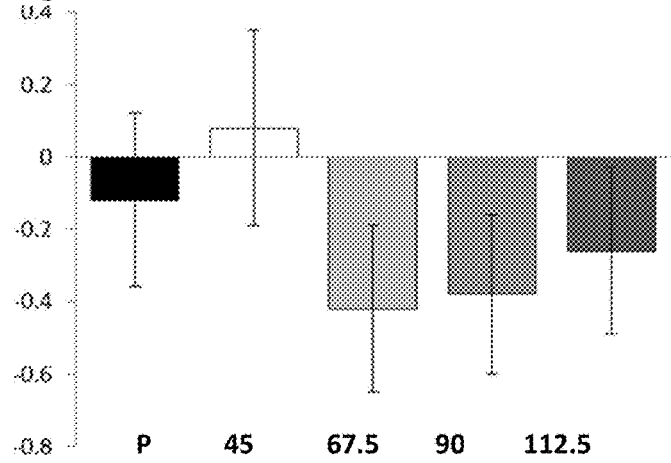

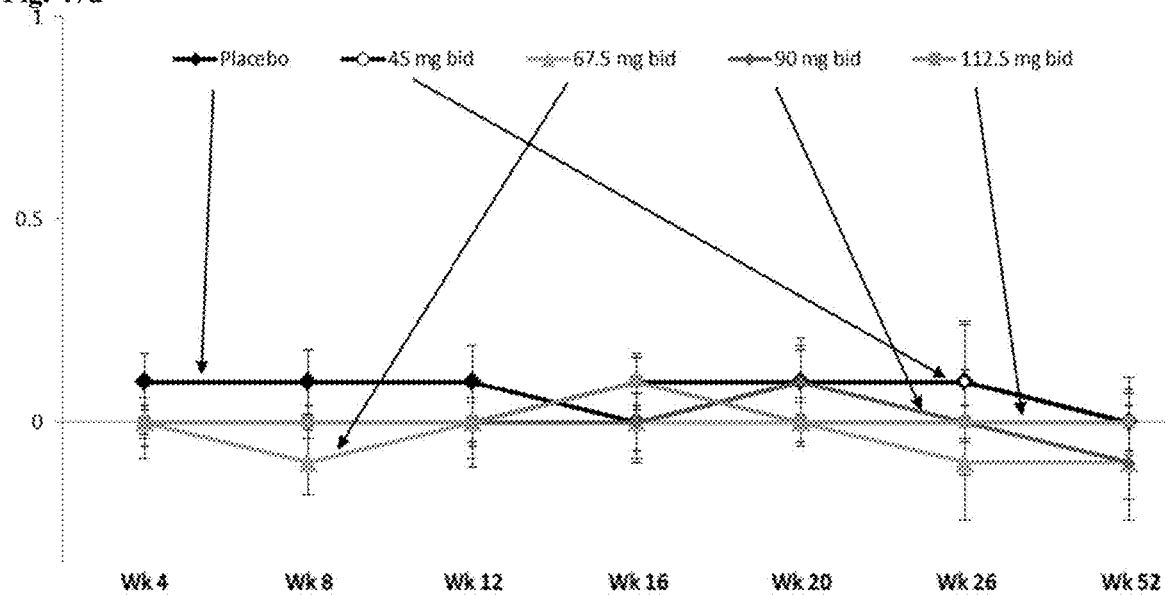
Fig. 47u
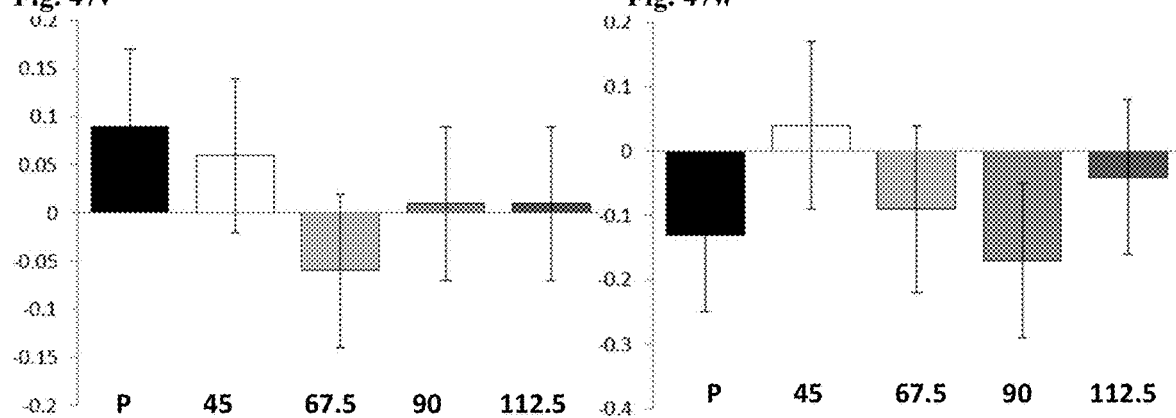
Fig. 47v
Fig. 47w
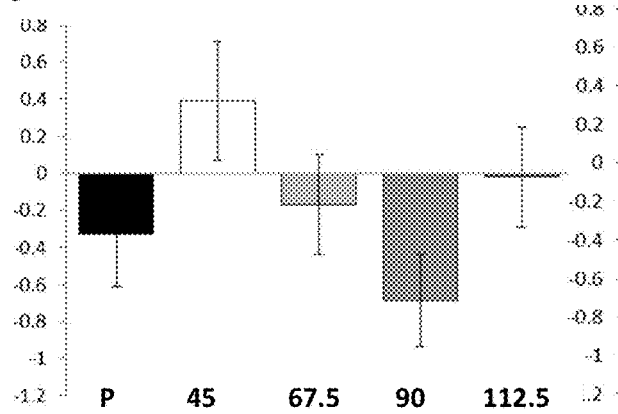
Fig. 47x
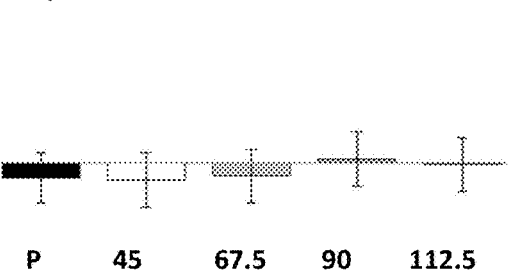
Fig. 47y

USE OF PRIDOPIDINE FOR TREATING FUNCTIONAL DECLINE

This application claims the benefit of U.S. Provisional Application No. 62/416,685, filed Nov. 2, 2016, U.S. Provisional Application No. 62/411,511, filed Oct. 21, 2016, U.S. Provisional Application No. 62/395,263, filed Sep. 15, 2016, and U.S. Provisional Application No. 62/379,175, filed Aug. 24, 2016, the contents of each of which are hereby incorporated by reference in their entirety.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND OF INVENTION

Huntington's Disease

Huntington's disease (HD) is a fatal neurodegenerative disorder with an autosomal dominant mode of inheritance. The disease is associated with a triad of motor, behavioral, and cognitive symptoms. Motor disturbances are the defining feature of the disease, with chorea the most evident motor symptom. Although useful for diagnosis, chorea is a poor marker of disease severity. Rather, disability and disease severity best correlate with negative motor features such as impairment in fine motor skills, bradykinesia, and gross motor coordination skills, including speech difficulties, gait, and postural dysfunction (Mahant 2003).

Dopamine is widely regarded as an important neurotransmitter modulating several aspects of brain functions including motor function (Nieoullon 2003). A disrupted dopaminergic signaling has been implicated in a number of neurological and psychiatric conditions, (Zhan 2011, Dunlop 2007) and there is considerable clinical and preclinical evidence suggesting that dopaminergic functions are also compromised in HD (Kung 2007, Huot 2007).

A number of medications are prescribed to ameliorate the motor and emotional problems associated with HD; however, the scientific evidence for the usefulness of various drugs in HD is poor (Mestre 2009, Mestre 2009). Only tetrabenazine and deutetrabenazine, which reduce dopamine availability and transmission, are registered specifically for the treatment of patients with HD for the management of chorea. No registered drugs are available for the management of the multifaceted symptoms of HD resulting in inexorable functional capacity decline throughout the course of the disease. As such, there is a significant unmet medical need to develop medications to retard or ameliorate functional deficits in HD.

Pridopidine

Pridopidine (4-[3-(methylsulfonyl)phenyl]-1-propyl-piperidine) (formerly known as ACR16) is a drug under development for treatment of Huntington's disease. Pridopidine has been shown to modulate motor activity by either suppressing hyperactivity or enhancing hypoactivity. The neuroprotective properties of pridopidine are suggested to be attributed to its high affinity to the sigma-1 receptor (S1R, binding IC50~100 nM), while the motor activity of pridopidine may be mediated primarily by its low-affinity, antagonistic activity at the dopamine D2 receptor (D2R) (binding IC50~10 μM) (Ponten 2010). Pridopidine shows low-affinity binding to additional receptors in the micromolar range.

The S1R is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the BDNF, dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival and to be impaired in HD. Moreover, pridopidine gene expression profile showed a reversed pattern of the HD disease gene expression profile in a Q175 knock-in (Q175 KI) HD mouse model (Geva 2016). Pridopidine also enhances secretion of the neuroprotective brain-derived neurotrophic factor (BDNF) in a neuroblastoma cell line, in a S1R-dependent manner (Geva 2016).

BRIEF SUMMARY OF THE INVENTION

This invention provides a method of maintaining functional capacity, improving functional capacity, or lessening the decline of functional capacity in a human patient comprising periodically orally administering to the patient a pharmaceutical composition comprising pridopidine such that a dose of 90-225 mg of pridopidine is administered to the patient per day, so as to thereby maintain functional capacity, improve functional capacity, or lessen the decline of functional capacity in the human patient. In some embodiments the method includes a dose of 90 mg or 180 mg of pridopidine administered to the patient per day. In some embodiments the method includes a dose of 90 mg of pridopidine administered to the patient per day. In some embodiments the patient is a Huntington's disease (HD) patient.

This invention provides a method of maintaining functional capacity, improving functional capacity, or reducing the rate of decline of functional capacity in a human patient comprising periodically orally administering to the patient a pharmaceutical composition comprising pridopidine such that a dose of 90-225 mg of pridopidine is administered to the patient per day, so as to thereby maintain functional capacity, improve functional capacity, or reduce the rate of decline of functional capacity in the human patient. In some embodiments the method includes a dose of 90 mg or 180 mg of pridopidine administered to the patient per day. In some embodiments the method includes a dose of 90 mg of pridopidine administered to the patient per day. In some embodiments the patient is a HD patient.

The invention additionally provides a method of slowing the clinical progression of HD as measured by total functional capacity in a human patient comprising periodically orally administering to the patient afflicted with HD a pharmaceutical composition comprising pridopidine such that a dose of 90-225 mg of pridopidine is administered to the patient per day, so as to thereby slow the clinical progression of HD in the patient as measured by total functional capacity. In some embodiments the method includes a dose of 90 mg or 180 mg of pridopidine administered to the patient per day. In some embodiments the method includes a dose of 90 mg of pridopidine administered to the patient per day. In some embodiments the 90 mg daily dose is administered to the patient as 45 mg bid.

Further provided is a method of decreasing functional decline in a human HD patient comprising periodically orally administering to the patient a pharmaceutical composition comprising pridopidine such that a dose of 90-180 mg of pridopidine is administered to the patient per day, so as to thereby decrease the functional decline in the patient. In some embodiments, functional decline from baseline in comparison to placebo (a HD subject not receiving pridopidine) is decreased by at least 10%, by at least 15%, by at least 20%, by at least 25%, by at least 30%, by at least 35% or by at least 40%. In some embodiments the method includes a dose of about 90 mg to about 180 mg of pridopidine administered to the patient per day. In some embodiments the method includes a dose of 90 mg of pridopidine administered to the patient per day. In some embodiments of the method, the 90 mg dose is administered to the patient as 45 mg bid. In some embodiments of the method, the pridopidine is administered orally. In some embodiments of the method, the administration continues for at least 26 weeks, at least 52 weeks, about 78 weeks or at least 78 weeks. In some embodiments of the method, the HD patient is an adult patient. HD patient is classified as an early stage patient, for example, as a stage 1 or stage 2 HD (HD1 or HD2) patient. In some embodiments, the patient has a baseline TFC score of 7-13 or at least 7, at least 8, at least 9, at least 10, at least 11, at least 12, 13 or 7-10 or 11-13. In some embodiments, functional capacity of a patient is measured using the Total Functional Capacity (TFC) scale of the Unified Huntington's Disease Rating Scale (UHDRS), UHDRS-TFC or TFC. In some embodiments of the method, the patient's baseline functional capacity and one or more subsequent functional capacity assessments is performed to determine any change in functional decline.

Further provided is a method of achieving a reduced change from baseline in the UHDRS-TFC score in a human HD patient comprising periodically orally administering to the patient a pharmaceutical composition comprising pridopidine such that a dose of 90-180 mg of pridopidine is administered to the patient per day, so as to thereby effect a change in the UHDRS-TFC score in the patient when compared to a HD subject not receiving pridopidine. In some embodiments the method includes a dose of about 90 mg to about 180 mg of pridopidine administered to the patient per day. In some embodiments the method includes a dose of 90 mg of pridopidine administered to the patient per day. In some embodiments of the method, the administration continues for at least 26 weeks, or at least 52 weeks or about 78 weeks or at least 78 weeks. In some embodiments of the method, the HD patient is classified as a stage 1 or stage 2 HD patient based on the patient's UHDRS-TFC score. In some embodiments, the patient has a baseline TFC score of 7-13 or at least 7, at least 8, at least 9, at least 10, at least 11, at least 12, 13 or 7-10 or 11-13. In some embodiments of the method, the difference in change from baseline in the UHDRS-TFC score, when compared to a HD subject not receiving pridopidine is reduced by at least 0.2 points over a period of 26 weeks or by at least 0.3 points over 52 weeks or by 0.5 over 78 weeks. In some embodiments of the method, the difference in change from baseline in the UHDRS-TFC score, when compared to a HD subject not receiving pridopidine, is a decrease in the rate of TFC decline by at least 20%, by at least 30% by at least 40% or by at least 50% at 78 weeks.

In some embodiments of the methods disclosed herein, TFC includes one or more of maintaining occupation, taking care of finances, domestic chores, requiring low level of care and activities of daily living (ADL).

The invention additionally provides a method of achieving a reduced change from baseline in the Timed Up and Go (TUG) test in a human HD patient comprising periodically orally administering to the patient a pharmaceutical composition comprising pridopidine such that a dose of 90-180 mg of pridopidine is administered to the patient per day, so as to thereby reduce the change in the TUG test in the patient compared to a HD subject not receiving pridopidine.

The invention additionally provides a method of achieving a reduced change from baseline in the TUG test in a human HD patient comprising periodically orally administering to the patient a pharmaceutical composition comprising pridopidine such that a dose of 90-180 mg of pridopidine is administered to the patient per day, so as to thereby reduce the change in the TUG test in the patient compared to a HD subject not receiving pridopidine.

The invention additionally provides a method of achieving a reduced change from baseline in the Symbol Digit Modalities test (SDMT) test in a human HD patient comprising periodically orally administering to the patient a pharmaceutical composition comprising pridopidine such that a dose of 90-180 mg of pridopidine is administered to the patient per day, so as to thereby reduce the change in the SDMT test in the patient compared to a HD subject not receiving pridopidine.

The invention additionally provides a method of achieving a reduced change from baseline in the Stroop Word test in a human HD patient comprising periodically orally administering to the patient a pharmaceutical composition comprising pridopidine such that a dose of 90-180 mg of pridopidine is administered to the patient per day, so as to thereby reduce the change in the Stroop Word test in the patient compared to a HD subject not receiving pridopidine.

The invention additionally provides a method of achieving a reduced change from baseline in the UHDRS-Independence Scale (UHDRS-IS) in a human HD patient comprising periodically orally administering to the patient a pharmaceutical composition comprising pridopidine such that a dose of 90-180 mg of pridopidine is administered to the patient per day, so as to thereby reduce the change in the UHDRS-IS in the patient compared to a HD subject not receiving pridopidine.

The invention additionally provides a method of achieving a reduced change from baseline in the gait and balance score as defined by the sum of the UHDRS-Total Motor Score (UHDRS-TMS) domains gait, tandem walking and retropulsion pull test in a human HD patient comprising periodically orally administering to the patient a pharmaceutical composition comprising pridopidine such that a dose of 90-180 mg of pridopidine is administered to the patient per day, so as to thereby reduce the change in the gait and balance score in the patient compared to a HD subject not receiving pridopidine.

The invention additionally provides a method of achieving a reduced change from baseline in the UHDRS-TMS chorea subscore in a human HD patient comprising periodically orally administering to the patient a pharmaceutical composition comprising pridopidine such that a dose of 90-180 mg of pridopidine is administered to the patient per day, so as to thereby reduce the change in the UHDRS-TMS chorea subscore in the patient compared to a HD subject not receiving pridopidine.

This invention also provides a method of maintaining or improving a human patient's ability to perform activities of daily living comprising periodically orally administering to the patient a pharmaceutical composition comprising pridopidine such that a dose of 90-225 mg of pridopidine is administered to the patient per day, so as to thereby maintain or improve the human patient's ability to perform activities of daily living.

The invention further provides a method of reducing dystonia or maintaining a level of dystonia in a human patient comprising periodically orally administering to the patient a pharmaceutical composition comprising pridopidine such that a dose of 90-225 mg of pridopidine is administered to the patient per day, so as to thereby reduce dystonia or maintain a level of dystonia in the human patient.

The invention also provides a method of treating limb Dystonia in a human patient comprising periodically orally administering to the patient a pharmaceutical composition comprising pridopidine such that a dose of 90-225 mg of pridopidine is administered to the patient per day, so as to thereby treat the limb dystonia in the human patient.

The invention further provides a method of improving or maintaining, a human patient's gait and balance comprising periodically orally administering to the patient a pharmaceutical composition comprising pridopidine such that a dose of 90-225 mg of pridopidine is administered to the patient per day, so as to thereby improve or maintain, a human patient's gait and balance.

Additionally provided is a method of improving, maintaining, or slowing the decline of, a human patient's gait and balance comprising periodically orally administering to the patient a pharmaceutical composition comprising pridopidine such that a dose of 90 mg of pridopidine is administered to the patient per day, so as to thereby improve, maintain, or slow the decline of, a human patient's gait and balance.

The invention also provides a method of improving or maintaining, a human patient's independence comprising periodically orally administering to the patient a pharmaceutical composition comprising pridopidine such that a dose of 90-225 mg of pridopidine is administered to the patient per day, so as to thereby improve or maintain a human patient's independence.

The invention also provides a method of improving, maintaining, or slowing the decline of, a human patient's independence comprising periodically orally administering to the patient a pharmaceutical composition comprising pridopidine such that a dose of 90 mg of pridopidine is administered to the patient per day, so as to thereby improve, maintain, or slow the decline of, a human patient's independence.

The invention also provides a method of improving or maintaining a human patient's cognitive domains comprising periodically orally administering to the patient a pharmaceutical composition comprising pridopidine such that a dose of 90-225 mg of pridopidine is administered to the patient per day, so as to thereby improve or maintain the human patient's cognitive domains.

Further provided is a method of improving, maintaining, or slowing the decline of, a human patient's cognitive domains comprising periodically orally administering to the patient a pharmaceutical composition comprising pridopidine such that a dose of 90 mg of pridopidine is administered to the patient per day, so as to thereby improve, maintain, or slow the decline of, a human patient's cognitive domains. A patient's cognitive domains may also be the patient's cognitive performance across a variety of domains The human patient's cognitive domains may be measured, for example, by the cognitive assessment battery (CAB) and/or the Hopkins Verbal Learning Test—Revised (HVLT-R). The cognitive domains may also be measured by the trail making test B (TMT-B). The cognitive domains may also be measured by the HD Cognitive Assessment Battery (HD-CAB), which includes 6 tests.

The invention also provides a method of reducing the severity of the sustained or intermittent muscle contractions associated with dystonia in a human patient comprising periodically orally administering to the patient a pharmaceutical composition comprising pridopidine such that a dose of 90-225 mg of pridopidine is administered to the patient per day, so as to thereby reduce the severity of the sustained or intermittent muscle contractions associated with dystonia in the human patient. In one embodiment of this method, the patient is afflicted with HD.

The severity of the sustained or intermittent muscle contractions associated with dystonia in a human patient may be measured by, for example, the UHDRS TMS Dystonia score.

Further provided is a method of improving or maintaining motor ability in a human patient comprising periodically orally administering to the patient a pharmaceutical composition comprising pridopidine such that a dose of 90-225 mg of pridopidine is administered to the patient per day, so as to thereby improve motor ability in the human patient.

The motor ability may be measured, for example, by the UHDRS Total Motor Score (TMS) score, the UHDRS TMS score excluding chorea or UHDRS TMS score excluding dystonia.

The invention also provides a method of reducing or maintaining the level of chorea in a human patient comprising periodically orally administering to the patient a pharmaceutical composition comprising pridopidine such that a dose of 90-225 mg of pridopidine is administered to the patient per day, so as to thereby reduce or maintain the level of chorea in a human patient.

The level of chorea may also be slowed. Accordingly, the invention provides a method of reducing, maintaining, or slowing the increase of, chorea in a human patient comprising periodically orally administering to the patient a pharmaceutical composition comprising pridopidine such that a dose of 90 mg of pridopidine is administered to the patient per day, so as to thereby reduce, maintain, or slow the increase of, chorea in a human patient.

The human patient's chorea may be measured by the UHDRS TMS chorea score.

The invention further provides a method of improving or maintaining a human patient's behavior and/or psychiatric state comprising periodically orally administering to the patient a pharmaceutical composition comprising pridopidine such that a dose of 90-225 mg of pridopidine is administered to the patient per day, so as to thereby improve or maintain the human patient's behavior and/or psychiatric state.

The human patient's behavior and/or psychiatric state may be measured, for example, by the Problem Behaviors Assessment total score. The human patient's behavior and/or psychiatric state may also be measured by the Problem Behaviors Assessment for depressed mood. The human patient's behavior and/or psychiatric state may also be measured by the Problem Behaviors Assessment for irritability. The human patient's behavior and/or psychiatric state may also be measured by the Problem Behaviors Assessment for lack of initiative or apathy. The human patient's behavior and/or psychiatric state may be measured, for example, by the Problem Behaviors Assessment for obsessive-compulsiveness. The human patient's behavior and/or psychiatric state may also be measured by the Problem Behaviors Assessment for disoriented behavior.

Further provided is a method of improving or lessening decline of lack of initiative or apathy in a human HD patient comprising periodically orally administering to the patient a pharmaceutical composition comprising pridopidine such that a dose of 90-225 mg of pridopidine is administered to the patient per day, so as to thereby improve or lessen decline of lack of initiative or apathy in the patient.

The invention also provides a method of reducing or maintaining a human patient's involuntary movements comprising periodically orally administering to the patient a pharmaceutical composition comprising pridopidine such that a dose of 90-225 mg of pridopidine is administered to the patient per day, so as to thereby reduce or maintain a human patient's involuntary movements.

The invention further provides method of improving or maintaining a human patient's mobility comprising periodically orally administering to the patient a pharmaceutical composition comprising pridopidine such that a dose of 90-225 mg of pridopidine is administered to the patient per day, so as to thereby improve or maintain the human patient's mobility.

This invention also provides a method of improving or maintaining a human patient's ability to perform physical tasks comprising periodically orally administering to the patient a pharmaceutical composition comprising pridopidine such that a dose of 90-225 mg of pridopidine is administered to the patient per day, so as to thereby improve or maintain the human patient's ability to perform physical tasks.

In some embodiments of the methods disclosed above, a dose of 90 mg or 180 mg of pridopidine is administered to the patient per day. In some embodiments of the methods disclosed above, a dose of 90 mg of pridopidine administered to the patient per day. In preferred embodiments of the methods disclosed above, the dose of 90 mg of pridopidine administered to the patient per day is administered to the patient as 45 mg bid.

In some embodiments, the patient is administered 45 mg pridopidine qd for about one to two weeks and 45 mg pridopidine bid thereafter. In some embodiments of the methods disclosed above, the administration continues for at least 12 weeks, at least 26 weeks, more than 26 weeks, at least 52 weeks or at least 78 weeks. In some embodiments of the methods disclosed above, the administration continues for 52 weeks or 78 weeks. In some embodiments of the methods disclosed above, the HD patient is an early stage HD patient and has a baseline TFC score of at least 7, at least 8, at least 9, at least 10, at least 11, at least 12, 13, or 7-10 or 11-13. In some embodiments of the methods disclosed above, the HD patient has been diagnosed as having at least 36 CAG repeats in the huntingtin gene. In some embodiments, the HD patient has been diagnosed as having at least 44 repeats in the huntingtin gene. In some embodiments of the methods disclosed above the HD patient is an adult patient and is at least 18 years old or is at least 21 years old. In some embodiments of the methods disclosed above, the HD patient is an early stage HD patient. In some embodiments the patient is a stage 1 HD (HD1) patient or stage 2 HD (HD2) patient. In some embodiments, the patient is HD1 patient and is experiencing one or more symptom of HD. In some embodiments, the HD patient is not a pre-manifest HD patient.

Provided herein is a pharmaceutical composition comprising pridopidine for use in lessening the decline of functional capacity in a human patient wherein the pharmaceutical composition is to be periodically orally administered to the patient such that a dose of 90-225 mg of pridopidine is to be administered to the patient per day. In some embodiments functional capacity is total functional capacity. In some embodiments the daily dose is 90 mg pridopidine. In some embodiments the daily dose is 45 mg bid.

Provided herein is a pharmaceutical composition comprising pridopidine for use in maintaining functional capacity in a human patient wherein the pharmaceutical composition is to be periodically orally administered to the patient such that a dose of 90-225 mg of pridopidine is to be administered to the patient per day. In some embodiments functional capacity includes activities of daily living (ADL).

Provided herein is use of an amount of pridopidine in the manufacture of a medicament maintaining functional capacity in a human patient wherein the medicament is formulated for periodic oral administration to the patient such that a dose of 90-225 mg of pridopidine is to be administered to the patient per day. In some embodiments functional capacity includes ADL.

Provided herein is a pharmaceutical composition comprising pridopidine for use in slowing the clinical progression of HD as measured by total functional capacity in a human patient wherein the pharmaceutical composition is to be periodically orally administered to the patient such that a dose of 90-225 mg of pridopidine is to be administered to the patient per day. In many embodiments, (a) the pharmaceutical composition is administered for more than 26 weeks or (b) a titration dose of an amount different from the intended dose is administered for a period of time at the start of the periodic administration, or (c) the human patient is afflicted with early stage Huntington's disease In some embodiments of the pharmaceutical compositions and uses, TFC includes one or more of maintaining occupation, taking care of finances, domestic chores, requiring low level of care and activities of daily living (ADL).

Provided herein is a use of an amount of pridopidine in the manufacture of a medicament for slowing the clinical progression of HD as measured by total functional capacity in a human patient wherein the medicament is formulated for periodic oral administration to the patient such that a dose of 90-225 mg of pridopidine is to be administered to the patient per day.

Provided herein is a pharmaceutical composition comprising pridopidine for use in maintaining a human patient's ability to perform activities of daily living in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in maintaining a human patient's ability to perform activities of daily living in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing dystonia or maintaining a level of dystonia in a human patient wherein the pharmaceutical composition is to be periodically orally administered to the patient such that a dose of 90-225 mg of pridopidine is to be administered to the patient per day. In some embodiments dystonia includes limb dystonia.

Provided herein is use of an amount of pridopidine in the manufacture of a medicament for use in reducing dystonia or maintaining a level of dystonia in a human patient wherein the medicament is formulated for periodic oral administration to the patient such that a dose of 90-225 mg of pridopidine is to be administered to the patient per day. In some embodiments dystonia includes limb dystonia.

Provided herein is a pharmaceutical composition comprising pridopidine for use in treating limb dystonia in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in treating limb dystonia in a human patient wherein the medicament is formulated for periodic oral administration to the patient such that a dose of 90-225 mg of pridopidine is to be administered to the patient per day.

Provided herein is a pharmaceutical composition comprising pridopidine for use in improving or maintaining gait and balance in a human patient wherein the pharmaceutical composition is to be periodically orally administered to the patient such that a dose of 90-225 mg of pridopidine is to be administered to the patient per day. In some embodiments the administration slows the decline of a patients gait and balance.

Provided herein is use of an amount of pridopidine in the manufacture of a medicament for use in improving or maintaining, a human patient's gait and balance in a human patient wherein the medicament is formulated for periodic oral administration to the patient such that a dose of 90-225 mg of pridopidine is to be administered to the patient per day. In some embodiments the administration slows the decline of a patients gait and balance.

Provided herein is a pharmaceutical composition comprising pridopidine for use in improving, maintaining, or slowing the decline of gait and balance in a human patient wherein the pharmaceutical composition is to be periodically orally administered to the patient such that a dose of 90 mg of pridopidine is to be administered to the patient per day. In some embodiments the administration slows the decline of a patients gait and balance.

Provided herein is use of an amount of pridopidine in the manufacture of a medicament for use in improving, maintaining, or slowing the decline of, a human patient's gait and balance in a human patient wherein the medicament is formulated for periodic oral administration to the patient such that a dose of 90 mg of pridopidine is to be administered to the patient per day. In some embodiments the administration slows the decline of a patients gait and balance.

Provided herein is a pharmaceutical composition comprising pridopidine for use in improving or maintaining independence in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining, a human patient's independence wherein the medicament is formulated for periodic oral administration to the patient such that a dose of 90-225 mg of pridopidine is to be administered to the patient per day.

Provided herein is a pharmaceutical composition comprising pridopidine for use in improving or maintaining or slowing the decline of a human patient's independence wherein the pharmaceutical composition is to be periodically orally administered to the patient such that a dose of 90 mg of pridopidine is to be administered to the patient per day.

Provided herein is use of an amount of pridopidine in the manufacture of a medicament for use in improving or maintaining, or slowing the decline of a human patient's independence wherein the medicament is formulated for periodic oral administration to the patient such that a dose of 90 mg of pridopidine is to be administered to the patient per day.

Provided herein is a pharmaceutical composition comprising pridopidine for use in improving or maintaining a human patient's cognitive domains wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's cognitive domains wherein the medicament is formulated for periodic oral administration to the patient such that a dose of 90 mg of pridopidine is to be administered to the patient per day.

Provided herein is a pharmaceutical composition comprising pridopidine for use in improving or maintaining or slowing the decline of a human patient's cognitive domains wherein the pharmaceutical composition is to be periodically orally administered to the patient such that a dose of 90 mg of pridopidine is to be administered to the patient per day.

Provided herein is use of an amount of pridopidine in the manufacture of a medicament for use in improving or maintaining or slowing the decline of a human patient's cognitive domains wherein the medicament is formulated for periodic oral administration to the patient such that a dose of 90-225 mg of pridopidine is to be administered to the patient per day.

Provided herein is a pharmaceutical composition comprising pridopidine for use in reducing the severity of the sustained or intermittent muscle contractions associated with dystonia in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing the severity of the sustained or intermittent muscle contractions associated with dystonia in a human patient wherein the medicament is formulated for periodic oral administration to the patient such that a dose of 90-225 mg of pridopidine is to be administered to the patient per day.

Provided herein is a pharmaceutical composition comprising pridopidine for use in improving or maintaining motor ability in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining motor ability in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining the level of chorea in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing or maintaining the level of chorea in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining or slowing the increase of chorea in a human patient wherein the pharmaceutical composition is to be periodically orally administered to the patient such that a dose of 90 mg of pridopidine is to be administered to the patient per day.

Provided herein is use of an amount of pridopidine in the manufacture of a medicament for use in reducing or maintaining or slowing the increase of chorea in a human patient wherein the medicament is formulated for periodic oral administration to the patient such that a dose of 90 mg of pridopidine is to be administered to the patient per day.

Provided herein is a pharmaceutical composition comprising pridopidine for use in improving or maintaining a human patient's behavior and/or psychiatric state wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's behavior and/or psychiatric state wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining a human patient's involuntary movements wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing or maintaining a human patient's involuntary movements wherein the medicament is formulated for periodic oral administration to the patient such that a dose of 90-225 mg of pridopidine is to be administered to the patient per day.

Provided herein is a pharmaceutical composition comprising pridopidine for use in improving or maintaining a human patient's mobility wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's mobility wherein the medicament is formulated for periodic oral administration to the patient such that a dose of 90-225 mg of pridopidine is to be administered to the patient per day.

Provided herein is a pharmaceutical composition comprising pridopidine for use in improving or maintaining a human patient's ability to perform physical tasks wherein the pharmaceutical composition is to be periodically orally administered to the patient such that a dose of 90-225 mg of pridopidine is to be administered to the patient per day.

Provided herein is a use of an amount of pridopidine in the manufacture of a medicament for use in improving or maintaining a human patient's ability to perform physical tasks wherein the medicament is formulated for periodic oral administration to the patient such that a dose of 90-225 mg of pridopidine is to be administered to the patient per day.

The methods, compositions and uses disclosed herein are applicable, for example, to a human patient afflicted with Huntington's disease. In some embodiments of the methods compositions and uses, the human patient is afflicted with HD and has a baseline TMS score which is in the least severe quarter of the overall population of patients afflicted with Huntington's disease; or the human patient is afflicted with HD and has a baseline TMS score which is in the two least severe quarters of the overall population of patients afflicted with Huntington's disease; or the human patient is afflicted with HD and has a baseline TMS score which is in the three least severe quarters of the overall population of patients afflicted with Huntington's disease; or the human patient is afflicted with HD and has a baseline TMS score which is in the three least severe quarters of the overall population of patients afflicted with HD or a baseline TFC score which is greater than or equal to 9; or the human patient is afflicted with HD and has a baseline TMS score which is in the three least severe quarters of the overall population of patients afflicted with HD or a baseline TFC score which is greater than or equal to 9 or less than 44 CAG repeats in the Huntingtin gene; or the human patient is afflicted with HD and has a baseline TMS score which is in the two least severe quarters of the overall population of patients afflicted with HD; or the human patient is afflicted with HD and has a baseline TFC score which is greater than or equal to 7; or the human patient is afflicted with HD and has a baseline TFC score of 11-13; or the human patient is afflicted with HD and has a baseline TFC score which is greater than or equal to 9 or greater than 44 CAG repeats in the huntingtin gene; or the human patient is afflicted with HD and has a baseline TMS score which is in the three least severe quarters of the overall population of patients afflicted with HD or less than 44 CAG repeats in the huntingtin gene; or the human patient is afflicted with HD and has a baseline TFC score which is greater than or equal to 9 or a baseline TMS score which is in the three least severe quarters of the overall population of patients afflicted with HD.

In some embodiments of the methods, compositions and uses disclosed herein the pridopidine or a pharmaceutically acceptable salt thereof is pridopidine hydrochloride.

A pharmaceutical composition comprising pridopidine or a pharmaceutically acceptable salt thereof, for example pridopidine hydrochloride, is to be periodically orally administered to the patient such that a dose of 90-225 mg of pridopidine is to be administered to the patient per day.

In some embodiments of the compositions and uses disclosed above, a dose of 90 mg or 180 mg of pridopidine is to be administered to the patient per day. In some embodiments of the methods disclosed above, a dose of 90 mg of pridopidine is to be administered to the patient per day. In preferred embodiments of the methods disclosed above, the dose of 90 mg of pridopidine to be administered to the patient per day is to be administered to the patient as 45 mg bid.

In some embodiments, the patient is to be administered 45 mg pridopidine once daily (qd) for about one to two weeks and 45 mg pridopidine bid thereafter. In some embodiments of the methods disclosed above, the administration continues for at least 12 weeks, at least 26 weeks, at least 52 weeks or at least 78 weeks. In some embodiments of the methods disclosed above, the administration continues for 52 weeks or 78 weeks. In some embodiments of the methods disclosed above, the HD patient is a stage 1 or stage 2 HD patient and has a baseline TFC score of at least 7, at least 8, at least 9, at least 10, at least 11, at least 12, 13, or 7-10 or 11-13. In some embodiments of the methods disclosed above, the HD patient has been diagnosed as having at least 36 CAG repeats in the huntingtin gene. In some embodiments of the methods disclosed above the HD patient is 21 years old or older.

In some embodiments of the methods, compositions and uses disclosed above, the HD patient is a HD1 or HD2 patient and is not a pre-manifest HD patient.

BRIEF DESCRIPTION OF THE SEVERAL VIEWS OF THE DRAWINGS

In the following brief descriptions of the figures and the corresponding figures, efficacy was assessed throughout the 52-week period using Mixed Models Repeated Measures (MMRM) analyses of change from baseline (prior to administration of pridopidine at week 0) in the UHDRS-TMS, UHDRS-Behavioral, UHDRS-Cognitive, TFC, UHDRS-Functional Assessment, UHDRS-Independence Scale, the modified Physical Performance Test (mPPT), individual TMS subscales, HD-Cognitive Assessment Battery (HD-CAB), Problem Behavior Assessment Short-Form (PBA-s), and other outcomes.

Figure 1:
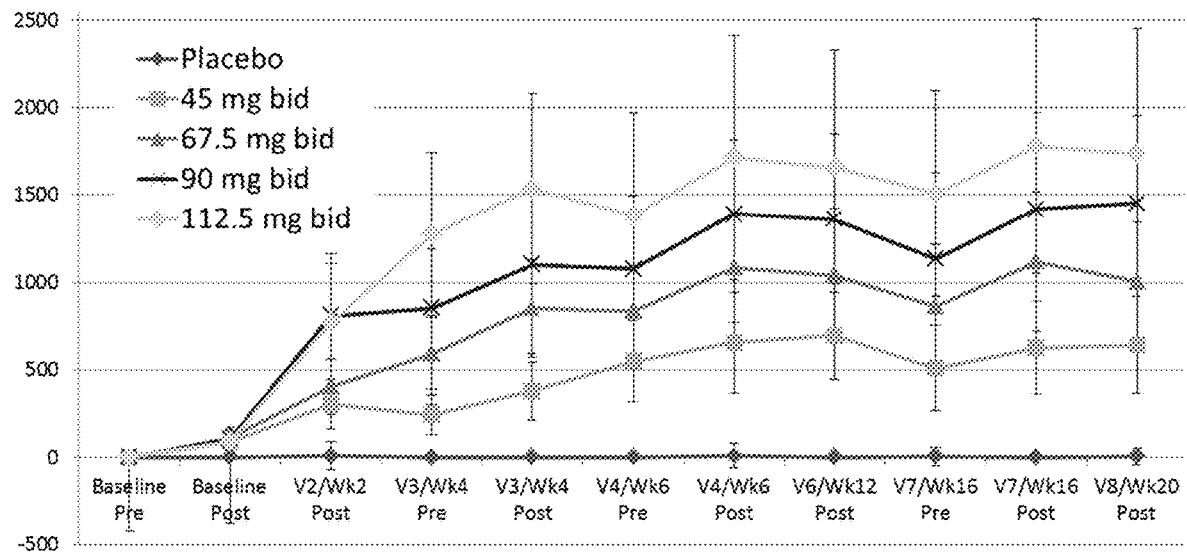
FIG. 1: Pridopidine concentration in patient's blood (ng/mL; Mean (+/−sd) measured values). "Pre" means predose and "post" mean post dose. V2 means visit 2, V3 means visit 3, etc. Wk2 means second week, Wk3 means third week, etc.
Figure 2:
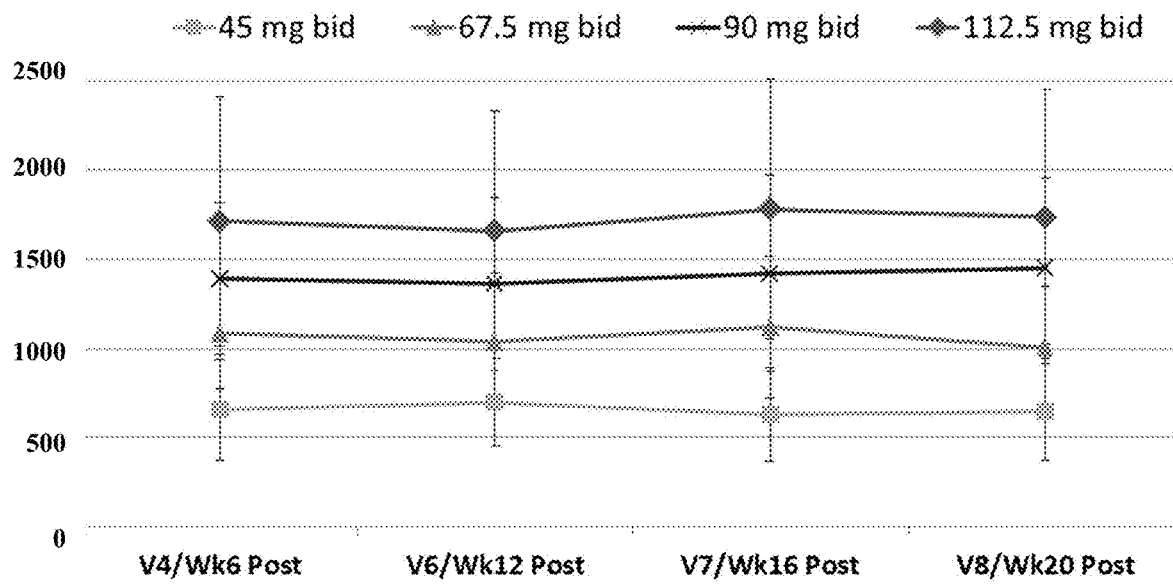
FIG. 2: Pridopidine concentration in patient's blood (ng/mL). Post-dose ("Cmax") (+/−sd) at Steady State.

For FIGS. 1 and 2, a % coefficient variation (CV) of around 40% for measured values is considered adequate for this setting [1-2 hours post dose, patient population, sparse sampling]. Variability is expected to decrease once true sampling times are taken into consideration.

Figure 3:
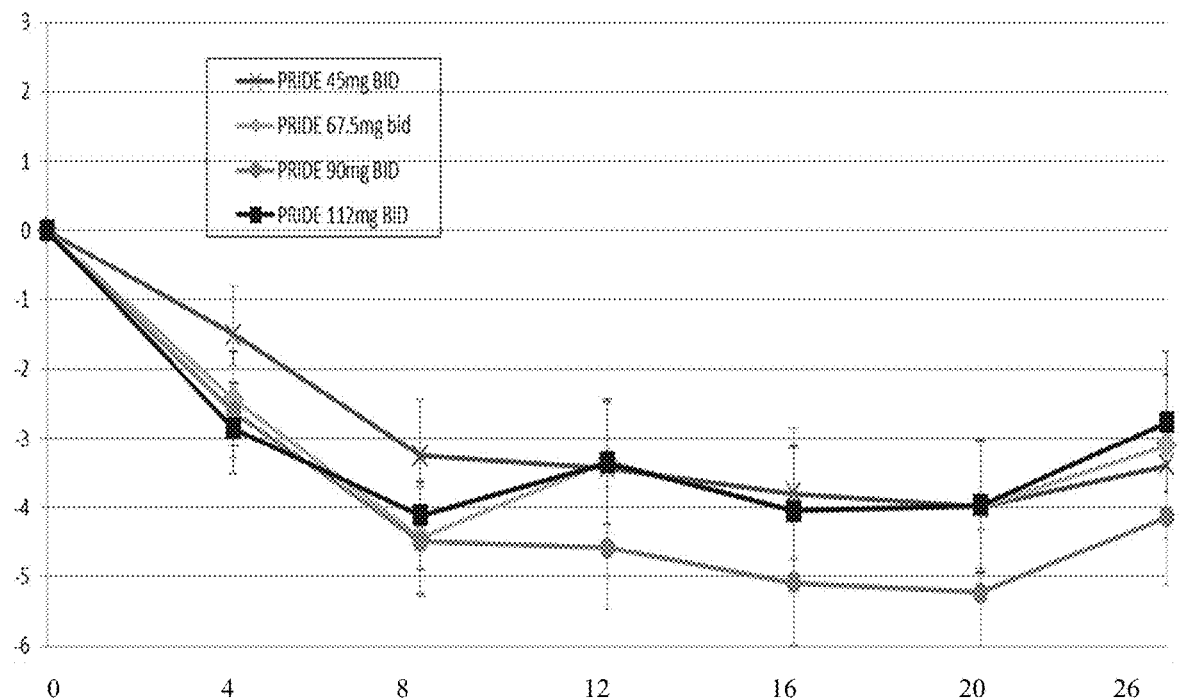

FIG. 3: Total Motor Score (TMS) Change from Baseline (BL) with pridopidine administration. The 90 mg bid dose (circles) demonstrated the largest treatment effect. A decrease in TMS indicates an improvement. Table 1 below shows the P-Values corresponding to FIG. 3.

TABLE 1

| Week | 45 mg bid | 67.5 mg bid | 90 mg bid | 112.5 mg bid |
|---|---|---|---|---|
| 4 | 0.0304 | 0.0004 | <.0001 | <.0001 |
| 8 | <.0001 | <.0001 | <.0001 | <.0001 |
| 12 | 0.0002 | 0.0003 | <.0001 | 0.0002 |
| 16 | <.0001 | <.0001 | <.0001 | <.0001 |
| 20 | <.0001 | <.0001 | <.0001 | <.0001 |
| 26 | 0.0013 | 0.0024 | <.0001 | 0.0063 |

Figure 4:
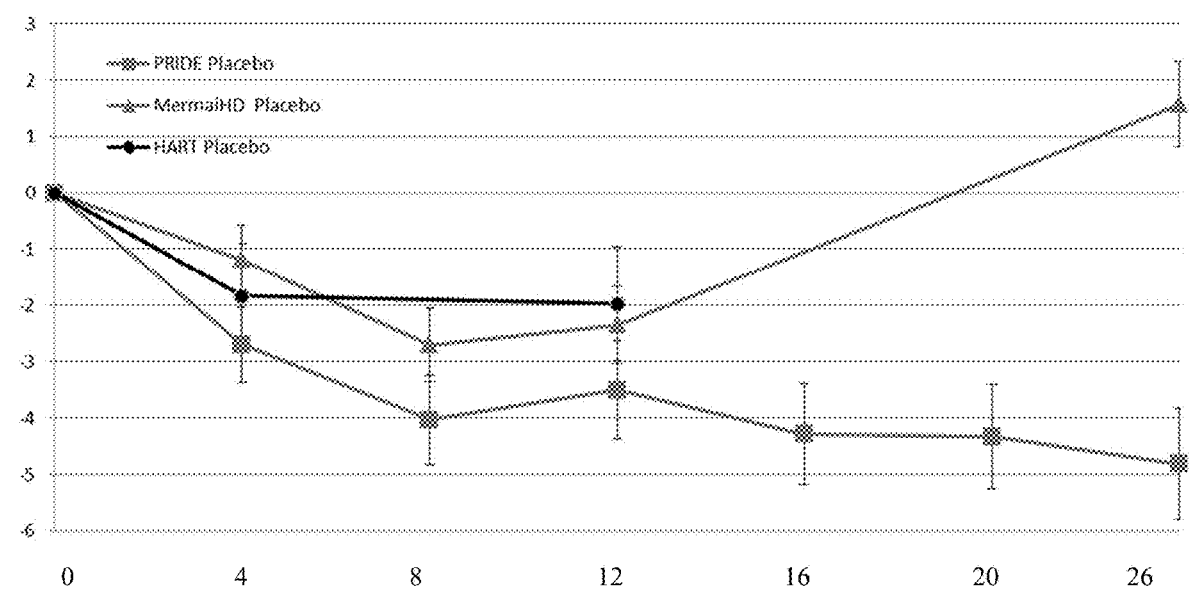

FIG. 4: Total Motor Score (TMS)—Change from Baseline PRIDE-HD placebo vs historical placebo in HART and MermaiHD clinical trials. A lower number indicates improvement. There is about a 6.5 TMS point difference at week 26.

Figure 5A:
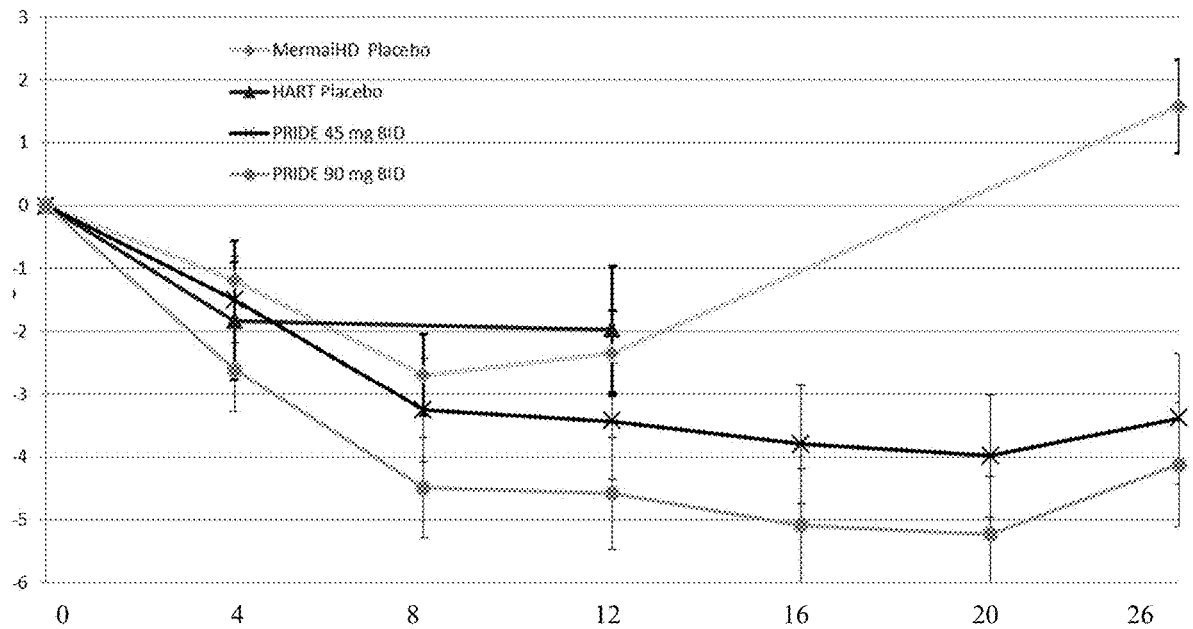
Figure 5B:
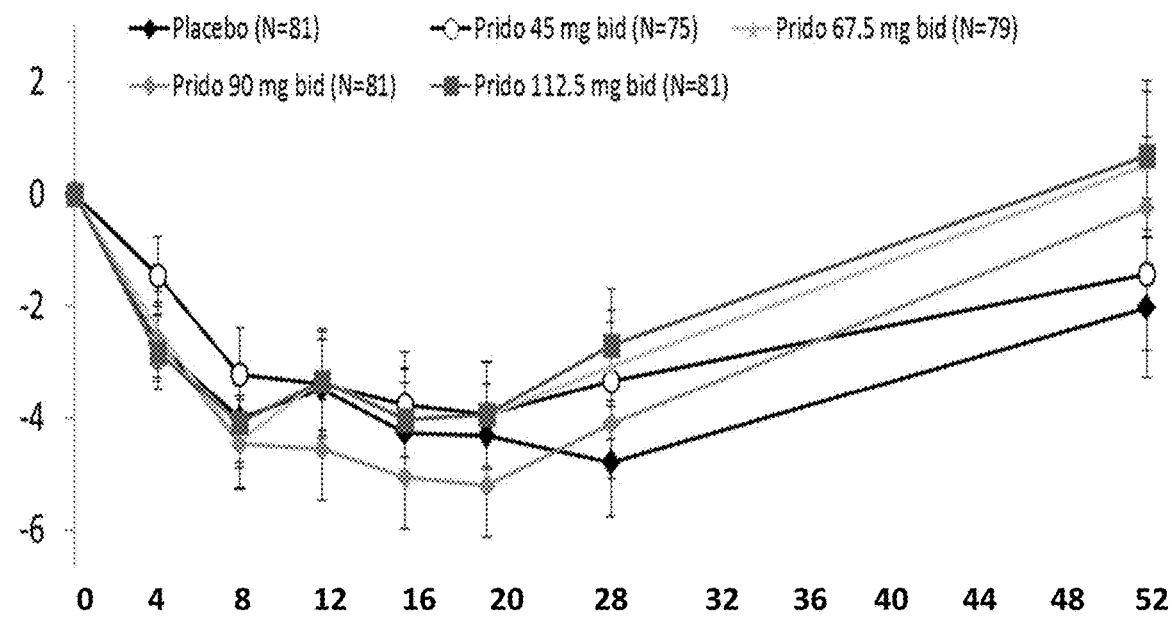

FIGS. 5a and 5b: Change from baseline in TMS. FIG. 5a: Using historical placebo in HART and MermaiHD clinical trials, TMS (change from baseline) results are significant for both 45 mg pridopidine bid and 90 mg pridopidine bid. A lower number indicates improvement. FIG. 5b: Change from baseline UHDRS-TMS full analysis set plotted over time. PRIDE-HD replicates previous data in TMS changes from baseline as the change from baseline values were similar to those in HART and MermaiHD. In this graph, a decrease in TMS change from baseline indicates improvement. Dark line with diamonds represents placebo, line with open circles represents 45 mg bid, gray line with triangles represents 67.5 mg bid, gray line with diamonds represents 90 mg bid, line with squares represents 112.5 mg bid. The 90 mg bid dose demonstrated the largest treatment effect.

Figure 6A:
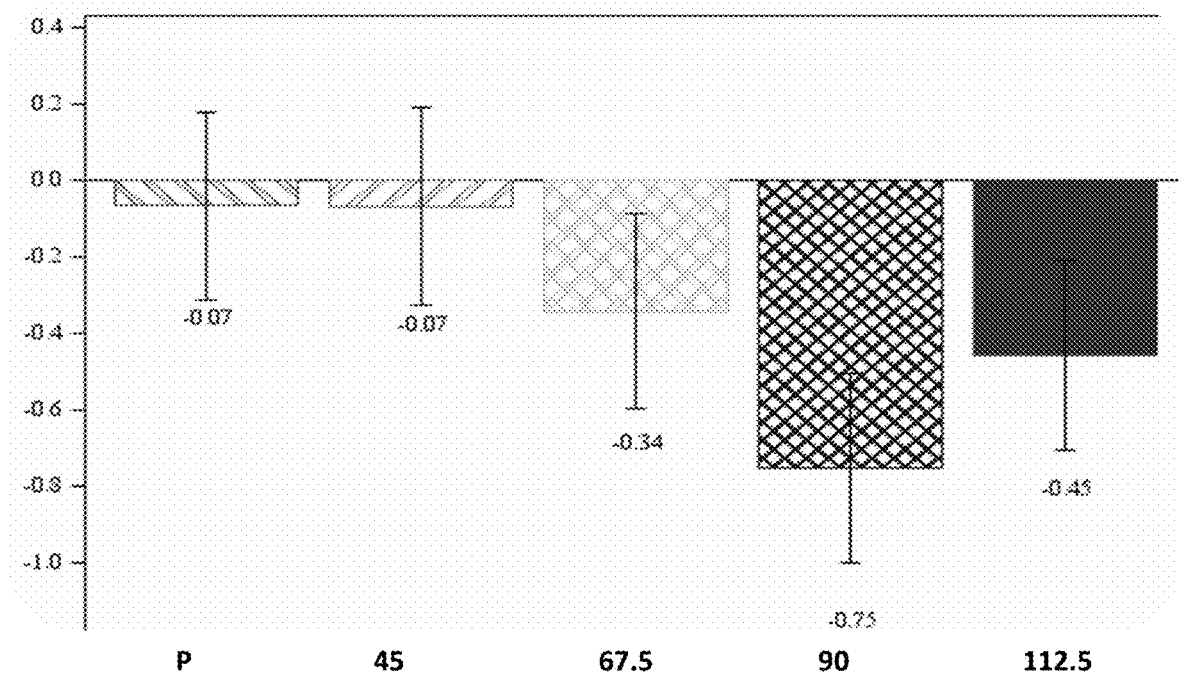
Figure 6B:
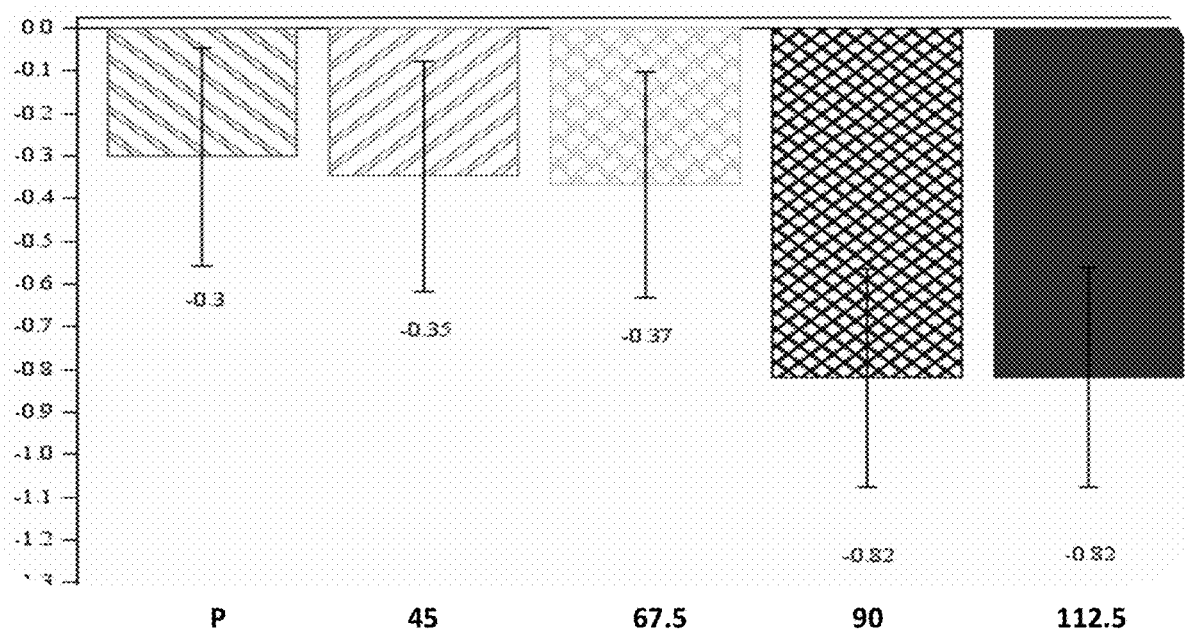
Figure 6C:
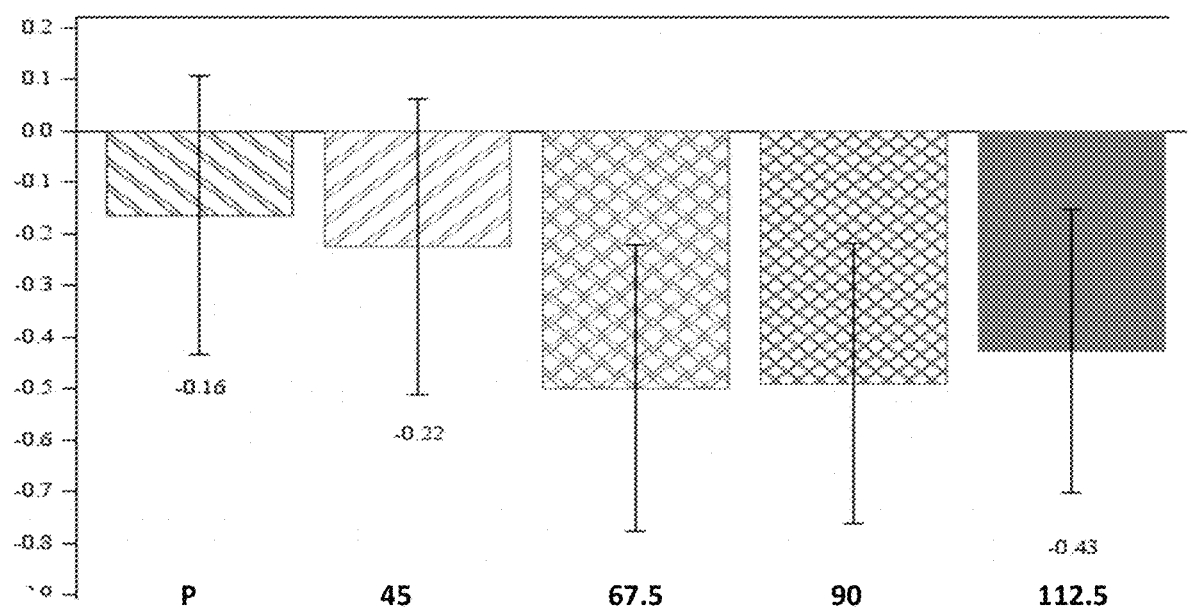

FIGS. 6a, 6b and 6c: Total Dystonia at week 12 (6a); at week 20 (6b); and at week 26 (6c) in patient groups administered different doses of pridopidine. Y-axis is change in dystonia from baseline. All data refer to adjusted means±SE of change in dystonia in full analysis set. A lower number indicates improvement.

FIGS. 6d-6h show data relating to various aspects of dystonia.

Figure 6D:
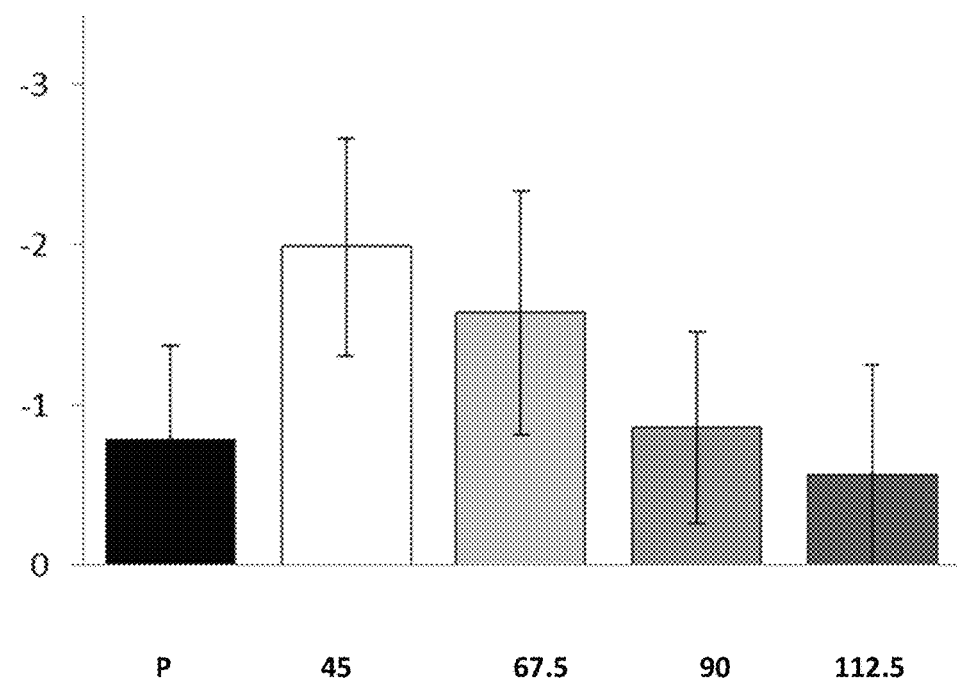

FIG. 6d. Comparison of patients with baseline (BL) dystonia score of ≥4 at 52 weeks after dosage with either placebo, 45 mg pridopidine b.i.d, 67.5 mg pridopidine b.i.d., 90 mg pridopidine b.i.d., or 112.5 mg pridopidine b.i.d. Within the full analysis set, no clinically meaningful changes from baseline were noted for patients at Week 26 or Week 52 in the dystonia score across the placebo and all active treatment groups (not shown). In patients with a baseline total dystonia score greater than or equal to 4 assessed at Week 52, a directional clinical improvement in dystonia was noted for all treatment groups, with the greatest decreases observed for the 45, 67.5, and 90 mg bid treatment groups. The table below shows change from baseline in UHDRS dystonia score over time.

| | week | | | | | | |
|---|---|---|---|---|---|---|---|
| | 4 | 8 | 12 | 16 | 20 | 26 | 52 |
| Placebo n= | 115 | 90 | 111 | 38 | 37 | 83 | 33 |
| Pridop n= | 109 | 82 | 102 | 25 | 24 | 81 | 21 |
| Δ to placebo | −0.35 | −0.24 | −0.96 | −0.35 | −1.09 | −1.01 | −1.54 |
| p value | 0.3414 | 0.5783 | 0.0232 | 0.5515 | 0.0722 | 0.0326 | 0.0571 |

Figure 6E:
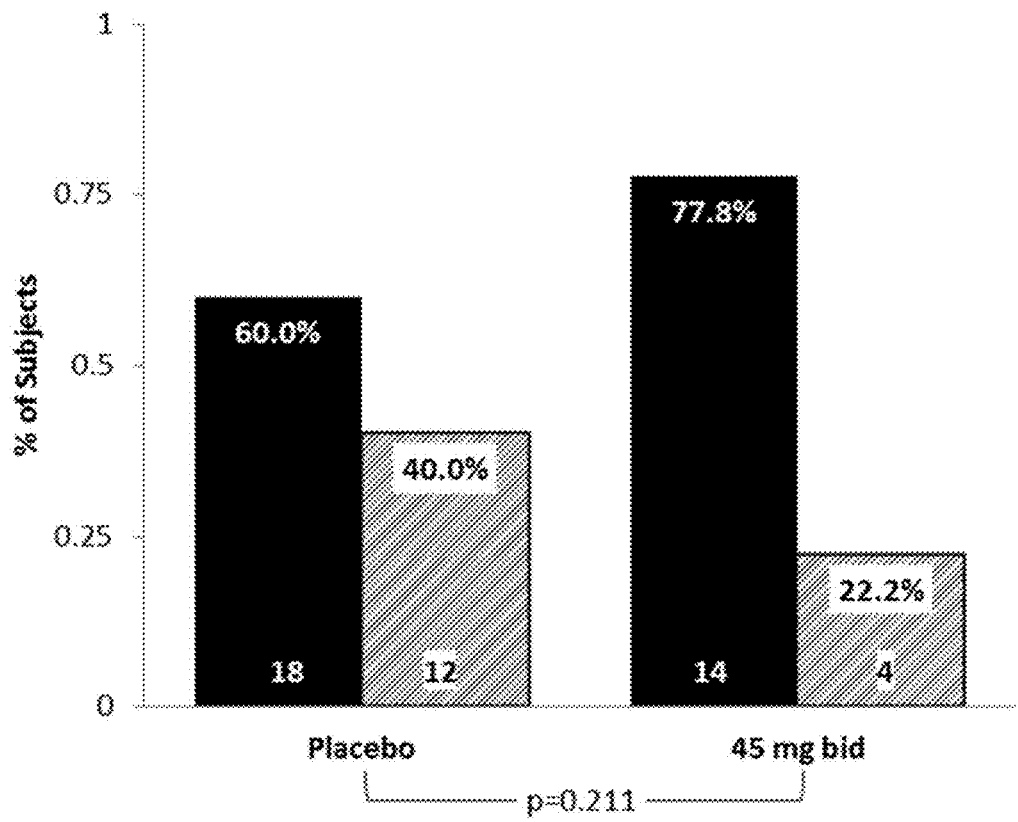
Figure 6F:
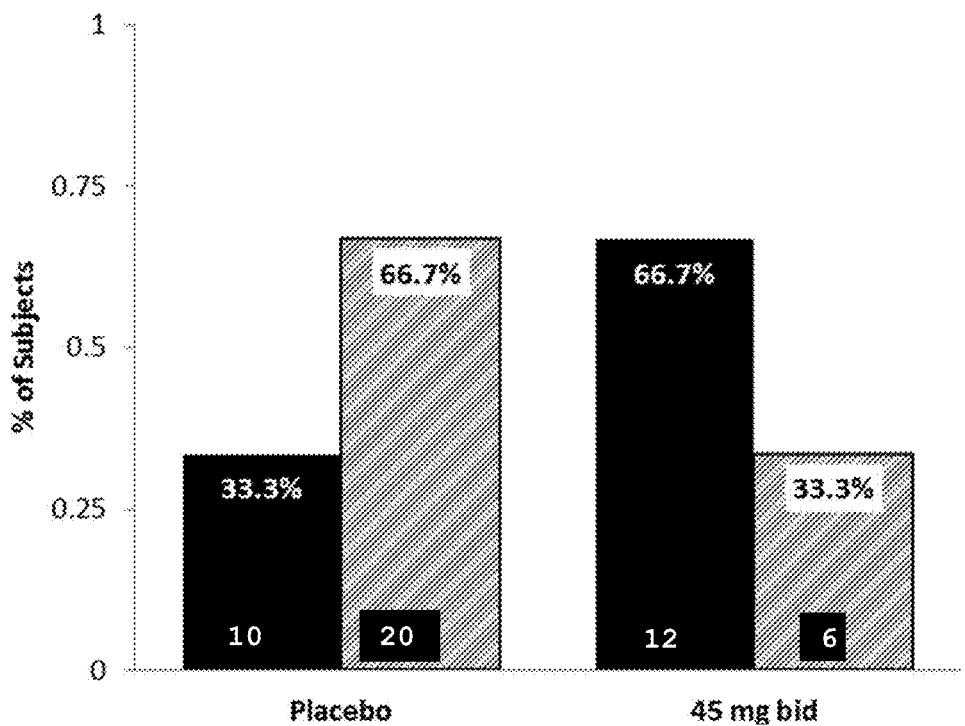

FIGS. 6e-6f: Black columns refer to responders: subjects with improvement or no change in UHDRS dystonia score. Gray columns refer to non-responders: subjects who exhibited a worsening in the UHDRS dystonia score. The number in the base of each column refers to the number of subjects. Improvement or no change is reflected in a score of greater than or equal to 0, respectively.

FIG. 6e: Percentage of subjects with UHDRS TMS dystonia (≥0) receiving either placebo or 45 mg pridopidine b.i.d. that were either responders or non-responders. Of those patients with baseline (BL) dystonia score of ≥4 who completed 52 weeks of treatment with either placebo or 45 mg pridopidine b.i.d., the percentage who were categorized based on the change in UHDRS TMS dystonia from BL to 52 weeks as responders (improved or no change, e.g. change≥0) or non-responders (worsened, change <0).

FIG. 6f: Of those patients with baseline (BL) dystonia score of ≥4 who completed 52 weeks of treatment with either placebo or 45 mg pridopidine b.i.d., the percentage who were categorized based on the change in UHDRS TMS dystonia from BL to 52 weeks as responders (improved, e.g.

change ≥1) or non-responders (worsened or no change <1). Results of the Responder Analysis for dystonia items further support this trend toward improvement by showing that a greater percentage of patients were categorized as Responders within the dystonia items in the 45 mg bid treatment group compared to the placebo group (14 patients [77.8%] and 18 patients [60.0%], respectively) and the chorea+ dystonia items in the 45 mg bid treatment group compared to the placebo group (14 patients [77.8%] and 20 patients [66.7%], respectively) (not shown).

Figure 6G:
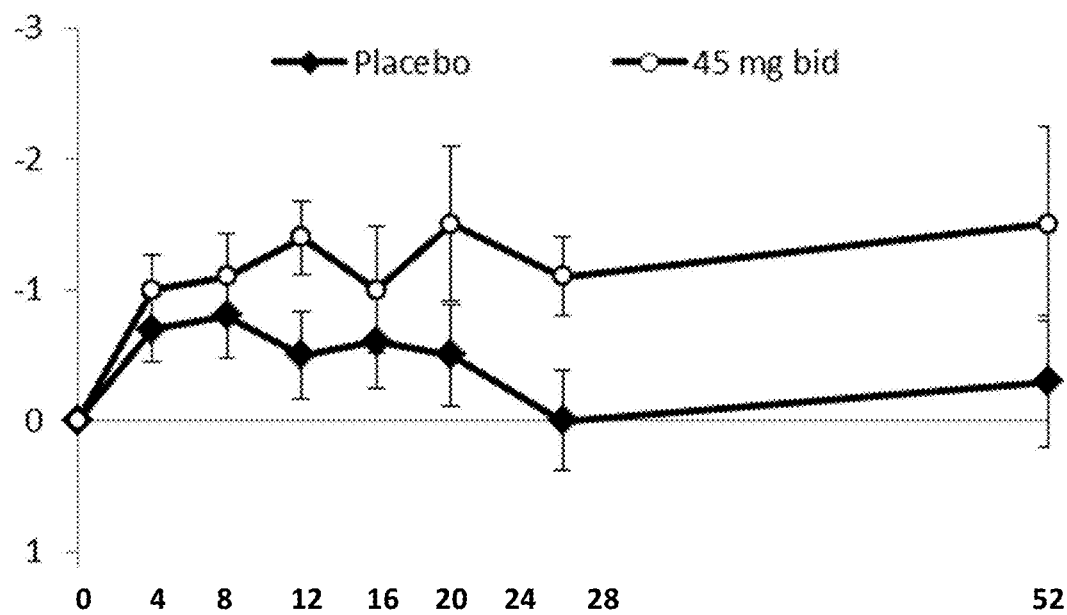

FIG. 6g: Plot of change in UHDRS Dystonia score over time for subjects pooled from MermaiHD, HART and Pride-HD studies with baseline (BL) dystonia (≥4) who received either placebo or 45 mg pridopidine b.i.d. At Week 26, patients taking 45 mg pridopidine b.i.d showed a statistically significant improvement in the dystonia score compared to those taking placebo. A trend toward this improvement was maintained at Week 52.

Figure 6H:
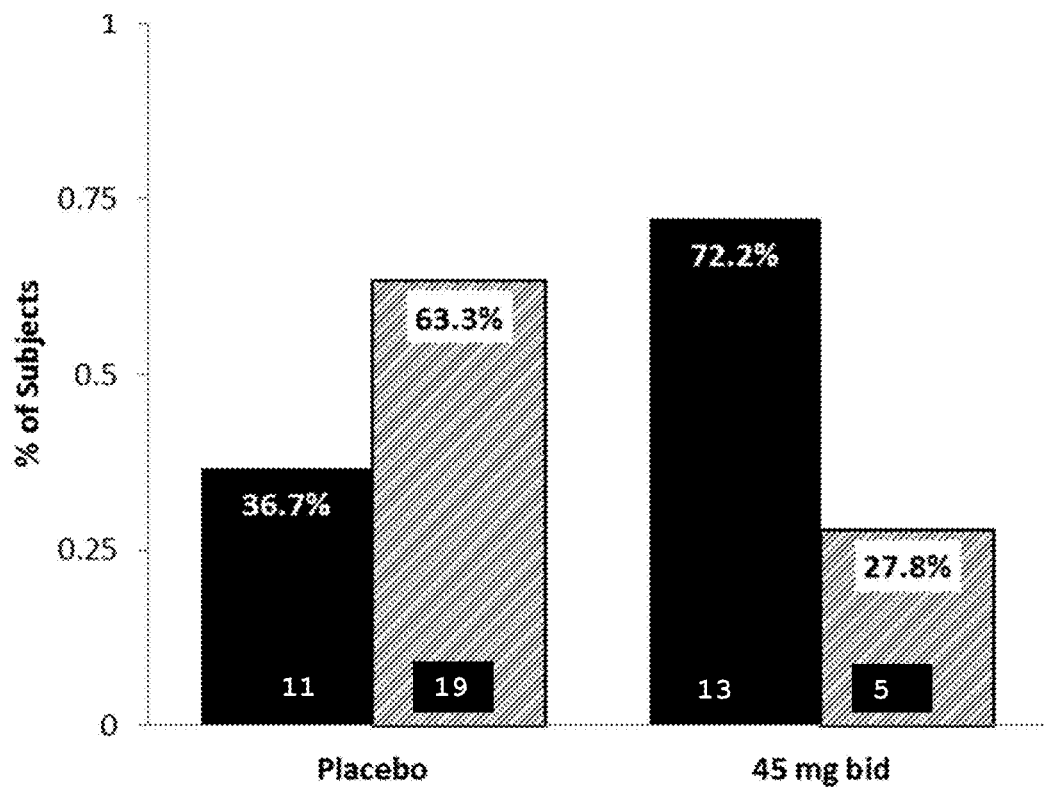

FIG. 6h: Of those PRIDE-HD patients with baseline (BL) dystonia score of ≥4 who completed 52 weeks of treatment with either placebo or 45 mg pridopidine b.i.d., the percentage who were categorized based on the change in UHDRS limb dystonia from BL to 52 weeks as responders (improved, e.g. change ≥1) or non-responders (worsened or no change <1).

Figure 7A:
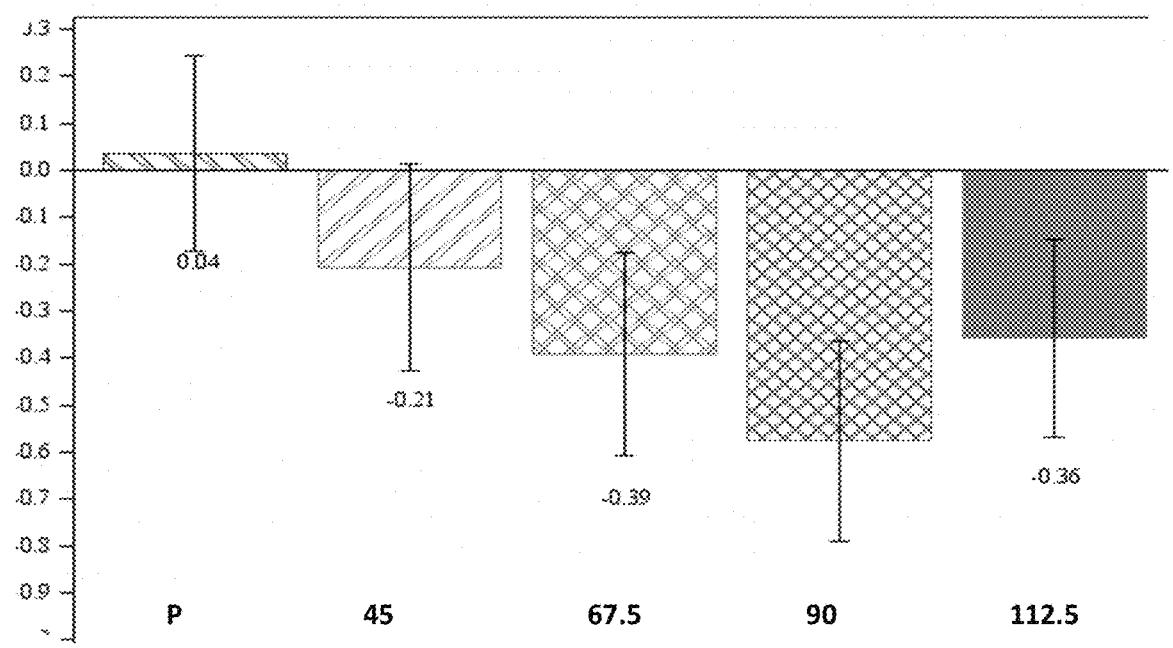
Figure 7B:
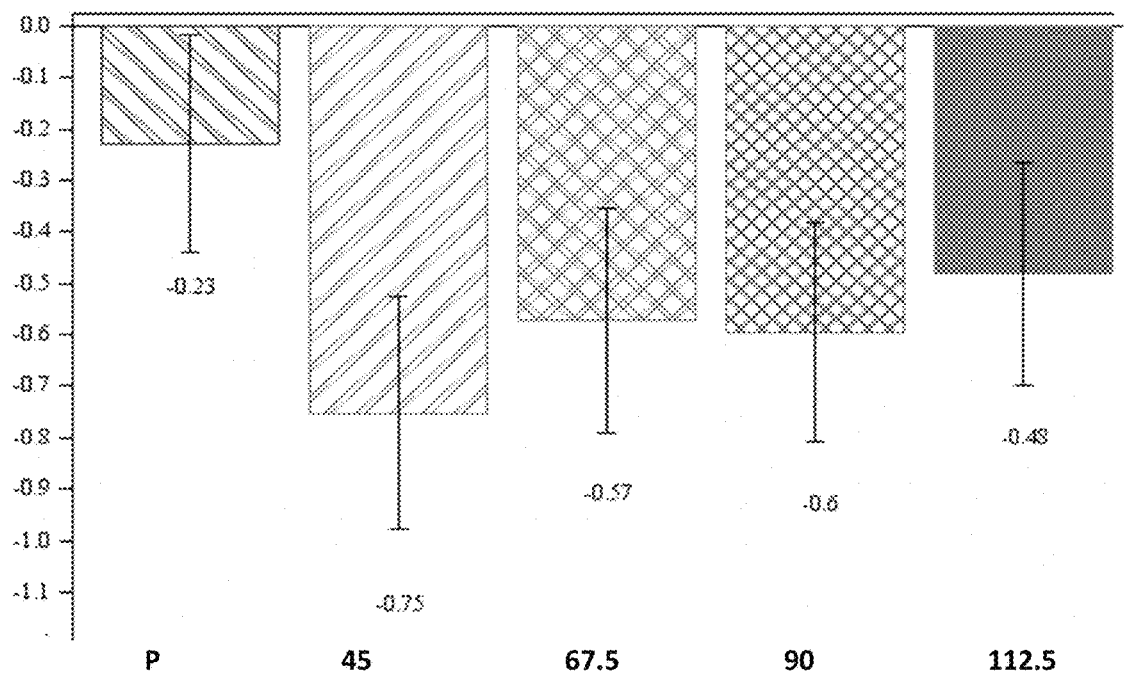
Figure 7C:
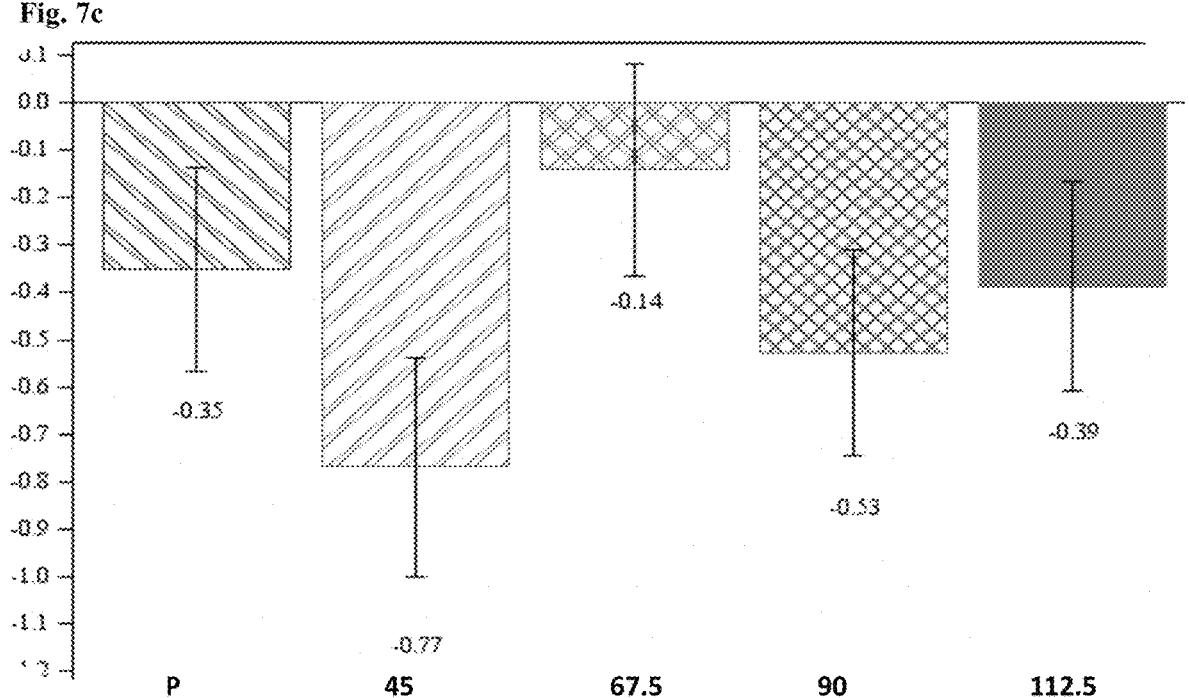

A statistically significant greater percentage of patients were categorized as Responders for the UHDRS-Limb Dystonia item in the pridopidine 45 mg bid treatment group compared to the placebo group (77.2% and 36.7%, respectively). FIG. 7a: Change in dystonia in limbs (UHDRS-dystonia limbs) at week 12; FIG. 7b: Finger Taps and Pronate-Supinate (P/S) hands at week 20; FIG. 7c: Finger Taps and P/S hands at week 26. Finger Taps and Pronate-Supinate (P/S) hands is a combination of finger tapping (the ability to tap the fingers of both hands where 15 repetitions in 5 seconds is considered normal) with pronation/supination (the ability to rotate the forearm and hand such that the palm is down (pronation) and to rotate the forearm and hand such that the palm is up (supination) on both sides of the body). Pronate-Supinate Hands is also known as the "Q-Motor: Pro-Sup-Frequency-MN-Hand (Hz)". All data show to adjusted means+SE of change in dystonia in full analysis set for FIGS. 7a-7c. In the tables below, data and the P-Values corresponding to the figures are provided. N refers to number of patients. Wk26 refers to relevant score at week 26. Wk52 refers to relevant score at week 52. "Δ to placebo" refers to the difference in score compared to placebo, specifically, the average change from baseline in the placebo group compared to the average change from baseline of the relevant group. "ALL" refers to pridopidine treated patients irrespective of disease stage. Y-axes are change from baseline for characteristic listed above the table. X-axes are dose whereby P means "placebo", 45 means "45 mg bid," 67.5 means "67.5 mg bid," 90 means "90 mg bid," and 112.5 means "112.5 mg bid." In the figures, improvement is in the direction from bottom of the graph to top of the graph.

Figure 8A:
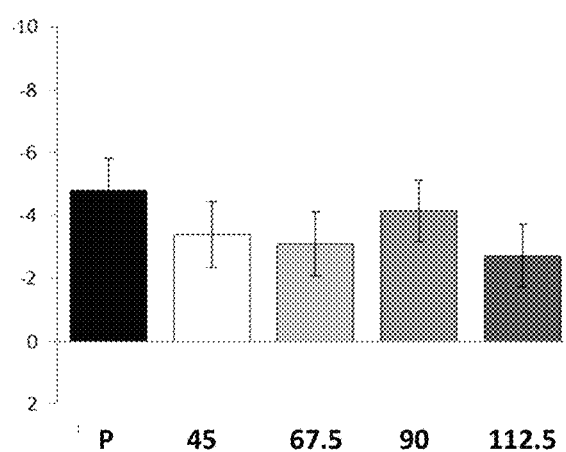
Figure 8B:
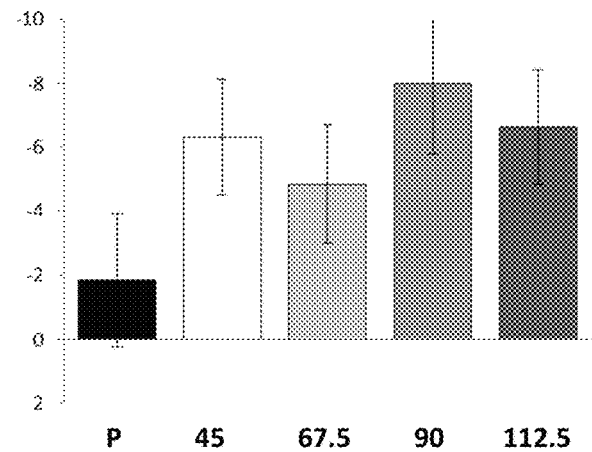

For example, FIG. 8b shows the average difference in the UHDRS TMS score of the indicated group of patients (i.e. patients having a TFC score of 11-13 at baseline, i.e. HD1) between the score at baseline and the score after 26 weeks of administration of pridopidine (at week 26). In this figure, the 90 mg bid dose shows the greatest improvement because its data point is the top most data point in the figure, showing an approximately 8 point improvement compared to baseline (i.e. a −8 UHDRS TMS score at week 26 compared to baseline). The table below the description of FIG. 8b shows that the 90 mg bid group had 11 patients ("N" row) and an average UHDRS TMS score of 39.1 at baseline ("Baseline" row). The table below the description of FIG. 8b also shows that the 90 mg bid group's change from baseline (about −8, shown in figure, not shown in table) is 6.15 points better (−6.15) than the placebo group's change from placebo (about −2, shown in figure, not shown in table)("Δ to placebo" row). Additionally, the table below the description of FIG. 8b shows a p value of 0.0361 for the 90 mg bid group ("p value" row). HD1 refers to an early stage HD patient with a baseline TFC score of 11-13. HD2 refers to an early stage HD patient with a baseline TFC score of 7-10.

FIG. 8a: Change from baseline in UHDRS TMS Week 26 ALL The table below and FIG. 8a show no significant improvement in UHDRS TMS in all pridopidine treated patients at 26 weeks compared to placebo. Improvement is evidenced by a more negative value in the UHDRS TMS score.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 46.9 | 44.5 | 46.9 | 47 | 46.7 |
| Δ to placebo |  | 1.42 | 1.71 | 0.67 | 2.1 |
| p value |  | 0.3199 | 0.2235 | 0.6282 | 0.1337 |

FIG. 8b: Change from baseline in UHDRS TMS Week 26 Stage 1 BL TFC 11-13. (The UHDRS TMS score at week 26 of pridopidine treated patients with a baseline Total Functional Capacity (BL TFC) score of 11 to 13). HD patients with a baseline TFC score of 11-13 are generally considered to be first stage (stage 1) HD patients. The table below and FIG. 8b show trend towards improvement in UHDRS TMS in HD1 pridopidine treated patients at 26 weeks compared to placebo.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 37.3 | 35.4 | 36.4 | 39.1 | 38.7 |
| Δ to placebo |  | −4.47 | −3 | −6.15 | −4.79 |
| p value |  | 0.0976 | 0.2505 | 0.0361 | 0.0676 |

Figure 8C:
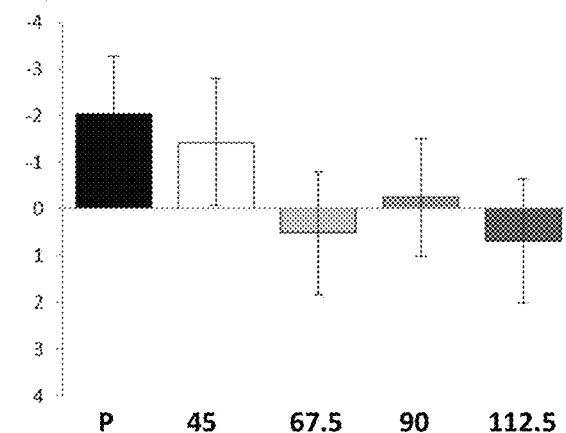

FIG. 8c: Change from baseline in UHDRS TMS Week 52 ALL. The table below and FIG. 8c show no significant improvement in UHDRS TMS in all pridopidine treated patients at 52 weeks, compared to placebo.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 46.9 | 44.5 | 46.9 | 47 | 46.7 |
| Δ to placebo |  | 0.59 | 2.55 | 1.78 | 2.71 |
| p value |  | 0.7468 | 0.1591 | 0.3144 | 0.137 |

Figure 8D:
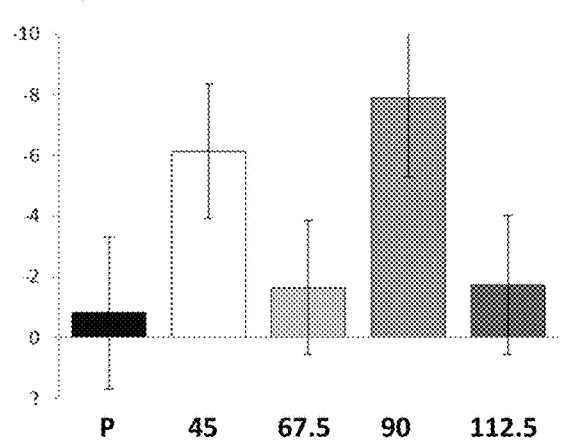

FIG. 8d: Change from baseline in UHDRS TMS Week 52 Stage 1 BL TFC 11-13. The table below and FIG. 8d show a trend towards improvement in UHDRS TMS in HD1 pridopidine treated patients at 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 37.3 | 35.4 | 36.4 | 39.1 | 38.7 |
| Wk52 Δ to placebo |  | −5.32 | −0.84 | −7.1 | −0.92 |
| p value |  | 0.1065 | 0.7918 | 0.047 | 0.7765 |

Figure 8E:
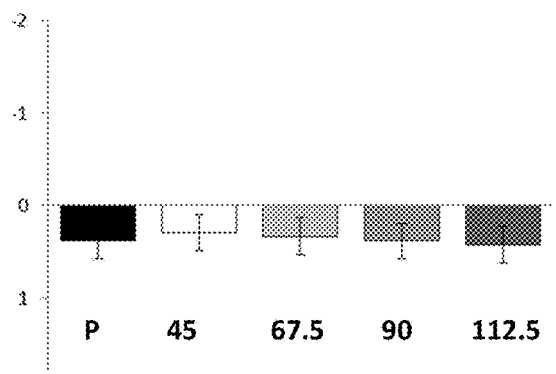

FIG. 8e: Change from baseline in UHDRS TMS Gait and Balances Week 52. The table below and FIG. 8e show no significant improvement in UHDRS TMS gait and balances in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.8 | 4.1 | 4.1 | 4 | 3.8 |
| Δ to placebo |  | −0.09 | −0.05 | −0.01 | 0.04 |
| p value |  | 0.7404 | 0.8532 | 0.9747 | 0.8923 |

Figure 8F:
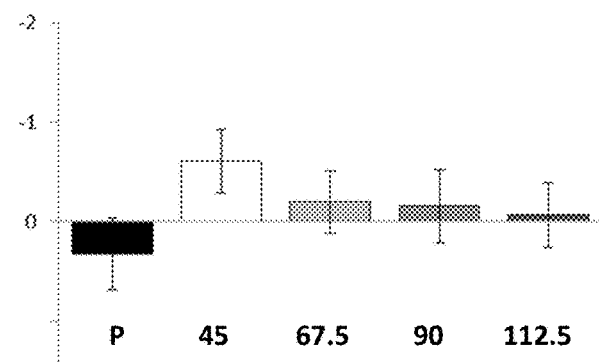

FIG. 8f: Change from baseline in UHDRS TMS Gait and Balances Week 52 Stage 1 BL TFC 11-13. The table below and FIG. 8f show a trend towards improvement in UHDRS TMS gait and balances in HD1 pridopidine treated patients at 52 weeks with significance for patients receiving 45 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.3 | 2.8 | 2.6 | 2.6 | 2.4 |
| Δ to placebo |  | −0.94 | −0.53 | −0.49 | −0.4 |
| p value |  | 0.0445 | 0.2294 | 0.3056 | 0.3797 |

Figure 8G:
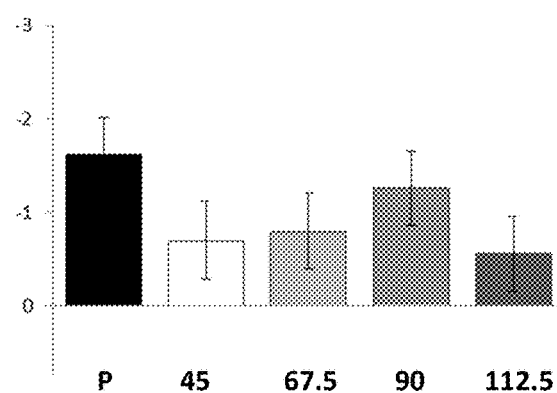

FIG. 8g: Change from baseline in UHDRS TMS Chorea Week 26 ALL. The table below and FIG. 8g show no significant improvement in UHDRS TMS chorea in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 11.4 | 10.9 | 11 | 11.2 | 10.9 |
| Δ to placebo |  | 0.92 | 0.81 | 0.36 | 1.05 |
| p value |  | 0.1083 | 0.1501 | 0.5185 | 0.0609 |

Figure 8H:
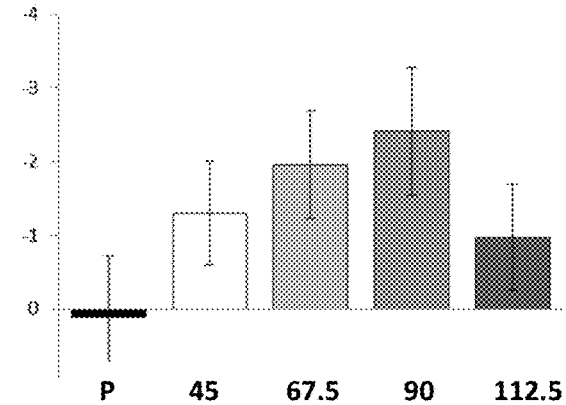

FIG. 8h: Change from baseline in UHDRS TMS Chorea Week 26 Stage 1 BL TFC 11-13. The table below and FIG. 8h show a trend towards improvement in UHDRS TMS chorea in HD1 pridopidine treated patients at 26 weeks with significance for patients receiving 90 mg bid pridopidine.

|  | 45 mg bid | 67.5 mg bid | 90 mg bid | 112.5 mg bid |
|---|---|---|---|---|
| N | 17 | 17 | 11 | 18 |
| Wk 26 Δ to placebo | −1.4 | −2.07 | −2.52 | −1.08 |
| p value | 0.1805 | 0.0438 | 0.0271 | 0.2932 |

Figure 8I:
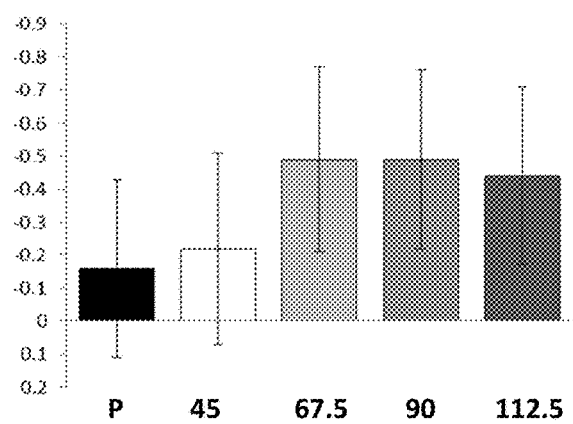

FIG. 8i: Change from baseline in UHDRS TMS Dystonia Week 26 ALL. The table below and FIG. 8i show a trend towards improvement in UHDRS TMS dystonia in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4.1 | 3.6 | 4.1 | 4.9 | 4.5 |
| Δ to placebo |  | −0.06 | −0.34 | −0.33 | −0.29 |
| p value |  | 0.8711 | 0.3778 | 0.3845 | 0.4507 |

Figure 8J:
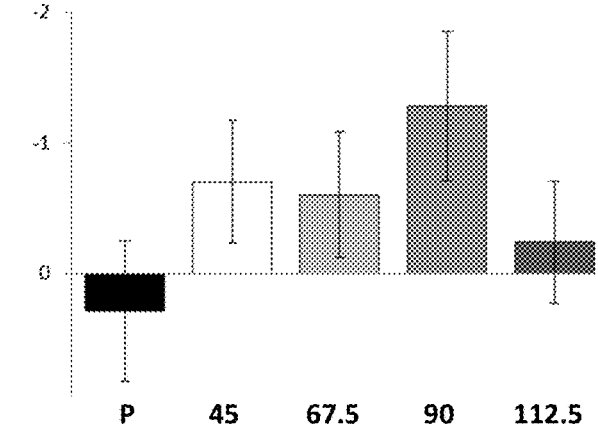

FIG. 8j: Change from baseline in UHDRS TMS Dystonia Week 26 Stage 1 BL TFC 11-13. The table below and FIG. 8j show a trend towards improvement in UHDRS TMS dystonia in HD1 pridopidine treated patients at 26 weeks with significance for patients receiving 90 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.8 | 2.1 | 2.2 | 3.2 | 2.4 |
| Δ to placebo |  | −0.99 | −0.89 | −1.56 | −0.53 |
| p value |  | 0.1569 | 0.1882 | 0.0396 | 0.4303 |

Figure 8K:
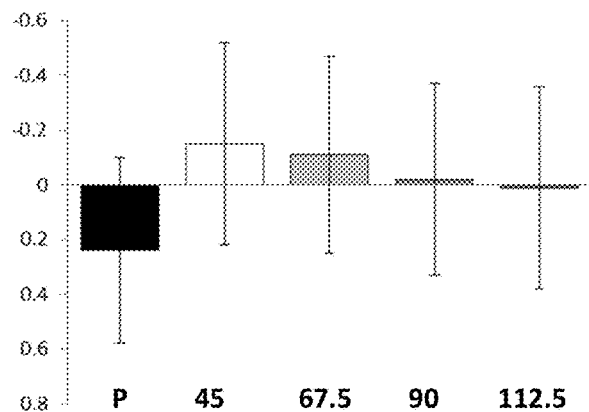

FIG. 8k: Change from baseline in UHDRS TMS Dystonia Week 52 The table below and FIG. 8k show a trend toward improvement in UHDRS TMS dystonia in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4.1 | 3.6 | 4.1 | 4.9 | 4.5 |
| Δ to placebo |  | −0.39 | −0.35 | −0.27 | −0.24 |
| p value |  | 0.4358 | 0.4795 | 0.5858 | 0.6382 |

Figure 8L:
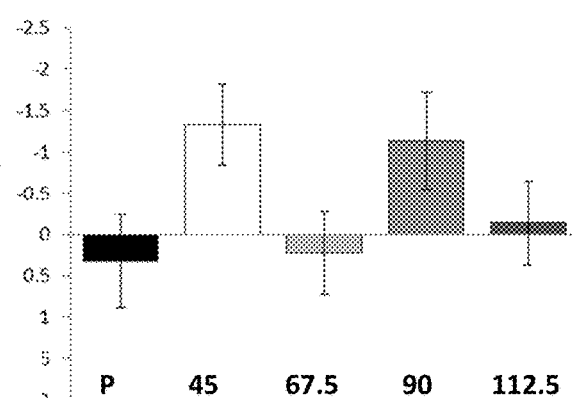

FIG. 8l: Change from baseline in UHDRS TMS Dystonia Week 52 Stage 1 BL TFC 11-13 The table below and FIG. 8l show a trend towards improvement in UHDRS TMS dystonia in HD1 pridopidine treated patients at 52 weeks with significance for patients receiving 45 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.8 | 2.1 | 2.2 | 3.2 | 2.4 |
| Δ to placebo |  | −1.65 | −0.1 | −1.46 | −0.46 |
| p value |  | 0.0243 | 0.8848 | 0.0575 | 0.5228 |

Figure 8M:
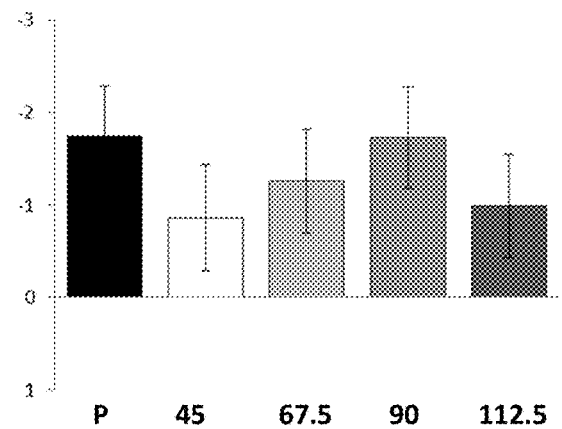

FIG. 8m: Change from baseline in UHDRS TMS Involuntary Movements Week 26 ALL. The table below and FIG. 8m show no significant improvement in UHDRS TMS Involuntary Movements in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 15.6 | 14.4 | 15.1 | 16 | 15.4 |
| Δ to placebo |  | 0.89 | 0.48 | 0.01 | 0.76 |
| p value |  | 0.2594 | 0.5328 | 0.9873 | 0.3268 |

Figure 8N:
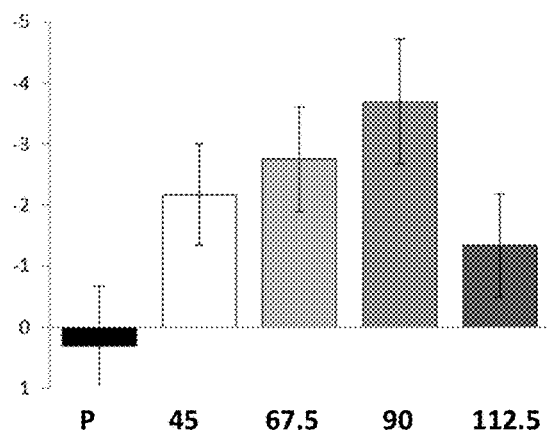

FIG. 8n: Change from baseline in UHDRS TMS Involuntary Movements Week 26 Stage 1 BL TFC 11-13. The table below and FIG. 8n show significant improvement in UHDRS TMS Involuntary Movements at 26 weeks in HD1 pridopidine treated patients receiving 45 mg bid, 67.5 bid and 90 mg bid pridopidine.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 11.5 | 12 | 12.2 | 12.9 | 13.2 |
| Δ to placebo |  | −2.49 | −3.07 | −4 | −1.64 |
| p value |  | 0.0469 | 0.0117 | 0.0033 | 0.1731 |

Figure 8O:
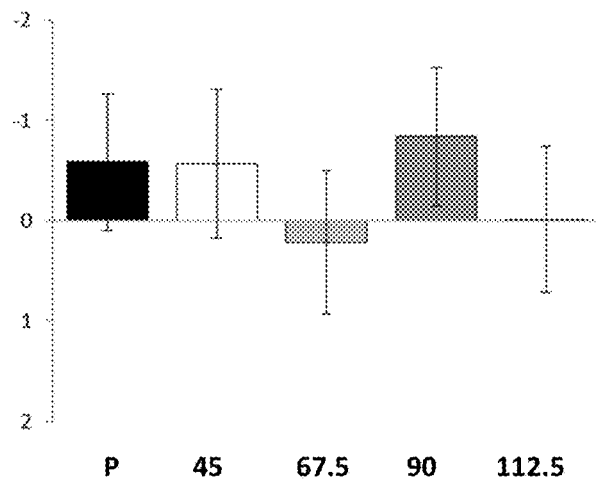

FIG. 8o: Change from baseline in UHDRS TMS Involuntary Movements Week 52. The table below and FIG. 8o show no significant improvement in UHDRS TMS Involuntary Movements in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 15.6 | 14.4 | 15.1 | 16 | 15.4 |
| Δ to placebo |  | 0.02 | 0.8 | −0.26 | 0.57 |
| p value |  | 0.9867 | 0.4196 | 0.7893 | 0.5648 |

Figure 8P:
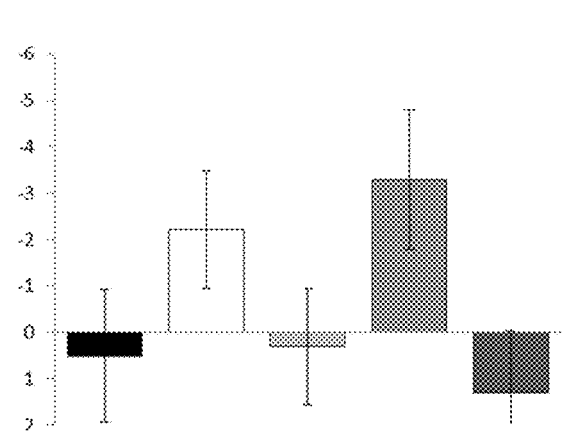

FIG. 8p: Change from baseline in UHDRS TMS Involuntary Movements Week 52 Stage 1 BL TFC 11-13. The table below and FIG. 8p show a trend towards improvement in UHDRS TMS Involuntary Movements in HD1 pridopidine treated patients at 52 weeks, in particular in 45 mg bid and 90 mg bid treated patients.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 11.5 | 12 | 12.2 | 12.9 | 13.2 |
| Δ to placebo |  | −2.73 | −0.2 | −3.8 | 0.8 |
| p value |  | 0.1487 | 0.9111 | 0.0643 | 0.6751 |

Figure 8Q:
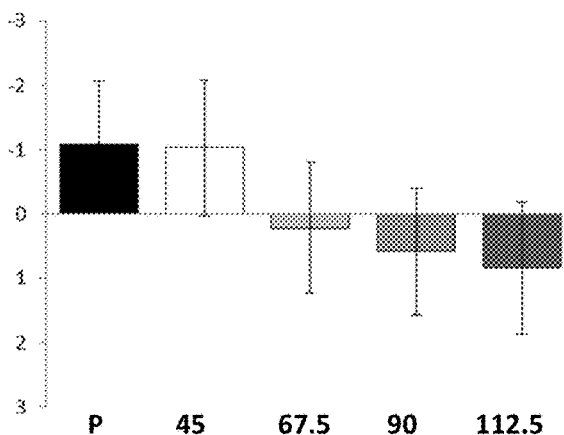

FIG. 8q: Change from baseline in UHDRS TMS Excluding Chorea Week 52. The table below and FIG. 8q show no significant improvement in UHDRS TMS excluding chorea in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 35.5 | 33.6 | 35.9 | 35.8 | 35.8 |
| Δ to placebo |  | 0.05 | 1.31 | 1.67 | 1.94 |
| p value |  | 0.9693 | 0.3495 | 0.2234 | 0.1704 |

Figure 8R:
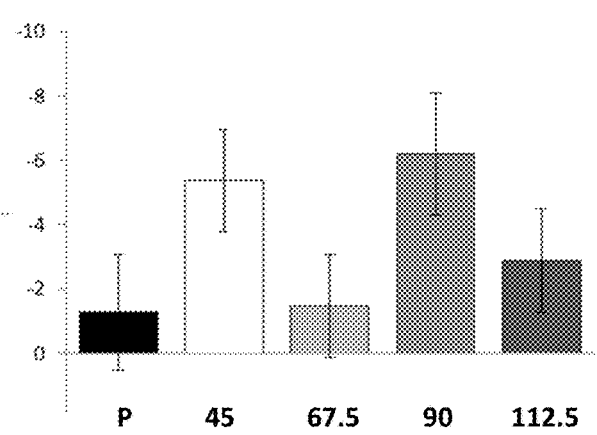

FIG. 8r: Change from baseline in UHDRS TMS Excluding Chorea Week 52 Stage 1 BL TFC 11-13. The table below and FIG. 8r show a trend towards improvement in UHDRS TMS excluding chorea in HD1 pridopidine treated patients at 52 weeks, in particular in the 45 mg bid and 90 mg bid treated patients.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 28.6 | 25.5 | 26.4 | 29.4 | 27.8 |
| Δ to placebo |  | −4.09 | −0.18 | −4.92 | −1.59 |
| p value |  | 0.083 | 0.9358 | 0.0505 | 0.4924 |

Figure 8S:
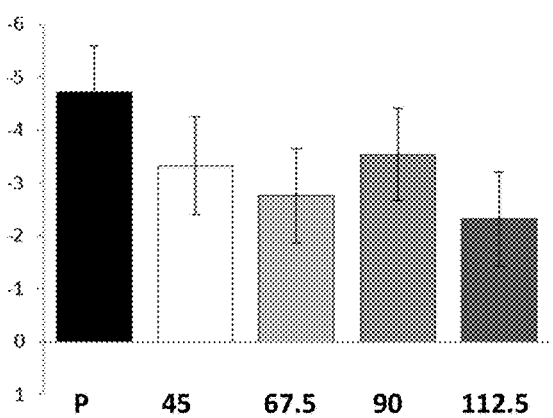

FIG. 8s: Change from baseline in UHDRS TMS Excluding Dystonia Week 26 ALL. The table below and FIG. 8s show no significant improvement in UHDRS TMS excluding dystonia in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 42.7 | 40.9 | 42.8 | 42.1 | 42.2 |
| Δ to placebo |  | 1.39 | 1.97 | 1.2 | 2.4 |
| p value |  | 0.2733 | 0.1137 | 0.3314 | 0.0539 |

Figure 8T:
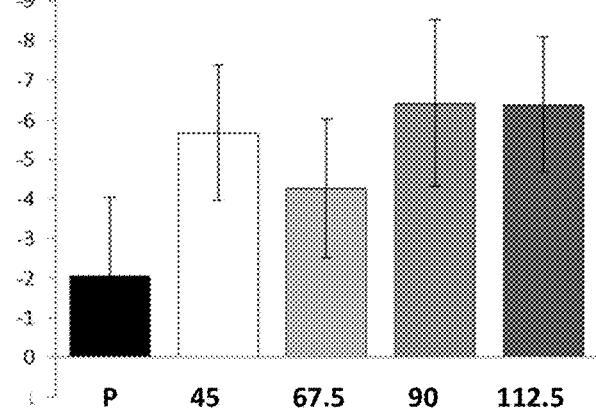

FIG. 8t: Change from baseline in UHDRS TMS Excluding Dystonia Week 26 Stage 1 BL TFC 11-13. The table below and FIG. 8t show a trend towards improvement in UHDRS TMS excluding dystonia in HD1 pridopidine treated patients, at 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 34.6 | 33.4 | 34.1 | 35.9 | 36.3 |
| Δ to placebo |  | −3.6 | −2.2 | −4.35 | −4.31 |
| p value |  | 0.1594 | 0.376 | 0.1167 | 0.0842 |

Figure 9A:
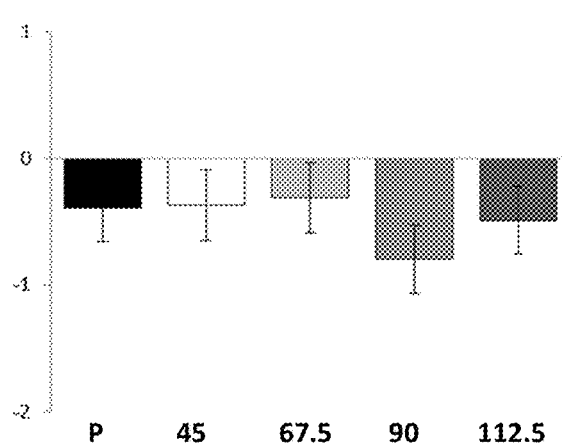

FIG. 9a: Change from baseline in UHDRS Total Functional Assessment Week 26 ALL. The table below and FIG. 9a show no significant improvement in UHDRS TFC in all pridopidine treated patients at 26 weeks. Improvement is evidenced by a higher TFC score.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 18.6 | 19 | 18.6 | 18.8 | 19.1 |
| Δ to placebo |  | 0.02 | 0.09 | −0.41 | −0.1 |
| p value |  | 0.9511 | 0.8211 | 0.277 | 0.7979 |

Figure 9B:
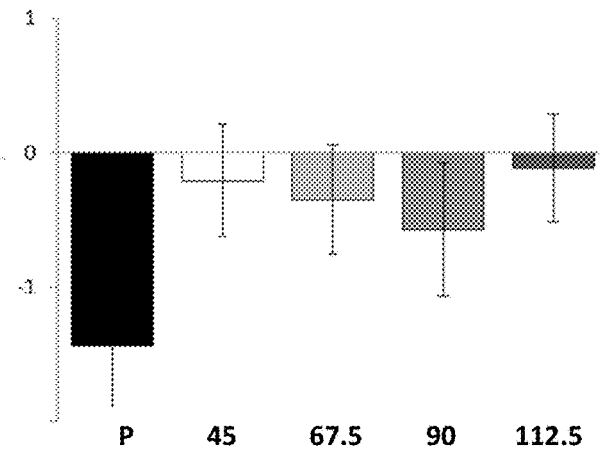

FIG. 9b: Change from baseline in UHDRS Total Functional Assessment Week 26 Stage 1 BL TFC 11-13. The table below and FIG. 9b show a trend towards improvement in UHDRS TFC in HD1 pridopidine treated patients, at 52 weeks, in particular in the 45 mg bid treated patients.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 22.8 | 23.9 | 23 | 23.1 | 22.9 |
| Δ to placebo |  | 1.23 | 1.08 | 0.87 | 1.33 |
| p value |  | 0.0516 | 0.0696 | 0.1899 | 0.0273 |

Figure 9C:
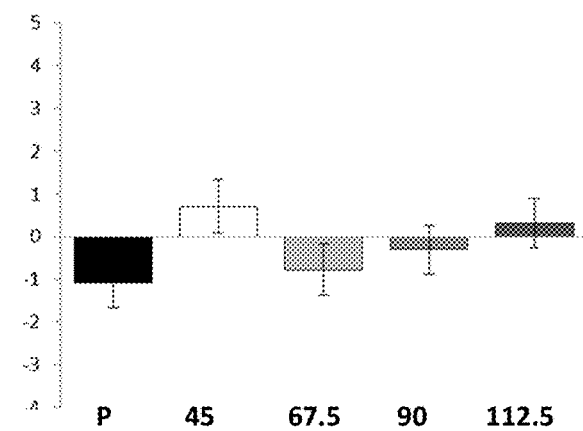

FIG. 9c: Change from baseline in UHDRS Independence Scale Week 26 ALL. The table below and FIG. 9c show significant improvement in UHDRS IS in all 45 mg pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 76.4 | 76.1 | 74.6 | 76.3 | 75.6 |
| Δ to placebo |  | 1.79 | 0.3 | 0.78 | 1.41 |
| p value |  | 0.0328 | 0.7124 | 0.341 | 0.0887 |

Figure 9D:
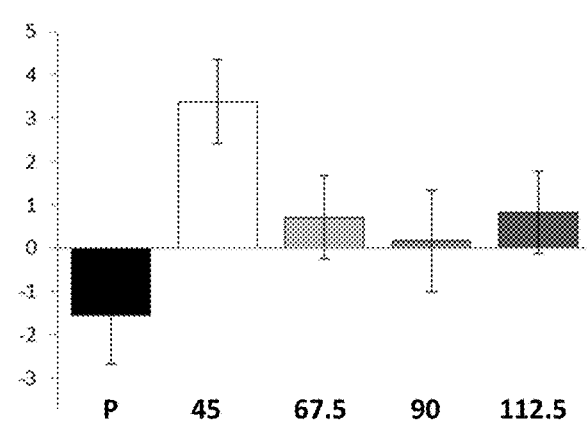

FIG. 9d: Change from baseline in UHDRS Independence Scale Week 26 Stage 1 BL TFC 11-13. The table below and FIG. 9d show improvement in UHDRS IS in 45 mg bid treated HD1 patients, after 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 83.8 | 84.1 | 81.5 | 84.1 | 83.1 |
| Δ to placebo |  | 4.94 | 2.27 | 1.73 | 2.38 |
| p value |  | 0.001 | 0.1126 | 0.2738 | 0.0958 |

Figure 9E:
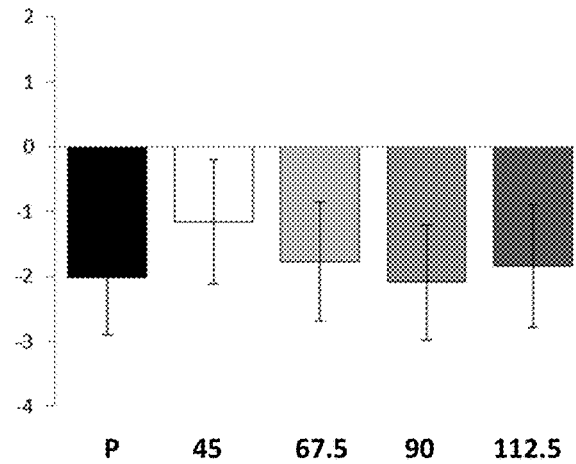

FIG. 9e: Change from baseline in 9e UHDRS Independence Scale Week 52 ALL. The table below and FIG. 9e show no significant improvement in UHDRS IS in all patients treated patients after 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 76.4 | 76.1 | 74.6 | 76.3 | 75.6 |
| Δ to placebo |  | 0.86 | 0.25 | -0.07 | 0.18 |
| p value |  | 0.5082 | 0.8431 | 0.9558 | 0.8871 |

Figure 9F:
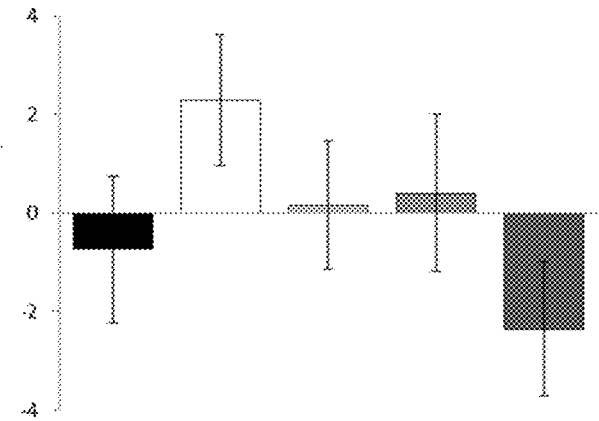

FIG. 9f: Change from baseline in UHDRS Independence Scale Week 52 Stage 1 BL TFC 11-13. The table below and FIG. 9f show a trend towards improvement in UHDRS IS in 45 mg bid treated HD1 patients, after 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 83.8 | 84.1 | 81.5 | 84.1 | 83.1 |
| Δ to placebo |  | 3.05 | 0.91 | 1.16 | -1.61 |
| p value |  | 0.1289 | 0.6415 | 0.5899 | 0.4193 |

Figure 9G:
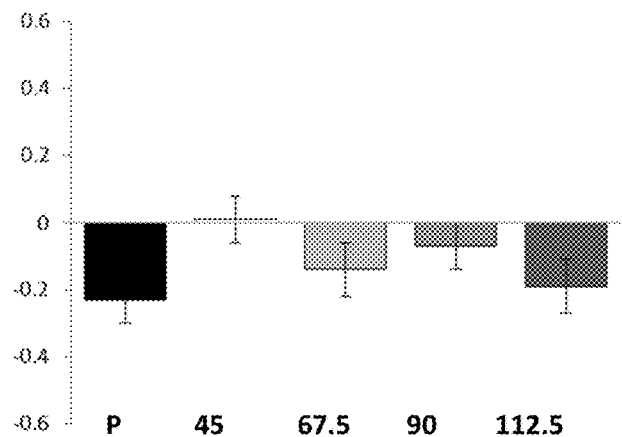

FIG. 9g: Domestic Chores at 52 weeks, Early Stage HD (TFC≥7). The table below provides data and the P-Values corresponding to FIG. 9g. Significant improvement in TFC domestic chores was observed in 45 mg bid pridopidine administered HD1 and HD2 patients, for 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 1.4 | 1.5 | 1.4 | 1.4 | 1.4 |
| Δ to placebo |  | 0.24 | 0.09 | 0.16 | 0.04 |
| p value |  | 0.0196 | 0.3829 | 0.1155 | 0.7145 |

Figure 9H:
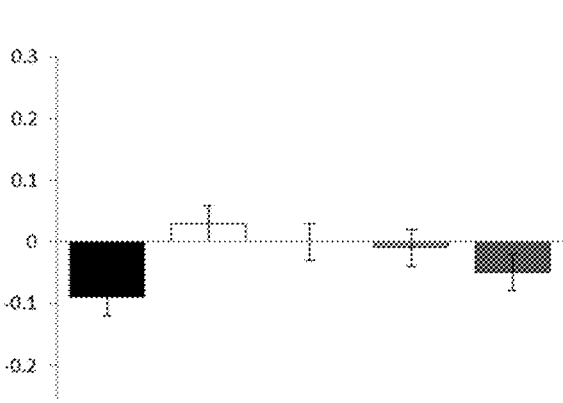

FIG. 9h: Care Level at 52 weeks, Early Stage HD (TFC≥7). The table below provides data and the P-Values corresponding to FIG. 9h. Significant improvement in TFC Care level was observed in 45 mg bid to 90 mg bid pridopidine administered HD1 and HD2 patients for 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2 | 1.9 | 2 | 2 | 2 |
| Δ to placebo |  | 0.12 | 0.09 | 0.08 | 0.04 |
| p value |  | 0.0044 | 0.0319 | 0.0411 | 0.403 |

Figure 10A:
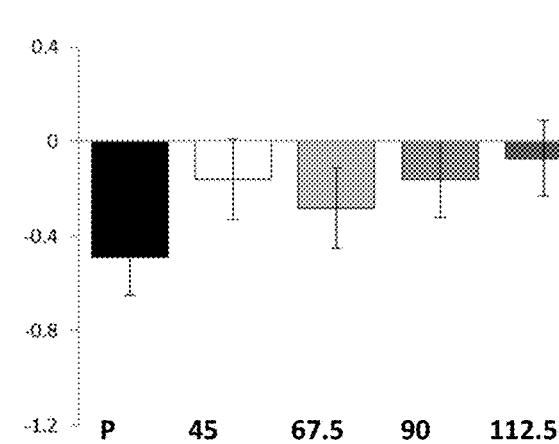

FIG. 10a: Change from baseline in UHDRS Total Functional Capacity Week 26 ALL. The table below and FIG. 10a show a trend toward improvement in UHDRS TFC in all pridopidine treated patients after 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 7.9 | 8.1 | 7.8 | 7.8 | 8 |
| Δ to placebo |  | 0.34 | 0.21 | 0.33 | 0.42 |
| p value |  | 0.1474 | 0.3639 | 0.1465 | 0.0676 |

Figure 10B:
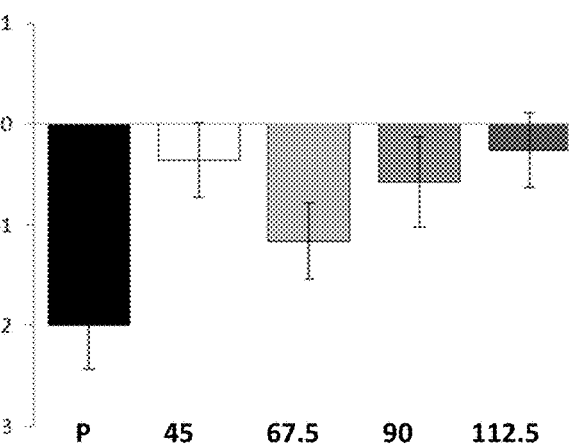

FIG. 10b: Change from baseline in UHDRS Total Functional Capacity Week 26 Stage 1 BL TFC 11-13. The table below and FIG. 10b show improvement in UHDRS IS in 45 mg bid and 90 mg bid HD1 pridopidine treated patients, for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 11.8 | 11.5 | 11.5 | 11.7 | 11.8 |
| Δ to placebo |  | 1.65 | 0.84 | 1.43 | 1.75 |
| p value |  | 0.004 | 0.1245 | 0.0191 | 0.0019 |

Figure 10C:
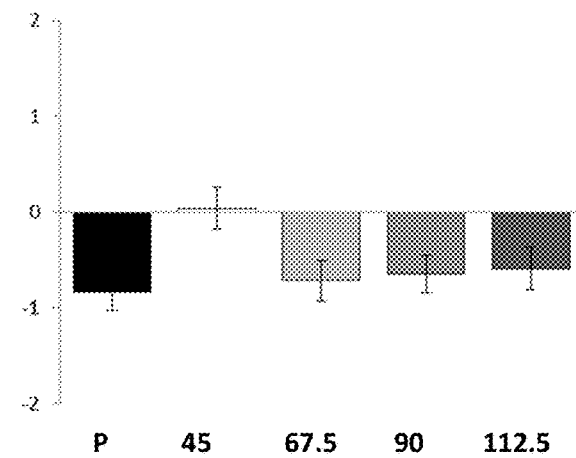

FIG. 10c: Change from baseline in UHDRS Total Functional Capacity Week 52. The table below and FIG. 10c show reduction in functional decline as measured by TFC score in all patients receiving 45 mg bid pridopidine for 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 7.9 | 8.1 | 7.8 | 7.8 | 8 |
| Δ to placebo |  | 0.87 | 0.11 | 0.19 | 0.24 |
| p value |  | 0.0032 | 0.7042 | 0.5099 | 0.4061 |

Figure 10D:
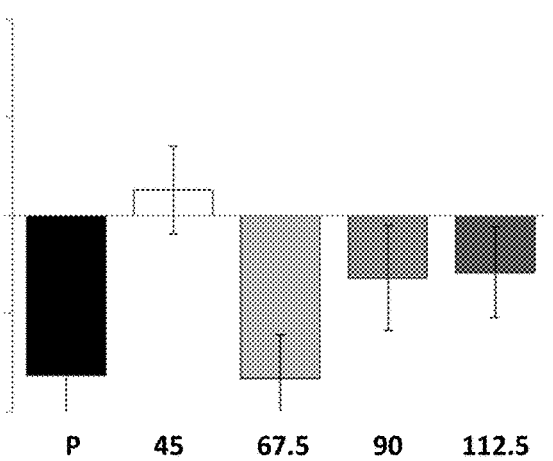

FIG. 10d: Change from baseline in UHDRS Total Functional Capacity Week 52 Stage 1 BL TFC 11-13. The table below and FIG. 10d show statistically significant reduced functional decline as measured by TFC in HD1 patient, receiving 45 mg bid pridopidine for 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 11.8 | 11.5 | 11.5 | 11.7 | 11.8 |
| Δ to placebo |  | 1.89 | -0.03 | 0.99 | 1.06 |
| p value |  | 0.0059 | 0.9588 | 0.1678 | 0.1154 |

Figure 10E:
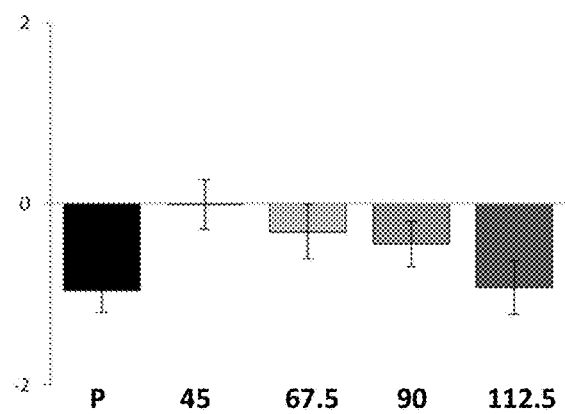

FIG. 10e: Change from baseline in UHDRS Total Functional Capacity Week 52 Stage 2 BL TFC 7-10. The table below and FIG. 10e show statistically significant reduced functional decline as measured by TFC in HD2 patients receiving 45 mg bid pridopidine for 52 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 8.3 | 8.2 | 8.4 | 8.5 | 8.2 |
| Δ to placebo |  | 0.94 | 0.64 | 0.51 | 0.03 |
| p value |  | 0.009 | 0.0924 | 0.1448 | 0.9331 |

Figure 11A:
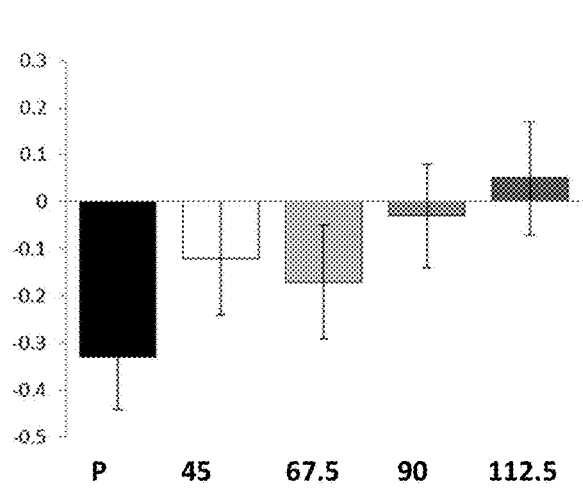

FIG. 11a: Change from baseline in UHDRS TFC Finance ADL Week 26 ALL. The table below and FIG. 11a show a trend towards improvement in ADL finance as measured as part of the UHDRS TFC score in all patients receiving pridopidine for 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4 | 4.1 | 3.9 | 4 | 4 |
| Δ to placebo |  | 0.22 | 0.16 | 0.31 | 0.38 |
| p value |  | 0.1782 | 0.3184 | 0.0543 | 0.0168 |

Figure 11B:
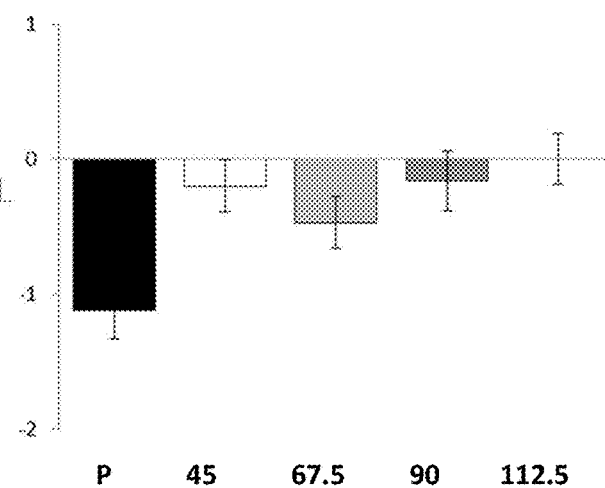

FIG. 11b: Change from baseline in UHDRS TFC Finance ADL Week 26 Stage 1 BL TFC 11-13. The table below and FIG. 11b show statistically significant improvement in ADL finances as measured as part of the TFC score in HD1 patients receiving all doses pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 5.8 | 5.7 | 5.8 | 5.9 | 5.9 |
| Δ to placebo |  | 0.92 | 0.65 | 0.97 | 1.12 |
| p value |  | 0.0012 | 0.0168 | 0.0017 | <.0001 |

Figure 11C:
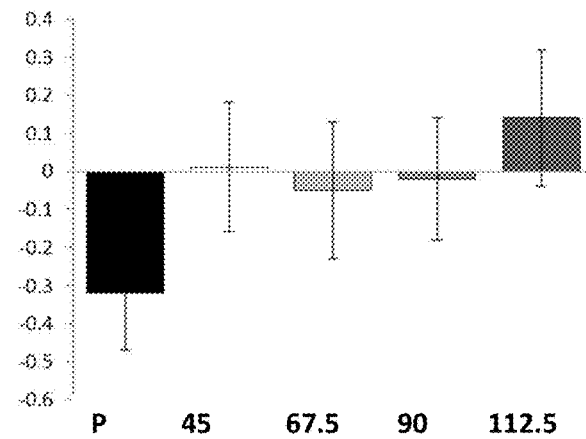

FIG. 11c: Change from baseline in UHDRS TFC Finance ADL Week 26 Stage 2 BL TFC 7-10. The table below and FIG. 11c show statistically significant improvement in ADL finances as measured as part of the TFC score in HD2 patients, receiving highest dose pridopidine for 26 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 4.4 | 4.3 | 4.4 | 4.5 | 4.2 |
| Δ to placebo |  | 0.33 | 0.26 | 0.3 | 0.46 |
| p value |  | 0.1492 | 0.2634 | 0.1674 | 0.0459 |

Figure 11D:
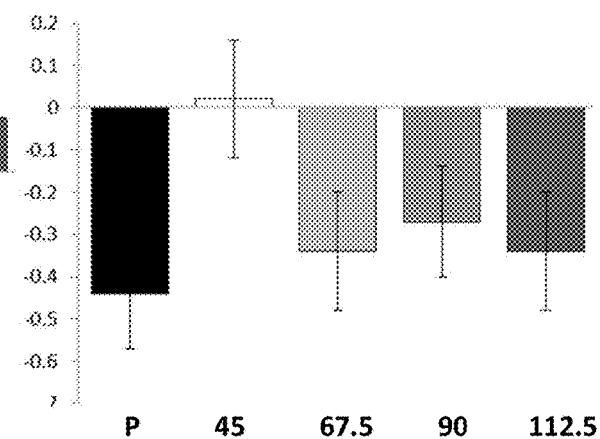

FIG. 11d: Change from baseline in UHDRS TFC Finance ADL Week 52 ALL. The table below and FIG. 11d show a statistically significant improvement in ADL finance as measured as part of the UHDRS TFC score in all patients receiving 45 mg bid pridopidine for 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4 | 4.1 | 3.9 | 4 | 4 |
| Δ to placebo |  | 0.46 | 0.1 | 0.17 | 0.1 |
| p value |  | 0.0164 | 0.5831 | 0.3558 | 0.6018 |

FIG. 11e: Change from baseline in UHDRS TFC Finance ADL Week 52 Stage 1 BL TFC 11-13. The table below and FIG. 11e show statistically significant improvement in ADL finances as measured as part of the TFC score in HD1 patients, receiving 45 mg bid pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 5.8 | 5.7 | 5.8 | 5.9 | 5.9 |
| Δ to Placebo |  | 0.77 | −0.18 | 0.4 | 0.64 |
| p value |  | 0.0277 | 0.5997 | 0.2805 | 0.0697 |

FIG. 11f: Change from baseline in UHDRS TFC Finance ADL Week 26 Stage 2 BL TFC 7-10. The table below and FIG. 11f show statistically significant improvement in ADL finances as measured as part of the TFC score in HD2 patients, receiving 45-90 mg bid pridopidine for 26 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 4.4 | 4.3 | 4.4 | 4.5 | 4.2 |
| Δ to Placebo |  | 0.7 | 0.54 | 0.56 | 0.18 |
| p value |  | 0.0045 | 0.0407 | 0.0199 | 0.4962 |

FIG. 12a: Change from baseline in UHDRS TFC Finances Week 26 ALL. The table below and FIG. 12a show no significant improvement in UHDRS TFC finances in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.6 | 1.8 | 1.7 | 1.7 | 1.7 |
| Δ to Placebo |  | 0.1 | 0.05 | 0.15 | 0.21 |
| p value |  | 0.3629 | 0.6131 | 0.1389 | 0.0449 |

FIG. 12b: Change from baseline in UHDRS TFC Finances Week 26 Stage 1 BL TFC 11-13. The table below and FIG. 12b show statistically significant improvement in UHDRS TFC finances in HD1 patients, receiving ≥67.5 mg bid pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.8 | 2.9 | 2.8 | 2.9 | 2.9 |
| Δ to Placebo |  | 0.25 | 0.31 | 0.43 | 0.44 |
| p value |  | 0.1183 | 0.0494 | 0.0162 | 0.0062 |

FIG. 12c: Change from baseline in UHDRS TFC Finances Week 52. The table below and FIG. 12c show statistically significant improvement in TFC finances in HD1 patients, receiving 45 mg bid pridopidine for 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.6 | 1.8 | 1.7 | 1.7 | 1.7 |
| Δ to Placebo |  | 0.31 | 0.05 | 0.16 | 0.05 |
| p value |  | 0.0143 | 0.6644 | 0.1976 | 0.7059 |

FIG. 12d: Change from baseline in UHDRS TFC Finances Week 52 Stage 2 BL TFC 7-10. The table below and FIG. 12b show statistically significant improvement in UHDRS TFC finances in HD2 patients, receiving 45 and 90 mg bid pridopidine for 26 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 1.8 | 1.9 | 1.9 | 1.9 | 1.8 |
| Δ to Placebo |  | 0.39 | 0.23 | 0.4 | 0.01 |
| p value |  | 0.0336 | 0.24 | 0.0248 | 0.9559 |

Figure 13A:
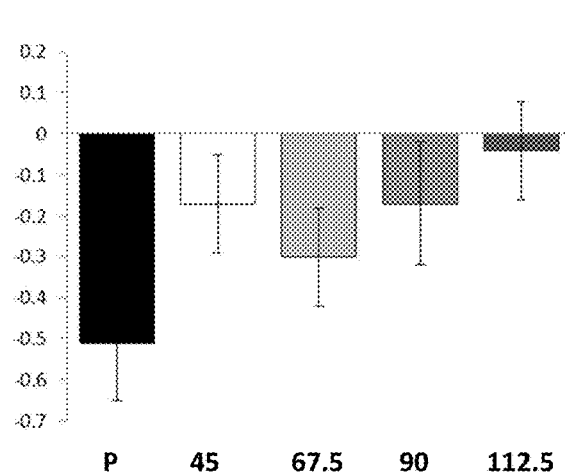

FIG. 13a: Change from baseline in UHDRS TFC Domestic Chores Week 26 ALL. The table below and FIG. 13a show no significant improvement in UHDRS TFC domestic chores in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.2 | 1.3 | 1.3 | 1.2 | 1.2 |
| Δ to Placebo |  | −0.01 | 0.02 | 0 | 0.06 |
| p value |  | 0.9015 | 0.8331 | 0.977 | 0.438 |

Figure 13B:
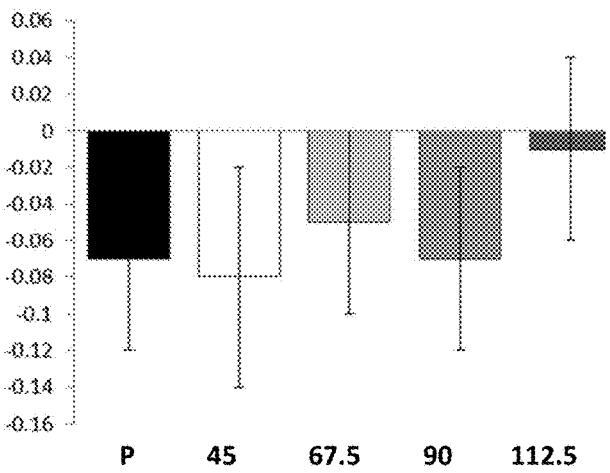

FIG. 13b: Change from baseline in UHDRS TFC Domestic Chores Week 26 Stage 1 BL TFC 11-13. The table below and FIG. 13b show a trend towards improvement in TFC domestic chores in HD1 patients receiving pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2 | 1.8 | 1.9 | 1.7 | 1.9 |
| Δ to Placebo |  | 0.34 | 0.21 | 0.34 | 0.47 |
| p value |  | 0.0589 | 0.2169 | 0.0872 | 0.0079 |

Figure 13C:
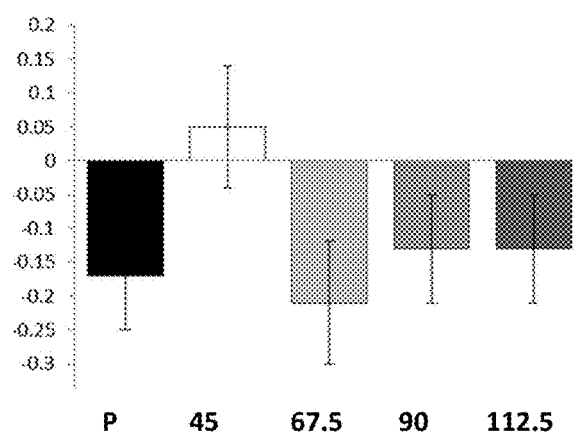

FIG. 13c: Change from baseline in UHDRS TFC Domestic Chores Week 52 ALL. The table below and FIG. 13c show no significant improvement in UHDRS TFC domestic chores in all pridopidine treated patients at 52 weeks.

|  | Placebo | 45 mg bid | 67.5 mg bid | 90 mg bid | 112.5 mg bid |
|---|---|---|---|---|---|
| N | 59 | 56 | 59 | 62 | 67 |
| Baseline | 1.3 | 1.3 | 1.3 | 1.2 | 1.2 |
| Δ to Placebo |  | 0.23 | −0.03 | 0.05 | 0.04 |
| p value |  | 0.0647 | 0.7825 | 0.6869 | 0.7093 |

Figure 13D:
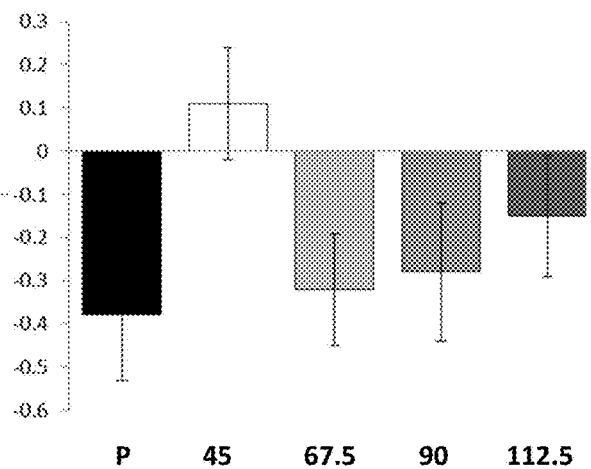

FIG. 13d: Change from baseline in UHDRS TFC Domestic Chores Week 52 Stage 1 BL TFC 11-13. The table below and FIG. 13d show statistically significant improvement in TFC domestic chores in HD1 patients receiving 45 mg bid pridopidine for 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2 | 1.8 | 1.9 | 1.7 | 1.9 |
| Δ to Placebo |  | 0.49 | 0.05 | 0.1 | 0.23 |
| p value |  | 0.0161 | 0.7793 | 0.6442 | 0.2463 |

Figure 14A:
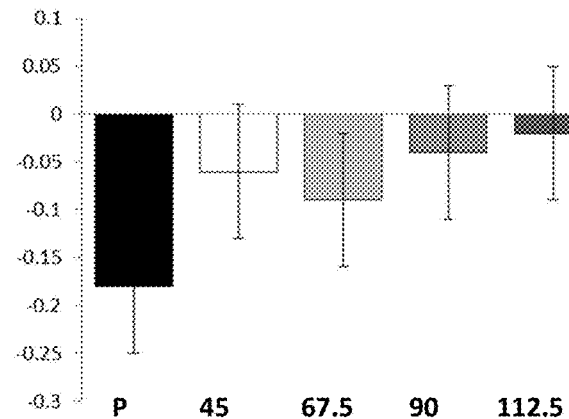

FIG. 14a: Change from baseline in UHDRS TFC ADL Week 26 ALL. The table below and FIG. 14a show no significant improvement in TFC ADL in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.4 | 2.3 | 2.2 | 2.3 | 2.3 |
| Δ to Placebo |  | 0.12 | 0.09 | 0.14 | 0.17 |
| p value |  | 0.205 | 0.3427 | 0.1296 | 0.0773 |

Figure 14B:
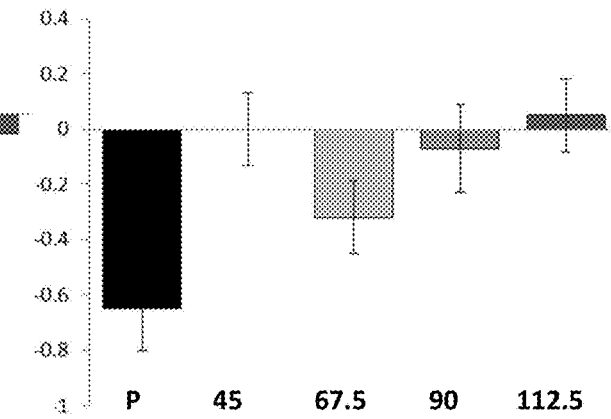

FIG. 14b: Change from baseline in UHDRS TFC ADL Week 26 Stage 1 BL TFC 11-13. The table below and FIG. 14b show statistically significant improvement in UHDRS TFC ADL in HD1 patients receiving 45 mg bid, 90 mg bid and 112.5 mg bid pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.9 | 2.8 | 2.9 | 3 | 3 |
| Δ to Placebo |  | 0.65 | 0.34 | 0.58 | 0.7 |
| p value |  | 0.0011 | 0.0715 | 0.0062 | 0.0003 |

Figure 14C:
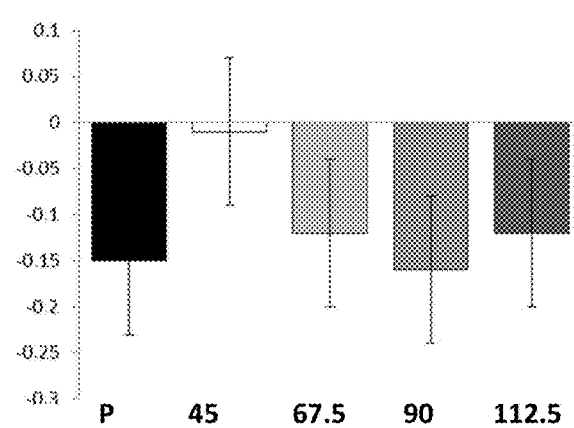

FIG. 14c: Change from baseline in UHDRS TFC ADL Week 52 ALL. The table below and FIG. 14c show no significant improvement in UHDRS TFC ADL in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.4 | 2.3 | 2.2 | 2.3 | 2.3 |
| Δ to Placebo |  | 0.14 | 0.03 | −0.01 | 0.03 |
| p value |  | 0.2216 | 0.7943 | 0.9318 | 0.7868 |

Figure 14D:
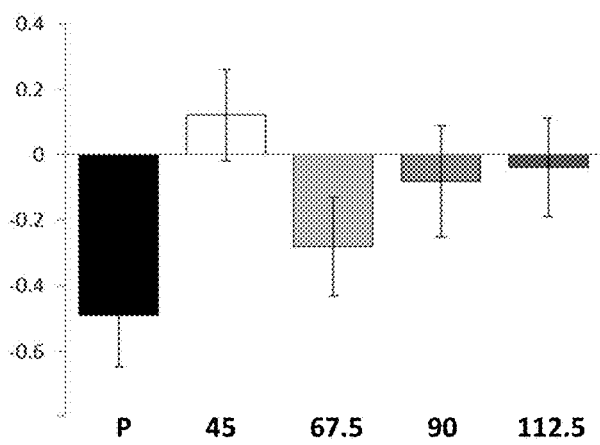

FIG. 14d: Change from baseline in UHDRS TFC ADL Week 52 Stage 1 BL TFC 11-13. The table below and FIG. 14d show statistically significant improvement in UHDRS TFC ADL in HD1 patients receiving 45 mg bid or 112.5 mg bid pridopidine for 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.9 | 2.8 | 2.9 | 3 | 3 |
| Δ to Placebo |  | 0.62 | 0.21 | 0.42 | 0.46 |
| p value |  | 0.0044 | 0.3054 | 0.0646 | 0.0345 |

Figure 14E:
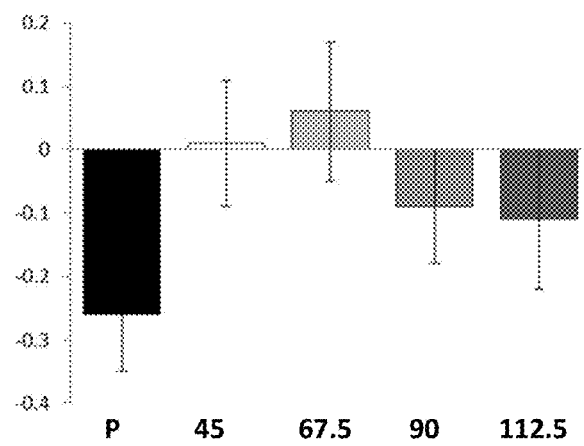

FIG. 14e: Change from baseline in UHDRS TFC ADL Week 52 Stage 2 BL TFC 7-10. The table below and FIG. 14e show statistically significant improvement in UHDRS TFC ADL in HD2 patients receiving 45 mg bid pridopidine for 52 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 2.6 | 2.5 | 2.5 | 2.5 | 2.4 |
| Δ to Placebo |  | 0.27 | 0.31 | 0.16 | 0.15 |
| p value |  | 0.0356 | 0.0244 | 0.1894 | 0.2776 |

Figure 15A:
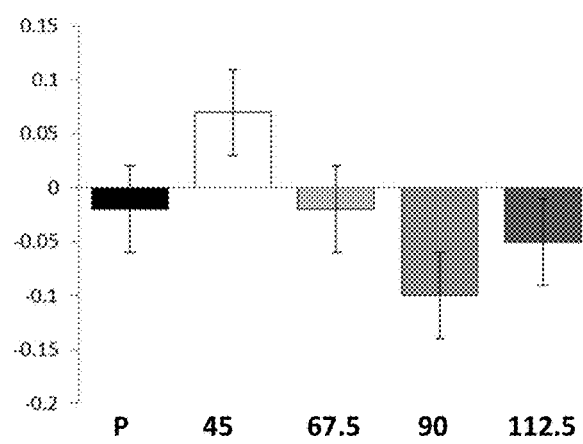

FIG. 15*a*: Change from baseline in UHDRS TFC Care Level Week 52 ALL. The table below and FIG. 15*a* show no significant improvement in UHDRS TFC care level in all pridopidine treated patients at 52 weeks.

|  | Placebo | 45 mg bid | 67.5 mg bid | 90 mg bid | 112.5 mg bid |
|---|---|---|---|---|---|
| N | 59 | 56 | 59 | 62 | 67 |
| Baseline | 1.9 | 1.9 | 1.9 | 1.9 | 1.9 |
| Δ to placebo |  | 0.09 | 0 | −0.08 | −0.03 |
| p value |  | 0.1153 | 0.9365 | 0.1509 | 0.5713 |

Figure 15B:
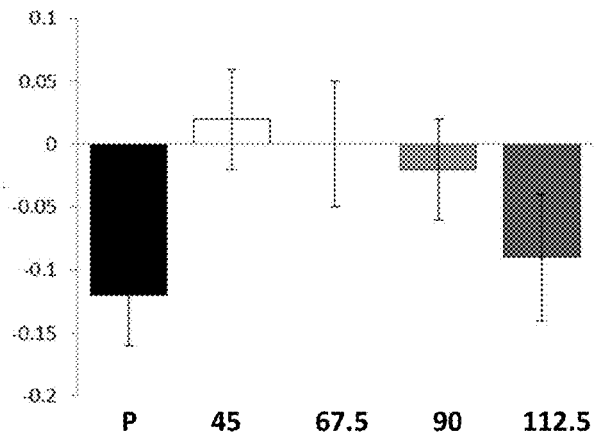

FIG. 15*b*: Change from baseline in UHDRS TFC Care Level Week 52 Stage 2 BL TFC 7-10. The table below and FIG. 15*b* show statistically significant improvement in UHDRS TFC care level in HD2 patients receiving 45 mg bid pridopidine for 52 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 1.9 | 1.9 | 2 | 2 | 2 |
| Δ to placebo |  | 0.13 | 0.12 | 0.1 | 0.03 |
| p value |  | 0.0156 | 0.0395 | 0.0585 | 0.6168 |

Figure 16A:
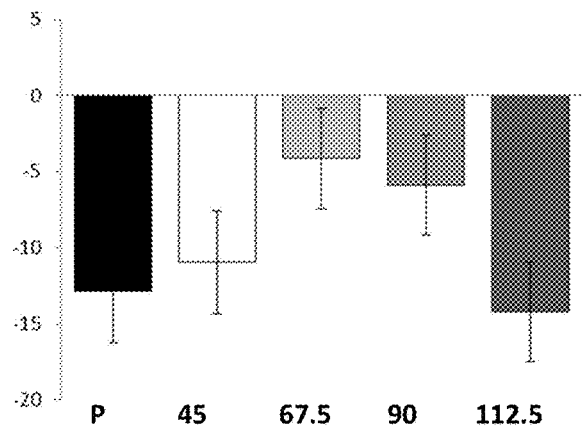

FIG. 16*a*: Change from baseline in HD-QoL Participant Total Score Week 26 ALL. The table below and FIG. 16*a* show no significant improvement in HD-QoL in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 68.1 | 67.3 | 76.5 | 73.3 | 69.9 |
| Δ to placebo |  | 1.91 | 8.7 | 6.95 | −1.36 |
| p value |  | 0.6775 | 0.0572 | 0.1251 | 0.7663 |

Figure 16B:
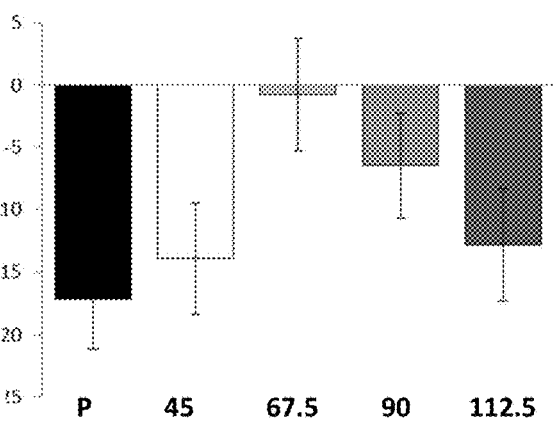

FIG. 16*b*: Change from baseline in HD-QoL Participant Total Score Week 26 Stage 2 BL TFC 7-10. The table below and FIG. 16*b* show significant improvement in HD-QoL in 67.5 mg bid pridopidine treated HD2 patients at 26 weeks.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 62.5 | 64.3 | 82.8 | 74.3 | 78 |
| Δ to placebo |  | 3.22 | 16.33 | 10.64 | 4.29 |
| p value |  | 0.5601 | 0.0054 | 0.0566 | 0.4577 |

Figure 17A:
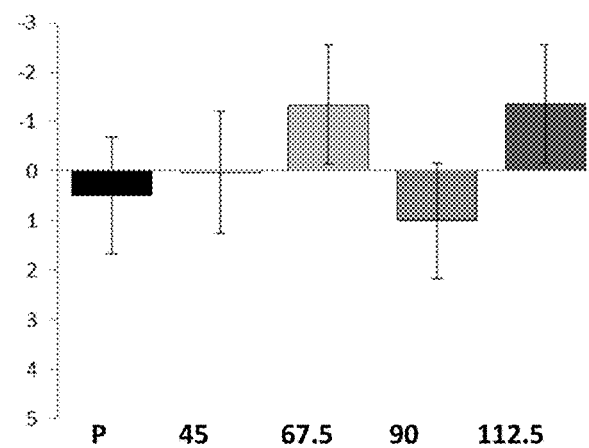

FIG. 17*a*: Change from baseline in PBA Total Score Week 26 ALL, full analysis set. The table below and FIG. 17*a* show change in baseline in PBA total score total in pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 12 | 10.9 | 13.8 | 11.2 | 11.8 |
| Δ to placebo |  | −0.46 | −1.83 | 0.51 | −1.85 |
| p value |  | 0.7838 | 0.2748 | 0.7567 | 0.2659 |

Figure 17B:
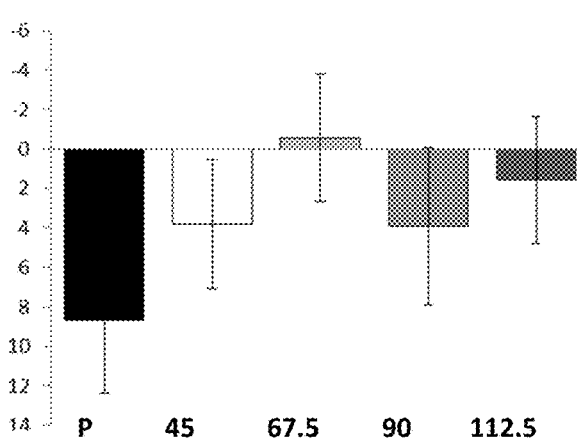

FIG. 17*b*: Change from baseline in PBA Total Score Week 26 Stage 1 BL TFC 11-13. The table below and FIG. 17*b* show a trend towards improvement in PBA total score in HD1 patients receiving pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 8.8 | 8.1 | 10.2 | 4 | 7.7 |
| Δ to placebo |  | −4.83 | −9.22 | −4.74 | −7.08 |
| p value |  | 0.319 | 0.0533 | 0.3721 | 0.1351 |

Figure 17C:
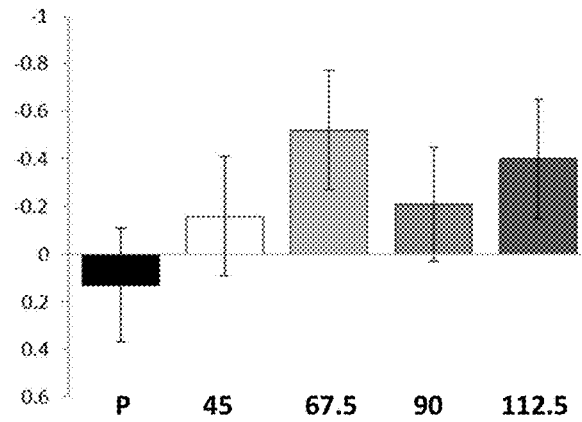

FIG. 17*c*: Change from baseline in PBA Depressed Mood, Severity×Frequency Week 26 ALL. The table below and FIG. 17*c* show no significant improvement in PBD depressed mood in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.5 | 1.8 | 1.9 | 1.2 | 1.3 |
| Δ to placebo |  | −0.29 | −0.65 | −0.34 | −0.52 |
| p value |  | 0.4015 | 0.0583 | 0.3174 | 0.1237 |

Figure 17D:
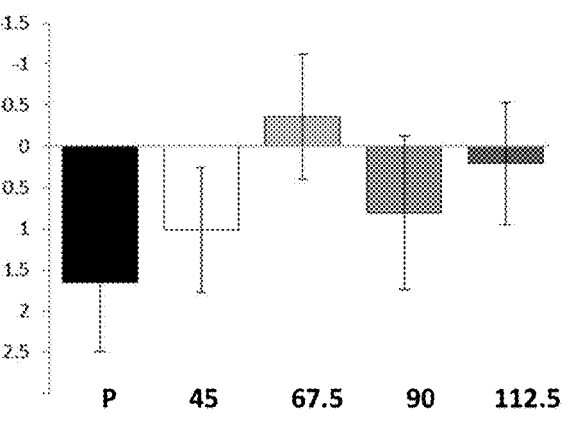

FIG. 17*d*: Change from baseline in PBA Depressed Mood, Severity×Frequency Week 26 Stage 1 BL TFC 11-13. The table below and FIG. 17*d* show no significant improvement in PBA depressed mood in HD1 pridopidine treated patients at 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 1.9 | 1.3 | 2.2 | 0.8 | 1.1 |
| Δ to placebo |  | −0.63 | −2.01 | −0.84 | −1.43 |
| p value |  | 0.5782 | 0.0704 | 0.4957 | 0.1942 |

FIG. 17*e*: PBA Change from baseline in Total Score Week 52 Full analysis set. The table below and FIG. 17*e* show trend to improvement in PBA total score in 45 mg bid pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 12 | 10.9 | 13.8 | 11.2 | 11.8 |
| Δ to placebo |  | −3.98 | −0.63 | −0.38 | 0.3 |
| p value |  | 0.0603 | 0.7602 | 0.851 | 0.8845 |

FIG. 17*f*: Change from baseline in PBA Total Score Week 52 Full analysis set BL TFC≥7. The table below and FIG. 17*f* show trend to improvement in PBA total score in 45 mg bid pridopidine treated HD1 and HD2 patients at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 11.4 | 10.1 | 14.4 | 10.9 | 10.4 |
| Δ to placebo |  | −2.74 | 0.61 | 0.9 | 1.4 |
| p value |  | 0.1911 | 0.7785 | 0.6653 | 0.5171 |

FIG. 17g: Change from baseline PBA Irritability, Severity×Frequency Week 52 ALL. The table below and FIG. 17g show significant improvement in PBA irritability in most (excluding 67.5 mg bid) pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2 | 1.6 | 1.7 | 1.4 | 1.5 |
| Δ to placebo |  | −1.03 | −0.63 | −1.01 | −0.84 |
| p value |  | 0.0126 | 0.1176 | 0.0108 | 0.0419 |

FIG. 17h: Change from baseline in PBA Irritability, Severity×Frequency Week 52 Stage 3-5 BL TFC 0-6. The table below and FIG. 17h show significant improvement in PBA irritability in pridopidine treated patients with baseline TFC 0-6 at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 1.3 | 0.9 | 0.9 | 1.3 | 1.6 |
| Δ to placebo |  | −2.42 | −1.78 | −1.79 | −1.71 |
| p value |  | 0.0165 | 0.0429 | 0.0422 | 0.0542 |

FIG. 17i: Change from baseline in PBA Lack of Initiative (Apathy), Severity×Frequency Week 26 ALL. The table below and FIG. 17i show no significant improvement in PBA apathy in all pridopidine treated patients at 26 weeks

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.6 | 2.5 | 3.1 | 2.9 | 3 |
| Δ to placebo |  | −0.87 | −0.53 | −0.2 | −0.26 |
| p value |  | 0.1235 | 0.3437 | 0.7198 | 0.6445 |

FIG. 17j: Change from baseline in PBA Lack of Initiative (Apathy), Severity×Frequency Week 26 Stage 1 BL TFC 11-13. The table below and FIG. 17j show trend towards improvement in PBA apathy in HD1 patients receiving pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 1.2 | 1 | 1.3 | 0.4 | 1.5 |
| Δ to placebo |  | −1.85 | −1.51 | −1.46 | −2.62 |
| p value |  | 0.0703 | 0.1267 | 0.1822 | 0.0089 |

Figure 17K:
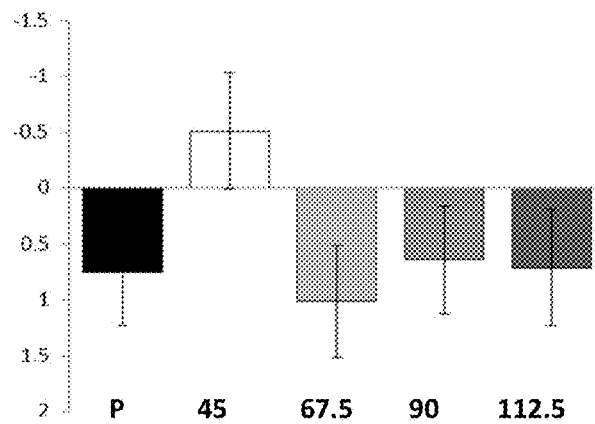

FIG. 17k: Change from baseline in PBA Lack of Initiative (Apathy), Severity×Frequency Week 52 Full analysis set. The table below and FIG. 17k show trend towards improvement in PBA apathy in BL stage 1 patients receiving pridopidine for 52 weeks.

|  | Placebo | 45 mg bid | 67.5 mg bid | 90 mg bid | 112.5 mg bid | Placebo |
|---|---|---|---|---|---|---|
| N | 81 | 75 | 79 | 81 | 81 |  |
| Baseline | 2.6 | 2.5 | 3.1 | 2.9 | 3 |  |
| Δ to placebo |  | −1.27 | 0.26 | −0.12 | −0.04 |  |
| p value |  | 0.0704 | 0.7052 | 0.8599 | 0.9523 |  |

Figure 17L:
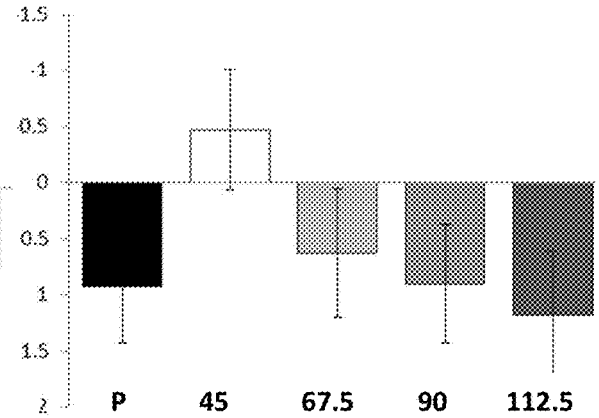

FIG. 17l: PBA Change from baseline in PBA Lack of Initiative (Apathy), Severity×Frequency Week 52 1 BL TFC>7. The table below and FIG. 17l show trend towards improvement in PBA apathy in HD1 and HD2 pridopidine treated patients for 52 weeks.

|  | Placebo | 45 mg bid | 67.5 mg bid | 90 mg bid | 112.5 mg bid | Placebo |
|---|---|---|---|---|---|---|
| N | 62 | 59 | 54 | 56 | 58 |  |
| Baseline | 2.5 | 2 | 3 | 2.7 | 2.8 |  |
| Δ to placebo |  | −1.39 | −0.29 | −0.02 | 0.26 |  |
| p value |  | 0.0608 | 0.703 | 0.9734 | 0.7346 |  |

Figure 17M:
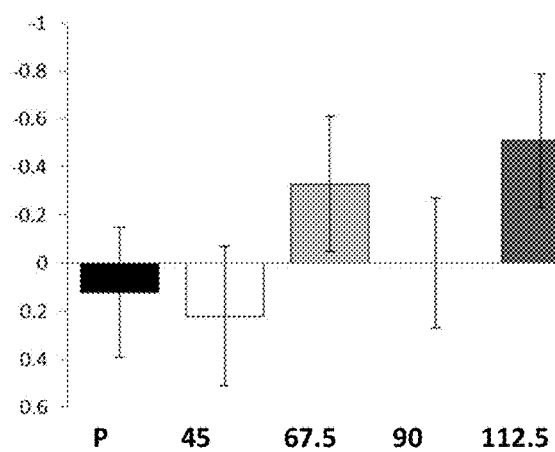

FIG. 17m: Change from baseline in PBA Obsessive-Compulsive, Severity×Frequency Week 26 ALL. The table below and FIG. 17m show no significant improvement in PBA O-C in all pridopidine treated patients at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.2 | 1.1 | 1.3 | 1.1 | 1 |
| Δ to placebo |  | 0.1 | −0.45 | −0.12 | −0.63 |
| p value |  | 0.8081 | 0.2512 | 0.7541 | 0.1061 |

Figure 17N:
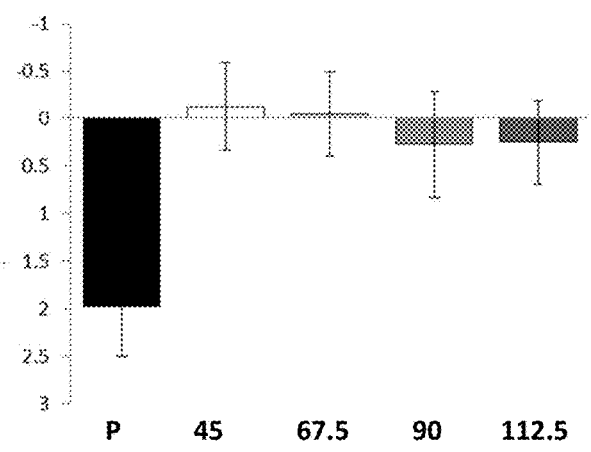

FIG. 17n Change from baseline in PBA Obsessive-Compulsive, Severity×Frequency Week 26 Stage 1 BL TFC 11-13. The table below and FIG. 17n show statistically significant improvement in PBA O-C in HD1 patients receiving pridopidine for 26 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 0 | 1 | 0.4 | 0.1 | 0.1 |
| Δ to placebo |  | −2.11 | −2.03 | −1.71 | −1.73 |
| p value |  | 0.0035 | 0.0035 | 0.0251 | 0.0114 |

Figure 17O:
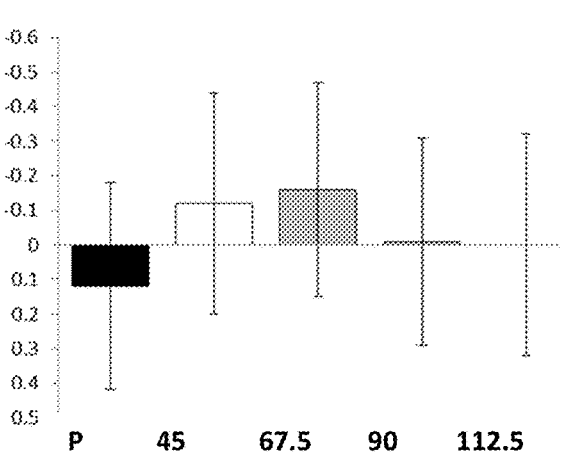

FIG. 17o: Change from baseline in PBA Obsessive-Compulsive, Severity×Frequency Week 52 ALL. The table below and FIG. 17o show no significant improvement in PBA O-C in all pridopidine treated patients at 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 1.2 | 1.1 | 1.3 | 1.1 | 1 |
| Δ to placebo |  | −0.24 | −0.28 | −0.13 | −0.12 |
| p value |  | 0.5733 | 0.5068 | 0.7508 | 0.7789 |

Figure 17P:
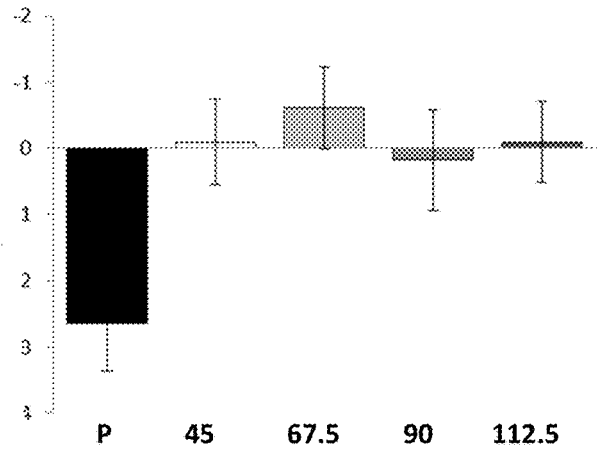

FIG. 17p: Change from baseline in PBA Obsessive-Compulsive, Severity×Frequency Week 52 Stage 1 BL TFC 11-13. The table below and FIG. 17p show statistically significant improvement in PBA 0-C in HD1 patients receiving pridopidine for 52 weeks

|  | Placebo | 45 mg bid | 67.5 mg bid | 90 mg bid | 112.5 mg bid |
| --- | --- | --- | --- | --- | --- |
| N | 12 | 17 | 17 | 11 | 18 |
| Baseline | 0 | 1 | 0.4 | 0.1 | 0.1 |
| Δ to placebo |  | −2.73 | −3.24 | −2.47 | −2.73 |
| p value |  | 0.007 | 0.0011 | 0.021 | 0.005 |

Figure 17Q:
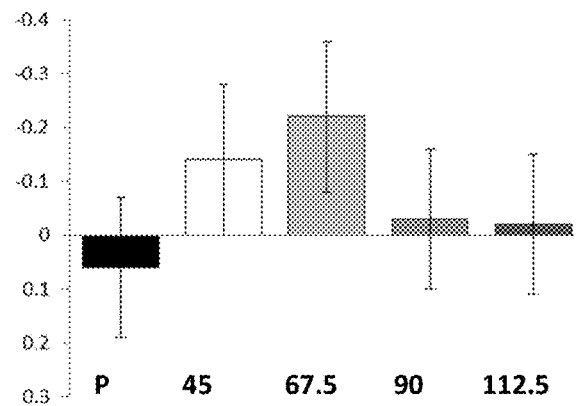

FIG. 17q: Change from baseline in PBA Disoriented Behavior, Severity×Frequency Week 26 ALL. The table below and FIG. 17q show no significant improvement in PBA Disoriented Behavior in all pridopidine treated patients at 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 0.6 | 0.4 | 0.8 | 0.6 | 0.6 |
| Δ to placebo |  | −0.2 | −0.28 | −0.09 | −0.08 |
| p value |  | 0.2864 | 0.1357 | 0.607 | 0.6771 |

Figure 17R:
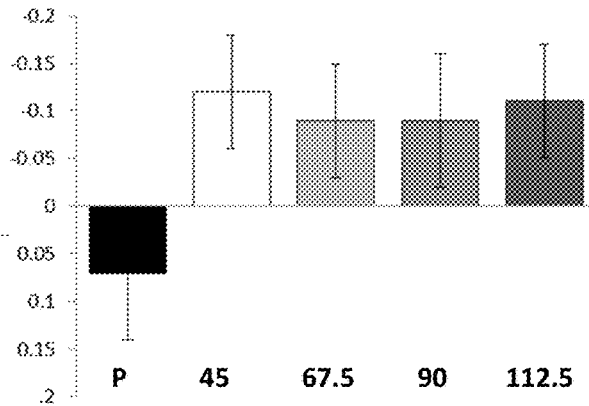

FIG. 17r: Change from baseline in PBA Disoriented Behavior, Severity×Frequency Week 26 Stage 1 BL TFC 11-13. The table below and FIG. 17r show significant improvement in PBA Disoriented Behavior in HID1 patients receiving 45 mg bid or 112.5 mg bid pridopidine at 26 weeks.

|  | Placebo | 45 mg bid | 67.5 mg bid | 90 mg bid | 112.5 mg bid |
| --- | --- | --- | --- | --- | --- |
| N | 12 | 17 | 17 | 11 | 18 |
| Baseline | 0.1 | 0 | 0.3 | 0 | 0.3 |
| Δ to placebo |  | −0.19 | −0.16 | −0.16 | −0.18 |
| p value |  | 0.0381 | 0.0615 | 0.093 | 0.0357 |

Figure 18A:
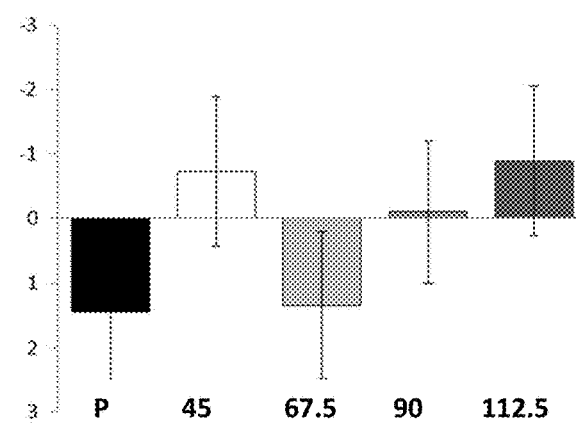

FIG. 18a: Change from baseline in Timed Up and Go Test (sec) Week 26 ALL. The table below and FIG. 18a show no significant improvement in Timed up and go test in all pridopidine treated patients at 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 12.1 | 12.1 | 10.4 | 10.3 | 11.6 |
| Δ to placebo |  | −2.16 | −0.09 | −1.54 | −2.33 |
| p value |  | 0.1765 | 0.9571 | 0.3255 | 0.1456 |

Figure 18B:
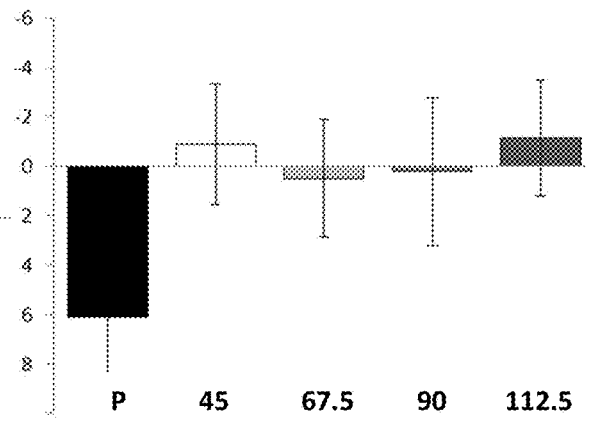

FIG. 18b: Change from baseline in Timed Up and Go Test (sec) Week 26 Stage 1 BL TFC 11-13. The table below and FIG. 18b show a trend towards improvement in the Timed up and go test in pridopidine treated HD1 patients at 26 weeks.

|  | Placebo | 45 mg bid | 67.5 mg bid | 90 mg bid | 112.5 mg bid |
| --- | --- | --- | --- | --- | --- |
| N | 12 | 17 | 17 | 11 | 18 |
| Baseline | 9.7 | 8.6 | 8.7 | 9.6 | 9.4 |
| Δ to placebo |  | −6.98 | −5.59 | −5.87 | −7.24 |
| p value |  | 0.0612 | 0.1259 | 0.1498 | 0.0482 |

Figure 18C:
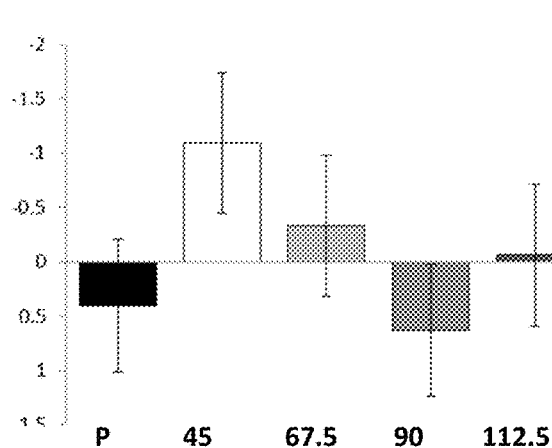

FIG. 18c: Change from baseline in Timed Up and Go Test (sec) Week 52. The table below and FIG. 18c show no statistically significant improvement in the Timed up and go test in all pridopidine treated patients at 52 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 12.1 | 12.1 | 10.4 | 10.3 | 11.6 |
| Δ to placebo |  | −1.49 | −0.74 | 0.22 | −0.47 |
| p value |  | 0.0899 | 0.4022 | 0.7918 | 0.595 |

Figure 18D:
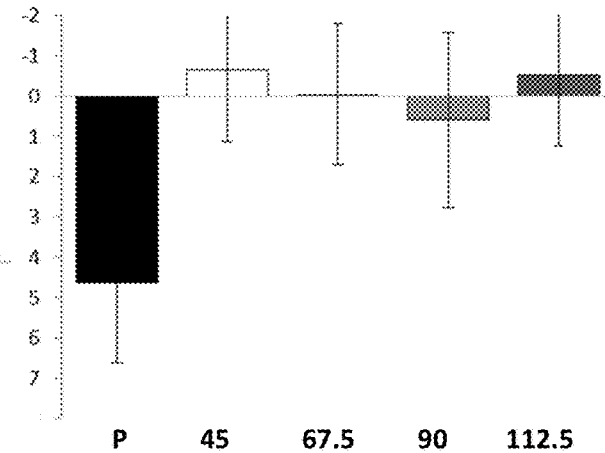

FIG. 18d: Change from baseline in Timed Up and Go Test (sec) Week 52 Stage 1 BL TFC 11-13. The table below and FIG. 18d show trend toward improvement in the Timed up and go test in pridopidine treated HD1 patients at 52 weeks.

|  | Placebo | 45 mg bid | 67.5 mg bid | 90 mg bid | 112.5 mg bid |
| --- | --- | --- | --- | --- | --- |
| N | 12 | 17 | 17 | 11 | 18 |
| Baseline | 9.7 | 8.6 | 8.7 | 9.6 | 9.4 |
| Δ to placebo |  | −5.26 | −4.65 | −4.02 | −5.13 |
| p value |  | 0.0627 | 0.0921 | 0.1859 | 0.0652 |

Figure 19A:
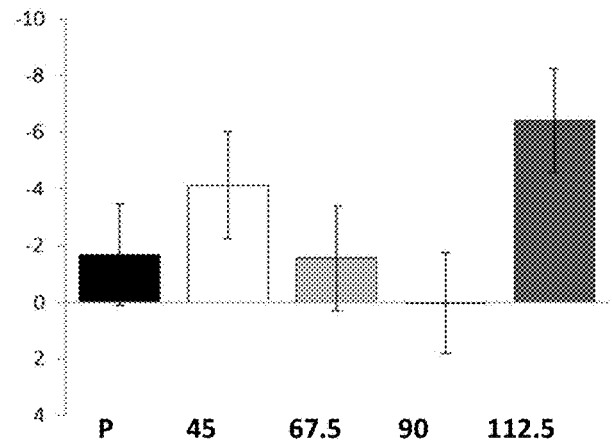

FIG. 19a: Change from baseline in Walk-12 Total Score Week 26 ALL. The table below and FIG. 19a show no significant improvement in the Walk-12 TS in all pridopidine treated patients at 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 31.5 | 32.1 | 32.8 | 29.7 | 29.7 |
| Δ to placebo |  | −2.45 | 0.13 | 1.7 | −4.71 |
| p value |  | 0.3359 | 0.9604 | 0.4931 | 0.0622 |

Figure 19B:
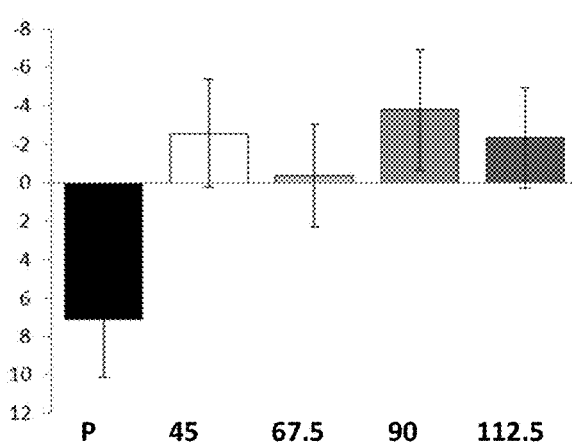

FIG. 19b: Change from baseline in Walk-12 Total Score Week 26 Stage 1 BL TFC 11-13. The table below and FIG. 19b show statistically significant improvement in the Walk-12 TS in pridopidine treated HD1 patients having at 26 weeks.

|  | Placebo | 45 mg bid | 67.5 mg bid | 90 mg bid | 112.5 mg bid |
| --- | --- | --- | --- | --- | --- |
| N | 12 | 17 | 17 | 11 | 18 |
| Baseline | 21.2 | 6.3 | 12.3 | 17.7 | 13 |
| Δ to placebo |  | −9.63 | −7.45 | −10.88 | −9.38 |
| p value |  | 0.0241 | 0.054 | 0.0116 | 0.0173 |

Figure 19C:
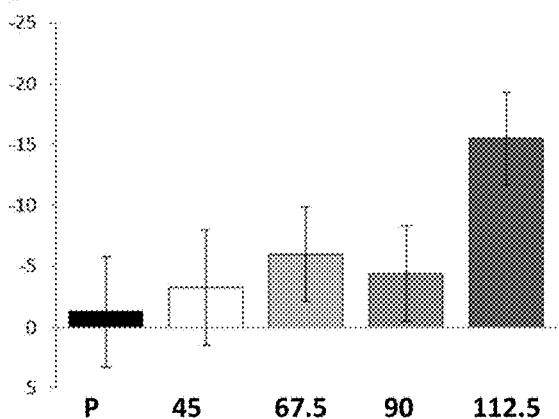

FIG. 19c: Change from baseline in Walk-12 Total Score Week 26 Stage 3-5 BL TFC 0-6. The table below and FIG. 19c show no significant improvement in the Walk-12 TS in late stage pridopidine treated patients (BL TFC 0-6) at 26 weeks.

|  | Placebo | 45 mg bid | 67.5 mg bid | 90 mg bid | 112.5 mg bid |
| --- | --- | --- | --- | --- | --- |
| N | 19 | 16 | 25 | 25 | 23 |
| Baseline | 56.6 | 55.4 | 48.3 | 39.6 | 45.9 |
| Δ to placebo |  | −1.97 | −4.7 | −3.18 | −14.22 |
| p value |  | 0.7524 | 0.4242 | 0.5934 | 0.0151 |

Figure 19D:
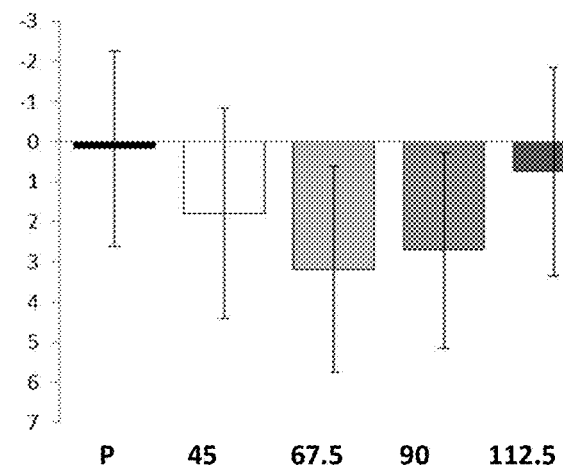

FIG. 19d: Change from baseline in Walk-12 Total Score Week 52 ALL. The table below and FIG. 19d show no statistically significant improvement in the Walk-12 TS in pridopidine treated patients at 52 weeks

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 31.5 | 32.1 | 32.8 | 29.7 | 29.7 |
| Δ to placebo |  | 1.62 | 3.01 | 2.53 | 0.56 |
| p value |  | 0.6486 | 0.3891 | 0.4587 | 0.8738 |

Figure 19E:
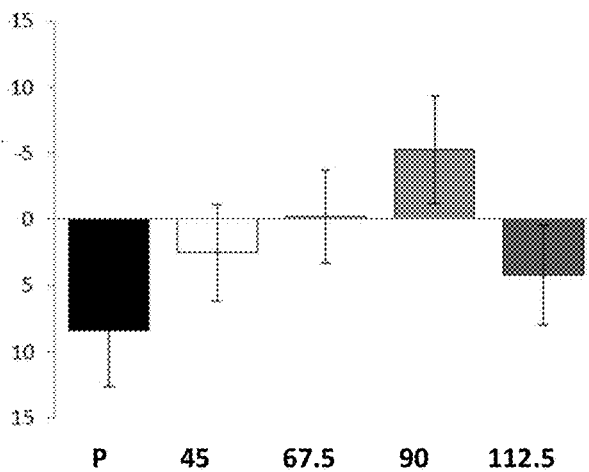

FIG. 19e: Change from baseline in Walk-12 Total Score Week 52 Stage 1 BL TFC 11-13. The table below and FIG. 19e show statistically significant improvement in the Walk-12 TS in 90 mg bid pridopidine treated HD1 patients at 52 weeks.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 21.2 | 6.3 | 12.3 | 17.7 | 13 |
| Δ to placebo |  | −5.86 | −8.57 | −13.6 | −4.13 |
| p value |  | 0.3018 | 0.1032 | 0.0193 | 0.4534 |

FIG. 20a: Change from baseline in UHDRS Independence Scale Week 26 BL TFC<7. The table below and FIG. 20a show no significant improvement in the UHDRS IS in pridopidine treated patients having BL TFC less than 7, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 65.5 | 63.8 | 64.8 | 68.2 | 66.3 |
| Δ to placebo |  | 0.3 | −0.44 | 0.2 | 1.65 |
| p value |  | 0.8796 | 0.8027 | 0.9116 | 0.3578 |

FIG. 20b: Change from baseline in UHDRS Independence Scale Week 26 BL TFC≥7. The table below and FIG. 20b show statistically significant improvement in the UHDRS IS in 45 mg bid pridopidine treated HD1 and HD2 patients, at 26 weeks.

|  | 45 mg bid | 67.5 mg bid | 90 mg bid | 112.5 mg bid |
|---|---|---|---|---|
| N | 59 | 54 | 56 | 58 |
| Wk 26 Δ to placebo | 2.22 | 0.99 | 1.48 | 1.51 |
| p value | 0.0128 | 0.2755 | 0.0949 | 0.0919 |

FIG. 20c: Change from baseline in UHDRS Independence Scale Week 52 BL TFC<7. The table below and FIG. 20a show no significant improvement in the UHDRS IS in pridopidine treated patients having baseline TFC less than 7, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 65.5 | 63.8 | 64.8 | 68.2 | 66.3 |
| Δ to placebo |  | −1.85 | −3.46 | −5.25 | −0.52 |
| p value |  | 0.5799 | 0.2415 | 0.0779 | 0.8613 |

FIG. 20d: Change from baseline in UHDRS Independence Scale Week 52 BL TFC≥7. The table below and FIG. 20d show statistically significant improvement in the UHDRS IS in 90 mg bid pridopidine treated HD1 and HD2 patients at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 79.8 | 79.4 | 79.2 | 79.9 | 79.3 |
| Δ to placebo |  | 1.99 | 2.22 | 2.79 | 0.44 |
| p value |  | 0.1047 | 0.0788 | 0.0228 | 0.7301 |

FIGS. 21a-21p, 22a-22b, 23a-23b, 24a-24b are graphs comparing characteristics in early stage (TFC≥7, HD1 and HD2) or late stage (TFC<7) HD patients.

Figure 21A:
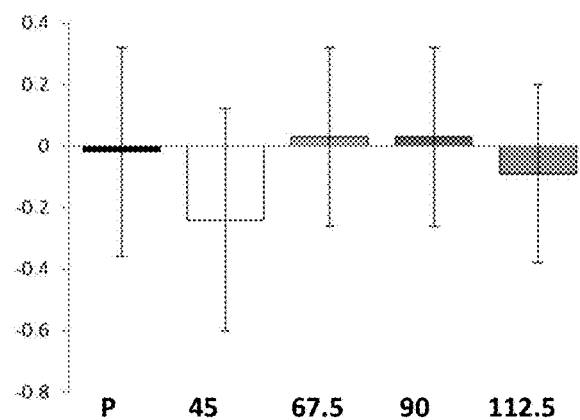

FIG. 21a: Change from baseline in UHDRS Total Functional Capacity Week 26 BL TFC<7. The table below and FIG. 21a show no significant improvement in the UHDRS TFC in pridopidine treated late stage patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 8.9 | 9.2 | 9.4 | 9.1 | 9.3 |
| Δ to placebo |  | 0.56 | 0.33 | 0.61 | 0.67 |
| p value |  | 0.0359 | 0.215 | 0.0199 | 0.0125 |

Figure 21B:
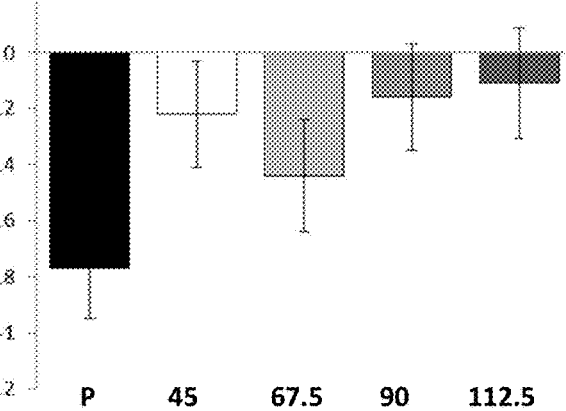

FIG. 21b: Change from baseline in UHDRS Total Functional Capacity Week 26 BL TFC≥7. The table below and FIG. 21b show statistically significant improvement in the UHDRS TFC in 45 mg bid and 90 mg bid and higher pridopidine treated HD1 and HD2 patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 8.9 | 9.2 | 9.4 | 9.1 | 9.3 |
| Wk 26 Δ to placebo |  | 0.56 | 0.33 | 0.61 | 0.67 |
| p value |  | 0.0359 | 0.215 | 0.0199 | 0.0125 |

Figure 21C:
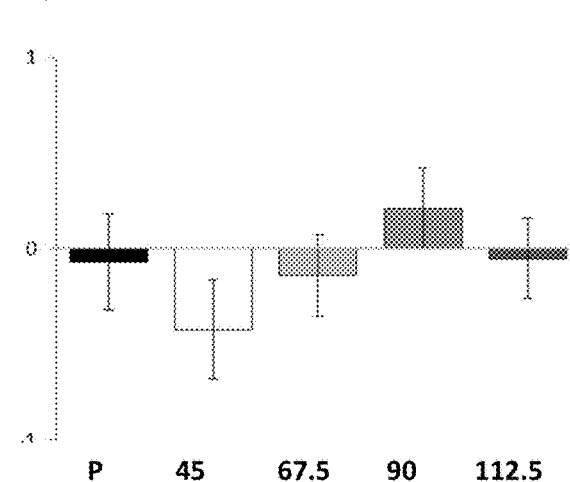

FIG. 21c: Change from baseline in UHDRS TFC Finance ADL Week 26 BL TFC<7. The table below and FIG. 21c show no significant improvement in the UHDRS TFC Finance ADL in pridopidine treated late stage patients, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 2 | 2 | 1.9 | 2.2 | 2.3 |
| Δ to placebo |  | −0.34 | −0.06 | 0.28 | 0.03 |
| p value |  | 0.3239 | 0.8408 | 0.3747 | 0.9361 |

Figure 21D:
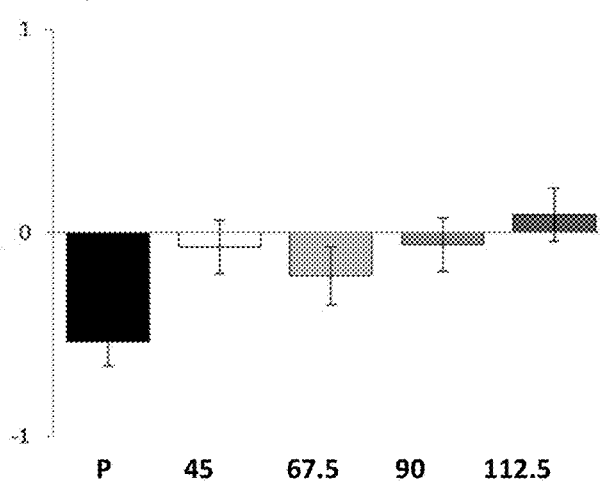

FIG. 21d: Change from baseline in UHDRS TFC Finance ADL Week 26 BL TFC≥7. The table below and FIG. 21d show statistically significant improvement in the UHDRS Finance ADL in 45 mg bid and 90 mg bid and higher pridopidine treated HD1 and HD2 patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 4.6 | 4.7 | 4.9 | 4.8 | 4.7 |
| Δ to placebo |  | 0.46 | 0.32 | 0.47 | 0.62 |
| p value |  | 0.0114 | 0.0817 | 0.0093 | 0.0007 |

Figure 21E:
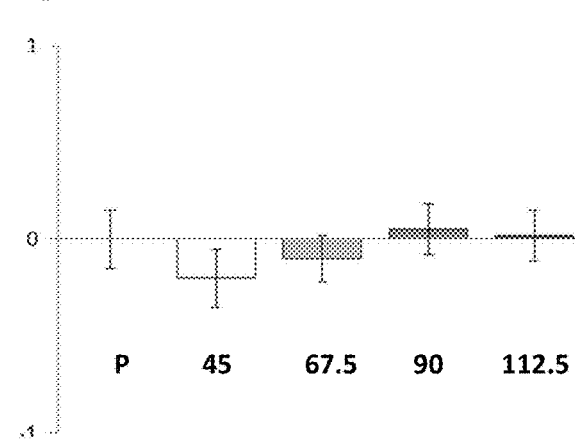

FIG. 21e: Change from baseline in UHDRS TFC Finances Week 26 BL TFC<7. The table below and FIG. 21e show no significant improvement in the UHDRS ITFC finances in pridopidine treated late stage patients, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 0.5 | 0.5 | 0.5 | 0.7 | 0.7 |
| Δ to placebo |  | −0.19 | −0.1 | 0.05 | 0.03 |
| p value |  | 0.3508 | 0.5934 | 0.774 | 0.8925 |

Figure 21F:
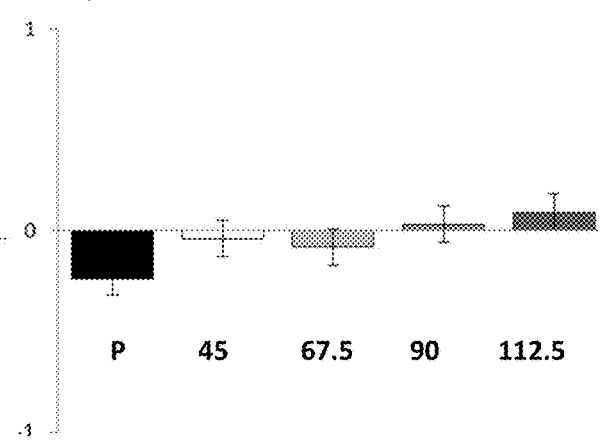

FIG. 21f: Change from baseline in UHDRS TFC Finances Week 26 BL TFC≥7. The table below and FIG. 21f show statistically significant improvement in the UHDRS TFC finances in 90 mg bid and higher HD1 and HD2 pridopidine treated patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2 | 2.2 | 2.2 | 2.1 | 2.2 |
| Δ to placebo |  | 0.2 | 0.16 | 0.27 | 0.33 |
| p value |  | 0.0853 | 0.1865 | 0.0236 | 0.0061 |

Figure 21G:
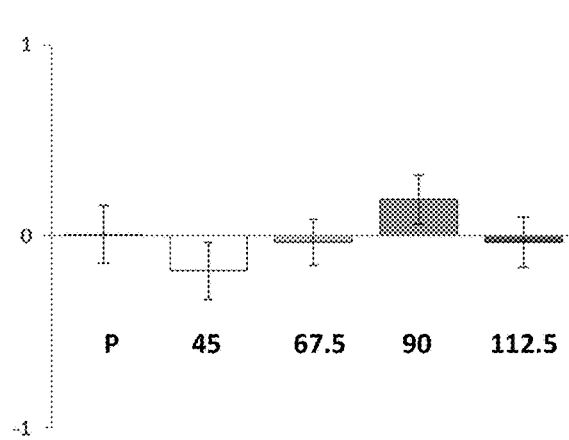

FIG. 21g: Change from baseline in UHDRS TFC ADL Week 26 BL TFC<7. The table below and FIG. 21g show no significant improvement in the UHDRS TFC ADL in pridopidine treated late stage patients, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 1.5 | 1.5 | 1.4 | 1.5 | 1.7 |
| Δ to placebo |  | −0.19 | −0.04 | 0.18 | −0.04 |
| p value |  | 0.3596 | 0.8518 | 0.3507 | 0.8438 |

Figure 21H:
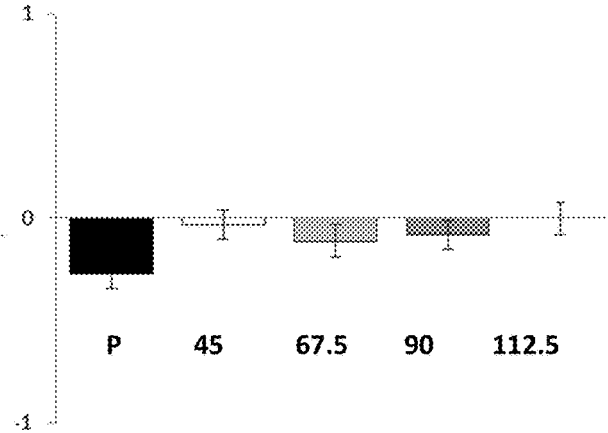

FIG. 21h: Change from baseline in UHDRS TFC ADL Week 26 BL TFC≥7. The table below and FIG. 21h show statistically significant improvement in the UHDRS TFC ADL in 45 mg bid and 90 mg bid and higher pridopidine treated HD1 and HD2 patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2.6 | 2.6 | 2.6 | 2.6 | 2.6 |
| Δ to placebo |  | 0.24 | 0.16 | 0.19 | 0.27 |
| p value |  | 0.0176 | 0.1132 | 0.0526 | 0.0076 |

Figure 21I:
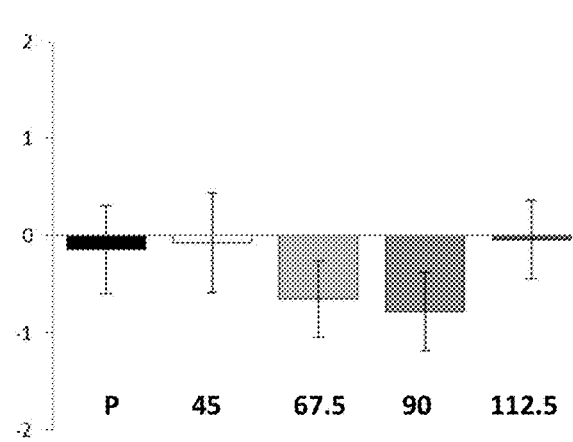

FIG. 21i: Change from baseline in UHDRS Total Functional Capacity Week 52 BL TFC<7. The table below and FIG. 21i show no significant improvement in the UHDRS IS in pridopidine treated late stage patients, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 4.5 | 4.1 | 4.5 | 4.9 | 4.7 |
| Δ to placebo |  | 0.07 | −0.5 | −0.64 | 0.1 |
| p value |  | 0.9108 | 0.3933 | 0.2828 | 0.8605 |

Figure 21J:
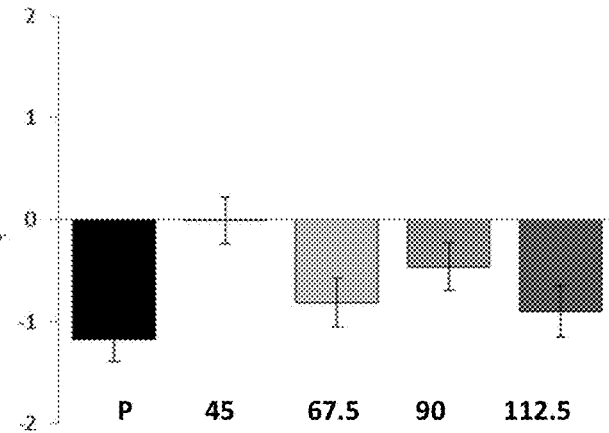

FIG. 21j: Change from baseline in UHDRS Total Functional Capacity Week 52 BL TFC≥7. The table below and FIG. 21j show slowing of functional decline as measured by UHDRS TFC in 45 mg bid and 90 mg bid pridopidine treated HD1 and HD2 patients, at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 8.9 | 9.2 | 9.4 | 9.1 | 9.3 |
| Wk 52 Δ to placebo |  | 1.16 | 0.36 | 0.71 | 0.27 |
| p value |  | 0.0003 | 0.2704 | 0.0239 | 0.4144 |

Figure 21K:
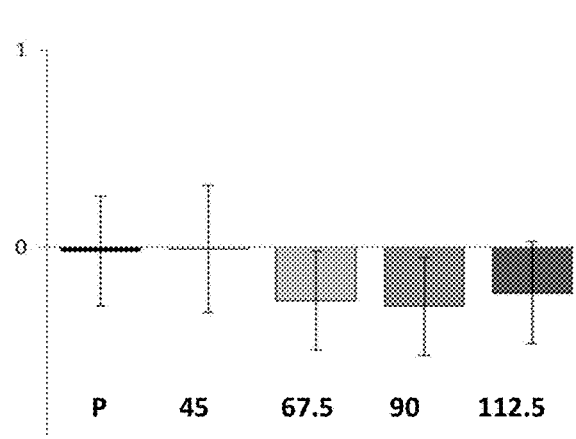

FIG. 21k: Change from baseline in UHDRS TFC Finance ADL Week 52 BL TFC<7. The table below and FIG. 21k show no significant improvement in the UHDRS TFC finance ADL in late stage pridopidine treated patients, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 2 | 2 | 1.9 | 2.2 | 2.3 |
| Δ to placebo |  | 0.01 | −0.25 | −0.29 | −0.22 |
| p value |  | 0.9863 | 0.497 | 0.4368 | 0.5626 |

Figure 21L:
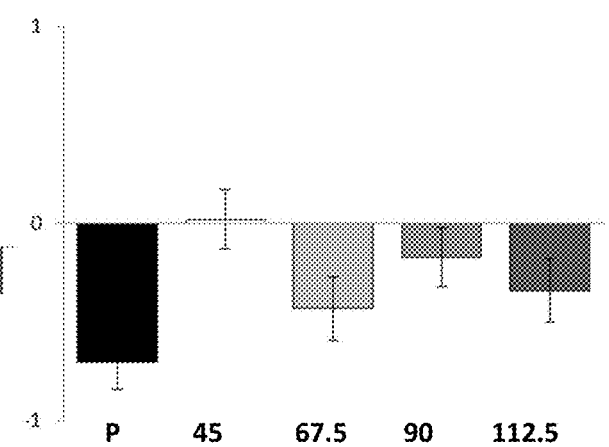

FIG. 21l: Change from baseline in UHDRS TFC Finance ADL week 52 BL TFC≥7. The table below and FIG. 21l show statistically significant improvement in the UHDRS TFC finance ADL in 45 mg bid and 90 mg bid pridopidine treated HD1 and HD2 patients, at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 4.6 | 4.7 | 4.9 | 4.8 | 4.7 |
| Δ to placebo |  | 0.72 | 0.27 | 0.53 | 0.36 |
| p value |  | 0.0004 | 0.1926 | 0.0088 | 0.0841 |

Figure 21M:
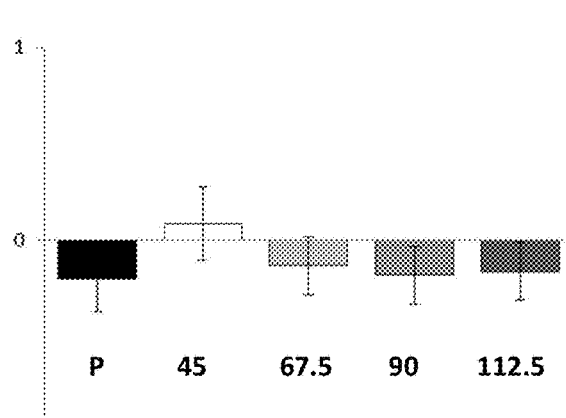

FIG. 21m: Change from baseline in UHDRS TFC Finances Week 52 BL TFC<7. The table below and FIG. 21m show no significant improvement in the UHDRS TFC finances in pridopidine treated late stage patients, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 0.5 | 0.5 | 0.5 | 0.7 | 0.7 |
| Δ to placebo |  | 0.29 | 0.07 | 0.02 | 0.04 |
| p value |  | 0.2468 | 0.7631 | 0.9318 | 0.8543 |

Figure 21N:
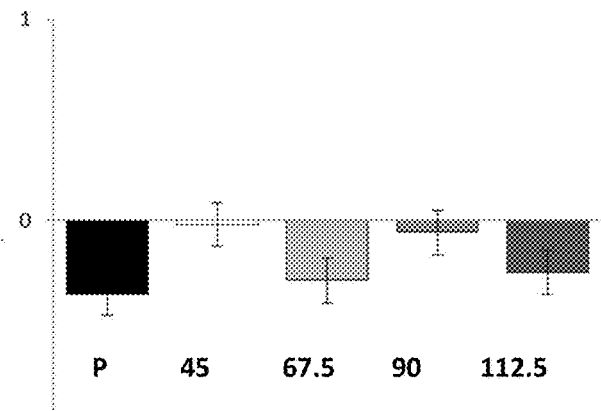

FIG. 21n: Change from baseline in UHDRS TFC Finances Week 52 BL TFC≥7. The table below and FIG. 21n show statistically significant improvement in the UHDRS IS in 45 mg bid and 90 mg bid pridopidine treated HD1 and HD2 patients, at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2 | 2.2 | 2.2 | 2.1 | 2.2 |
| Δ to placebo |  | 0.35 | 0.07 | 0.31 | 0.12 |
| p value |  | 0.0171 | 0.6373 | 0.0332 | 0.4466 |

Figure 21O:
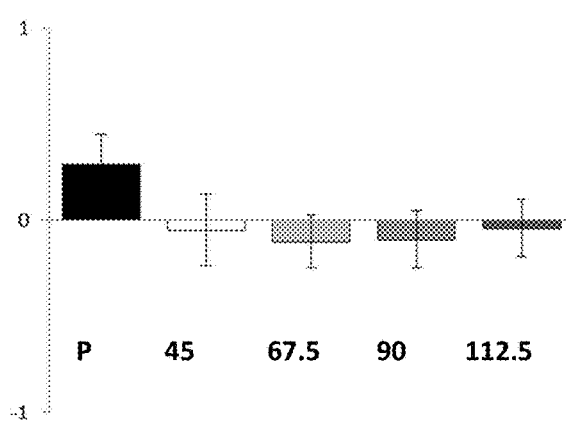

FIG. 21o: Change from baseline in UHDRS TFC ADL Week 52 BL TFC<7. The table below and FIG. 21o show no significant improvement in the UHDRS TFC ADL in pridopidine treated late stage patients, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 1.5 | 1.5 | 1.4 | 1.5 | 1.7 |
| Δ to placebo |  | −0.33 | −0.4 | −0.39 | −0.32 |
| p value |  | 0.178 | 0.0671 | 0.073 | 0.1393 |

Figure 21P:
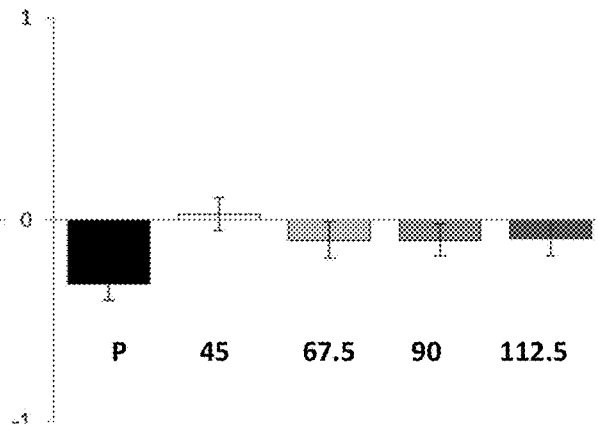

FIG. 21p: Change from baseline in UHDRS TFC ADL Week 52 BL TFC≥7. The table below and FIG. 21p show statistically significant improvement in the UHDRS TFC ADL in 45 mg bid pridopidine treated HD1 and HD2 patients, at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2.6 | 2.6 | 2.6 | 2.6 | 2.6 |
| Wk 52 Δ to placebo |  | 0.35 | 0.22 | 0.21 | 0.23 |
| p value |  | 0.0019 | 0.0598 | 0.0545 | 0.0493 |

Figure 22A:
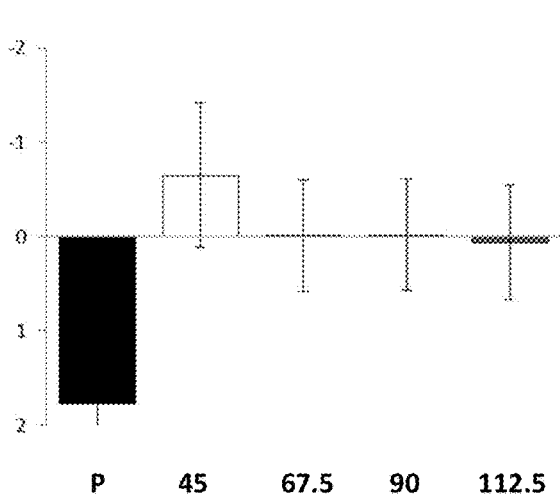

FIG. 22a: Change from baseline in PBA Irritability, Severity×Frequency Week 52 BL TFC<7. The table below and FIG. 22a show statistically significant improvement in PBA Irritability in pridopidine treated late stage patients, at 52 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 1.3 | 0.9 | 0.9 | 1.3 | 1.6 |
| Δ to placebo |  | −2.42 | −1.78 | −1.79 | −1.71 |
| p value |  | 0.0165 | 0.0429 | 0.0422 | 0.0542 |

Figure 22B:
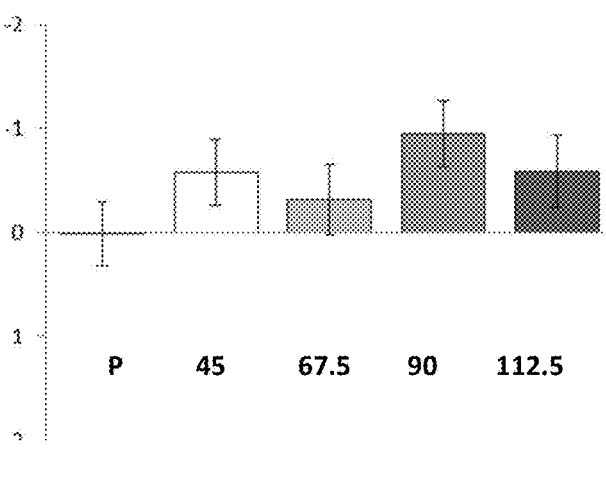

FIG. 22b: Change from baseline in PBA Irritability, Severity×Frequency Week 52 BL TFC≥7. The table below and FIG. 22b show statistically significant improvement in the PBA Irritability in 90 mg bid pridopidine treated HD1 and HD2 patients, at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2.1 | 1.8 | 2.1 | 1.4 | 1.4 |
| Wk 52 Δ to placebo |  | −0.59 | −0.33 | −0.95 | −0.6 |
| p value |  | 0.1789 | 0.466 | 0.0311 | 0.1927 |

Figure 23A:
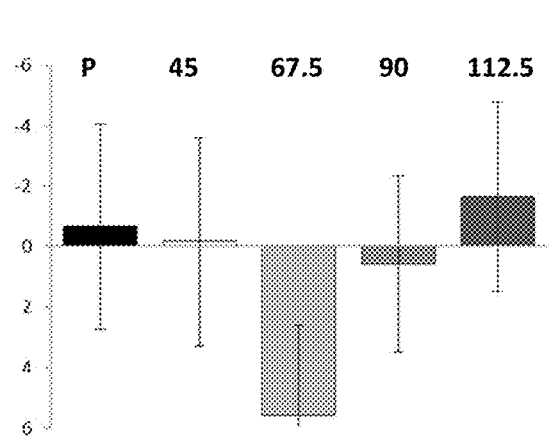

FIG. 23a: Change from baseline in Timed Up and Go Test (sec) Week 26 BL TFC<7. The table below and FIG. 23a show no significant improvement in Timed up and go test in pridopidine treated late stage patients, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 18.9 | 13.8 | 11.9 | 11.5 | 16.2 |
| Δ to placebo |  | 0.5 | 6.24 | 1.23 | −0.99 |
| p value |  | 0.9181 | 0.1715 | 0.7846 | 0.8295 |

Figure 23B:
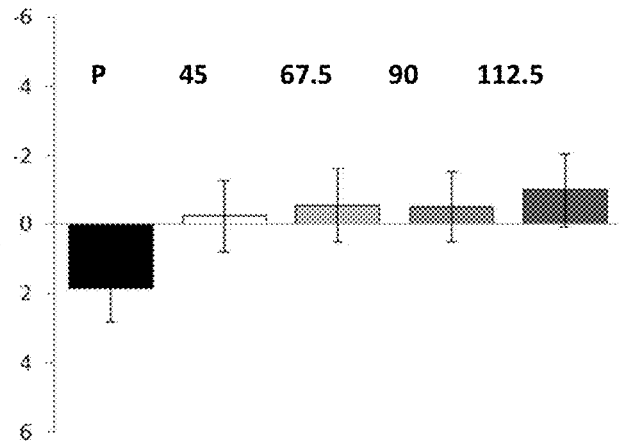

FIG. 23b: Change from baseline in Timed Up and Go Test (sec) Week 26 BL TFC≥7. The table below and FIG. 23b show statistically significant improvement in the PBA Irritability in 112.5 mg bid pridopidine treated HD1 and HD2 patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 10 | 11.7 | 9.7 | 9.8 | 9.8 |
| Δ to placebo |  | −2.09 | −2.41 | −2.37 | −2.84 |
| p value |  | 0.1397 | 0.0933 | 0.0896 | 0.0478 |

Figure 24A:
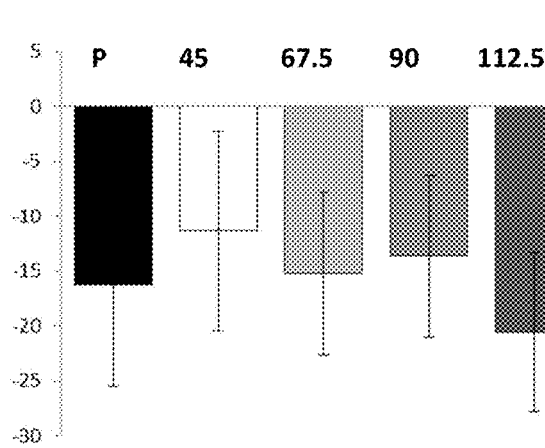

FIG. 24a: Change from baseline in HD-QoL Participant Total Score Week 26 BL TFC<7. The table below and FIG. 24a show no significant improvement in HD-QoL TS in pridopidine treated late stage patients, at 26 weeks.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 94.7 | 113.1 | 86.3 | 83 | 79.5 |
| Δ to placebo |  | 4.87 | 1 | 2.61 | −4.33 |
| p value |  | 0.6958 | 0.9304 | 0.817 | 0.7016 |

Figure 24B:
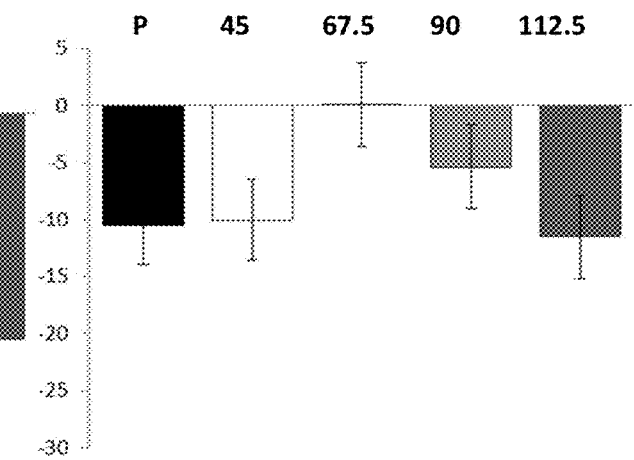

FIG. 24b: Change from baseline in HD-QoL Participant Total Score Week 26 BL TFC≥7. The table below and FIG. 24b show statistically significant improvement in the PBA Irritability in 67.5 mg bid pridopidine treated HD1 and HD2 patients, at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 61.2 | 55.1 | 73.5 | 68.8 | 67.3 |
| Δ to placebo |  | 0.51 | 10.63 | 5.17 | −0.99 |
| p value |  | 0.9144 | 0.0284 | 0.2834 | 0.8365 |

FIGS. 25a-25e show bar graphs of changes in UHDRS TMS Finger Tap scores in 26 and 52 week patient groups.

Figure 25A:
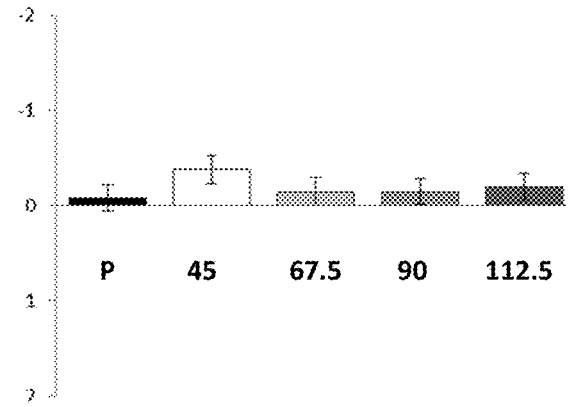

FIG. 25a: Change from Baseline in UHDRS TMS Finger Taps ALL Week 26. The table below provides P-Values corresponding to FIG. 25a. The table below and FIG. 25a show no significant improvement in the UHDRS TMS finger taps in all pridopidine treated patients, at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.8 | 3.5 | 4.1 | 3.7 | 3.9 |
| Δ to placebo |  | −0.3 | −0.07 | −0.07 | −0.12 |
| p value |  | 0.1466 | 0.7306 | 0.7114 | 0.5475 |

Figure 25B:
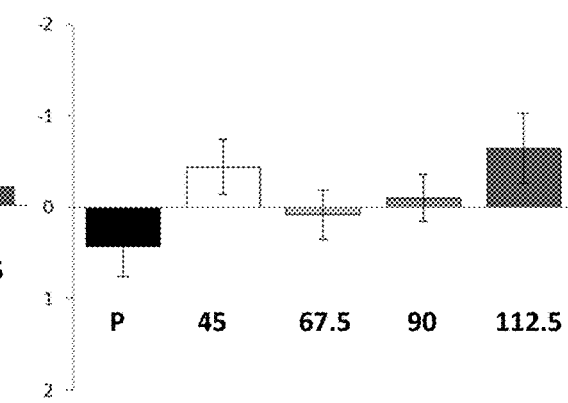

FIG. 25b: Change from Baseline in UHDRS TMS Finger Taps: Week 26 patients with baseline total functional capacity (BL TFC)≥9 and CAG Repeats >44. The table below provides the P-Values corresponding to FIG. 25b. The table below and FIG. 25b show statistically significant improvement in the UHDRS TMS finger taps in 45 mg bid and 112.5 mg bid pridopidine treated patients having BL TFC greater than or equal to 9 and greater than 44 CAG repeats in their htt gene, at 26 weeks.

|  | Placebo | 45 mg bid | 67.5 mg bid | 90 mg bid | 112.5 mg bid |
|---|---|---|---|---|---|
| N | 13 | 15 | 19 | 22 | 11 |
| Baseline | 2.6 | 2.7 | 3.3 | 3 | 3.6 |
| Δ to placebo |  | −0.86 | −0.34 | −0.52 | −1.07 |
| p value |  | 0.0499 | 0.4255 | 0.1972 | 0.0424 |

Figure 25C:
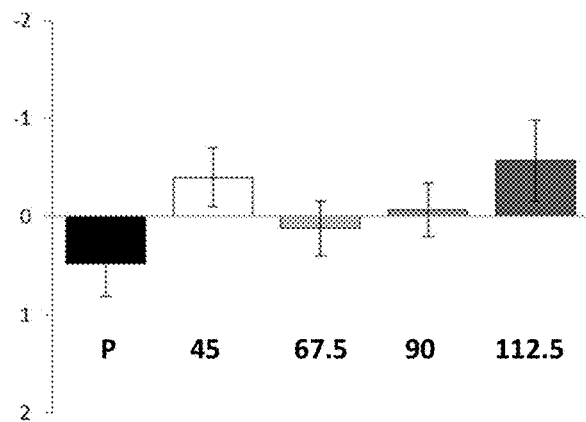

FIG. 25c: Change from baseline in UHDRS TMS Finger Taps: Week 26 patients with BL TFC≥9, CAG Repeats <44 and patients who represent three least severe TMS quarters (BL TMS 1st 3 Qs). The table below provides the P-Values corresponding to FIG. 25c. The table below and FIG. 25c show statistically significant improvement in the UHDRS TMS finger taps in 45 mg bid and 112.5 mg bid pridopidine treated patients having BL TFC greater than or equal to 9 and less than 44 CAG repeats in their htt gene, at 26 weeks.

|  | Placebo | 45 mg bid | 67.5 mg bid | 90 mg bid | 112.5 mg bid |
|---|---|---|---|---|---|
| N | 13 | 15 | 19 | 21 | 10 |
| Baseline | 2.6 | 2.7 | 3.3 | 3 | 3.5 |
| Δ to placebo |  | −0.87 | −0.36 | −0.54 | −1.05 |
| p value |  | 0.05 | 0.41 | 0.1888 | 0.0537 |

Figure 25D:
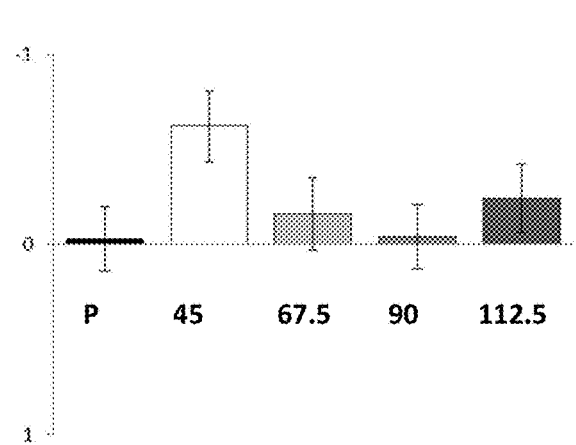

FIG. 25d: Change from baseline in UHDRS TMS Finger Taps: Patients who have completed 52 weeks of treatment: UHDRS TMS Finger Tap score at week 26. The table below provides the P-Values corresponding to FIG. 25d. The table below and FIG. 25d show statistically significant improvement in the UHDRS TMS finger taps in 45 mg bid pridopidine treated patients who completed 52 weeks, at 26 weeks.

|  | Placebo | 45 mg bid | 67.5 mg bid | 90 mg bid | 112.5 mg bid |
|---|---|---|---|---|---|
| N | 52 | 43 | 44 | 53 | 44 |
| Baseline | 3.8 | 3.2 | 4 | 3.5 | 3.8 |
| Δ to placebo |  | −0.59 | −0.13 | −0.01 | −0.21 |
| p value |  | 0.0182 | 0.5881 | 0.9554 | 0.3833 |

Figure 25E:
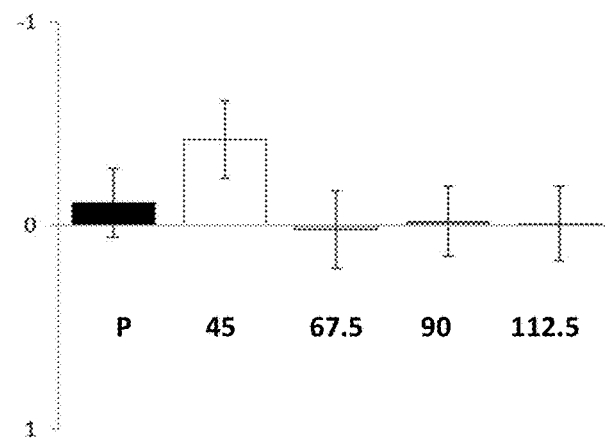

FIG. 25e: Change from baseline in UHDRS TMS Finger Taps: Patients who have completed 52 weeks of treatment: UHDRS TMS Finger Tap score at week 52. The table below provides the P-Values corresponding to FIG. 25e. The table below and FIG. 25e show no significant improvement in the UHDRS TMS finger taps in ALL pridopidine treated patients, at 52 weeks.

|  | Placebo | 45 mg bid | 67.5 mg bid | 90 mg bid | 112.5 mg bid |
|---|---|---|---|---|---|
| N | 52 | 43 | 44 | 53 | 44 |
| Baseline | 3.8 | 3.2 | 4 | 3.5 | 3.8 |
| Δ to placebo |  | −0.31 | 0.13 | 0.08 | 0.1 |
| p value |  | 0.2091 | 0.6027 | 0.7179 | 0.6835 |

Figure 26A:
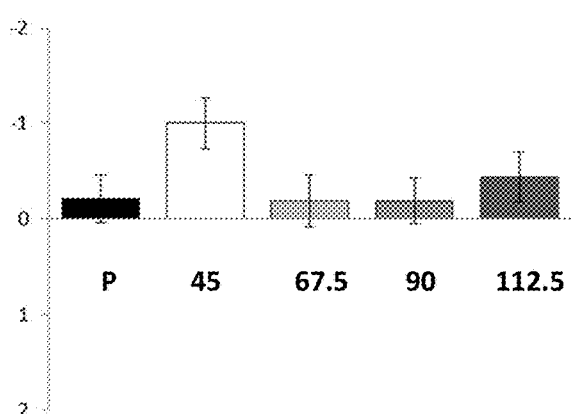

FIG. 26a: Change from baseline in UHDRS TMS Finger Tapping+Pronate-Supinate Hands: Patients who have completed 52 weeks of treatment—score at week 26. The table below provides the P-Values corresponding to FIG. 26a. The table below and FIG. 26a show statistically significant improvement in the UHDRS TMS finger taps and Pronate-Supinate Hands in 45 mg bid pridopidine treated patients who completed 52 weeks, at 26 weeks.

|  | Placebo | 45 mg bid | 67.5 mg bid | 90 mg bid | 112.5 mg bid |
|---|---|---|---|---|---|
| N | 52 | 43 | 44 | 53 | 44 |
| Baseline | 7.1 | 6.1 | 7 | 6.5 | 7 |
| Δ to placebo |  | −0.79 | 0.02 | 0.02 | −0.23 |
| p value |  | 0.0294 | 0.9443 | 0.9412 | 0.5268 |

Figure 26B:
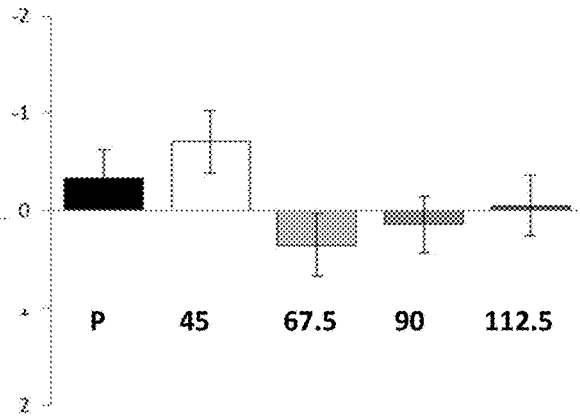

FIG. 26b: Change from baseline in UHDRS TMS Finger Tapping+Pronate-Supinate Hands: Patients who have completed 52 weeks of treatment—score at week 52. The table below provides the P-Values corresponding to FIG. 26b. The table below and FIG. 26b show no significant improvement in the UHDRS TMS finger taps and Pronate-Supinate Hands in pridopidine treated patients at 26 weeks.

|  | Placebo | 45 mg bid | 67.5 mg bid | 90 mg bid | 112.5 mg bid |
|---|---|---|---|---|---|
| N | 52 | 43 | 44 | 53 | 44 |
| Baseline | 7.1 | 6.1 | 7 | 6.5 | 7 |
| Δ to placebo |  | −0.37 | 0.68 | 0.48 | 0.28 |
| p value |  | 0.3801 | 0.1066 | 0.2337 | 0.4978 |

Figure 27A:
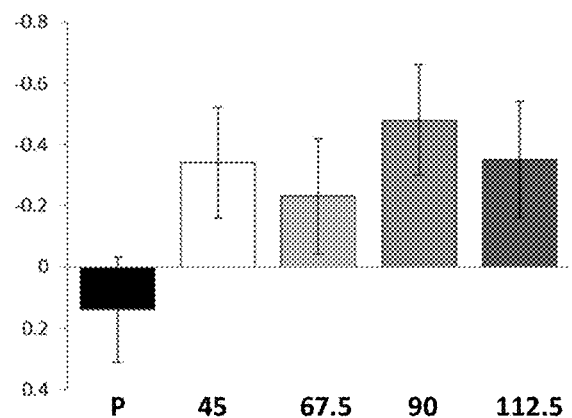

FIG. 27a: Change from baseline in UHDRS TMS Gait and Balance: Gait and balance scores at week 26 for patients with BL TFC≥7. The table below provides the P-Values corresponding to FIG. 27a. The table below and FIG. 27a show statistically significant improvement in the UHDRS TMS gait and balances in 90 mg bid pridopidine treated HD1 and HD2 patients at 26 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 3.2 | 3.7 | 3.4 | 3.5 | 3.1 |
| Δ to placebo |  | −0.48 | −0.37 | −0.62 | −0.49 |
| p value |  | 0.0563 | 0.1442 | 0.013 | 0.0518 |

Figure 27B:
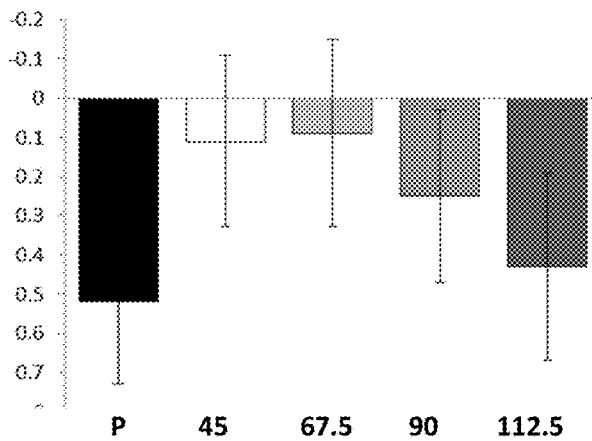

FIG. 27b: Change from baseline in UHDRS TMS Gait and Balance: Gait and balance scores at week 52 for patients with BL TFC≥7. The table below provides the P-Values corresponding to FIG. 27b. The table below and FIG. 27b show no significant improvement in the UHDRS TMS gait and balances in pridopidine treated HD1 and HD2 patients at 52 weeks.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 3.2 | 3.7 | 3.4 | 3.5 | 3.1 |
| Δ to placebo |  | −0.41 | −0.43 | −0.28 | −0.09 |
| p value |  | 0.1811 | 0.1691 | 0.365 | 0.7719 |

FIGS. 28a-28d provide bar graphs showing change from baseline in UHDRS TMS Dystonia scores in 26 and 52 week patient groups.

Figure 28A:
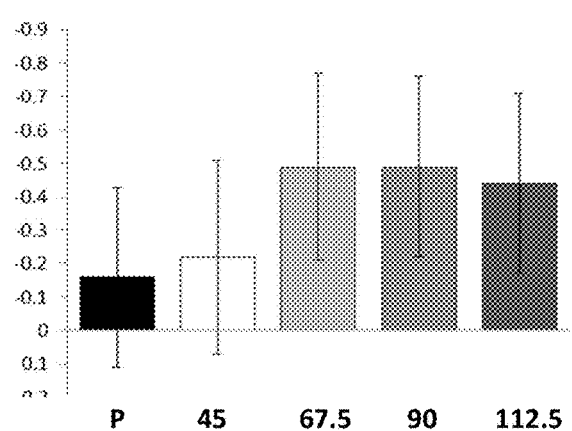

FIG. 28a: Change from baseline in UHDRS TMS Dystonia ALL: UHDRS TMS Dystonia scores at week 26 in all patients. The table below provides the P-Values corresponding to FIG. 28a. No significant improvement is observed.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 4.1 | 3.6 | 4.1 | 4.9 | 4.5 |
| Δ to placebo |  | −0.06 | −0.34 | −0.33 | −0.29 |
| p value |  | 0.8711 | 0.3778 | 0.3845 | 0.4507 |

Figure 28B:
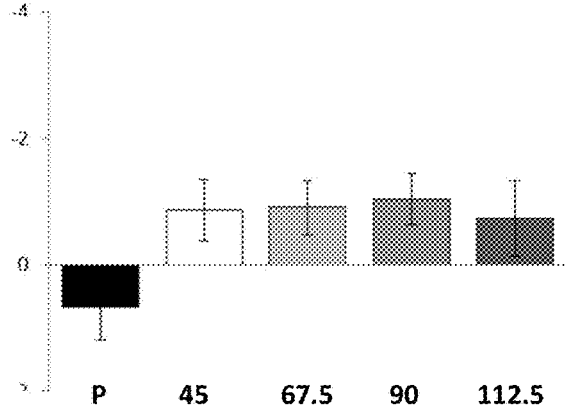

FIG. 28b: Change from baseline in UHDRS TMS Dystonia: UHDRS TMS Dystonia scores for patients with BL TFC≥9 AND CAG Repeats <44 at week 26. The table below provides the P-Values corresponding to FIG. 28b. Patients with baseline TFC greater than or equal to 9, show statistically significant improvement in the UHDRS TMS Dystonia score at 45 mg bid, 67.5 bid and 90 mg bid pridopidine for 26 weeks.

|  | Placebo | 45 mg bid | 67.5 mg bid | 90 mg bid | 112.5 mg bid |
|---|---|---|---|---|---|
| N | 13 | 15 | 19 | 22 | 11 |
| Baseline | 3.8 | 1.7 | 2.8 | 3.4 | 1.9 |
| Δ to placebo |  | −1.54 | −1.58 | −1.72 | −1.4 |
| p value |  | 0.0313 | 0.0191 | 0.0078 | 0.0847 |

Figure 28C:
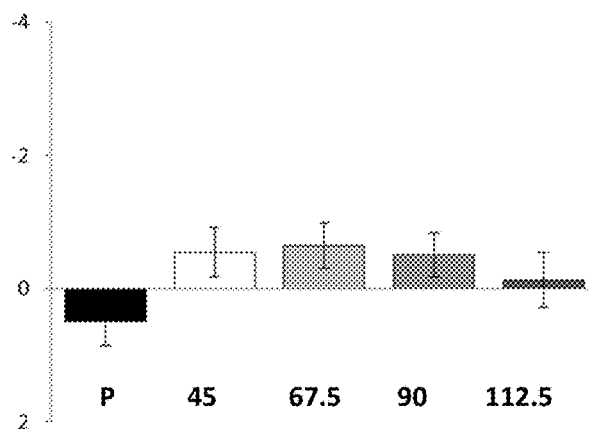

FIG. 28c: Change from baseline in UHDRS TMS Dystonia: UHDRS TMS Dystonia scores for patients with CAG Repeats <44 AND BL TMS 1st 3 Qs at week 26. The table below provides the P-Values corresponding to FIG. 28c. Patients with baseline TMS who represent three least severe TMS quarters and less than 44 CAG repeats in their htt gene, show statistically significant improvement in the UHDRS TMS Dystonia score at 45 mg bid, 67.5 bid and 90 mg bid pridopidine for 26 weeks.

|  | Placebo | 45 mg bid | 67.5 mg bid | 90 mg bid | 112.5 mg bid |
|---|---|---|---|---|---|
| N | 29 | 29 | 32 | 37 | 22 |
| Baseline | 3 | 2.6 | 2.6 | 2.9 | 2.6 |
| Δ to placebo |  | −1.04 | −1.15 | −1 | −0.62 |
| p value |  | 0.0437 | 0.0235 | 0.0399 | 0.2655 |

Figure 28D:
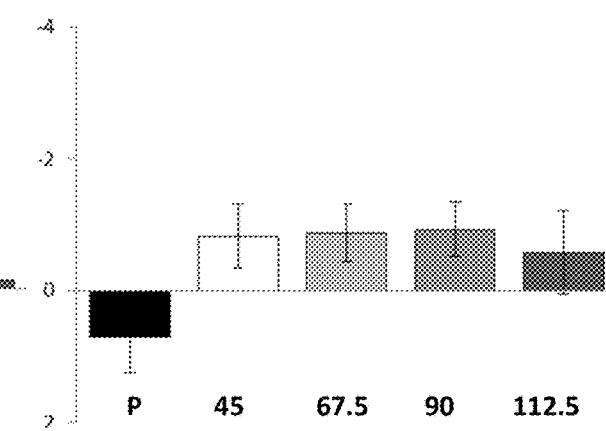

FIG. 28d: Change from baseline in UHDRS TMS Dystonia: UHDRS TMS Dystonia scores for patients with BL TFC≥9 and CAG Repeats <44 and BL TMS 1st 3 Qs at week 26. The table below provides the P-Values corresponding to FIG. 28d. Patients with baseline TFC greater than or equal to 9, baseline TMS representing three least severe TMS quarters and less than 44 CAG repeats in their htt gene, show statistically significant improvement in the UHDRS TMS Dystonia score at 45 mg bid 67.5 mg bid and 90 mg bid pridopidine for 26 weeks.

|  | Placebo | 45 mg bid | 67.5 mg bid | 90 mg bid | 112.5 mg bid |
|---|---|---|---|---|---|
| N | 13 | 15 | 19 | 21 | 10 |
| Baseline | 3.8 | 1.7 | 2.8 | 3.1 | 2.1 |
| Δ to placebo |  | −1.53 | −1.6 | −1.64 | −1.29 |
| p value |  | 0.0349 | 0.02 | 0.0132 | 0.1276 |

Figure 29A:
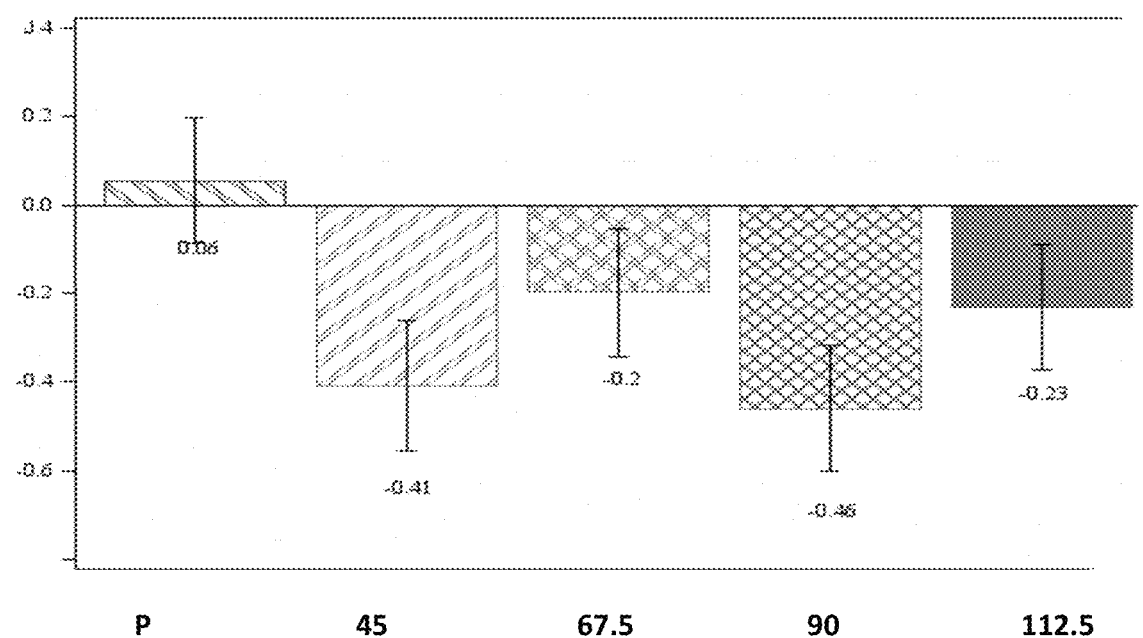
Figure 29B:
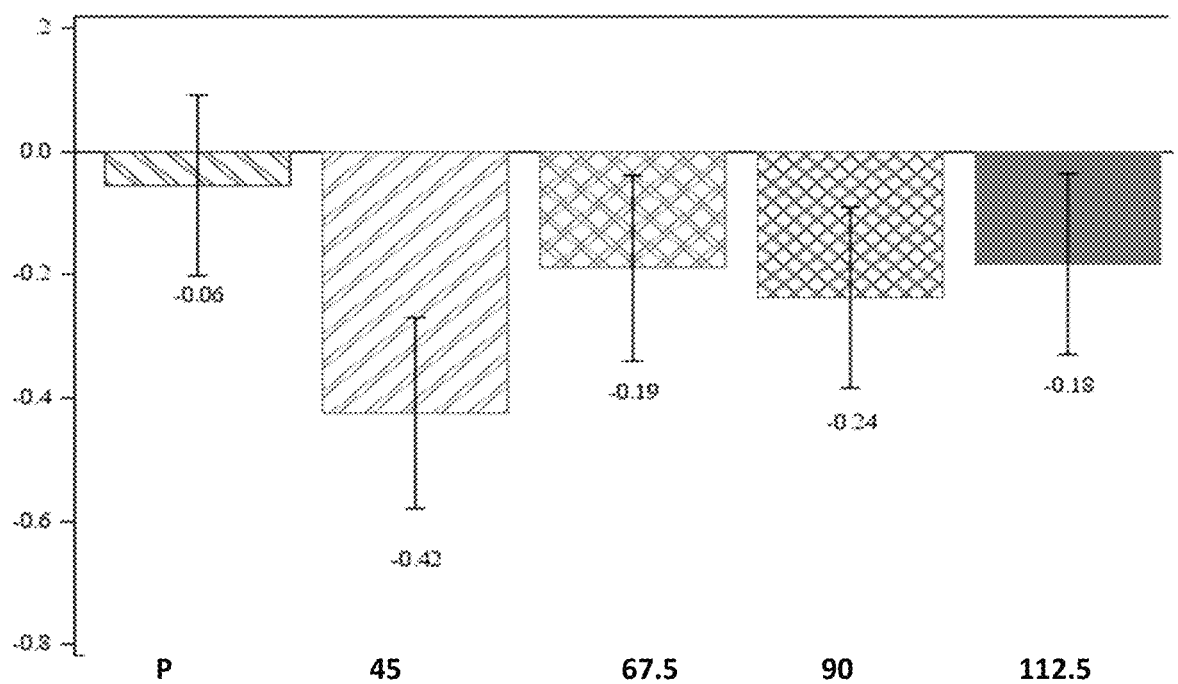
Figure 29C:
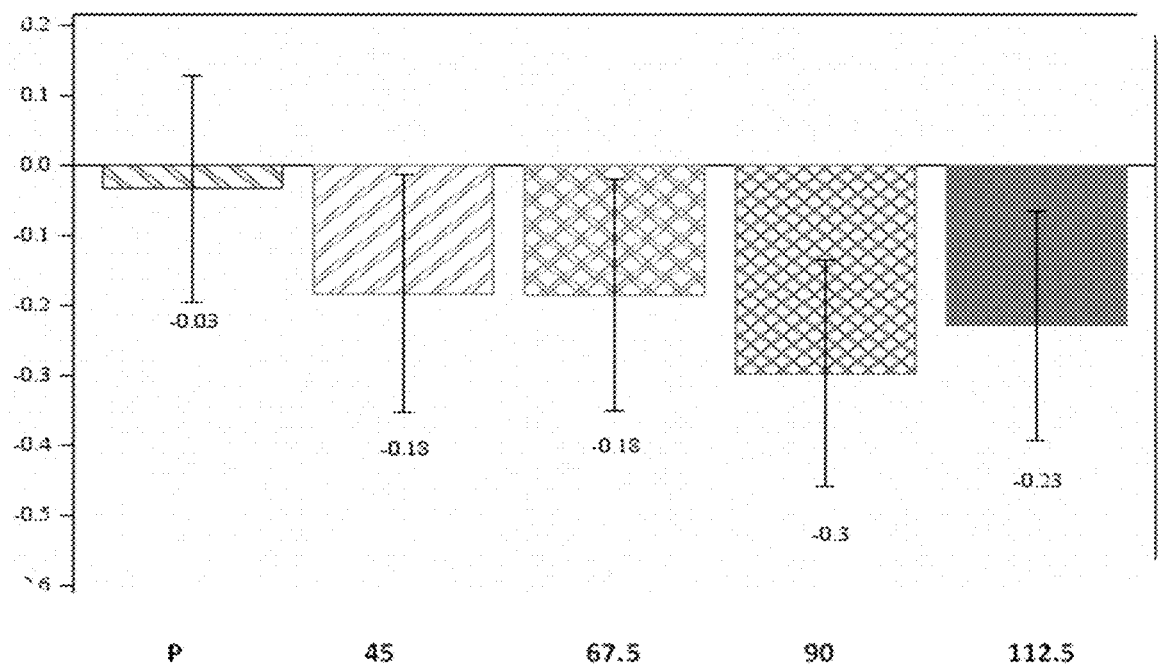

FIGS. 29a, 29b and 29c are bar graphs showing changes from baseline in Gait and Balance scores at week 12 (29a); week 20 (29b); and week 26 (29c). Y-axes are changes in UHDRS Gait and Balance score.

Figure 30:
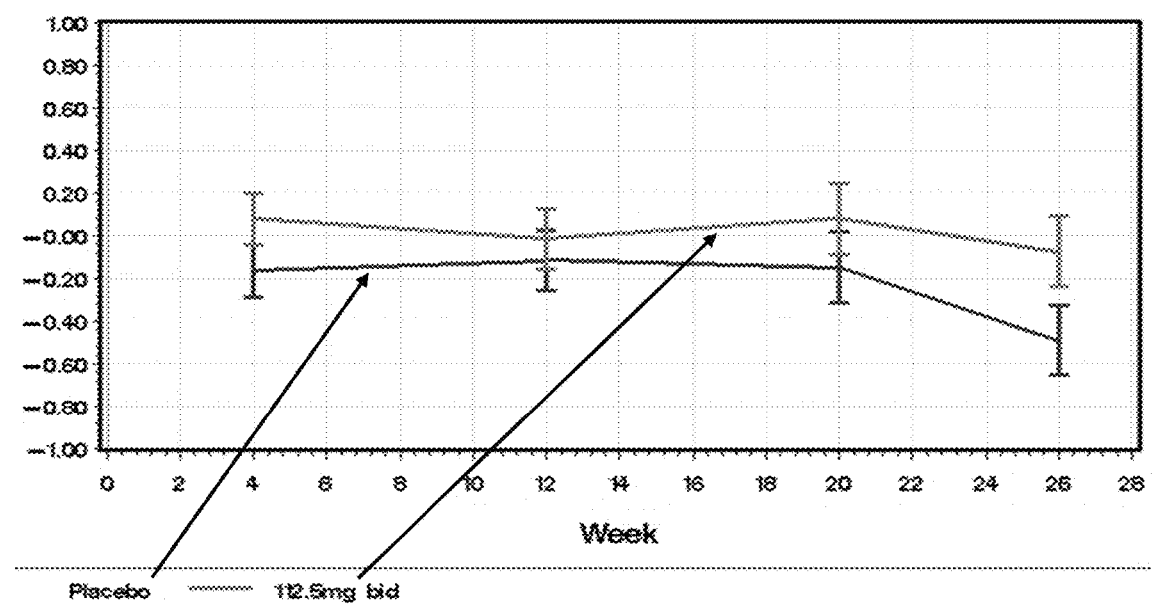

FIG. 30 is a graph showing changes from baseline in UHDRS TFC score over 26 weeks for treatment with pridopidine and placebo. The data for 112.5 mg pridopidine bid is shown by the top line in this graph and the data for the placebo is shown by the bottom line in this graph. Difference in p-value of 112.5 mg pridopidine bid from placebo was 0.1498 at week 4, 0.6065 at week 12, 0.3238 at week 20, and 0.0676 at week 26. Increase in Change in UHDRS TFC indicates delay/reduction in functional decline.

FIGS. 31a-31h provide bar graphs or line graphs showing changes from baseline of UHDRS TFC scores in 26 and 52 week patient groups.

Figure 31A:
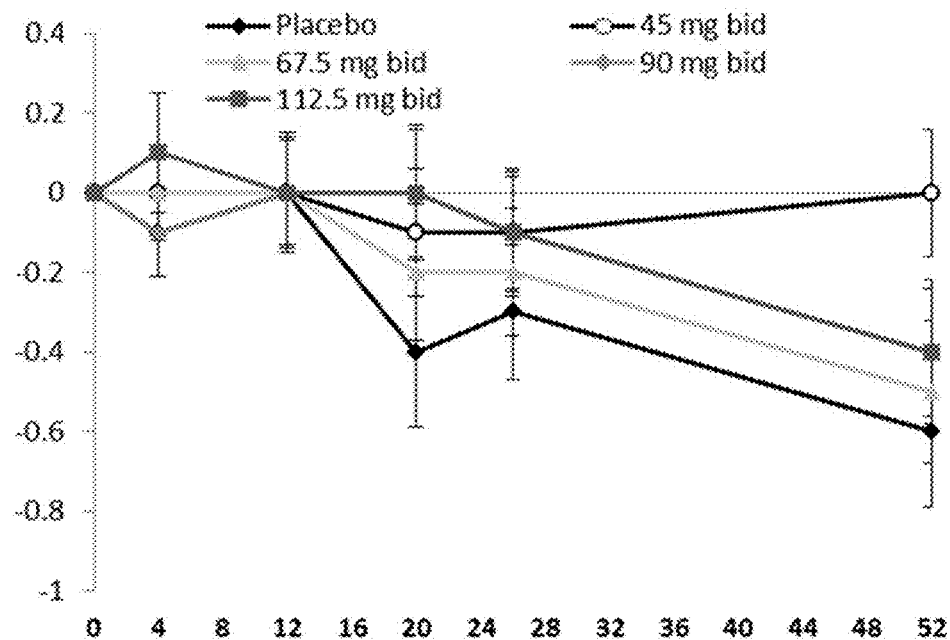
Figure 31B:
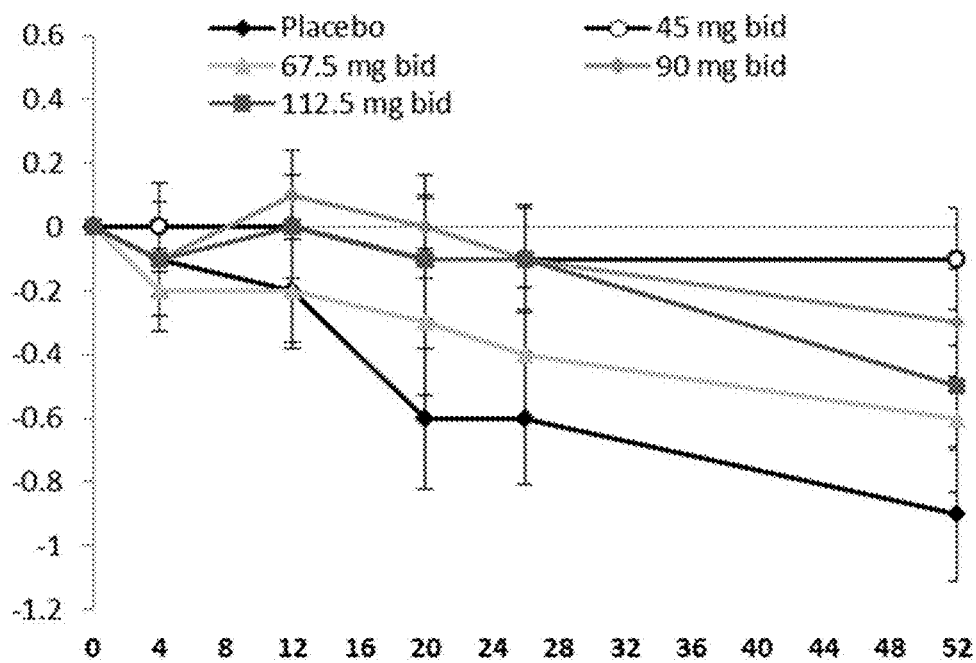

FIGS. 31a and 31b show change from baseline in UHDRS TFC score over time. Y axes represents change in TFC score, X axes represents pridopidine treatment time, in weeks. FIG. 31a shows the trend in full analysis set after 52 weeks. FIG. 31b shows trends in patients having BL TFC≥7 (n=54-62).

Figure 31C:
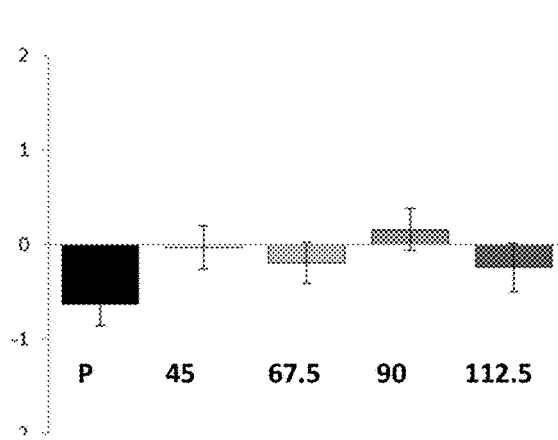

FIG. 31c: Change from baseline in UHDRS Total Functional Capacity for patients with BL CAG Repeats <44 at week 26. The table below provides the P-Values corresponding to FIG. 31c.

|  | Placebo | 45 mg bid | 67.5 mg bid | 90 mg bid | 112.5 mg bid |
|---|---|---|---|---|---|
| N | 37 | 37 | 38 | 42 | 29 |
| Baseline | 7.4 | 7.9 | 8.5 | 8.3 | 7.9 |
| Δ to placebo |  | 0.6 | 0.43 | 0.79 | 0.38 |
| p value |  | 0.056 | 0.1707 | 0.0102 | 0.2643 |

Figure 31D:
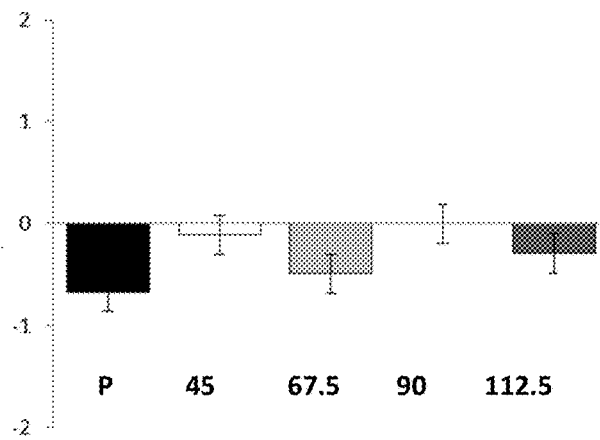

FIG. 31d: Change from baseline in UHDRS Total Functional Capacity for patients with BL TFC≥9 or CAG Repeats <44 at week 26. The table below provides the P-Values corresponding to FIG. 31d.

|  | Placebo | 45 mg bid | 67.5 mg bid | 90 mg bid | 112.5 mg bid |
|---|---|---|---|---|---|
| N | 56 | 56 | 53 | 52 | 49 |
| Baseline | 8.5 | 8.8 | 8.9 | 8.7 | 9.1 |
| Δ to placebo |  | 0.56 | 0.18 | 0.67 | 0.38 |
| p value |  | 0.0321 | 0.5069 | 0.0117 | 0.1665 |

Figure 31E:
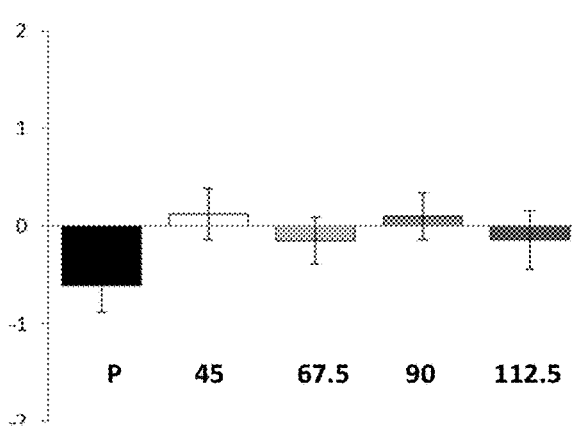

FIG. 31e: Change from baseline in UHDRS Total Functional Capacity for patients with BL CAG Repeats <44 AND BL TMS 1st 3 Qs at week 26. The table below provides the P-Values corresponding to FIG. 31e.

|          | Placebo | 45 mg bid | 67.5 mg bid | 90 mg bid | 112.5 mg bid |
|----------|---------|-----------|-------------|-----------|--------------|
| N        | 29      | 29        | 32          | 37        | 22           |
| Baseline | 8       | 8.7       | 9           | 8.6       | 8.6          |
| Δ to placebo |     | 0.73      | 0.47        | 0.71      | 0.48         |
| p value  |         | 0.0469    | 0.1952      | 0.0405    | 0.2324       |

Figure 31F:
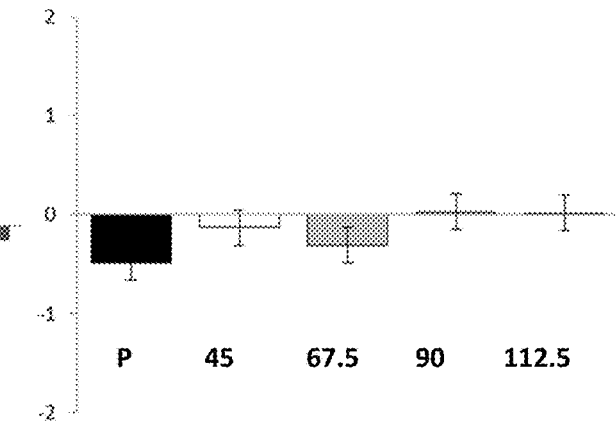

FIG. 31f: Change from baseline in UHDRS Total Functional Capacity for patients with BL CAG Repeats <44 OR BL TMS 1st 3 Qs at week 26 (baseline TMS in the first 3 quartiles). The table below provides the P-Values corresponding to FIG. 31f.

|          | Placebo | 45 mg bid | 67.5 mg bid | 90 mg bid | 112.5 mg bid |
|----------|---------|-----------|-------------|-----------|--------------|
| N        | 69      | 65        | 66          | 66        | 68           |
| Baseline | 8.1     | 8.4       | 8.3         | 8.3       | 8.5          |
| Δ to placebo |     | 0.36      | 0.18        | 0.52      | 0.51         |
| p value  |         | 0.1493    | 0.4727      | 0.0349    | 0.0379       |

Figure 31G:
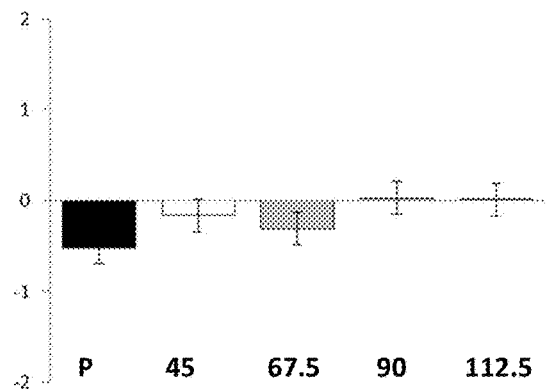

FIG. 31g: Change from baseline in UHDRS Total Functional Capacity for patients with Week 26 median BL TFC OR CAG Repeats <44 or BL TMS 1st 3 Qs at week 26. The table below provides the P-Values corresponding to FIG. 31g.

|          | Placebo | 45 mg bid | 67.5 mg bid | 90 mg bid | 112.5 mg bid |
|----------|---------|-----------|-------------|-----------|--------------|
| N        | 71      | 67        | 66          | 66        | 69           |
| Baseline | 8.2     | 8.5       | 8.3         | 8.3       | 8.5          |
| Δ to placebo |     | 0.36      | 0.21        | 0.55      | 0.53         |
| p value  |         | 0.1423    | 0.3863      | 0.0244    | 0.0289       |

Figure 31H:
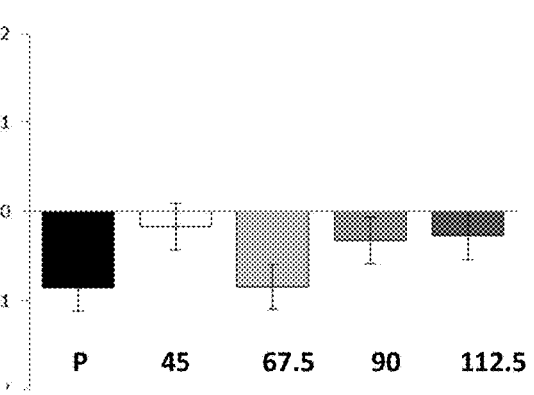

FIG. 31h: Change from baseline in UHDRS Total Functional Capacity for patients with BL TFC≥9 or BL TMS 1st 3 Qs at week 26. The table below provides the P-Values corresponding to FIG. 31h.

|          | Placebo | 45 mg bid | 67.5 mg bid | 90 mg bid | 112.5 mg bid |
|----------|---------|-----------|-------------|-----------|--------------|
| N        | 30      | 32        | 34          | 31        | 29           |
| Baseline | 10.3    | 10.5      | 10.4        | 10.3      | 10.9         |
| Δ to placebo |     | 0.69      | 0.01        | 0.54      | 0.6          |
| p value  |         | 0.0601    | 0.9741      | 0.1371    | 0.1136       |

Figure 32:
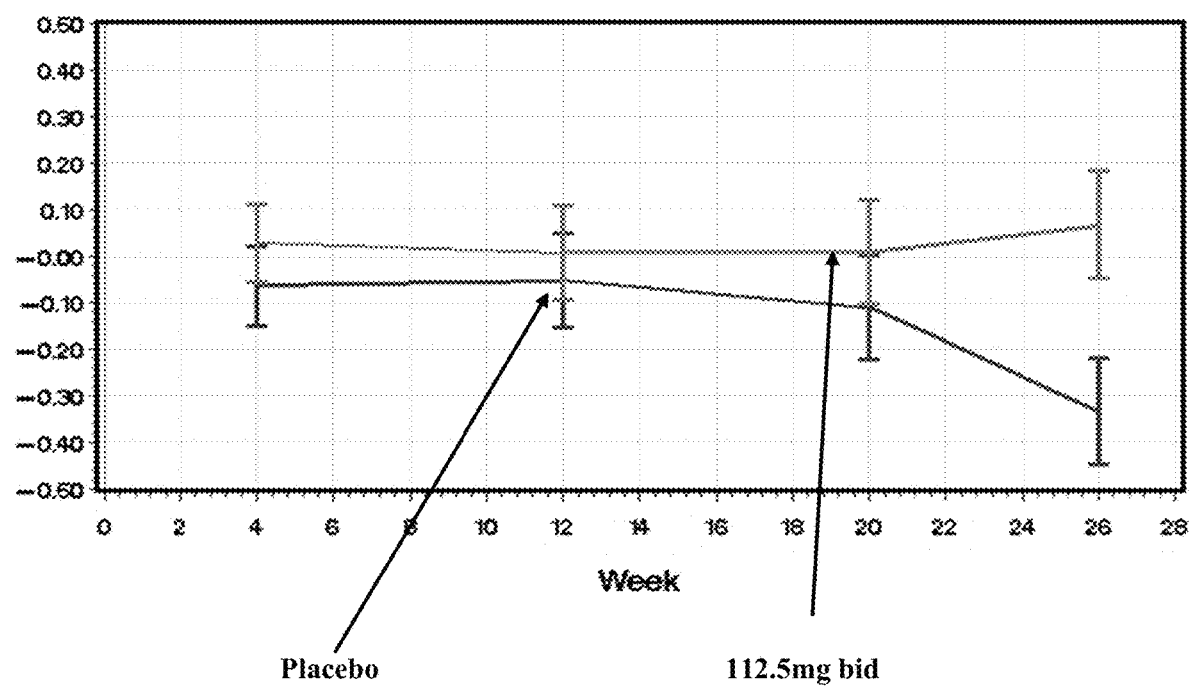

FIG. 32: A graph showing changes from baseline in Finances and ADL TFC scores over 26 weeks for treatment with pridopidine and placebo. The data for 112.5 mg pridopidine bid is shown by the top line in this graph and the data for the placebo is shown by the bottom line in this graph. Difference in p-value of 112.5 mg pridopidine bid from placebo was 0.4382 at week 4, 0.6636 at week 12, 0.4437 at week 20, and 0.0125 at week 26. An increase in Change in TFC Finance and ADL indicates a lessening in functional decline.

Figure 33A:
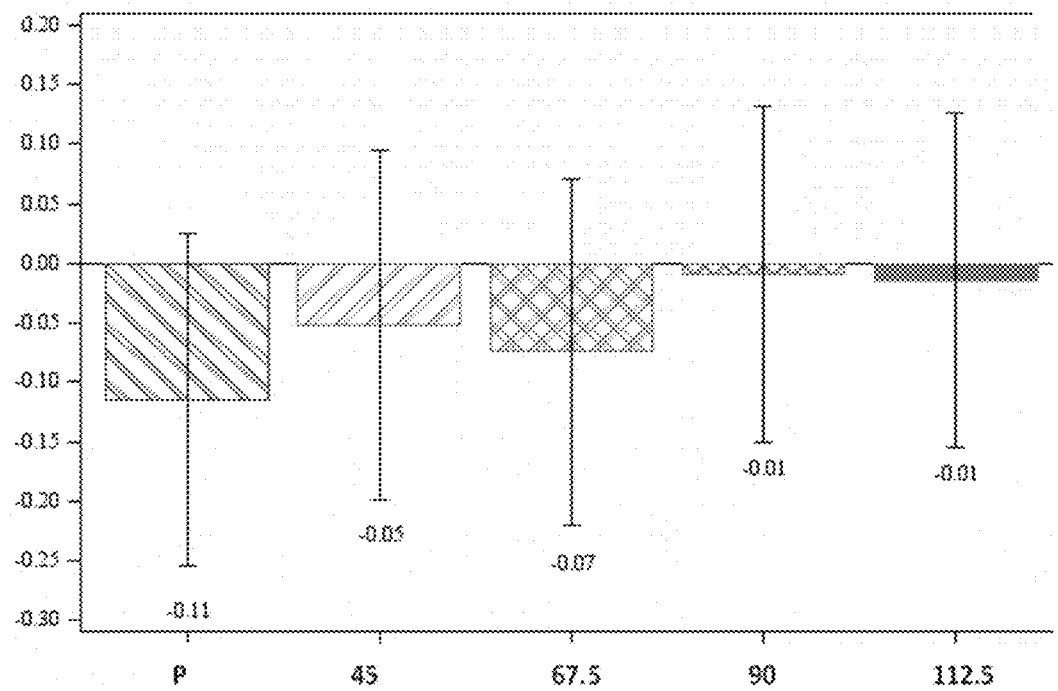
Figure 33B:
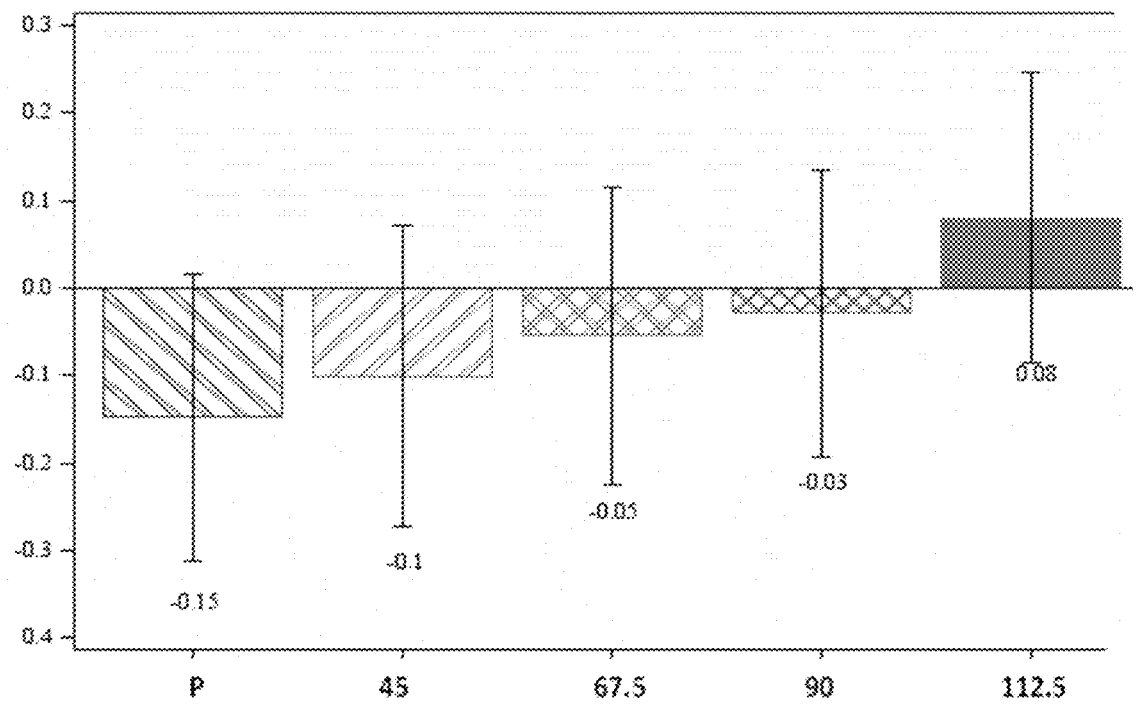
Figure 33C:
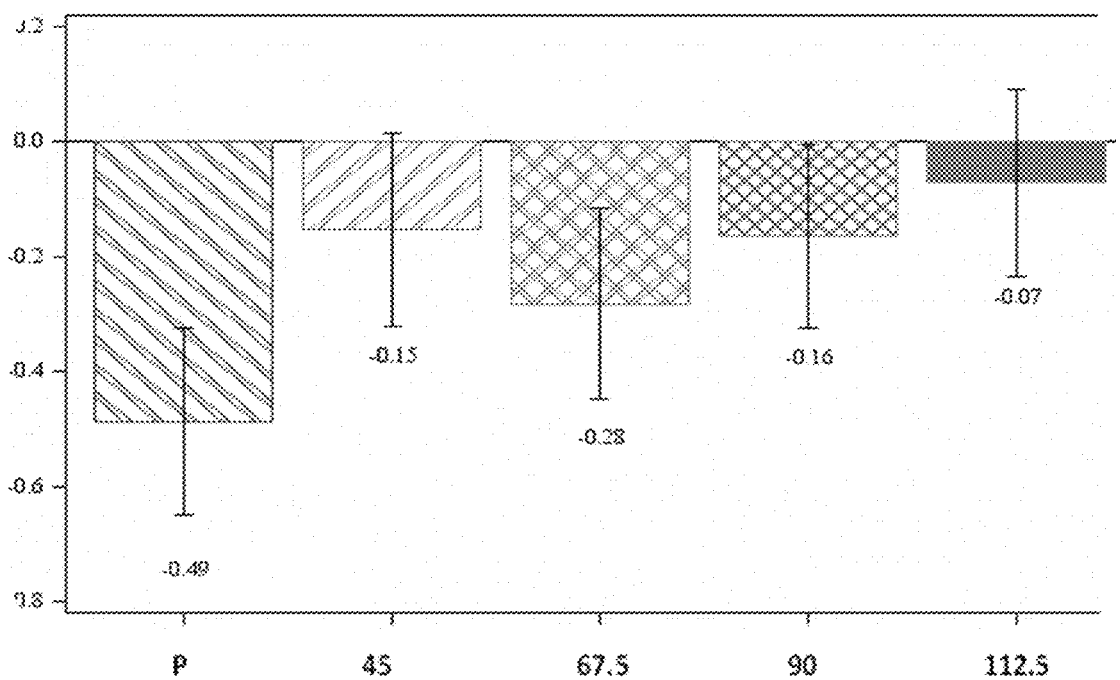

FIGS. 33a, 33b, and 33c: Change from baseline in TFC score in pridopidine treated HD patients. Doses at week 12 (FIG. 33a), week 20 (FIG. 33b) and week 26 (FIG. 33c). Score is adjusted means±SE of change in TFC for full analysis set.

Figure 34A:
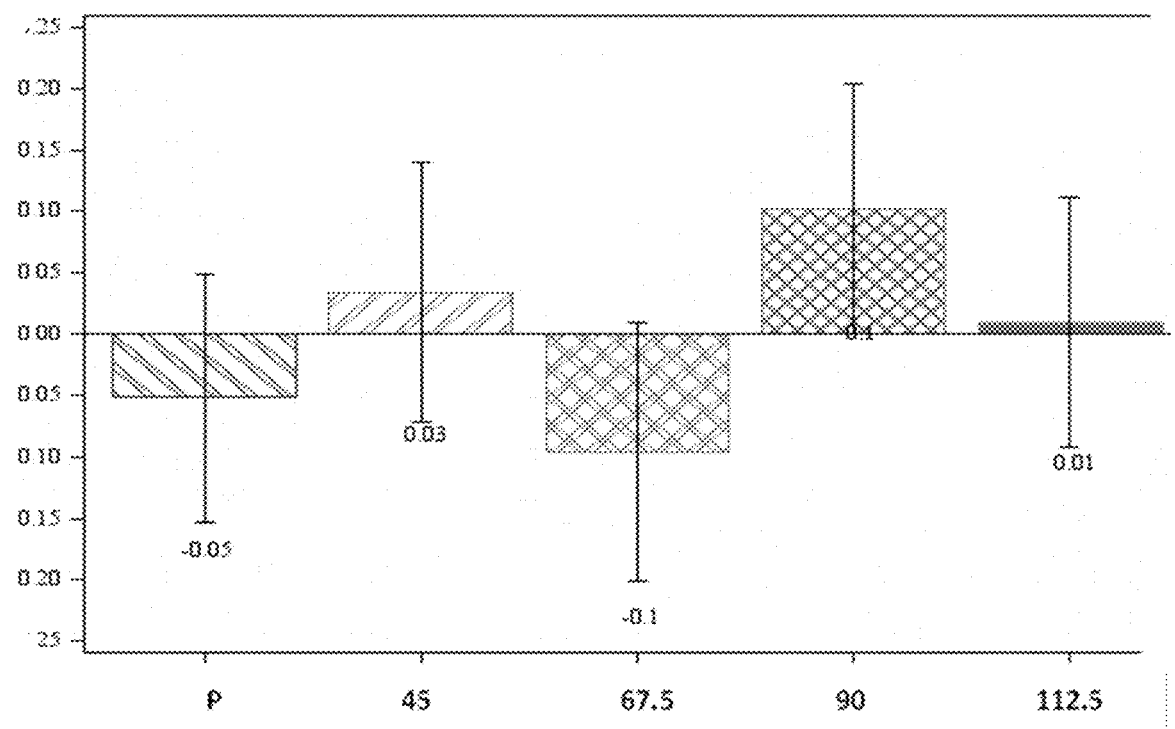
Figure 34B:
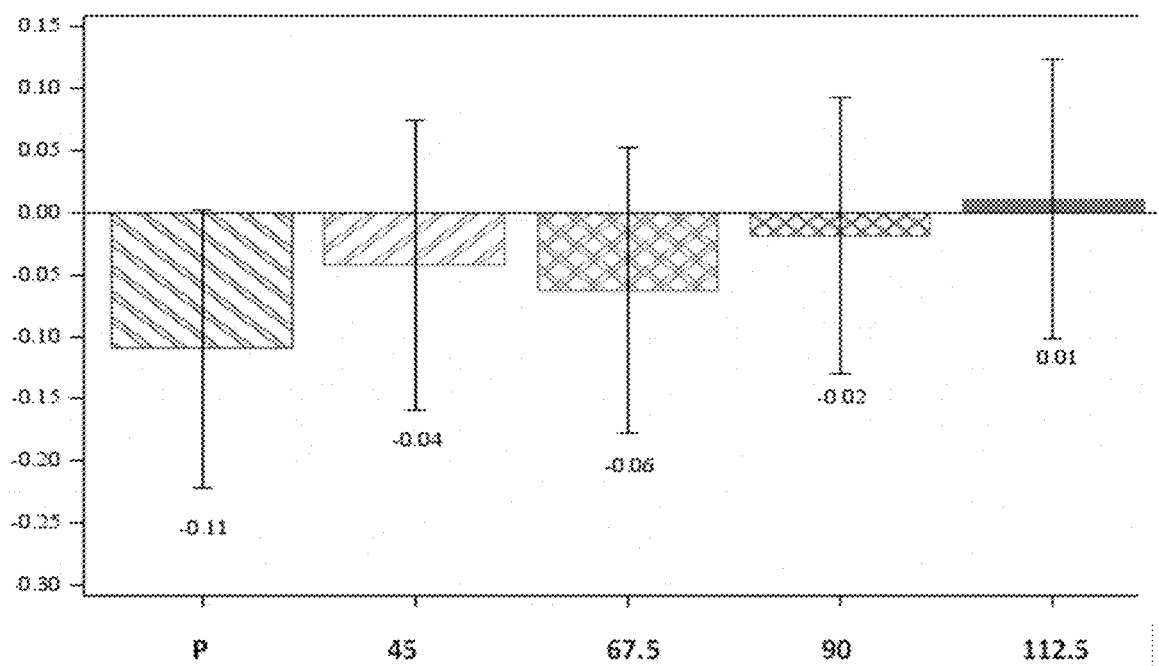

FIGS. 34a, 34b, and 34c: Change from baseline in TFC ADL & Finances score in pridopidine treated HD patients. Doses at week 12 (34a), week 20 (34b) and week 26 (34c). Score is adjusted means±SE of change in TFC Finance and ADL for full analysis set.

Figure 35C:
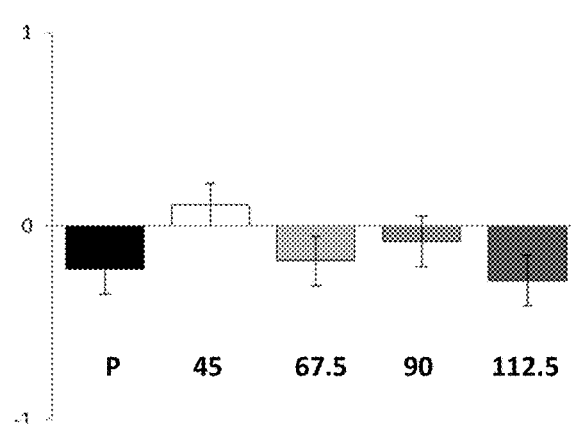
Figure 35D:
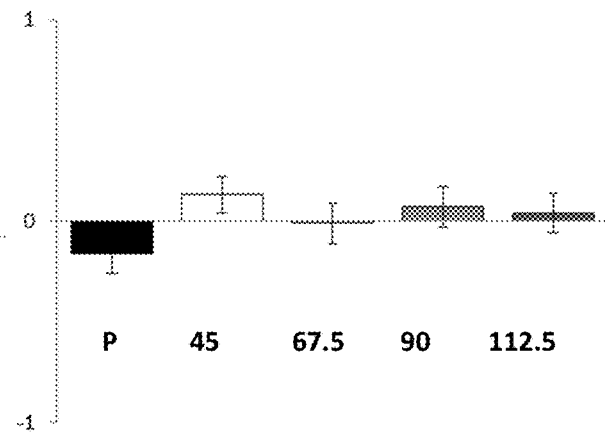
Figure 35E:
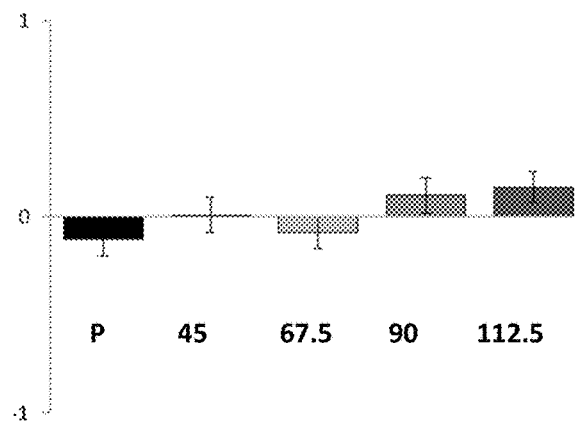
Figure 35F:
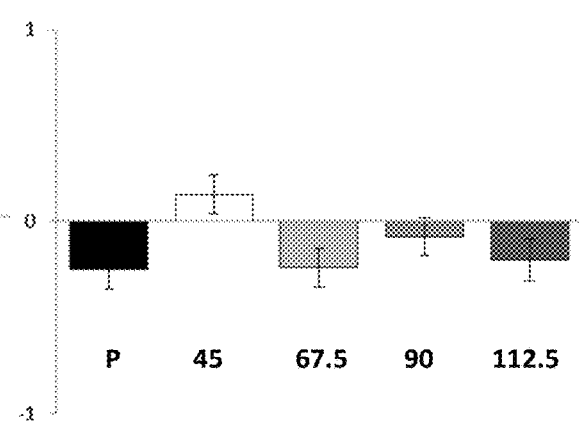
Figure 35G:
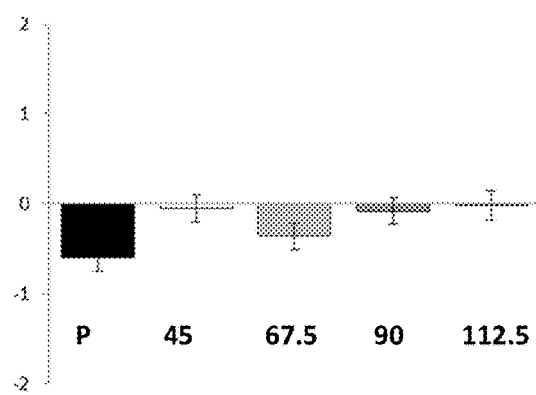
Figure 35H:
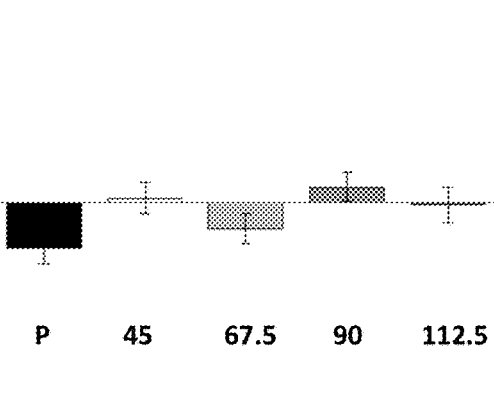
Figure 35I:
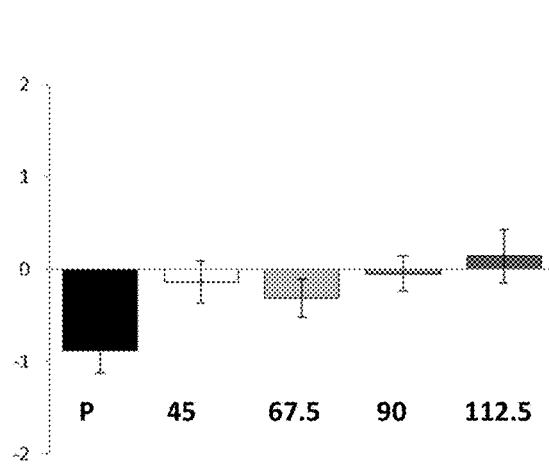
Figure 35J:
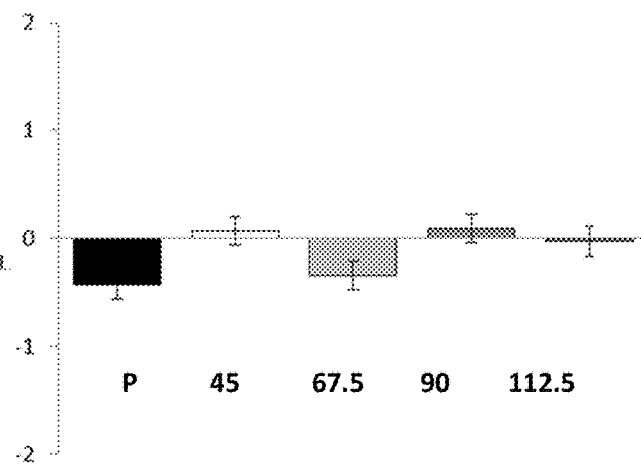
Figure 35K:
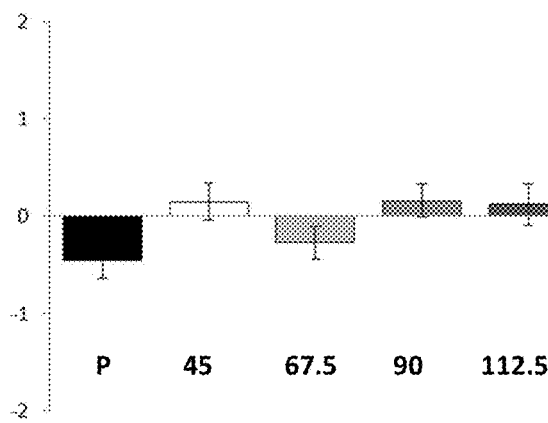
Figure 35L:
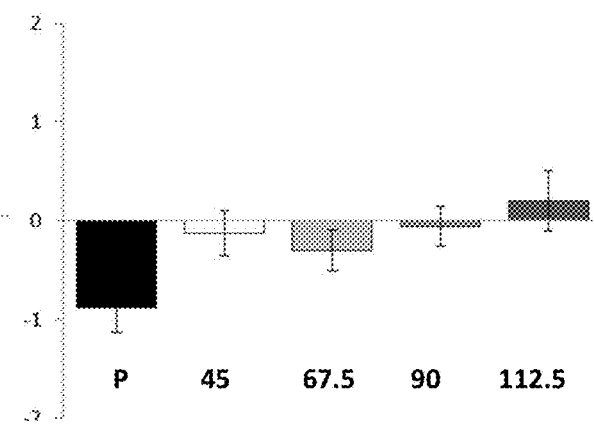
Figure 35M:
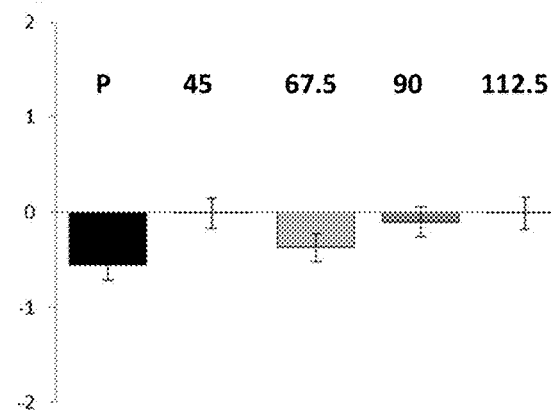
Figure 35N:
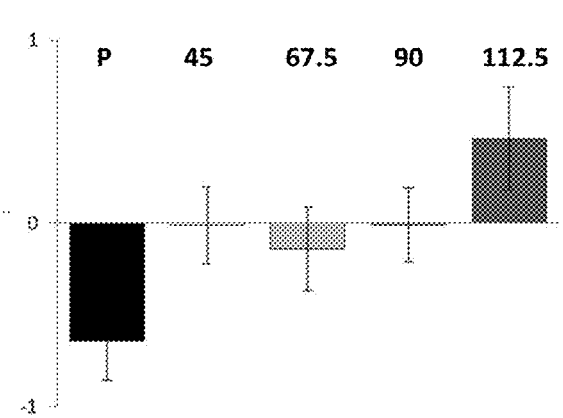
Figure 35O:
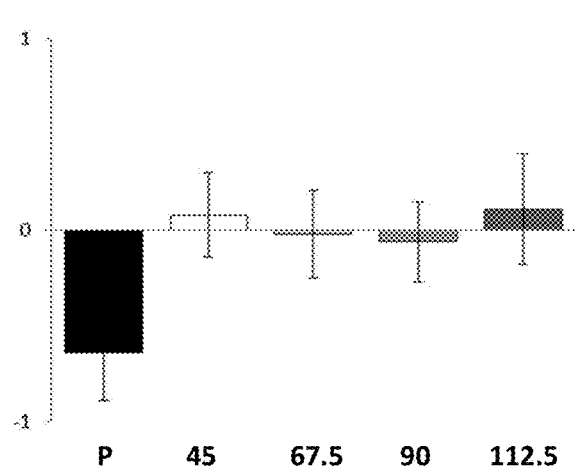
Figure 35P:
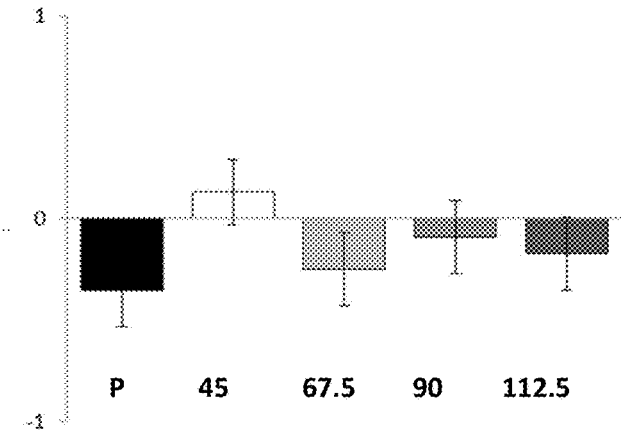
Figure 35Q:
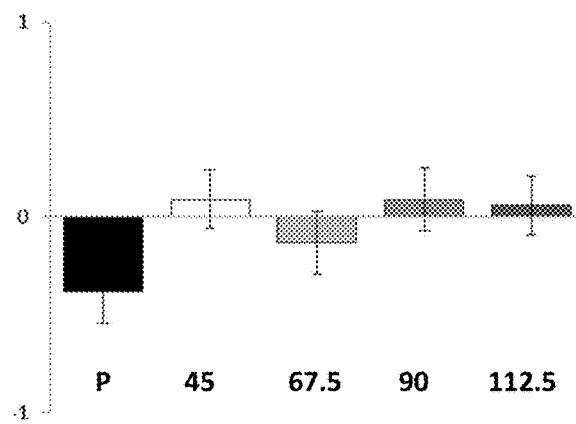
Figure 35R:
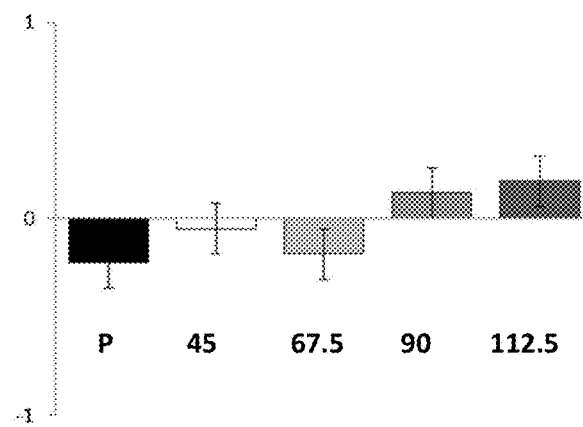
Figure 35S:
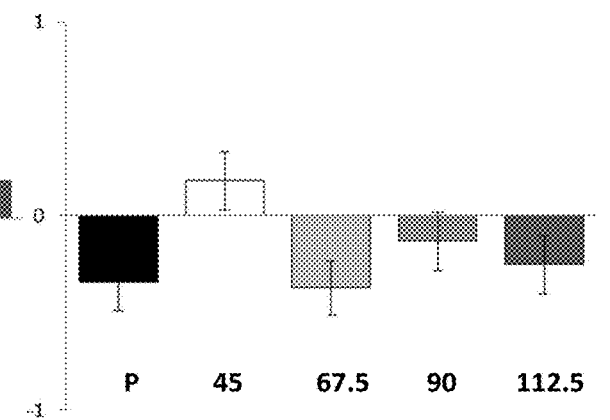

FIGS. 35a-35s are bar graphs showing changes from baseline of UHDRS TFC Finances and UHDRS TFC Finances and ADL scores in 26 and 52 week patient groups according to quartiles.

FIG. 35a: Change from baseline in UHDRS TFC Finances score for patients with TMS 1st Q (first least severe TMS quarter) at week 26. The table below provides the P-Values corresponding to FIG. 35a. Significant improvement in TFC finances in 45 mg bid pridopidine administered first least severe TMS quarter patients for 26 weeks.

|          | Placebo | 45 mg bid | 67.5 mg bid | 90 mg bid | 112.5 mg bid |
|----------|---------|-----------|-------------|-----------|--------------|
| N        | 21      | 24        | 20          | 25        | 15           |
| Baseline | 2.2     | 2.1       | 2.3         | 2.2       | 2.6          |
| Δ to placebo |     | 0.38      | 0.27        | 0.26      | 0.63         |
| p value  |         | 0.0347    | 0.1556      | 0.1336    | 0.0038       |

FIG. 35b: Change from baseline in UHDRS TFC Finances score for patients with TMS 1st Q at week 52. The table below provides the P-Values corresponding to FIG. 35b. Trend towards improvement in TFC finances was observed in 45 mg bid pridopidine administered first least severe TMS quarter patients for 52 weeks.

|          | Placebo | 45 mg bid | 67.5 mg bid | 90 mg bid | 112.5 mg bid |
|----------|---------|-----------|-------------|-----------|--------------|
| N        | 21      | 24        | 20          | 25        | 15           |
| Baseline | 2.2     | 2.1       | 2.3         | 2.2       | 2.6          |
| Δ to placebo |     | 0.43      | 0.25        | 0.21      | 0.32         |
| p value  |         | 0.0673    | 0.3084      | 0.3653    | 0.2369       |

FIG. 35c: Change from baseline in UHDRS TFC Finances score for patients with TMS 1st 2Qs (first two least severe TMS quarters) at week 26. The table below provides the P-Values corresponding to FIG. 35c. Trend towards improvement in TFC finances was observed in 45 mg bid pridopidine administered first two least severe TMS quarter patients for 26 weeks.

|          | Placebo | 45 mg bid | 67.5 mg bid | 90 mg bid | 112.5 mg bid |
|----------|---------|-----------|-------------|-----------|--------------|
| N        | 42      | 44        | 39          | 40        | 43           |
| Baseline | 2       | 2.1       | 2.2         | 2.1       | 2.1          |
| Δ to placebo |     | 0.33      | 0.04        | 0.14      | −0.06        |
| p value  |         | 0.0566    | 0.8406      | 0.4275    | 0.7529       |

FIG. 35d: Change from baseline in UHDRS TFC Finances score for patients with TMS 1st 2Qs at week 52. The table below provides the P-Values corresponding to FIG. 35d. Significant improvement in TFC finances was observed in 45 mg bid pridopidine administered first two least severe TMS quarters patients for 52 weeks.

|          | Placebo | 45 mg bid | 67.5 mg bid | 90 mg bid | 112.5 mg bid |
|----------|---------|-----------|-------------|-----------|--------------|
| N        | 42      | 44        | 39          | 40        | 43           |
| Baseline | 2       | 2.1       | 2.2         | 2.1       | 2.1          |

-continued

|  | Placebo | 45 mg bid | 67.5 mg bid | 90 mg bid | 112.5 mg bid |
|---|---|---|---|---|---|
| Δ to placebo |  | 0.29 | 0.15 | 0.23 | 0.2 |
| p value |  | 0.0299 | 0.2941 | 0.0994 | 0.1432 |

FIG. 35e: Change from baseline in UHDRS TFC Finances score for patients with TMS 1st 3Qs at week 26. The table below provides the P-Values corresponding to FIG. 35e. Trend towards improvement in TFC finances in 45 mg bid pridopidine administered first three least severe TMS quarter patients for 26 weeks.

|  | Placebo | 45 mg bid | 67.5 mg bid | 90 mg bid | 112.5 mg bid |
|---|---|---|---|---|---|
| N | 58 | 59 | 62 | 58 | 62 |
| Baseline | 1.8 | 2 | 1.9 | 1.9 | 2 |
| Δ to placebo |  | 0.12 | 0.03 | 0.22 | 0.26 |
| p value |  | 0.315 | 0.8115 | 0.0665 | 0.0323 |

FIG. 35f: Change from baseline in UHDRS TFC Finances score for patients with TMS 1st 3Qs at week 52. The table below provides the P-Values corresponding to FIG. 35f. Significant improvement in TFC finances was observed in 45 mg bid pridopidine administered first three least severe TMS quarter patients for 52 weeks.

|  | Placebo | 45 mg bid | 67.5 mg bid | 90 mg bid | 112.5 mg bid |
|---|---|---|---|---|---|
| N | 58 | 59 | 62 | 58 | 62 |
| Baseline | 1.8 | 2 | 1.9 | 1.9 | 2 |
| Δ to placebo |  | 0.39 | 0.01 | 0.17 | 0.05 |
| p value |  | 0.0072 | 0.97 | 0.2295 | 0.7396 |

FIG. 35g: Change from baseline in UHDRS TFC Finance and ADL score for patients with BL TFC≥9 at week 26. The table below provides the P-Values corresponding to FIG. 35g. Significant improvement in TFC finance and ADL was observed in 45 mg bid and 90 mg bid pridopidine administered patients having with baseline TFC greater than or equal to 9 for 26 weeks

|  | Placebo | 45 mg bid | 67.5 mg bid | 90 mg bid | 112.5 mg bid |
|---|---|---|---|---|---|
| N | 32 | 34 | 34 | 32 | 31 |
| Baseline | 5.2 | 5.1 | 5.4 | 5.4 | 5.4 |
| Δ to placebo |  | 0.53 | 0.23 | 0.51 | 0.57 |
| p value |  | 0.0143 | 0.2874 | 0.0197 | 0.0109 |

FIG. 35h: Change from baseline in UHDRS TFC Finance and ADL score for patients with BL CAG Repeat >44 at week 26. The table below provides the P-Values corresponding to FIG. 35h. Significant improvement in TFC finance and ADL was observed in 45 mg bid and 90 mg bid pridopidine administered patients having more than 44 CAG repeats in their htt gene, for 26 weeks.

|  | Placebo | 45 mg bid | 67.5 mg bid | 90 mg bid | 112.5 mg bid |
|---|---|---|---|---|---|
| N | 37 | 37 | 38 | 42 | 29 |
| Baseline | 3.7 | 4.1 | 4.2 | 4.2 | 4.1 |
| Δ to placebo |  | 0.55 | 0.21 | 0.67 | 0.47 |
| p value |  | 0.017 | 0.3497 | 0.0026 | 0.0597 |

FIG. 35i: Change from baseline in UHDRS TFC Finance and ADL score for patients with BL TFC≥9 and CAG Repeat >44 at week 26. The table below provides the P-Values corresponding to FIG. 35i. Significant improvement in TFC finance and ADL was observed in 45 mg bid and 90 mg bid pridopidine administered patients having baseline TFC greater than or equal to 9 and more than 44 CAG repeats in their htt gene, for 26 weeks.

|  | Placebo | 45 mg bid | 67.5 mg bid | 90 mg bid | 112.5 mg bid |
|---|---|---|---|---|---|
| N | 13 | 15 | 19 | 22 | 11 |
| Baseline | 5.1 | 5.2 | 5.5 | 5.4 | 5.5 |
| Δ to placebo |  | 0.74 | 0.57 | 0.83 | 1.02 |
| p value |  | 0.0296 | 0.083 | 0.0089 | 0.0094 |

FIG. 35j: Change from baseline in UHDRS TFC Finance and ADL score for patients with BL TFC≥9 or CAG Repeat >44 at week 26. The table below provides the P-Values corresponding to FIG. 35j Significant improvement in TFC finance and ADL was observed in 45 mg bid and 90 mg bid pridopidine administered patients having baseline TFC greater than or equal to 9 or more than 44 CAG repeats in their htt gene, for 26 weeks.

|  | Placebo | 45 mg bid | 67.5 mg bid | 90 mg bid | 112.5 mg bid |
|---|---|---|---|---|---|
| N | 56 | 56 | 53 | 52 | 49 |
| Baseline | 4.2 | 4.5 | 4.5 | 4.5 | 4.7 |
| Δ to placebo |  | 0.5 | 0.08 | 0.52 | 0.4 |
| p value |  | 0.0055 | 0.6381 | 0.0039 | 0.0317 |

FIG. 35k: Change from baseline in UHDRS TFC Finance and ADL score for patients with CAG Repeats <44 and BL TMS 1st 3 Qs at week 26. The table below provides the P-Values corresponding to FIG. 35k. Significant improvement in TFC finance and ADL was observed in 45 mg bid and 90 mg bid pridopidine administered patients having baseline TMS first 3 quarters and less than 44 CAG repeats in their htt gene, for 26 weeks.

|  | Placebo | 45 mg bid | 67.5 mg bid | 90 mg bid | 112.5 mg bid |
|---|---|---|---|---|---|
| N | 29 | 29 | 32 | 37 | 22 |
| Baseline | 4.1 | 4.6 | 4.5 | 4.4 | 4.6 |
| Δ to placebo |  | 0.59 | 0.18 | 0.6 | 0.57 |
| p value |  | 0.0236 | 0.4782 | 0.0145 | 0.0478 |

FIG. 35l: Change from baseline in UHDRS TFC Finance and ADL score for patients with BL TFC≥9 and CAG Repeats <44 and BL TMS 1st 3 Qs at week 26. The table below provides the P-Values corresponding to FIG. 35l. Significant improvement in TFC finance and ADL was observed in 45 mg bid and 90 mg bid pridopidine administered patients having baseline TFC greater than or equal to 9 and less than 44 CAG repeats in their htt gene, for 26 weeks.

|  | Placebo | 45 mg bid | 67.5 mg bid | 90 mg bid | 112.5 mg bid |
|---|---|---|---|---|---|
| N | 13 | 15 | 19 | 21 | 10 |
| Baseline | 5.1 | 5.2 | 5.5 | 5.3 | 5.5 |
| Δ to placebo |  | 0.74 | 0.57 | 0.81 | 1.08 |
| p value |  | 0.0315 | 0.0848 | 0.0118 | 0.009 |

FIG. 35m: Change from baseline in UHDRS TFC Finance and ADL score for patients with BL TFC≥9 and BL TMS 1st 3 Qs at week 26. The table below provides the P-Values corresponding to FIG. 35m. Significant improvement in TFC finance and ADL was observed in 45 mg bid and 90 mg bid pridopidine administered patients having baseline TFC greater than or equal to 9 or less than 44 CAG repeats in their htt gene or baseline TMS first three quarters, for 26 weeks.

|  | Placebo | 45 mg bid | 67.5 mg bid | 90 mg bid | 112.5 mg bid |
|---|---|---|---|---|---|
| N | 30 | 32 | 34 | 31 | 29 |
| Baseline | 5.1 | 5.1 | 5.4 | 5.4 | 5.5 |
| Δ to placebo |  | 0.53 | 0.18 | 0.45 | 0.54 |
| p value |  | 0.018 | 0.4039 | 0.0455 | 0.0193 |

FIG. 35n: Change from baseline in UHDRS TFC Finance and ADL score for patients with TMS 1st Q at week 26. The table below provides the P-Values corresponding to FIG. 35n. Significant improvement in TFC finance and ADL was observed in 45 mg bid and 90 mg bid pridopidine administered patients with TMS first three quarters, for 26 weeks.

|  | Placebo | 45 mg bid | 67.5 mg bid | 90 mg bid | 112.5 mg bid |
|---|---|---|---|---|---|
| N | 21 | 24 | 20 | 25 | 15 |
| Baseline | 4.9 | 4.8 | 5 | 4.8 | 5.3 |
| Δ to placebo |  | 0.63 | 0.5 | 0.63 | 1.1 |
| p value |  | 0.038 | 0.1136 | 0.0342 | 0.0024 |

FIG. 35o: Change from baseline in UHDRS TFC Finance and ADL score for patients with TMS 1st Q at week 52. The table below provides the P-Values corresponding to FIG. 35o. Significant improvement in TFC finance and ADL was observed in 45 mg bid pridopidine administered patients with TMS first quarter, for 52 weeks.

|  | Placebo | 45 mg bid | 67.5 mg bid | 90 mg bid | 112.5 mg bid |
|---|---|---|---|---|---|
| N | 21 | 24 | 20 | 25 | 15 |
| Baseline | 4.9 | 4.8 | 5 | 4.8 | 5.3 |
| Δ to placebo |  | 0.71 | 0.61 | 0.57 | 0.74 |
| p value |  | 0.0319 | 0.0744 | 0.0762 | 0.0534 |

FIG. 35p: Change from baseline in UHDRS TFC Finance and ADL score for patients with TMS 1st 2Qs at week 26. The table below provides the P-Values corresponding to FIG. 35p. Significant improvement in TFC finance and ADL was observed in 45 mg bid pridopidine administered patients with TMS first two quarters, for 26 weeks.

|  | Placebo | 45 mg bid | 67.5 mg bid | 90 mg bid | 112.5 mg bid |
|---|---|---|---|---|---|
| N | 42 | 44 | 39 | 40 | 43 |
| Baseline | 4.5 | 4.7 | 4.8 | 4.6 | 4.7 |
| Δ to placebo |  | 0.48 | 0.1 | 0.26 | 0.19 |
| p value |  | 0.045 | 0.6867 | 0.3021 | 0.4543 |

FIG. 35q: Change from baseline in UHDRS TFC Finance and ADL score for patients with TMS 1st 2Qs at week 52. The table below provides the P-Values corresponding to FIG. 35q. Significant improvement in TFC finance and ADL was observed in 45 mg bid and 90 mg bid pridopidine administered patients with TMS first two quarters, for 52 weeks.

|  | Placebo | 45 mg bid | 67.5 mg bid | 90 mg bid | 112.5 mg bid |
|---|---|---|---|---|---|
| N | 42 | 44 | 39 | 40 | 43 |
| Baseline | 4.5 | 4.7 | 4.8 | 4.6 | 4.7 |
| Δ to placebo |  | 0.47 | 0.25 | 0.47 | 0.44 |
| p value |  | 0.0294 | 0.255 | 0.0326 | 0.0433 |

FIG. 35r: Change from baseline in UHDRS TFC Finance and ADL score for patients with TMS 1st 3Qs at week 26. The table below provides the P-Values corresponding to FIG. 35r. No significant improvement in TFC finance and ADL was observed in pridopidine administered patients with TMS first three quarters, for 26 weeks.

|  | Placebo | 45 mg bid | 67.5 mg bid | 90 mg bid | 112.5 mg bid |
|---|---|---|---|---|---|
| N | 58 | 59 | 62 | 58 | 62 |
| Baseline | 4.3 | 4.5 | 4.3 | 4.4 | 4.5 |
| Δ to placebo |  | 0.18 | 0.04 | 0.35 | 0.41 |
| p value |  | 0.3393 | 0.8205 | 0.0555 | 0.0253 |

FIG. 35s: Change from baseline in UHDRS TFC Finance and ADL score for patients with TMS 1st 3Qs at week 52. The table below provides the P-Values corresponding to FIG. 35s. Significant improvement in TFC finance and ADL was observed in 45 mg bid pridopidine administered patients with TMS first three quarters, for 52 weeks.

|  | Placebo | 45 mg bid | 67.5 mg bid | 90 mg bid | 112.5 mg bid |
|---|---|---|---|---|---|
| N | 58 | 59 | 62 | 58 | 62 |
| Baseline | 4.3 | 4.5 | 4.3 | 4.4 | 4.5 |
| Δ to placebo |  | 0.52 | −0.03 | 0.21 | 0.09 |
| p value |  | 0.0122 | 0.8661 | 0.3033 | 0.6679 |

Figure 36A:
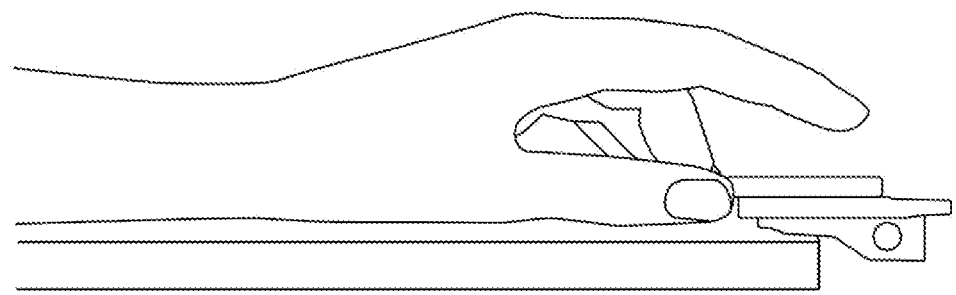
Figure 36B:
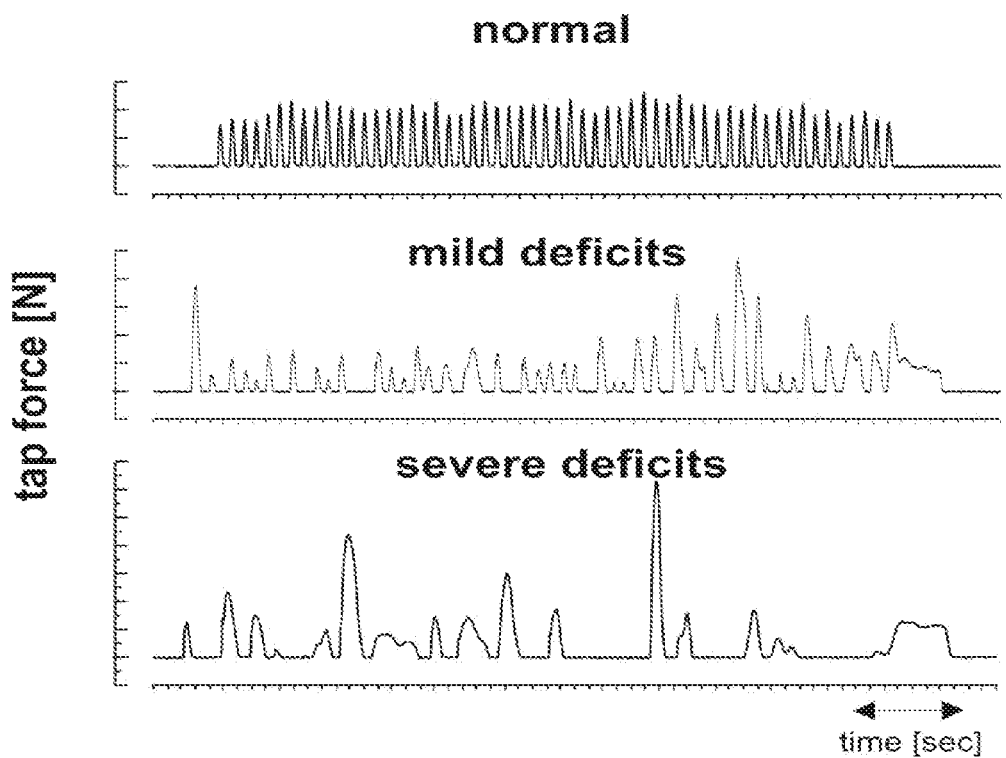

FIGS. 36a and 36b: General information regarding Finger tapping (Q-motor tap measurements). FIG. 36a shows a drawing of subject's arm with tapper. FIG. 36b shows normal and aberrant tapping measurements.

Figure 37A:
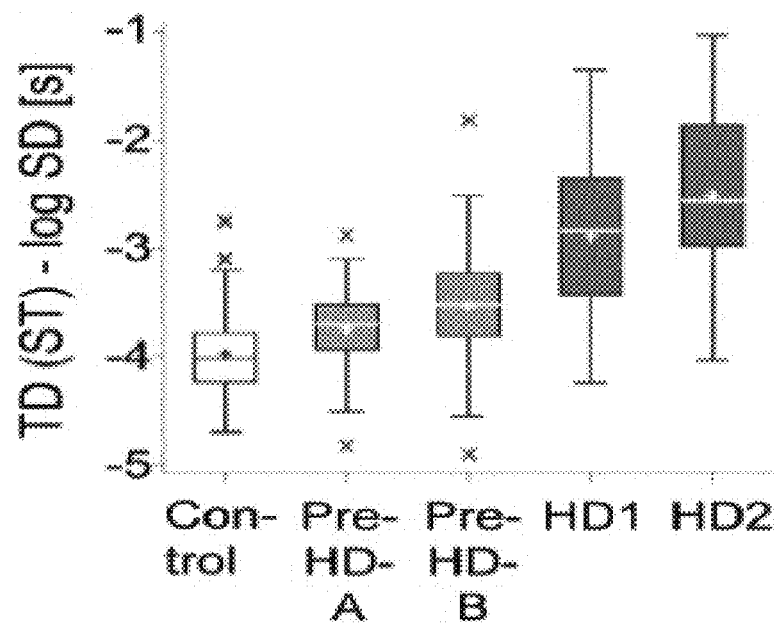
Figure 37B:
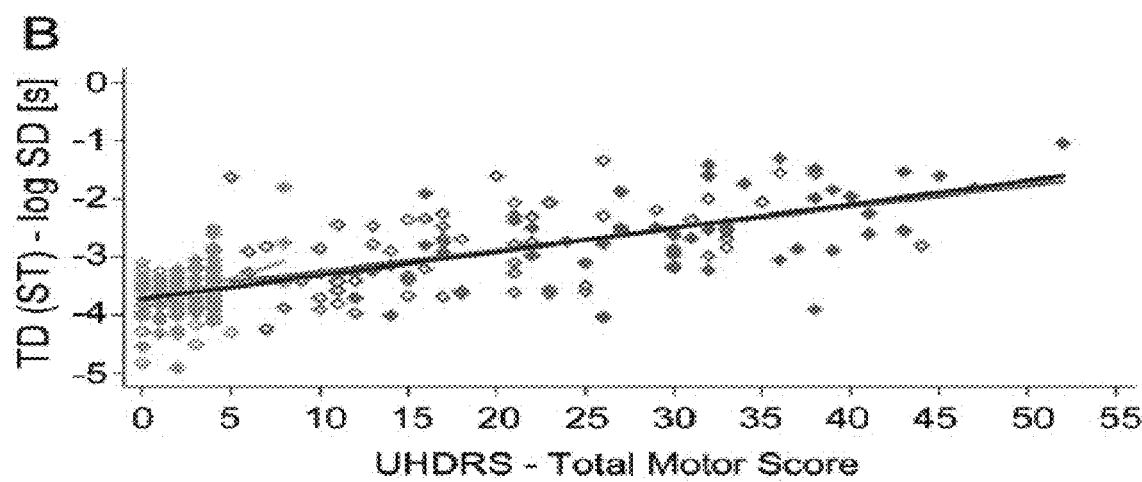

FIGS. 37a and 37b: Q-motor tap measurements: A well-validated objective measure. (Bechtel 2010).

Figure 38:
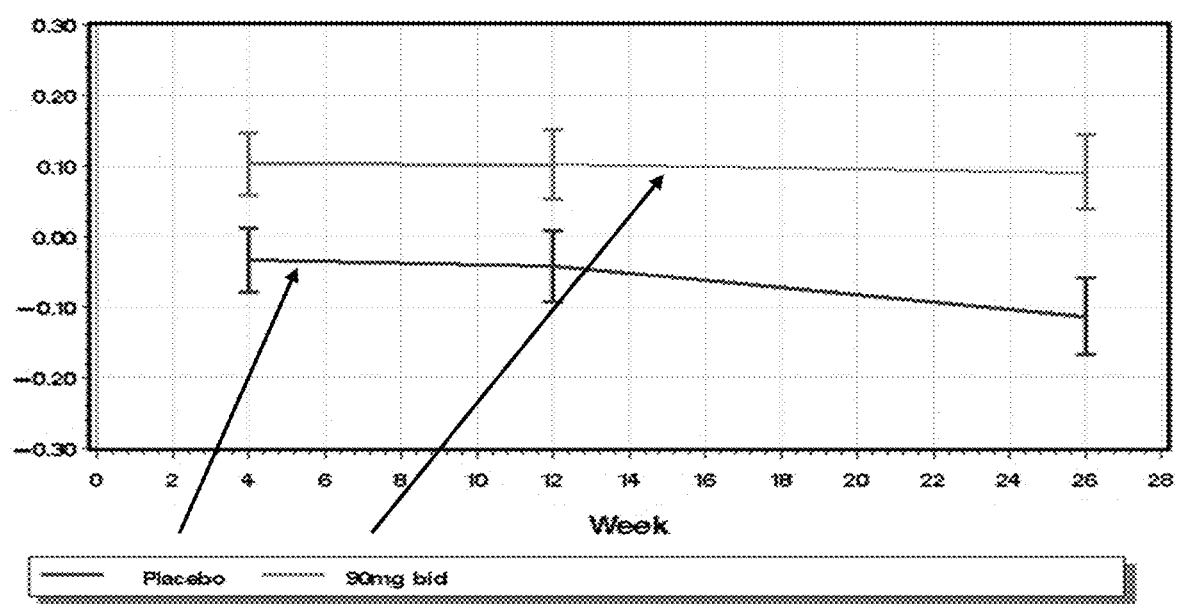

FIG. 38: Q-Motor Tap-Speed-Frequency. 90 mg pridopidine administered bid demonstrated consistent improvement from baseline. The data for 90 mg bid is shown by the top line in this graph and the data for the placebo is shown by the bottom line in this graph. Difference in p-value of 90 mg bid from placebo was 0.0259 at week 4, 0.0365 at week 12, and 0.0056 at week 26. Increase in tap speed indicates improvement. The unit of measurement of the Y-axis is Frequency (Hz).

Figure 39A:
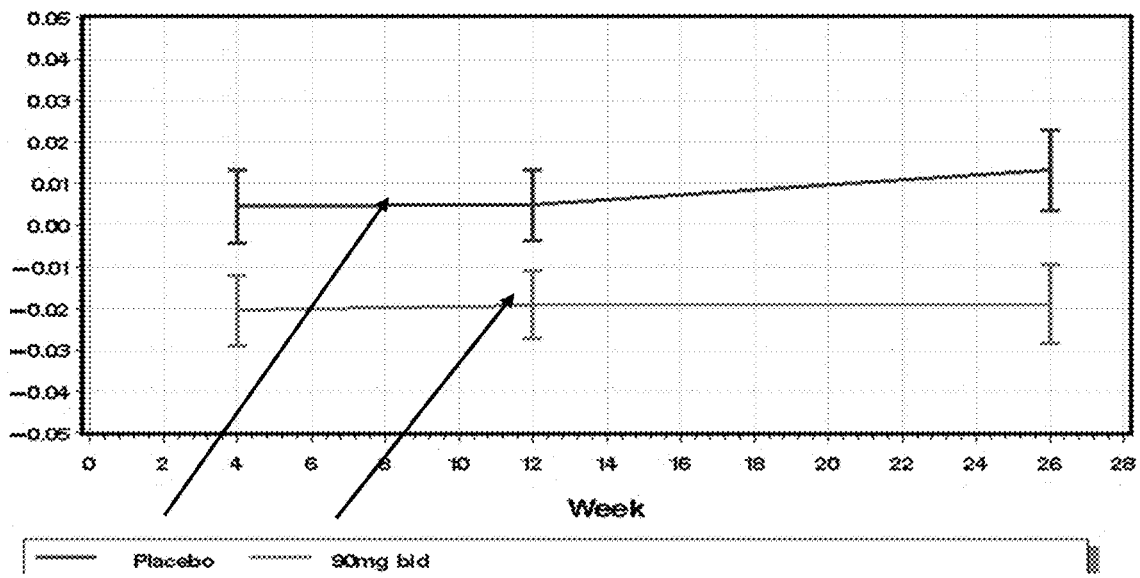
Figure 39B:
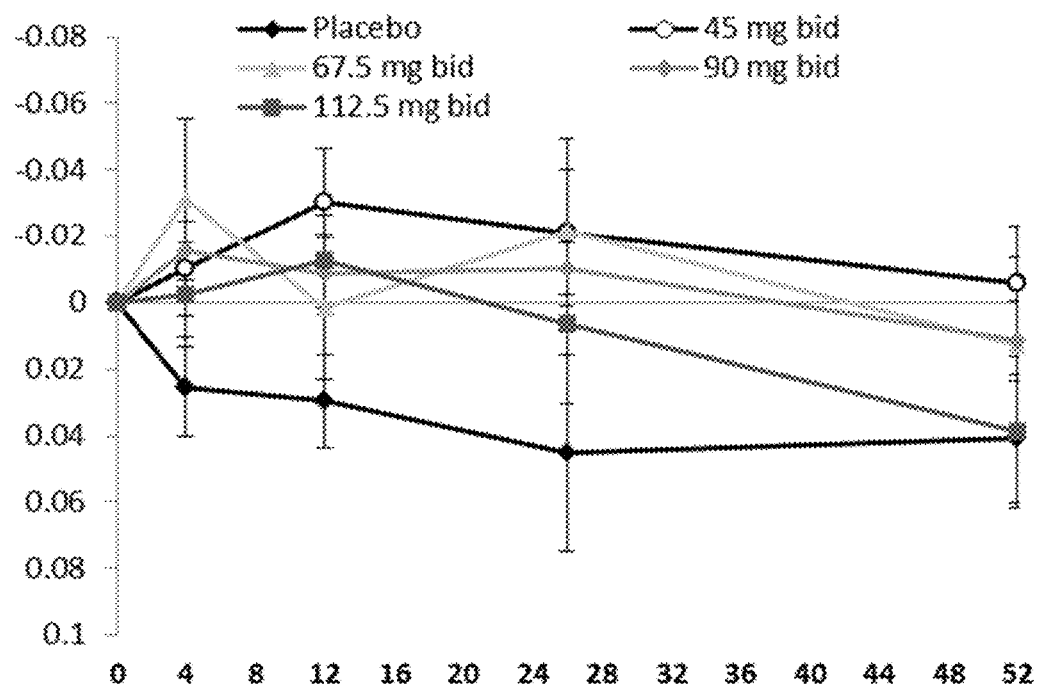

FIGS. 39a and 39b: Q-Motor Tap Speed Inter Onset Interval (IOI). 90 mg pridopidine administered bid demonstrated consistent and significant improvement from baseline for 90 mg bid. The data for 90 mg pridopidine bid is shown by the bottom line in this graph and the data for the placebo is shown by the top line in this graph. Difference in p-value of 90 mg pridopidine bid from placebo was 0.0342 at week 4, 0.0368 at week 12, and 0.0162 at week 26. Decrease in inter tap interval indicates improvement. The unit of measurement of the Y-axis in FIG. 39a is Frequency (Hz). FIG. 39b shows change from baseline in Tap-Speed-Inter-Onset-interval-MN-Hand-L (sec) over time (weeks) for full analysis set.

FIG. 39c: Improvement in objective pharmacodynamic measures of motor control: change from baseline in Q-Motor: Tap-Speed-Inter-Onset-interval-MN-Hand (sec), Week 52 FAS. The table below provides data and the P-Values corresponding to FIG. 39c. A trend towards improvement was noted in 45 mg bid treated patients.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 0.4065 | 0.4154 | 0.4608 | 0.4029 | 0.4366 |
| Δ to placebo |  | −0.0402 | 0.0152 | −0.0064 | −0.017 |
| p value |  | 0.1956 | 0.6063 | 0.8258 | 0.5689 |

FIG. 39d: Improvement in objective pharmacodynamic measures of motor control: change from baseline in Q-Motor: Tap-Speed-Inter-Onset-interval-MN-Hand (sec), Week 52 in pridopidine treated HD1 and HD2 patients. The table below provides the data and P-Values corresponding to FIG. 39d. A trend towards improvement was noted in all treatment arms.

|  | Placebo | 45 mg bid | 67.5 mg bid | 90 mg bid | 112.5 mg bid |
| --- | --- | --- | --- | --- | --- |
| N | 62 | 59 | 54 | 56 | 58 |
| Baseline | 0.3725 | 0.3605 | 0.3983 | 0.3789 | 0.4056 |
| Δ to placebo |  | −0.0351 | −0.0464 | −0.0291 | −0.022 |
| p value |  | 0.1347 | 0.0449 | 0.2039 | 0.3509 |

FIG. 39e: Improvement in objective pharmacodynamic measures of motor control, change from baseline in Q-Motor: Pro-Sup-Frequency-MN-Hand (Hz), Week 52 FAS. The table below provides the data and P-Values corresponding to FIG. 39e. A trend towards improvement was noted in 45 mg bid treated patients.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 1.6686 | 1.7789 | 1.7255 | 1.7505 | 1.7251 |
| Wk 52 Δ to placebo |  | 0.0599 | −0.0124 | −0.0087 | 0.0127 |
| p value |  | 0.3122 | 0.8278 | 0.8763 | 0.8261 |

FIG. 39f: Improvement in objective pharmacodynamic measures of motor control, change from baseline in Q-Motor: Pro-Sup-Frequency-MN-Hand (Hz), Week 52 Week 52 in pridopidine treated HD1 and HD2 patients. The table below provides the data and P-Values corresponding to FIG. 39f. A trend towards improvement was noted in 45 ma bid treated patients.

|  | Placebo | 45 mg bid | 67.5 mg bid | 90 mg bid | 112.5 mg bid |
| --- | --- | --- | --- | --- | --- |
| N | 62 | 59 | 54 | 56 | 58 |
| Baseline | 1.77 | 1.8513 | 1.8928 | 1.8658 | 1.841 |
| Wk 52 Δ to placebo |  | 0.1195 | 0.0548 | 0.0575 | 0.08 |
| p value |  | 0.0692 | 0.3996 | 0.3709 | 0.229 |

Figure 40A:
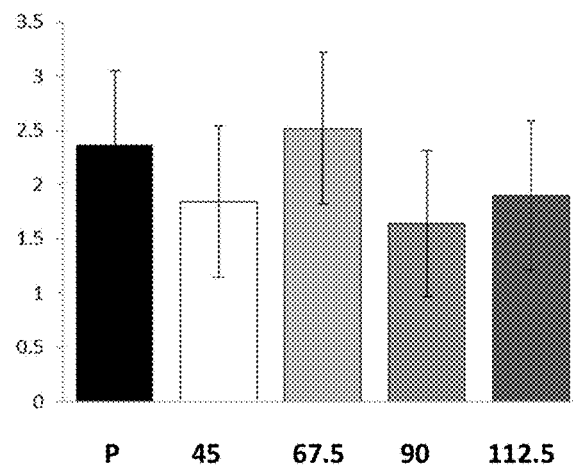

FIG. 40a: Change from baseline in Cognitive Assessment Battery Hopkins Verbal Learning Test, revised (CAB HVLT-R) score for patients at week 26. The table below provides the P-Values corresponding to FIG. 40a. No significant improvement in CAB HVLT-R score was observed in pridopidine administered patients, for 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 19.3 | 19.5 | 20.3 | 19.4 | 19.1 |
| Δ to placebo |  | −0.53 | 0.15 | −0.73 | −0.47 |
| p value |  | 0.5837 | 0.8758 | 0.4384 | 0.6217 |

Figure 40B:
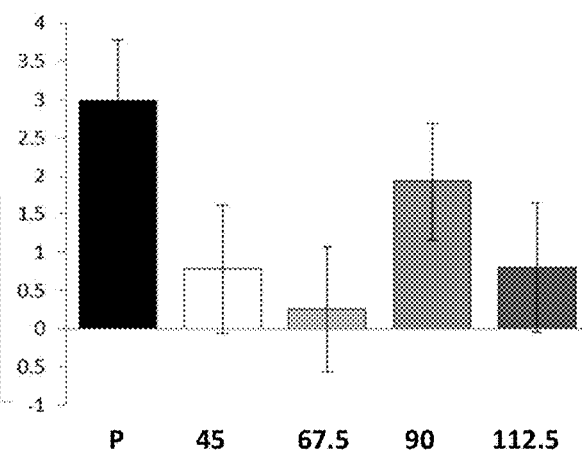

FIG. 40b: Change from baseline in Cognitive Assessment Battery Hopkins Verbal Learning Test, revised (CAB HVLT-R) score for patients at week 52. The table below provides the P-Values corresponding to FIG. 40b. A trend towards improvement in CAB HVLT-R score was observed in 45 mg bid pridopidine administered patients, for 52 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 19.3 | 19.5 | 20.3 | 19.4 | 19.1 |
| Δ to placebo |  | −2.21 | −2.74 | −1.07 | −2.19 |
| p value |  | 0.0517 | 0.0148 | 0.3265 | 0.0562 |

Figure 41A:
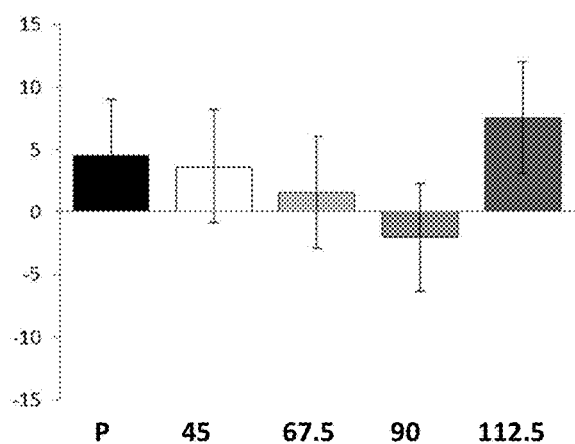

FIG. 41a: Change from baseline in Cognitive Assessment Battery CAB Trail Making Test score for patients at week 26. The table below provides the P-Values corresponding to FIG. 41a. No significant improvement in CAB Trail making test score was observed in pridopidine administered patients, for 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | −184.7 | −181.6 | −182.2 | −185 | −178.9 |
| Δ to placebo |  | −0.95 | −3.03 | −6.64 | 2.97 |
| p value |  | 0.8773 | 0.6211 | 0.2713 | 0.6283 |

Figure 41B:
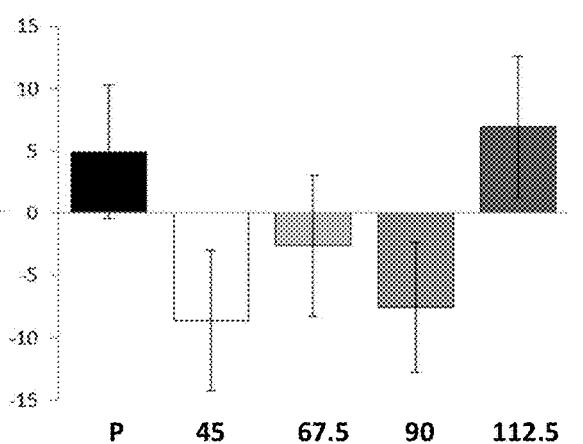

FIG. 41b: Change from baseline in Cognitive Assessment Battery CAB Trail Making Test score for patients at week 52. The table below provides the P-Values corresponding to FIG. 41b. A trend towards improvement in CAB Trail making test score was observed in pridopidine administered patients, for 52 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | −184.7 | −181.6 | −182.2 | −185 | −178.9 |
| Δ to placebo |  | −13.56 | −7.54 | −12.48 | 2.01 |
| p value |  | 0.0773 | 0.3266 | 0.0913 | 0.7951 |

Figure 41C:
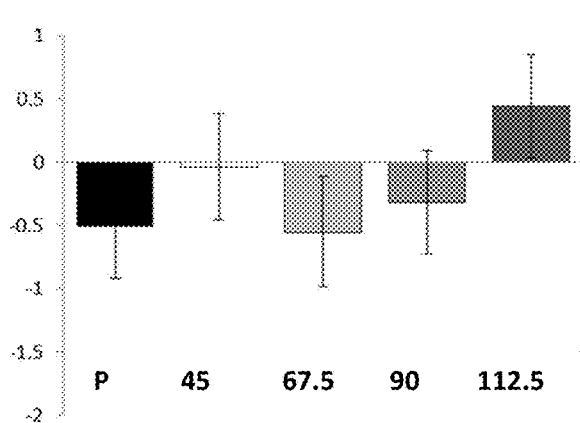

FIG. 41c: Change from baseline in Cognitive Assessment Battery CAB Paced Tapping at 3 Hz at 26 weeks. The table below provides data and the P-Values corresponding to FIG. 41c.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 5.935 | 6.035 | 5.027 | 4.943 | 5.572 |
| Δ to placebo |  | 0.4736 | −0.041 | 0.1975 | 0.9515 |
| p value |  | 0.4081 | 0.9441 | 0.7276 | 0.0937 |

Figure 41D:
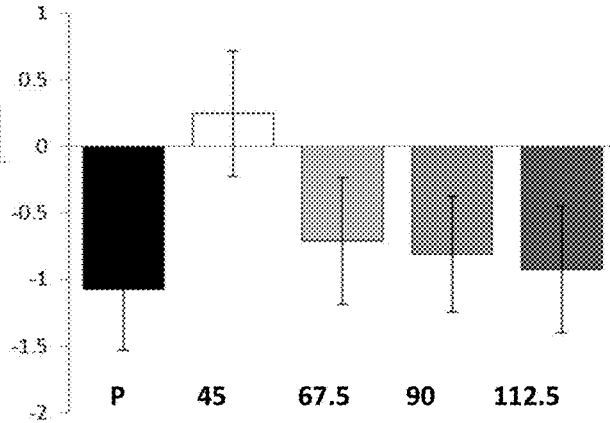

FIG. 41d: Change from baseline in Cognitive Assessment Battery CAB Paced Tapping at 3 Hz at 52 weeks. The table below provides data and the P-Values corresponding to FIG. 41d.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 5.935 | 6.035 | 5.027 | 4.943 | 5.572 |
| Δ to placebo |  | 1.3234 | 0.3701 | 0.2659 | 0.1523 |
| p value |  | 0.0402 | 0.5681 | 0.6681 | 0.8152 |

Figure 42:
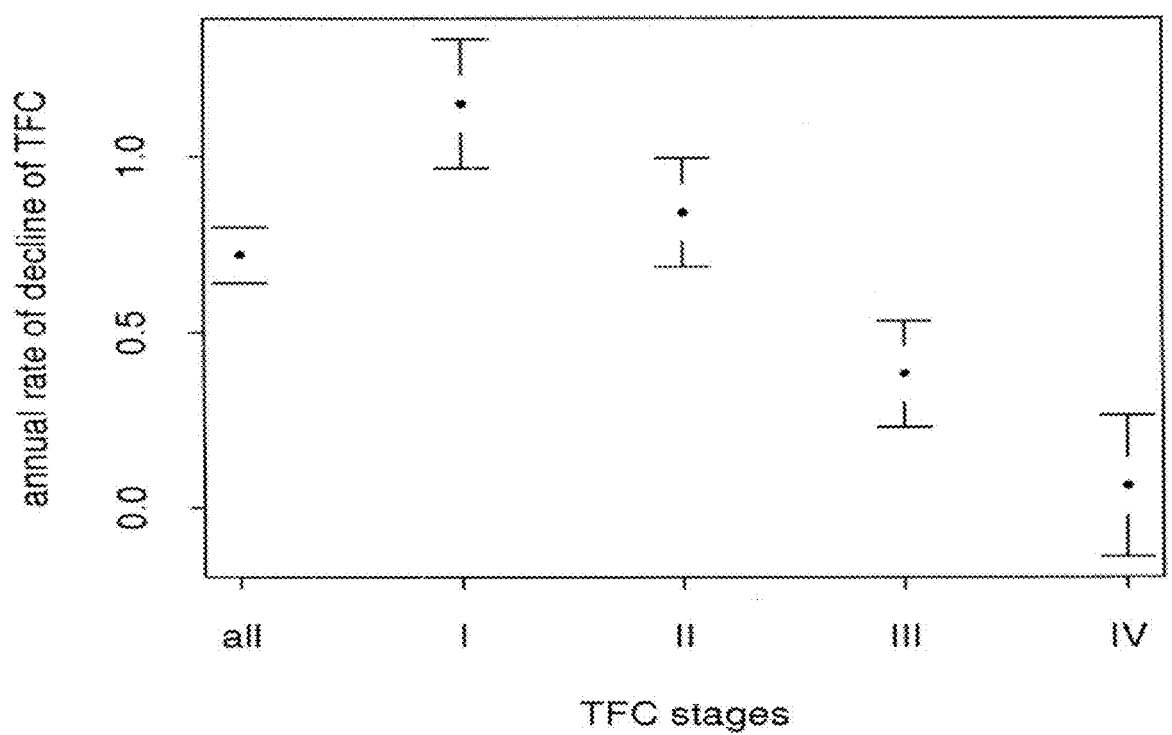

FIG. 42: Annual rates of decline (y axis) in TFC are higher in earlier stages of disease (Marder 2000).

Figure 43A:
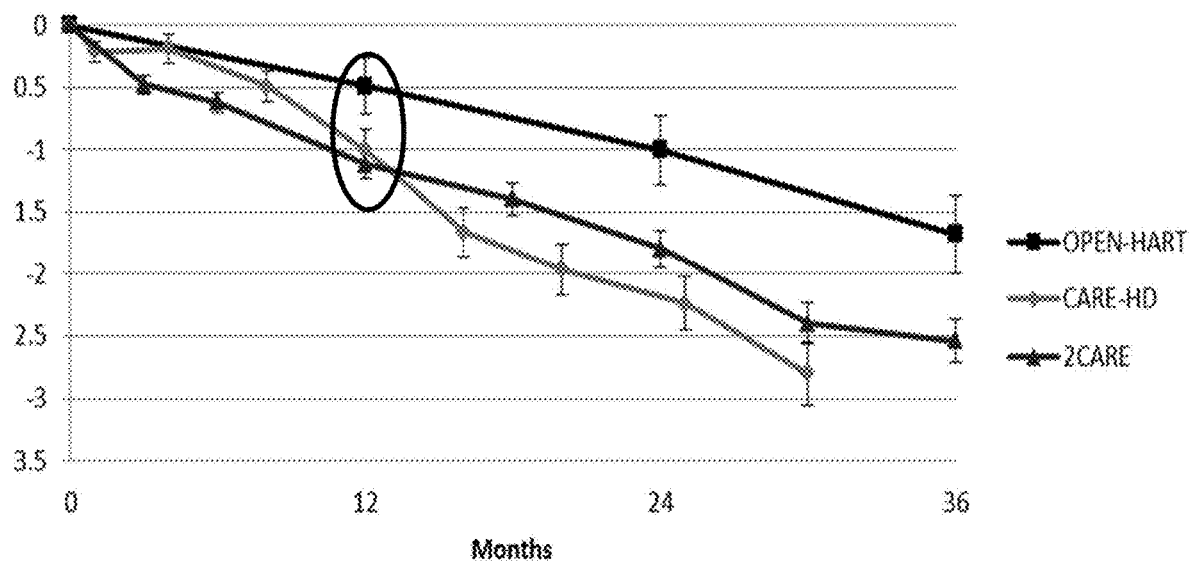

FIG. 43a: Mean change from baseline TFC in placebo arms of (1) Open-label Extension Study of Pridopidine (ACR16) in the Symptomatic Treatment of Huntington Disease (OPEN-HART) (n=50), (2) Co-Enzyme Q10 And Remacemide: Evaluation in HD (CARE-HD) (n=80) (Kieburtz 2001) and (3) Coenzyme Q10 in Huntington's Disease (HD) (2CARE) (n=213): TFC Score Change From Baseline (non-matched cohorts). The circle over the 12 months points reflects ~1-point difference that was observed in the rate of functional decline in Open-HART subjects treated with Pridopidine.

Figure 43B:
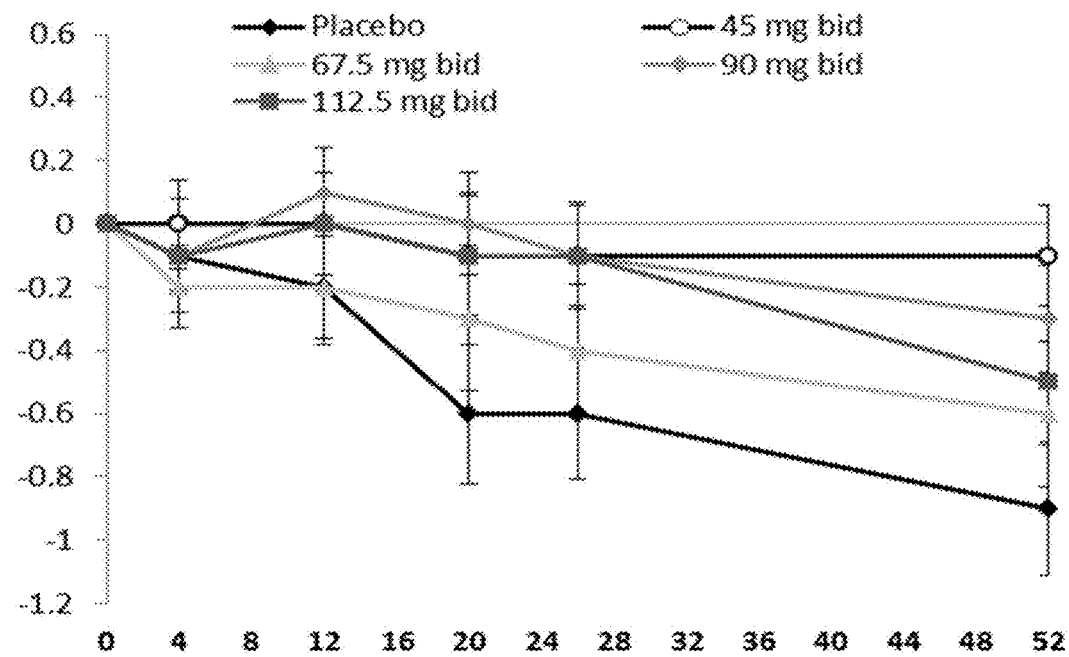

FIG. 43b: Change from baseline in TFC score plotted over time in Week 52 in pridopidine treated HD1 and HD2 treated subjects (n=54-62) in PRIDE-HD trial. The dark line with diamond represents placebo; line with open circle represents 45 mg bid, line with triangle represents 67.5 mg bid, line with grey diamond represents 90 mg bid, line with square represents 112.5 mg bid. Y axis represents change from baseline in TFC score from baseline, x axis represents treatment time in weeks.

Figure 44A:
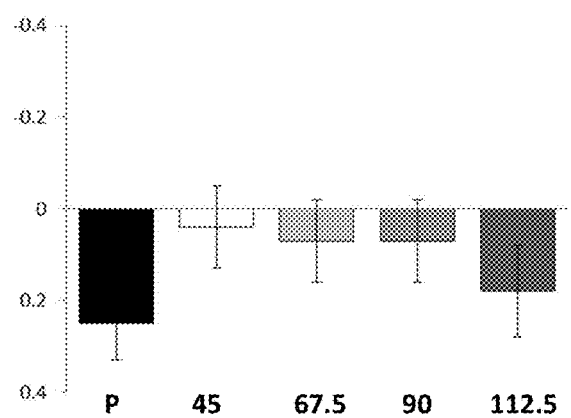
Figure 44B:
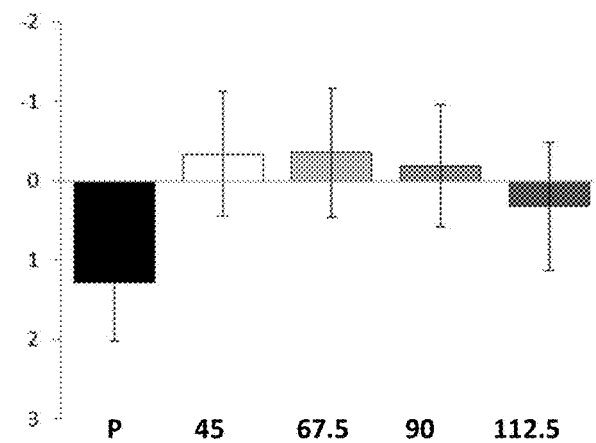
Figure 44C:
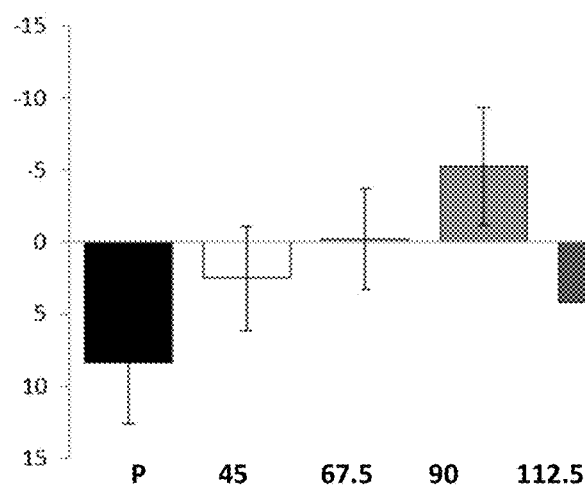

FIGS. 44a-44c are graphs which show multiple ambulation-related endpoints demonstrating trends favoring pridopidine in early HD (stage 1-2 patients). Data for TMS showed a strong placebo effect. A trend towards improvement in TMS was observed at 52 weeks.

FIG. 44a: UHDRS TMS Gait: Early HD at 52 weeks. The table below provides data and the P-Values corresponding to FIG. 44a.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 0.9 | 1.1 | 1 | 1.1 | 1 |
| Wk 52 Δ to placebo |  | −0.21 | −0.17 | −0.17 | −0.06 |
| p value |  | 0.0855 | 0.168 | 0.1521 | 0.628 |

FIG. 44b: Timed Up and Go Test (sec): Pridopidine treated HD1 and HD2 patients at 52 weeks. The table below provides data and the P-Values corresponding to FIG. 44b.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 10 | 11.7 | 9.7 | 9.8 | 9.8 |
| Wk52 Δ to placebo |  | −1.61 | −1.64 | −1.46 | −0.96 |
| p value |  | 0.1348 | 0.1369 | 0.171 | 0.3827 |

FIG. 44c: Walk-12 improved in pridopidine treated HD1 patients at 52 weeks. The table below provides data and the P-Values corresponding to FIG. 44c.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 21.2 | 6.3 | 12.3 | 17.7 | 13 |
| Δ to placebo |  | −5.86 | −8.57 | −13.6 | −4.13 |
| p value |  | 0.3018 | 0.1032 | 0.0193 | 0.4534 |

Figure 44D:
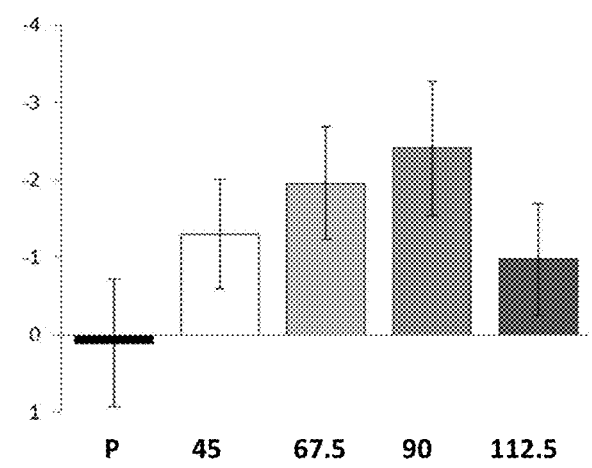
Figure 44E:
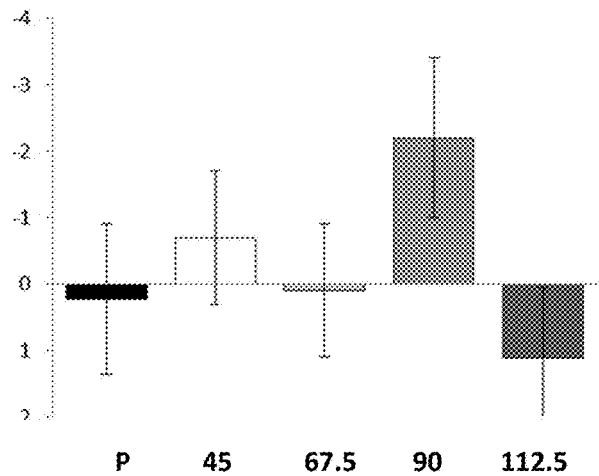

FIGS. 44d and 44e: Week 26 and week 52 HD, respectively, Pridopidine treated HD1 patients for Involuntary movements: Total Maximal Chorea (TMC). The table below provides the data and P-Values corresponding to FIG. 44d.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 12 | 17 | 17 | 11 | 18 |
| Δ to placebo |  | −1.4 | −2.07 | −2.52 | −1.08 |
| p value |  | 0.1805 | 0.0438 | 0.0271 | 0.2932 |

The table below provides the data and P-Values corresponding to FIG. 44e.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 12 | 17 | 17 | 11 | 18 |
| Δ to placebo |  | −0.93 | −0.13 | −2.43 | 0.88 |
| p value |  | 0.5315 | 0.931 | 0.1313 | 0.5622 |

Figure 45A:
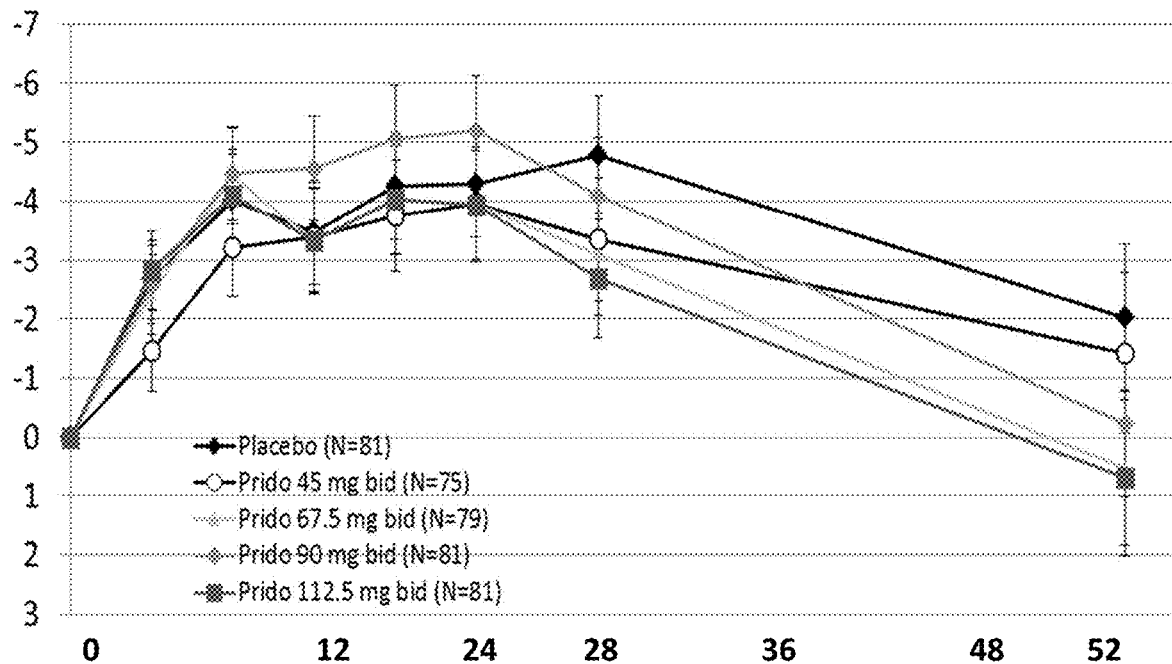
Figure 45B:
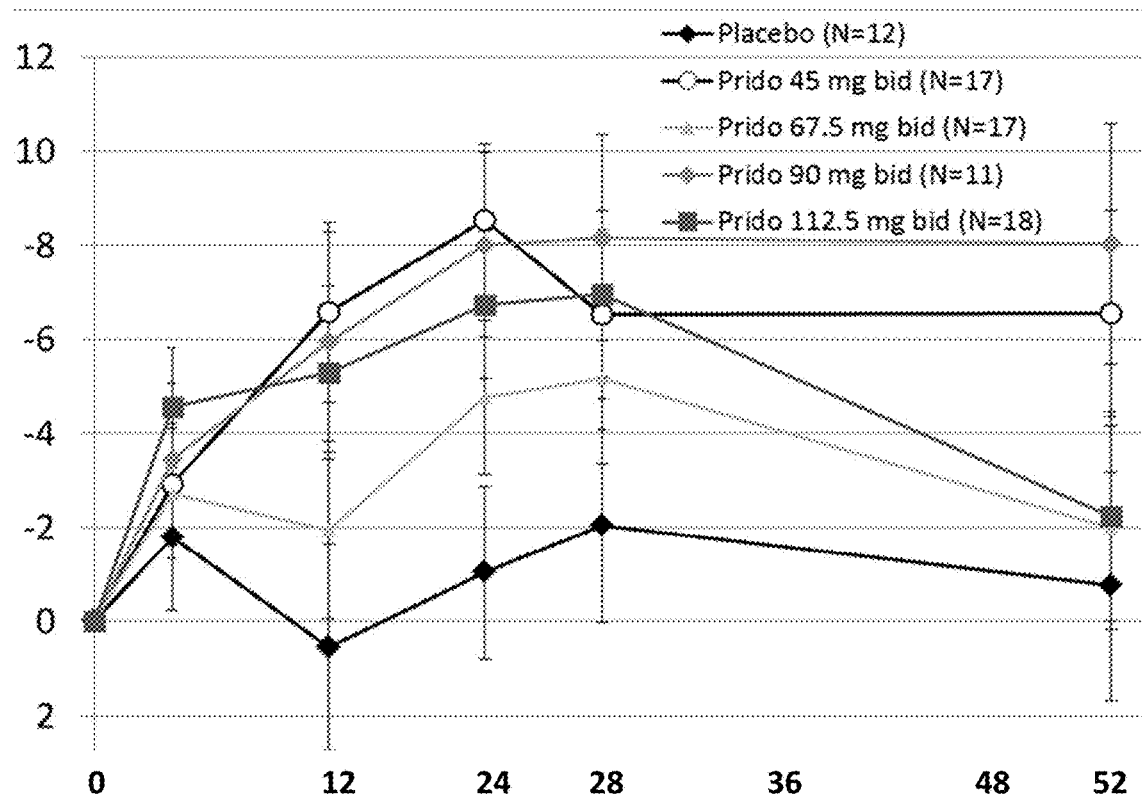

FIGS. 45a-45b: FIG. 45: Change from baseline in TMS plotted over time in TMS full analysis set plotted over time in PRIDE-HD. Data replicates previous data in changes from baseline in TMS as change from baseline values were similar to HART and MermaiHD. A decrease in TMS change from baseline indicates improvement. Y axis represents change from baseline in TMS from baseline, x axis represents treatment time in weeks. FIG. 45b: Change from baseline in TMS plotted over time in HD1 patients. Line with dark diamond represents placebo; line with open circle represents 45 mg bid, line with triangle represents 67.5 mg bid, line with grey diamond represents 90 mg bid, line with square represents 112.5 mg bid. 45 mg bid shows improvement in TMS score after 52 weeks. Y axis represents change from baseline in TMS from baseline, x axis represents treatment time in weeks.

FIGS. 46a-46v and 47a-47y, show ambulation related Modified Physical Performance Test (mPPT) data. The table provided below each graph provides data and P-values corresponding to the graph.

Figure 46A:
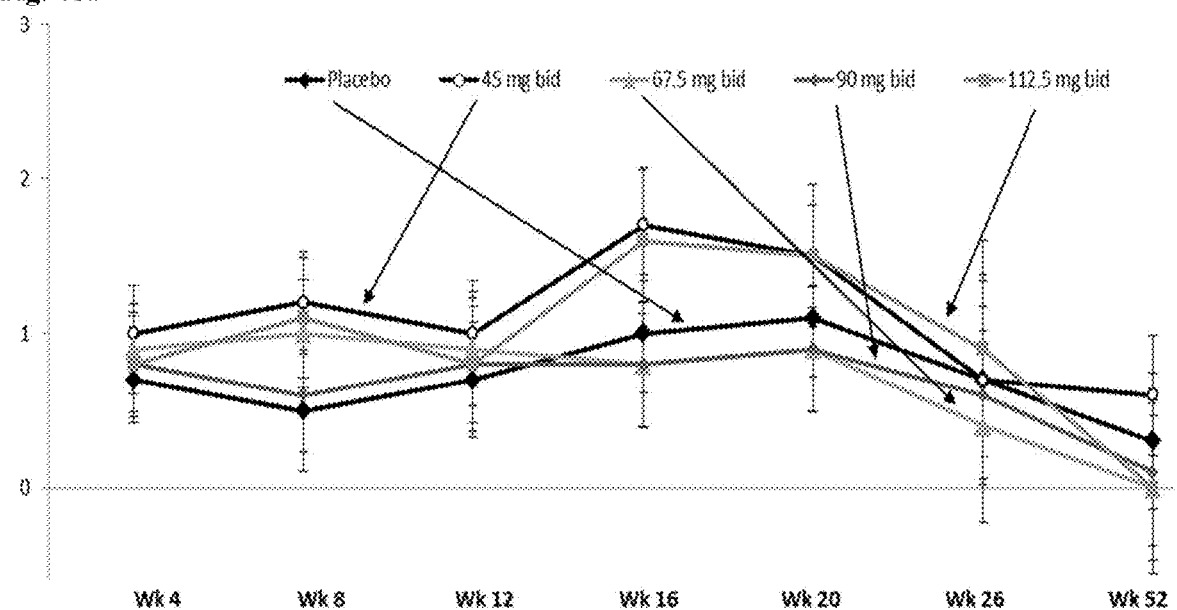

FIG. 46a: Change from baseline in mPPT Total Score, Full Analysis Set from week 4 of treatment through week 52. The mPPT quantifies the patient's performance in physical and functional tasks using a standardized 9-item test. Line with dark diamond represents placebo; line with open circle represents 45 mg bid, line with triangle represents 67.5 mg bid, line with grey diamond represents 90 mg bid, line with square represents 112.5 mg bid. Administration of 45 mg bid shows improvement on mPPT score after 52 weeks. Y axis represents change from baseline in mPPT from baseline, x axis represents treatment time in weeks.

Figure 46B:
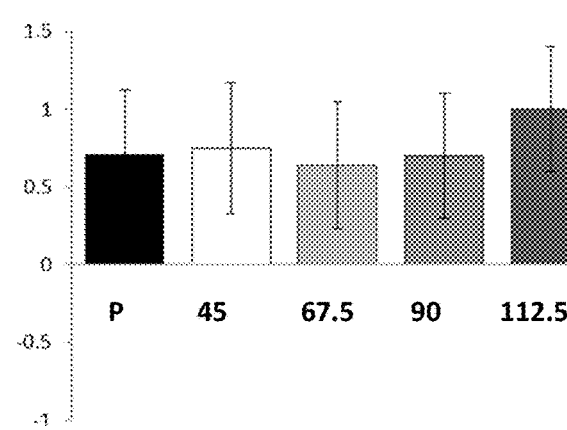

FIG. 46b: mPPT Total Score—Change from Baseline, Full Analysis Set, week 26. The table below provides the data and P-Values corresponding to FIG. 46b.

|   | Placebo | 45 mg bid | 67.5 mg bid | 90 mg bid | 112.5 mg bid |
|---|---|---|---|---|---|
| N | 81 | 75 | 79 | 81 | 81 |
| Baseline | 25.5 | 24.9 | 26.1 | 25.7 | 25.7 |
| Δ to placebo |  | 0.04 | −0.07 | −0.01 | 0.29 |
| p value |  | 0.9462 | 0.8968 | 0.9853 | 0.6063 |

Figure 46C:
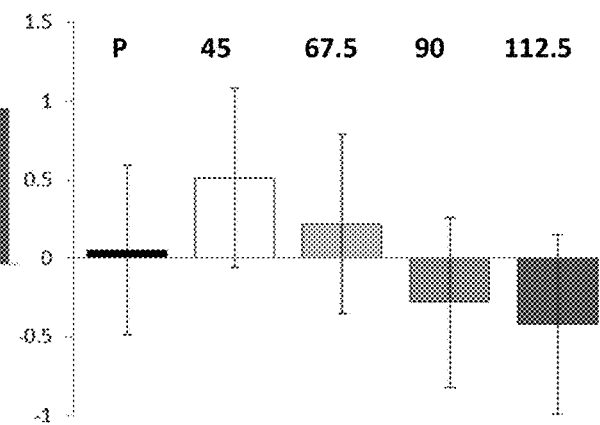

FIG. 46c: mPPT Total Score—Change from Baseline, Full Analysis Set, week 52. The table below provides the data and P-Values corresponding to FIG. 46c.

|   | Placebo | 45 mg bid | 67.5 mg bid | 90 mg bid | 112.5 mg bid |
|---|---|---|---|---|---|
| N | 81 | 75 | 79 | 81 | 81 |
| Baseline | 25.5 | 24.9 | 26.1 | 25.7 | 25.7 |
| Δ to placebo |  | 0.46 | 0.17 | −0.33 | −0.47 |
| p value |  | 0.5541 | 0.8284 | 0.661 | 0.5482 |

Figure 46D:
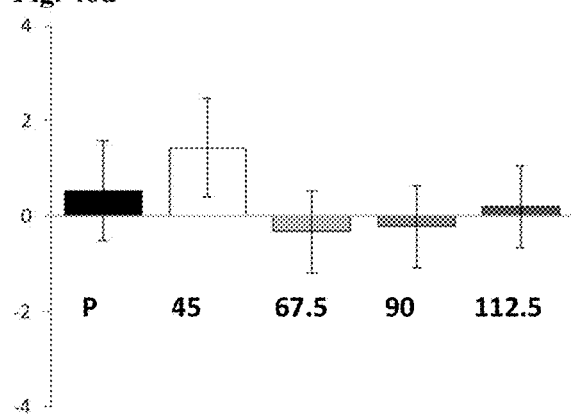

FIG. 46d: mPPT Total Score—Change from Baseline in pridopidine treated patients with baseline TFC<7 week 26. The table below provides the data and P-Values corresponding to FIG. 46d.

|   | Placebo | 45 mg bid | 67.5 mg bid | 90 mg bid | 112.5 mg bid |
|---|---|---|---|---|---|
| N | 19 | 16 | 25 | 25 | 23 |
| Baseline | 21.5 | 21.4 | 23.3 | 23.1 | 21.3 |
| Δ to placebo |  | 0.9 | −0.85 | −0.73 | −0.33 |
| p value |  | 0.5266 | 0.5247 | 0.5786 | 0.802 |

Figure 46E:
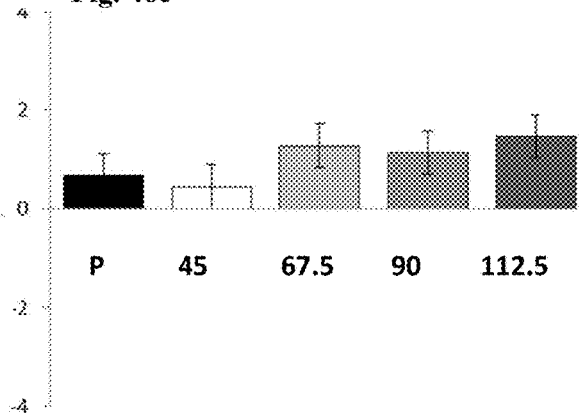

FIG. 46e: mPPT Total Score—Change from Baseline in pridopidine treated HD1 and HD2 patients week 26. The table below provides the data and P-Values corresponding to FIG. 46e.

|   | Placebo | 45 mg bid | 67.5 mg bid | 90 mg bid | 112.5 mg bid |
|---|---|---|---|---|---|
| N | 62 | 59 | 54 | 56 | 58 |
| Baseline | 26.6 | 25.9 | 27.4 | 26.9 | 27.5 |
| Δ to placebo |  | −0.24 | 0.59 | 0.46 | 0.79 |
| p value |  | 0.6903 | 0.3296 | 0.4429 | 0.1889 |

FIG. 46f: mPPT Total Score—Change from Baseline in pridopidine treated patients with baseline TFC<7 week 52. The table below provides the data and P-Values corresponding to FIG. 46f.

|   | Placebo | 45 mg bid | 67.5 mg bid | 90 mg bid | 112.5 mg bid |
|---|---|---|---|---|---|
| N | 19 | 16 | 25 | 25 | 23 |
| Baseline | 21.5 | 21.4 | 23.3 | 23.1 | 21.3 |
| Δ to placebo |  | 1.57 | −1.37 | −2.73 | −0.49 |
| p value |  | 0.4267 | 0.4515 | 0.1288 | 0.7822 |

FIG. 46g: mPPT Total Score—Change from Baseline, in pridopidine treated HD1 and HD2 patients week 52. The table below provides the data and P-Values corresponding to FIG. 46g.

|   | Placebo | 45 mg bid | 67.5 mg bid | 90 mg bid | 112.5 mg bid |
|---|---|---|---|---|---|
| N | 62 | 59 | 54 | 56 | 58 |
| Baseline | 26.6 | 25.9 | 27.4 | 26.9 | 27.5 |
| Δ to placebo |  | 0.15 | 1.04 | 0.88 | −0.26 |
| p value |  | 0.8564 | 0.2087 | 0.2728 | 0.7532 |

FIG. 46h: Change from baseline in mPPT total score in pridopidine treated HD1 patients at 26 weeks. The table below provides the data and P-Values corresponding to FIG. 46h.

|   | Placebo | 45 mg bid | 67.5 mg bid | 90 mg bid | 112.5 mg bid |
|---|---|---|---|---|---|
| N | 12 | 17 | 17 | 11 | 18 |
| Baseline | 28.1 | 30.1 | 28.7 | 27.8 | 30.2 |
| Δ to placebo |  | −1.31 | −0.2 | 0.81 | 0.03 |
| p value |  | 0.2537 | 0.8574 | 0.5048 | 0.9789 |

FIG. 46i: Change from baseline in mPPT total score in pridopidine treated HD2 patients at 26 weeks. The table below provides the data and P-Values corresponding to FIG. 46i.

|   | Placebo | 45 mg bid | 67.5 mg bid | 90 mg bid | 112.5 mg bid |
|---|---|---|---|---|---|
| N | 50 | 42 | 37 | 45 | 40 |
| Baseline | 26.3 | 24.1 | 26.8 | 26.7 | 26.3 |
| Δ to placebo |  | −0.07 | 0.68 | 0.35 | 0.85 |
| p value |  | 0.9231 | 0.3603 | 0.6191 | 0.242 |

FIG. 46j: Change from baseline in mPPT total score in pridopidine treated HD patients BL stage 3-5 (TFC 0-6) at 26 weeks. The table below provides the data and P-Values corresponding to FIG. 46j.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 21.5 | 21.4 | 23.3 | 23.1 | 21.3 |
| Δ to placebo |  | 0.9 | −0.85 | −0.73 | −0.33 |
| p value |  | 0.5266 | 0.5247 | XX0.5786 | 0.802 |

FIG. 46*k*: Change from baseline in mPPT total score in pridopidine treated HD1 patients at 52 weeks. The table below provides the data and P-Values corresponding to FIG. 46*k*.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 28.1 | 30.1 | 28.7 | 27.8 | 30.2 |
| Δ to placebo |  | 0.76 | 0.45 | 1.11 | 0.08 |
| p value |  | 0.5292 | 0.7013 | 0.388 | 0.9456 |

FIG. 46*l*: Change from baseline in mPPT total score in pridopidine treated HD2 patients at 52 weeks. The table below provides the data and P-Values corresponding to FIG. 46*l*.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 26.3 | 24.1 | 26.8 | 26.7 | 26.3 |
| Δ to placebo |  | −0.39 | 1 | 0.71 | −0.65 |
| p value |  | 0.7028 | 0.3539 | 0.4672 | 0.5427 |

FIG. 46*m*: Change from baseline in mPPT total score in pridopidine treated HD patients BL stage 3-5 at 52 weeks. The table below provides the data and P-Values corresponding to FIG. 46*m*.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 21.5 | 21.4 | 23.3 | 23.1 | 21.3 |
| Δ to placebo |  | 1.57 | −1.37 | −2.73 | −0.49 |
| p value |  | 0.4267 | 0.4515 | 0.1288 | 0.7822 |

FIG. 46*n*: Graph showing change from baseline in mPPT standing static balance scores, full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

FIG. 46*o*: mPPT standing static balance scores, full analysis set at 26 weeks. The table below provides the data and P-Values corresponding to FIG. 46*o*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.1 | 2.9 | 2.9 | 3.1 | 3 |
| Δ to placebo |  | 0.07 | −0.2 | −0.1 | 0.05 |
| p value |  | 0.6768 | 0.2154 | 0.5123 | 0.7294 |

FIG. 46*p*: mPPT standing static balance scores, full analysis set at 52 weeks. The table below provides the data and P-Values corresponding to FIG. 46*p*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.1 | 2.9 | 2.9 | 3.1 | 3 |
| Δ to placebo |  | −0.15 | −0.19 | −0.14 | −0.12 |
| p value |  | 0.4019 | 0.3018 | 0.435 | 0.5024 |

Figure 46Q:
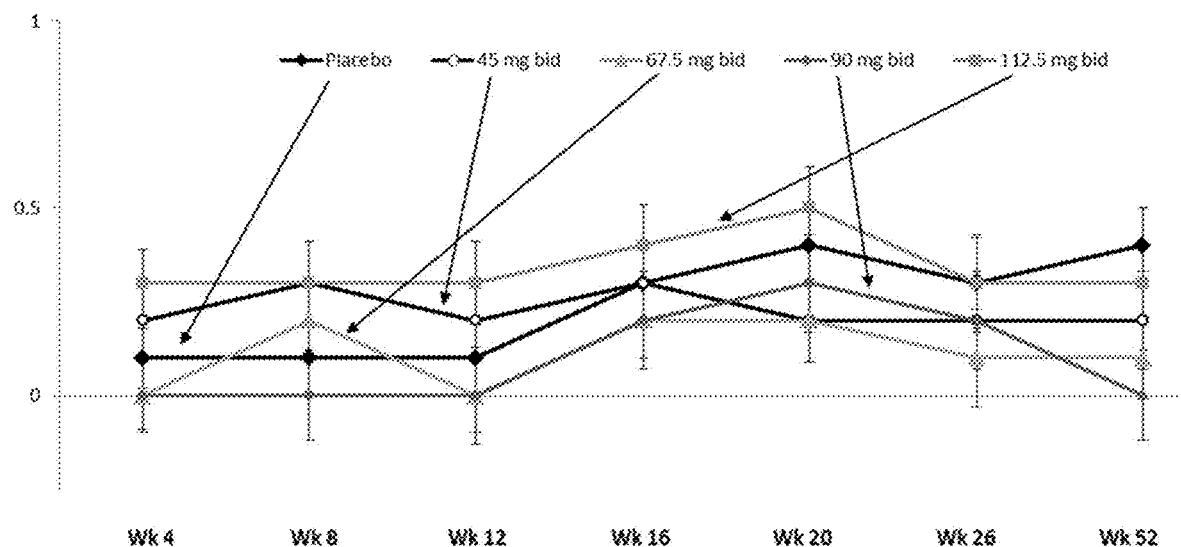

FIG. 46*q*: graph showing change from baseline in mPPT Chair Rise scores, full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 46R:
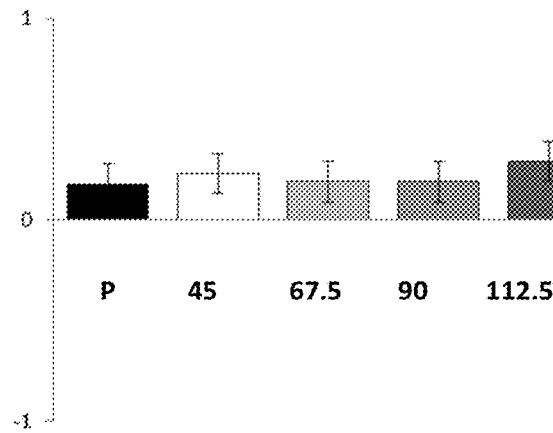

FIG. 46*r*: mPPT Chair Rise scores, full analysis set at 26 weeks. The table below provides the data and P-Values corresponding to FIG. 46*r*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.5 | 2.6 | 2.8 | 2.8 | 2.6 |
| Δ to placebo |  | 0.05 | 0.01 | 0.01 | 0.12 |
| p value |  | 0.7238 | 0.9436 | 0.9222 | 0.3883 |

Figure 46S:
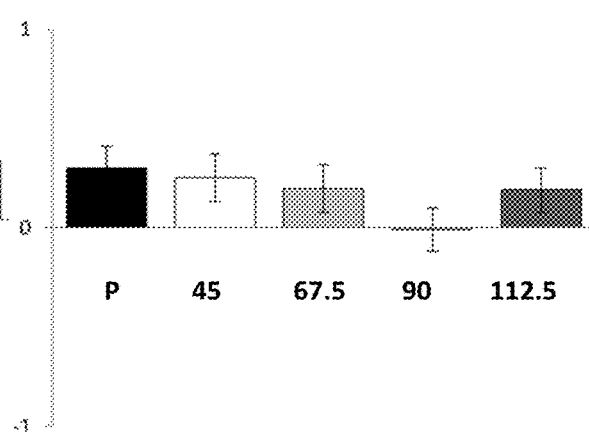

FIG. 46*s*: mPPT Chair Rise scores, full analysis set at 52 weeks. The table below provides the data and P-Values corresponding to FIG. 46*s*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.5 | 2.6 | 2.8 | 2.8 | 2.6 |
| Δ to placebo |  | −0.05 | −0.1 | −0.31 | −0.12 |
| p value |  | 0.7501 | 0.5267 | 0.0414 | 0.4515 |

Figure 46T:
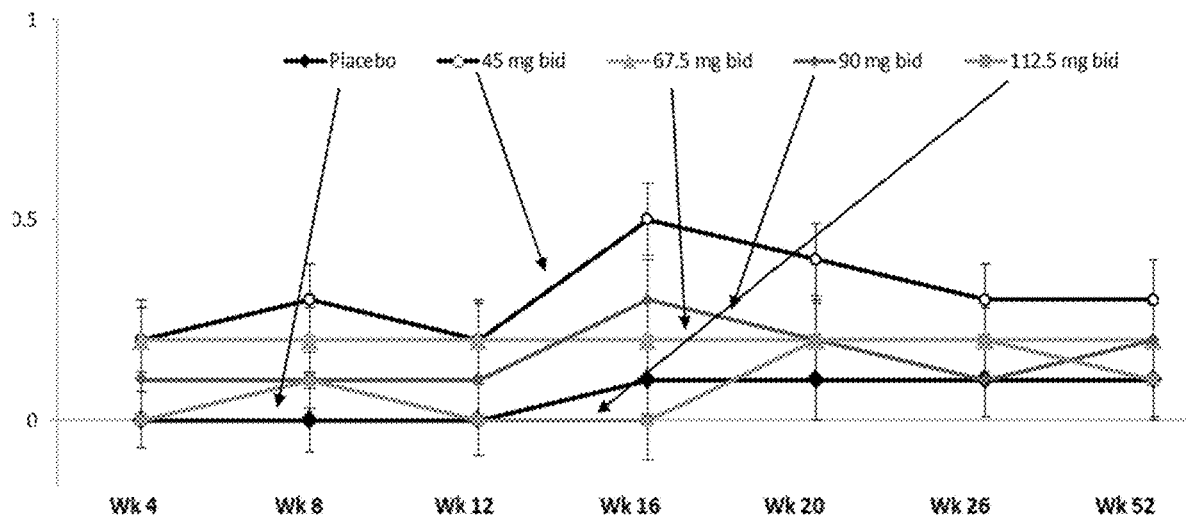

FIG. 46*t*: Graph showing change from baseline in mPPT Lift a Book and Put it on the Shelf scores, full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 46U:
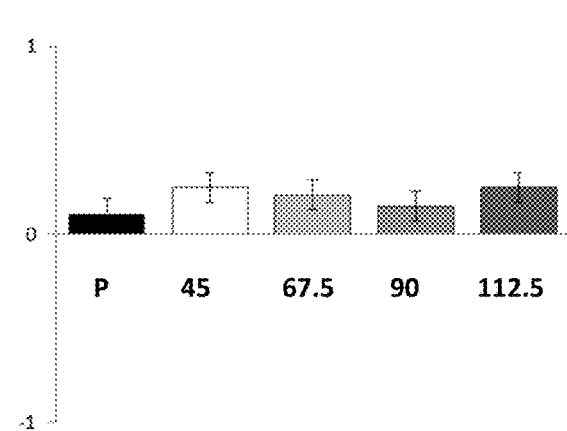

FIG. 46*u*: Change from baseline in mPPT Lift a Book and Put it on the Shelf scores, full analysis set at 26 weeks.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.6 | 2.4 | 2.6 | 2.6 | 2.7 |
| Δ to placebo |  | 0.14 | 0.1 | 0.04 | 0.14 |
| p value |  | 0.2277 | 0.3649 | 0.6982 | 0.2057 |

Figure 46V:
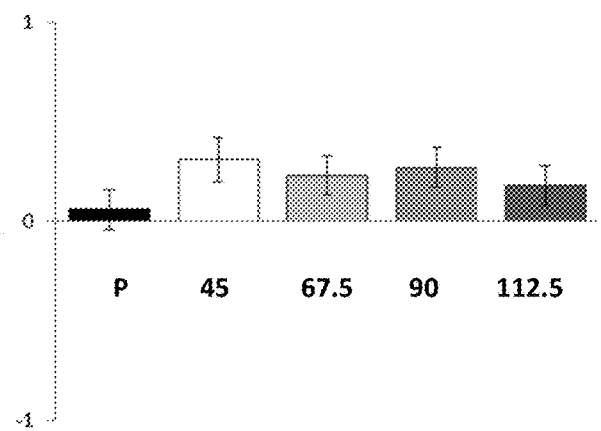

FIG. 46*v*: Change from baseline in mPPT Lift a Book and Put it on the Shelf scores, full analysis set at 52 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 2.6 | 2.4 | 2.6 | 2.6 | 2.7 |
| Δ to placebo |  | 0.25 | 0.17 | 0.22 | 0.12 |
| p value |  | 0.0755 | 0.224 | 0.1116 | 0.3956 |

Figure 47A:
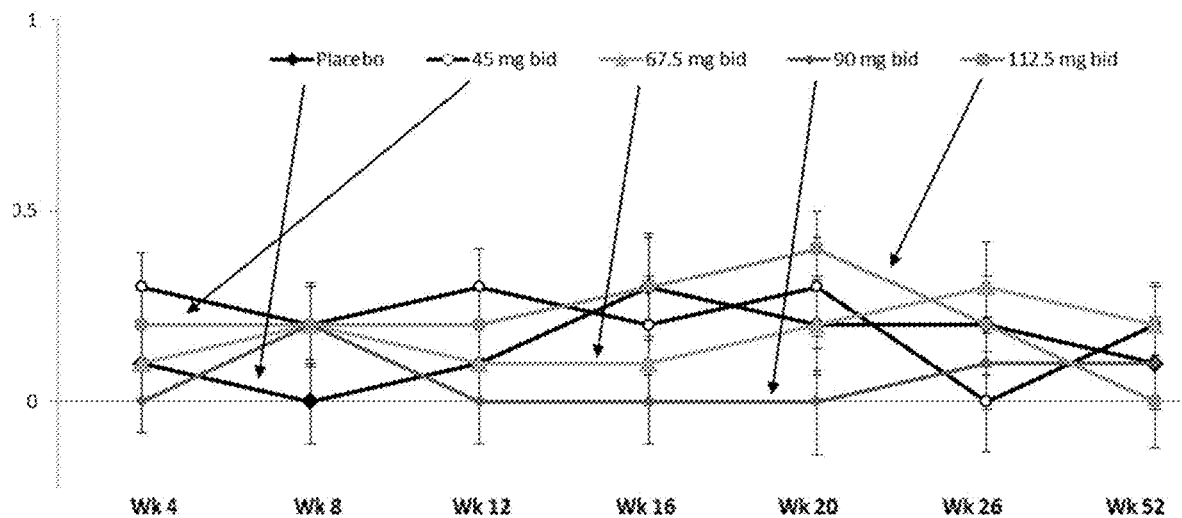

FIG. 47a: Graph showing change from baseline in mPPT Put on and Remove a Jacket full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 47B:
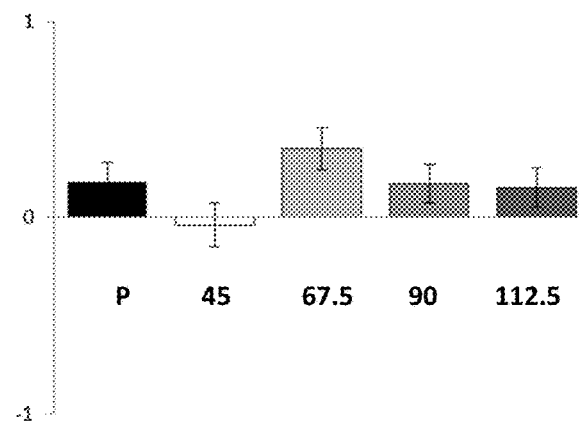

FIG. 47b: Change from baseline in mPPT Put on and Remove a Jacket scores, full analysis set at 26 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 2.2 | 2.1 | 2.3 | 2.3 | 2.2 |
| Δ to placebo |  | −0.22 | 0.17 | −0.01 | −0.03 |
| p value |  | 0.1319 | 0.2355 | 0.9331 | 0.8307 |

Figure 47C:
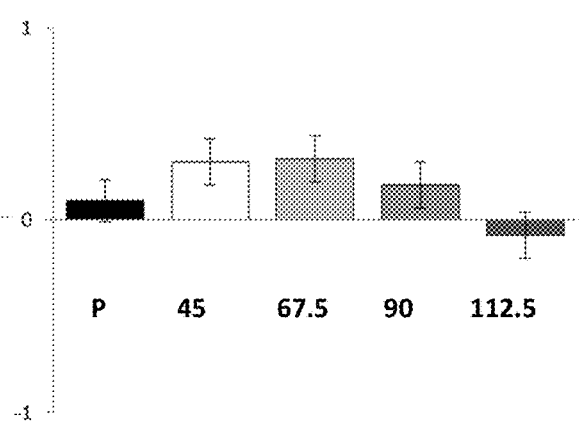

FIG. 47c: Change from baseline in mPPT Put on and Remove a Jacket scores, full analysis set at 52 weeks.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 2.2 | 2.1 | 2.3 | 2.3 | 2.2 |
| Δ to placebo |  | 0.2 | 0.21 | 0.08 | −0.18 |
| p value |  | 0.2306 | 0.1943 | 0.615 | 0.2614 |

Figure 47D:
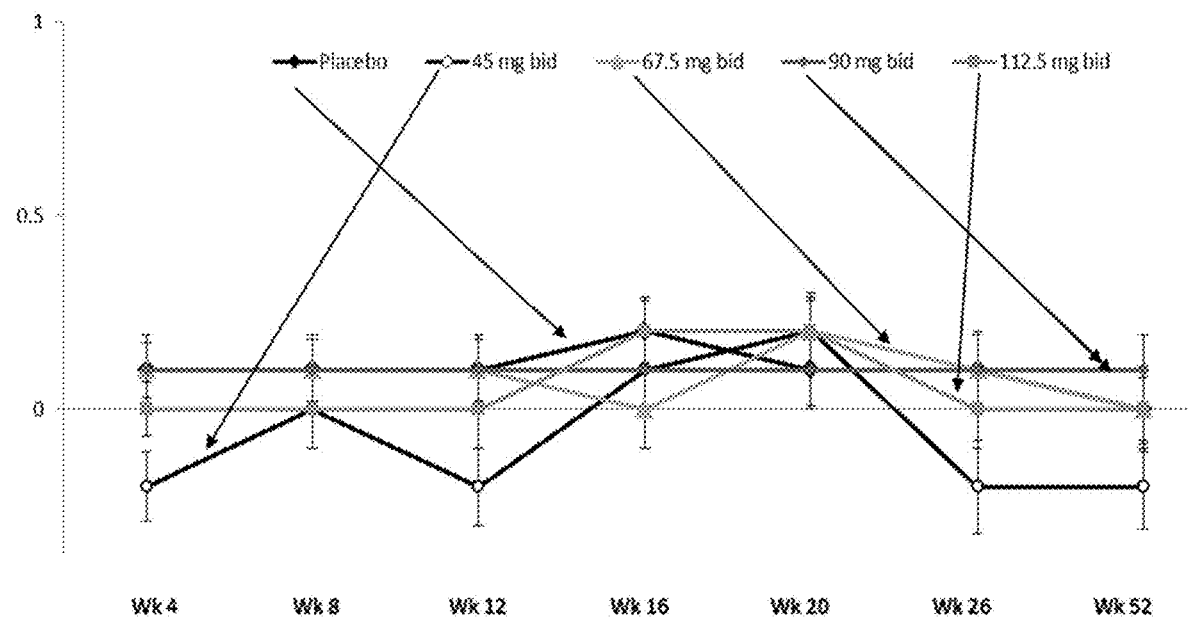

FIG. 47d: Graph showing change from baseline in mPPT Pick up a Penny from the Floor full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 47E:
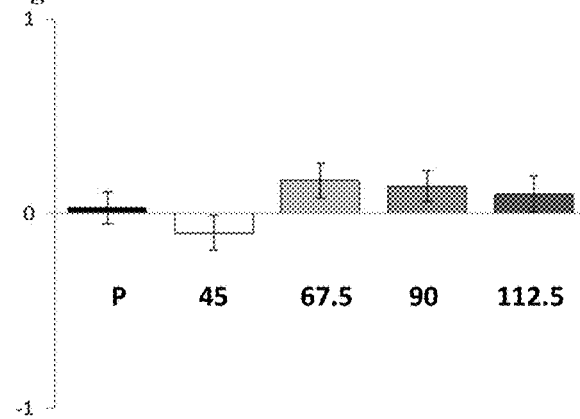

FIG. 47e: Change from baseline in mPPT Pick up a Penny from the Floor scores, full analysis set at 26 weeks. The table below provides the data and P-Values corresponding to FIG. 47e.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 2.6 | 2.7 | 2.8 | 2.6 | 2.7 |
| Δ to placebo |  | −0.13 | 0.14 | 0.1 | 0.07 |
| p value |  | 0.2702 | 0.2404 | 0.3764 | 0.5559 |

Figure 47F:
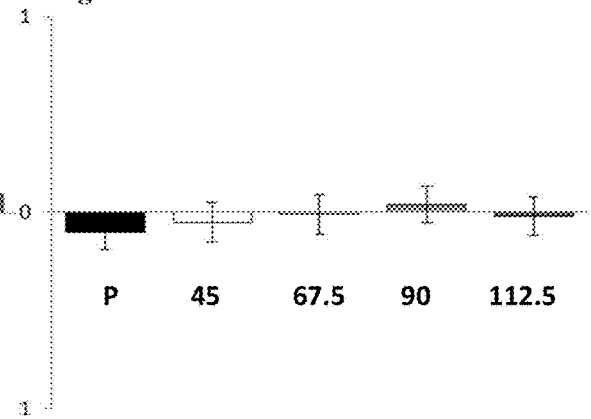

FIG. 47f: Change from baseline in mPPT Pick up a Penny from the Floor scores, full analysis set at 52 weeks. The table below provides the data and P-Values corresponding to FIG. 47f.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 2.6 | 2.7 | 2.8 | 2.6 | 2.7 |
| Δ to placebo |  | 0.04 | 0.09 | 0.14 | 0.07 |
| p value |  | 0.7523 | 0.5148 | 0.3007 | 0.5939 |

Figure 47G:
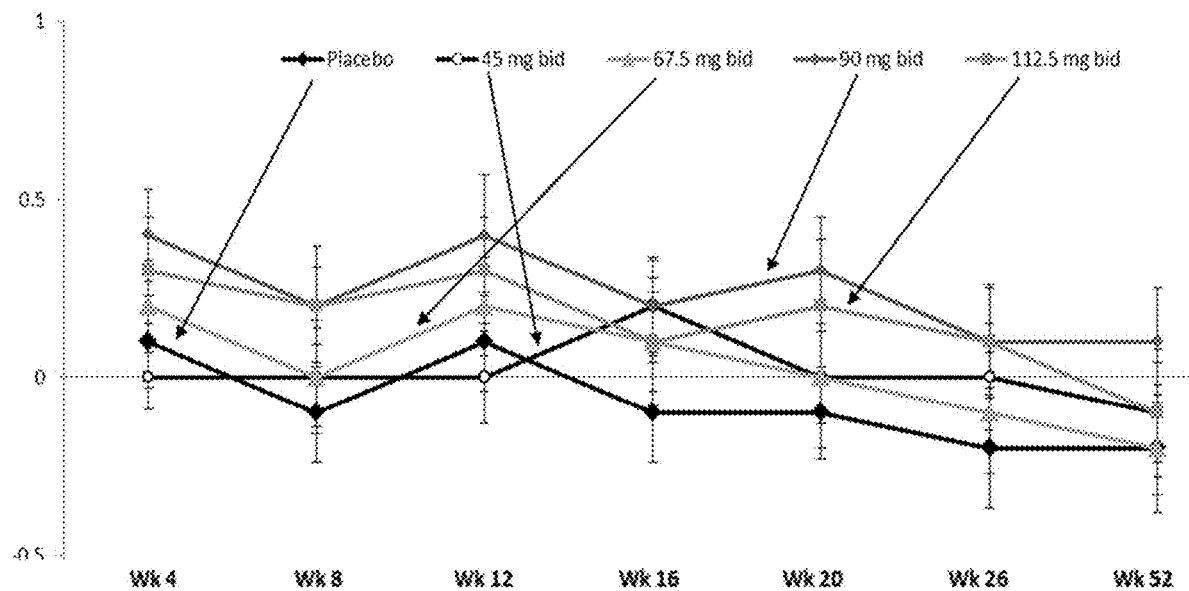

FIG. 47g: Graph showing change from baseline in mPPT Turn 360 Degrees scores full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 47H:
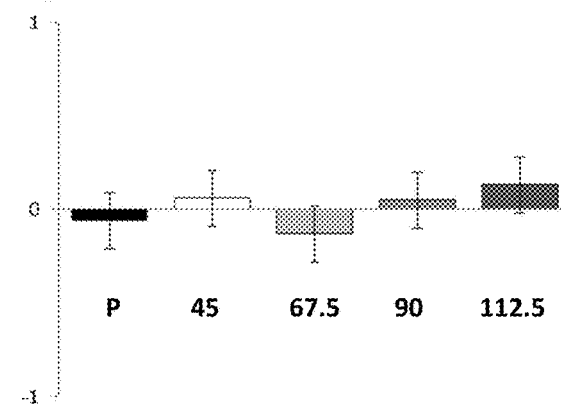

FIG. 47h: Change from baseline in mPPT Turn 360 Degrees scores, full analysis set at 26 weeks. The table below provides the data and P-Values corresponding to FIG. 47h.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 3.2 | 3.2 | 3.1 | 3 | 3.1 |
| Δ to placebo |  | 0.12 | −0.06 | 0.12 | 0.2 |
| p value |  | 0.557 | 0.7586 | 0.5746 | 0.3518 |

Figure 47I:
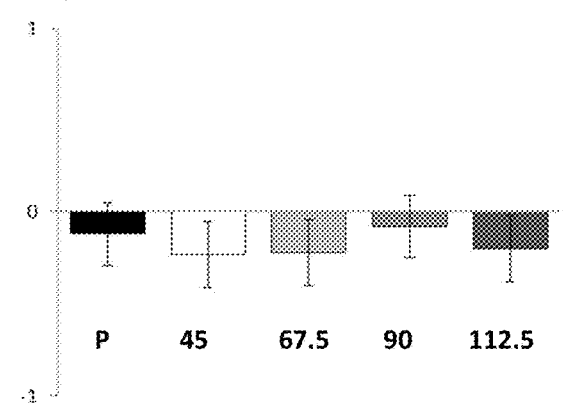

FIG. 47i: Change from baseline in mPPT Turn 360 Degrees scores, full analysis set at 52 weeks. The table below provides the data and P-Values corresponding to FIG. 47i.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 3.2 | 3.2 | 3.1 | 3 | 3.1 |
| Δ to placebo |  | −0.12 | −0.1 | 0.04 | −0.08 |
| p value |  | 0.636 | 0.6733 | 0.8805 | 0.7413 |

Figure 47J:
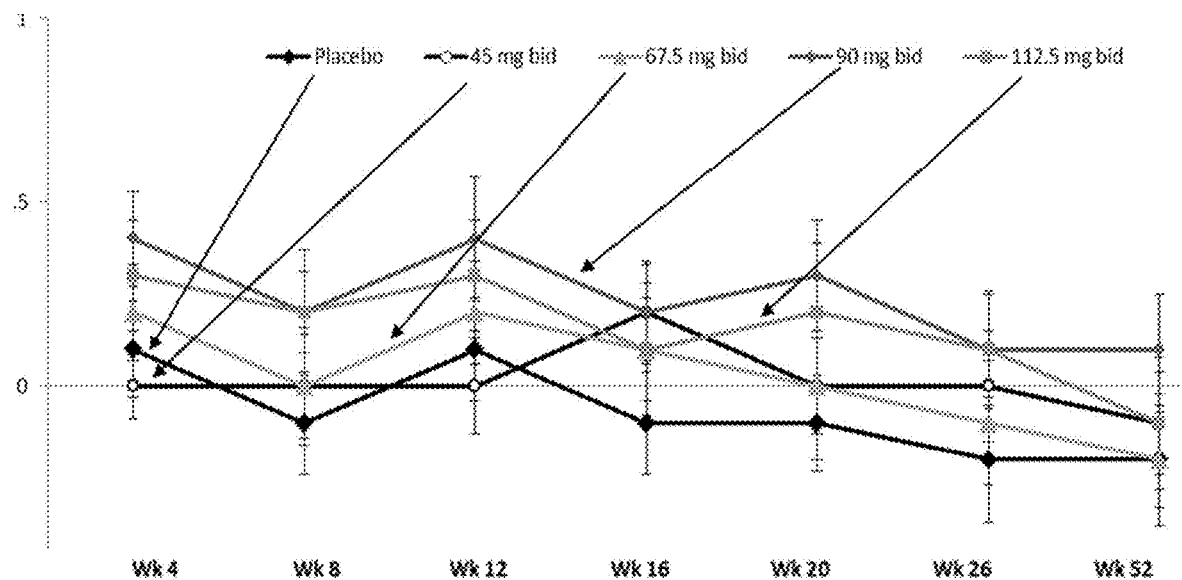

FIG. 47j: Graph showing change from baseline in mPPT 50 Feet Walk scores full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 47K:
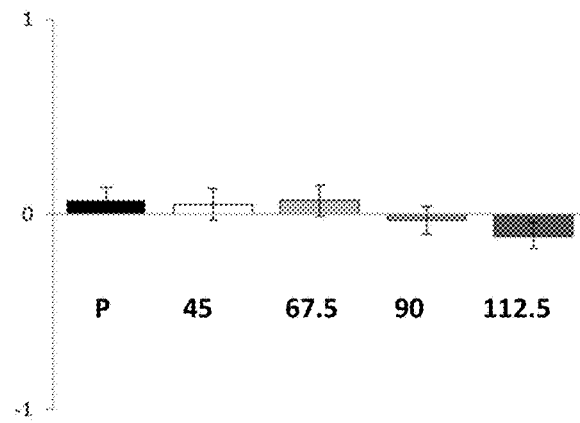

FIG. 47k: Change from baseline in mPPT 50 Feet Walk scores, full analysis set at 26 weeks. The table below provides the data and P-Values corresponding to FIG. 47k.

|  | Placebo | 45 mg bid | 67.5 mg bid | 90 mg bid | 112.5 mg bid |
| --- | --- | --- | --- | --- | --- |
| N | 81 | 75 | 79 | 81 | 81 |
| Baseline | 3.3 | 3.2 | 3.3 | 3.4 | 3.3 |
| Δ to placebo |  | −0.02 | 0 | −0.1 | −0.17 |
| p value |  | 0.8367 | 0.9738 | 0.3331 | 0.0945 |

Figure 47L:
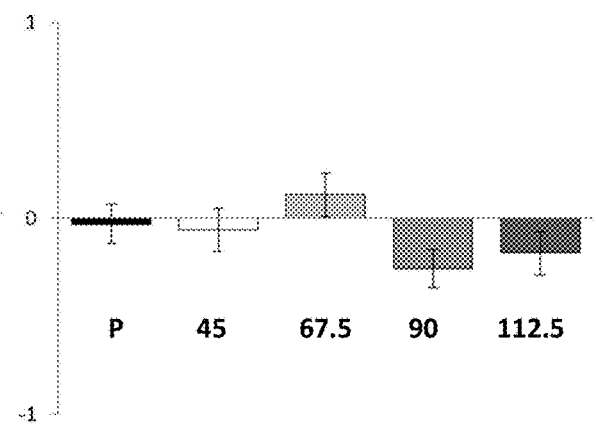

FIG. 47l: Change from baseline in mPPT 50 Feet Walk scores, full analysis set at 52 weeks. The table below provides the data and P-Values corresponding to FIG. 47l.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.3 | 3.2 | 3.3 | 3.4 | 3.3 |
| Δ to placebo |  | −0.03 | 0.15 | −0.23 | −0.15 |
| p value |  | 0.8302 | 0.3032 | 0.1087 | 0.3004 |

Figure 47M:
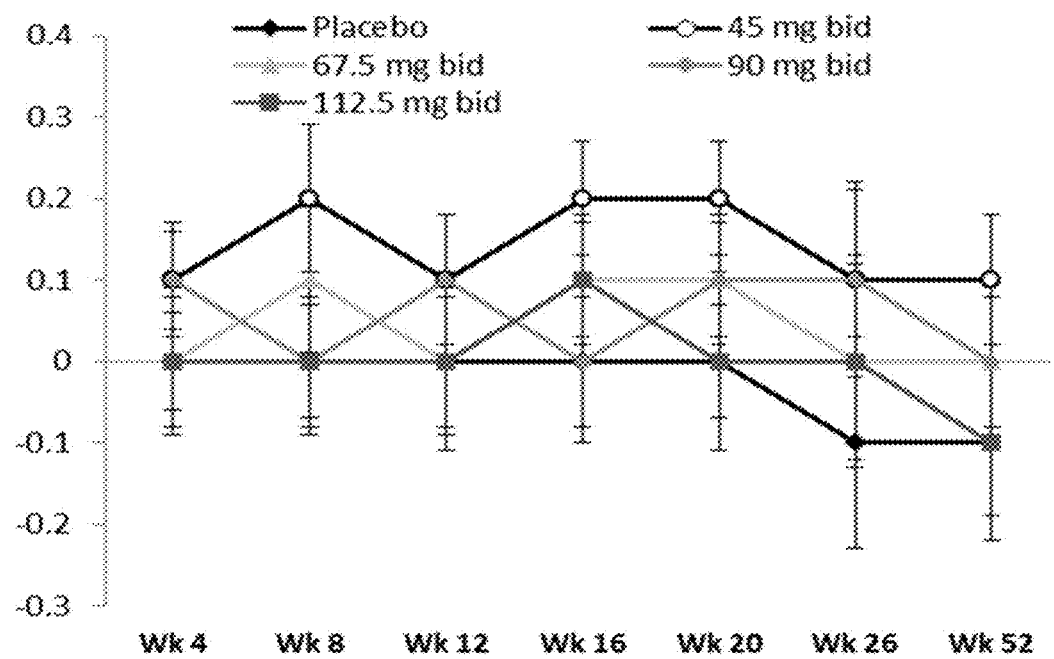

FIG. 47*m*: graph showing change from baseline in mPPT Climb One Flight of Stairs scores full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

Figure 47N:
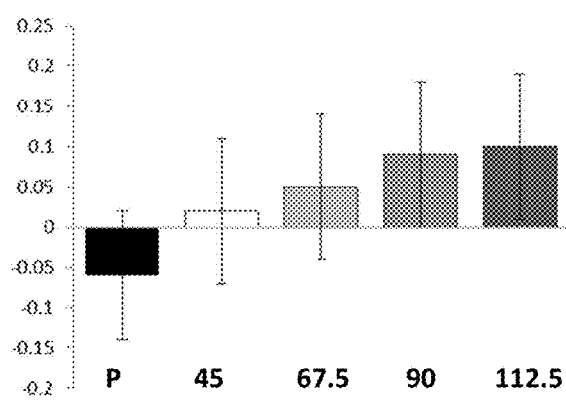

FIG. 47*n*: Change from baseline in mPPT Climb One Flight of Stairs scores, full analysis set at 26 weeks. The table below provides the data and P-Values corresponding to FIG. 47*n*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.6 | 2.6 | 2.7 | 2.6 | 2.8 |
| Δ to placebo |  | 0.08 | 0.11 | 0.15 | 0.16 |
| p value |  | 0.5139 | 0.3671 | 0.2061 | 0.1912 |

Figure 47O:
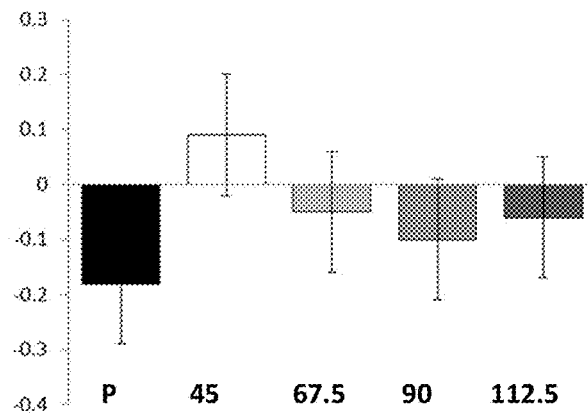

FIG. 47*o*: Change from baseline in mPPT Climb One Flight of Stairs scores, full analysis set at 52 weeks. The table below provides the data and P-Values corresponding to FIG. 47*o*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 2.6 | 2.6 | 2.7 | 2.6 | 2.8 |
| Δ to placebo |  | 0.26 | 0.13 | 0.08 | 0.11 |
| p value |  | 0.0896 | 0.4116 | 0.6043 | 0.4606 |

FIG. 47*p*: Change from baseline in mPPT Climb One Flight of Stairs scores in pridopidine treated late stage HD patients with BL TFC<7, at 52 weeks. The table below provides the data and P-Values corresponding to FIG. 47*p*.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 2.5 | 2.5 | 2.4 | 2.3 | 2.5 |
| Δ to placebo |  | 0.19 | −0.3 | −0.26 | −0.15 |
| p value |  | 0.5914 | 0.3609 | 0.4198 | 0.6539 |

FIG. 47*q*: Change from baseline in mPPT Climb One Flight of Stairs scores in pridopidine treated HD1 and HD2 patients, at 52 weeks. The table below provides the data and P-Values corresponding to FIG. 47*q*.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 2.7 | 2.6 | 2.8 | 2.7 | 2.9 |
| Δ to placebo |  | 0.27 | 0.3 | 0.22 | 0.23 |
| p value |  | 0.1076 | 0.0769 | 0.1955 | 0.1771 |

FIG. 47*r*: Change from baseline in mPPT Climb One Flight of Stairs scores in pridopidine treated HD1 patients, at 52 weeks. The table below provides the data and P-Values corresponding to FIG. 47*r*.

|  | Placebo | 45 mg bid | 67.5 mg bid | 90 mg bid | 112.5 mg bid |
|---|---|---|---|---|---|
| N | 12 | 17 | 17 | 11 | 18 |
| Baseline | 2.7 | 3.2 | 2.7 | 2.9 | 3.2 |
| Δ to placebo |  | −0.02 | 0.01 | −0.06 | 0.18 |
| p value |  | 0.9539 | 0.9627 | 0.86 | 0.5277 |

FIG. 47*s*: Change from baseline in mPPT Climb One Flight of Stairs scores in pridopidine treated HD2 patients, at 52 weeks. The table below provides the data and P-Values corresponding to FIG. 47*s*.

|  | Placebo | 45 mg bid | 67.5 mg bid | 90 mg bid | 112.5 mg bid |
|---|---|---|---|---|---|
| N | 50 | 42 | 37 | 45 | 40 |
| Baseline | 2.7 | 2.3 | 2.9 | 2.7 | 2.8 |
| Δ to placebo |  | 0.35 | 0.34 | 0.28 | 0.23 |
| p value |  | 0.0958 | 0.1189 | 0.1482 | 0.2731 |

FIG. 47*t*: Change from baseline in mPPT Climb One Flight of Stairs scores in pridopidine treated late stage HD patients with BL TFC 0-6, at 52 weeks. The table below provides the data and P-Values corresponding to FIG. 47*t*.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 2.5 | 2.5 | 2.4 | 2.3 | 2.5 |
| Δ to placebo |  | 0.19 | −0.3 | −0.26 | −0.15 |
| p value |  | 0.5914 | 0.3609 | 0.4198 | 0.6539 |

FIG. 47*u*: Graph showing change from baseline in mPPT Climb Stairs (Flights Up and Down) scores full analysis set from week 4 of treatment through week 52. Line with dark diamond represents placebo; line with open circle represents 45 mg bid, line with triangle represents 67.5 mg bid, line with grey diamond represents 90 mg bid, line with square represents 112.5 mg bid.

FIG. 47*v*: Change from baseline in mPPT Climb Stairs (Flights Up and Down) scores, full analysis set at 26 weeks. The table below provides the data and P-Values corresponding to FIG. 47*v*.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.4 | 3.5 | 3.6 | 3.6 | 3.7 |
| Δ to placebo |  | −0.03 | −0.14 | −0.08 | −0.08 |
| p value |  | 0.8134 | 0.195 | 0.464 | 0.4872 |

FIG. 47w: Change from baseline in mPPT Climb Stairs (Flights Up and Down) scores, full analysis set at 52 weeks. The table below provides the data and P-Values corresponding to FIG. 47w.

|  | Placebo | 45 mg bid | 67.5 mg bid | 90 mg bid | 112.5 mg bid |
|---|---|---|---|---|---|
| N | 81 | 75 | 79 | 81 | 81 |
| Baseline | 3.4 | 3.5 | 3.6 | 3.6 | 3.7 |
| Δ to placebo |  | 0.17 | 0.04 | −0.04 | 0.1 |
| p value |  | 0.3209 | 0.8251 | 0.8282 | 0.5759 |

FIG. 47x: Change from baseline in mPPT Climb Stairs (Flights Up and Down) scores in late stage HD patients with BL TFC<7, at 52 weeks. The table below provides the data and P-Values corresponding to FIG. 47x.

|  | Placebo | 45 mg bid | 67.5 mg bid | 90 mg bid | 112.5 mg bid |
|---|---|---|---|---|---|
| N | 19 | 16 | 25 | 25 | 23 |
| Baseline | 3.2 | 3.1 | 3.4 | 3.5 | 3.1 |
| Δ to placebo |  | 0.72 | 0.16 | −0.36 | 0.31 |
| p value |  | 0.0915 | 0.6827 | 0.3305 | 0.4235 |

FIG. 47y: Change from baseline in mPPT Climb Stairs (Flights Up and Down) scores in pridopidine treated HD1 and HD2 patients, at 52 weeks. The table below provides the data and P-Values corresponding to FIG. 47y.

|  | Placebo | 45 mg bid | 67.5 mg bid | 90 mg bid | 112.5 mg bid |
|---|---|---|---|---|---|
| N | 62 | 59 | 54 | 56 | 58 |
| Baseline | 3.5 | 3.6 | 3.7 | 3.6 | 3.9 |
| Δ to placebo |  | −0.01 | 0.01 | 0.1 | 0.07 |
| p value |  | 0.9572 | 0.9614 | 0.5816 | 0.7161 |

DETAILED DESCRIPTION OF THE INVENTION

This invention provides a method of maintaining functional capacity, improving functional capacity, or lessening the decline of functional capacity in a human patient in need thereof comprising periodically orally administering to the patient a pharmaceutical composition comprising pridopidine or a pharmaceutically acceptable salt thereof such that a dose of 90-225 mg of pridopidine is administered to the patient per day, so as to thereby maintain functional capacity, improve functional capacity, or lessening the decline of functional capacity in the human patient. In an embodiment, the method comprises maintaining functional capacity, improving functional capacity, or lessening the decline of functional capacity.

This invention provides a method of maintaining functional capacity, improving functional capacity, reducing the rate of decline of functional capacity, or slowing the rate of functional decline in a human patient in need thereof comprising periodically orally administering to the patient a pharmaceutical composition comprising pridopidine or a pharmaceutically acceptable salt thereof such that a dose of 90-225 mg of pridopidine is administered to the patient per day, so as to thereby maintain functional capacity, improve functional capacity, reduce the rate of decline of functional capacity or slow the rate of functional decline in the human patient. In an embodiment, the method comprises maintaining functional capacity, improving functional capacity, or reducing the rate of decline of functional capacity.

In an embodiment, the method comprises maintaining function capacity. In another embodiment, the method comprises improving functional capacity. In some embodiments, the functional capacity is maintained or improved, for at least 12 weeks, at least 20 weeks, at least 26 weeks, at least 52 weeks, at least 78 weeks, at least 3 years, or at least 5 years.

In another embodiment, the functional capacity is total functional capacity (TFC) measured by UHDRS-TFC and the human patient has an improvement of one (1) or more points in the UHDRS TFC. In some embodiments, the human patient has an improvement of one (1) or more points in the UHDRS TFC after 52 weeks of administration of pridopidine. In another embodiment, the rate of functional decline is less than one (1) point as measured by the UHDRS TFC after 52 weeks of administration of pridopidine.

In one embodiment, the method comprises lessening the decline of functional capacity. In another embodiment, the method comprises lessening the decline of functional capacity and (a) the pharmaceutical composition is administered for more than 26 weeks or (b) the human patient is afflicted with early stage HD. In one embodiment, the method comprises reducing the rate of decline of functional capacity. In another embodiment, the method comprises reducing the rate of decline of functional capacity and (a) the pharmaceutical composition is administered for more than 26 weeks or (b) the human patient is afflicted with early stage HD. In some embodiments, the method comprises lessening functional decline. In some embodiments, the decline in functional capacity is lessened by or the rate of functional decline is slowed for at least 20%, at least 30%, at least 40%, at least 50%, or at least 80%. In another embodiment, the rate of the decline in functional capacity is reduced for at least 12 weeks, at least 20 weeks, at least 26 weeks, at least 52 weeks, at least 78 weeks, at least 3 years, or at least 5 years. In another embodiment, rate of functional decline is slowed in functional capacity is reduced for at least 12 weeks, at least 20 weeks, at least 26 weeks, at least 52 weeks, at least 78 weeks, at least 3 years, or at least 5 years.

In one embodiment, the functional capacity is total functional capacity (TFC). The total functional capacity may be measured by UHDRS-TFC. The total functional capacity may also be measured by the UHDRS Functional Assessment Scale (UHDRS-FAS). In an embodiment the functional capacity is maintained for at least 12 weeks, at least 20 weeks, at least 26 weeks, at least 52 weeks, or at least 78 weeks.

In an embodiment, the human patient has no deterioration of functional capacity. In other embodiments, the human patient has no deterioration of functional capacity for at least 52 weeks.

The invention additionally provides a method of slowing the clinical progression of HD in a human patient comprising periodically orally administering to the patient afflicted with HD a pharmaceutical composition comprising pridopidine or a pharmaceutically acceptable salt thereof such that a dose of 90-225 mg of pridopidine is administered to the patient per day, so as to thereby slow the clinical progression of HD in the patient.

In an embodiment, the clinical progression of HD is measured by total functional capacity. In one embodiment, the clinical progression of HD is slowed by at least 20%, at least 30%, at least 50%, at least 80%, or between 20% and 90%. In another embodiment, the clinical progression of HD is slowed for at least 12 weeks, at least 20 weeks, at least 26 weeks, at least 52 weeks, at least 3 years, or at least 5 years. In a further embodiment, the total functional capacity is measured by the UHDRS-TFC.

This invention also provides a method of reducing functional decline as measured by UHDRS Total Functional Capacity, in a human patient in need thereof comprising periodically orally administering to the human patient a pharmaceutical composition comprising pridopidine or a pharmaceutically acceptable salt thereof such that a dose of 90-225 mg of pridopidine is administered to the patient per day, so as to thereby reduce functional decline in the human patient, wherein the human patient is afflicted with HD and has a baseline TFC score of 11-13.

In an embodiment, functional decline is measured by UHDRS-TFC. In another embodiment, the method comprises reducing functional decline for at least 12 weeks, at least 20 weeks, at least 26 weeks, at least 52 weeks, at least 78 weeks, at least 3 years, or at least 5 years.

This invention also provides a method of maintaining, improving, or lessening the decline of, a human patient's ability to perform activities of daily living, comprising periodically orally administering to the human patient in need thereof a pharmaceutical composition comprising pridopidine or a pharmaceutically acceptable salt thereof such that a dose of 90-225 mg of pridopidine is administered to the patient per day, so as to thereby maintain, improve, or lessen the decline of the human patient's ability to perform activities of daily living.

This invention also provides a method of maintaining, improving, or reducing the rate of decline of, a human patient's ability to perform activities of daily living, comprising periodically orally administering to the human patient in need thereof a pharmaceutical composition comprising pridopidine or a pharmaceutically acceptable salt thereof such that a dose of 90-225 mg of pridopidine is administered to the patient per day, so as to thereby maintain, improve, or reduce the rate of decline of the human patient's ability to perform activities of daily living.

In one embodiment, the human patient's ability to perform activities of daily living is maintained, improved, or the decline is lessened over a period of at least 12 weeks, at least 20 weeks, at least 26 weeks, at least 52 weeks, or at least 78 weeks. In one embodiment, the human patient's ability to perform activities of daily living is maintained, improved, or the rate of decline is reduced for at least 12 weeks, at least 20 weeks, at least 26 weeks, at least 52 weeks, or at least 78 weeks. In another embodiment, the method comprises maintaining the human patient's ability to perform activities of daily living. In an embodiment, the ability to perform activities of daily living is measured by the Activities of Daily Living (ADL) domain of the TFC.

The invention also provides a method of maintaining, improving, or lessening the decline of, a human patient's ability to manage finances, comprising periodically orally administering to the human patient in need thereof a pharmaceutical composition comprising pridopidine or a pharmaceutically acceptable salt thereof such that a dose of 90-225 mg of pridopidine is administered to the patient per day, so as to thereby maintain, improve, or lessen the rate of decline of the human patient's ability to manage finances.

The invention also provides a method of maintaining, improving, or reducing the rate of decline of, a human patient's ability to manage finances, comprising periodically orally administering to the human patient in need thereof a pharmaceutical composition comprising pridopidine or a pharmaceutically acceptable salt thereof such that a dose of 90-225 mg of pridopidine is administered to the patient per day, so as to thereby maintain, improve, or reduce the rate of decline of the human patient's ability to manage finances.

In another embodiment, administering further maintains, improves, or lessens the decline of the human patient's ability to manage finances. In an embodiment, the human patient's ability to manage finances is maintained, improved, or the decline of is lessened for at least 12 weeks, at least 20 weeks, at least 26 weeks, at least 52 weeks, or at least 78 weeks. In another embodiment, administering further maintains, improves, or reduces the rate of decline of the human patient's ability to manage finances. In an embodiment, the human patient's ability to manage finances is maintained, improved, or the rate of decline is reduced for at least 12 weeks, at least 20 weeks, at least 26 weeks, at least 52 weeks, or at least 78 weeks. In one embodiment, the method comprises maintaining the human patient's ability to manage finances. In another embodiment, the method comprises improving the human patient's ability to manage finances. In some embodiments, the ability to manage finances is measured by the Managing Finances domain of the TFC.

In one embodiment, administering further maintains, improves, or reduces the rate of decline of the human patient's ability to perform domestic chores. In another embodiment, administering further maintains, improves, or lessens the decline of the human patient's ability to perform domestic chores.

The invention also provides a method of maintaining, improving, or lessening the decline of, a human patient's ability to perform domestic chores, comprising periodically orally administering to the human patient in need therefore a pharmaceutical composition comprising pridopidine or a pharmaceutically acceptable salt thereof such that a dose of 90-225 mg of pridopidine is administered to the patient per day, so as to thereby maintain, improve, or lessen the decline of the human patient's ability to perform domestic chores.

The invention also provides a method of maintaining, improving, or reducing the rate of decline of, a human patient's ability to perform domestic chores, comprising periodically orally administering to the human patient in need therefore a pharmaceutical composition comprising pridopidine or a pharmaceutically acceptable salt thereof such that a dose of 90-225 mg of pridopidine is administered to the patient per day, so as to thereby maintain, improve, or reduce the rate of decline of the human patient's ability to perform domestic chores.

In an embodiment, the ability to perform domestic chores is measured by the Domestic Chores domain of the UHDRS TFC. In another embodiment, the human patient's ability to perform domestic chores is maintained or improved for at least 12 weeks, at least 20 weeks, at least 26 weeks, at least 52 weeks, or at least 78 weeks. In another embodiment, the method comprises maintaining the human patient's ability to perform domestic chores. In one embodiment, the method comprises improving the human patient's ability to perform domestic chores. In another embodiment, the human patient's ability to perform domestic chores is maintained or improved, or the rate of decline is reduced for at least 12 weeks, at least 20 weeks, at least 26 weeks, at least 52 weeks, or at least 78 weeks. In a further embodiment, the human patient's ability to perform domestic chores is maintained or improved, or the decline is lessened for at least 12 weeks, at least 20 weeks, at least 26 weeks, at least 52 weeks, or at least 78 weeks.

In one embodiment, administering further maintains, improves, or reduces the rate of decline of, the care level of the human patient. In another embodiment, administering further maintains, improves, or lessens the decline of, the care level of the human patient.

The invention also provides, a method of maintaining, improving, or lessening the decline of, a human patient's care level, comprising periodically orally administering to the human patient in need thereof a pharmaceutical composition comprising pridopidine such that a dose of 90-225 mg of pridopidine is administered to the patient per day, so as to thereby maintain, improve, or lessen the decline of the human patient's care level.

The invention also provides, a method of maintaining, improving, or reducing the rate of decline of, a human patient's care level, comprising periodically orally administering to the human patient in need thereof a pharmaceutical composition comprising pridopidine such that a dose of 90-225 mg of pridopidine is administered to the patient per day, so as to thereby maintain, improve, or reduce the rate of decline of the human patient's care level.

In an embodiment, the care level is measured by the Care level domain of the TFC. In another embodiment, the human patient's care level is maintained, improved, or the rate of decline is reduced for at least 12 weeks, at least 20 weeks, at least 26 weeks, at least 52 weeks, or at least 78 weeks. In another embodiment, the human patient's care level is maintained, improved, or the decline of is lessened for at least 12 weeks, at least 20 weeks, at least 26 weeks, at least 52 weeks, or at least 78 weeks. In another embodiment, the method comprises maintaining the care level of the human patient.

In one embodiment, a dose of 135-225 mg of pridopidine is administered to the patient per day. In another embodiment, a dose of 180-225 mg of pridopidine is administered to the patient per day. In another embodiment, a dose of 90 mg of pridopidine is administered to the patient per day, a dose of 135 mg of pridopidine is administered to the patient per day, a dose of 180 mg of pridopidine is administered to the patient per day, or a dose of 225 mg of pridopidine is administered to the patient per day. In another embodiment, a dose of 135 mg of pridopidine is administered to the patient per day, a dose of 180 mg of pridopidine is administered to the patient per day, or a dose of 225 mg of pridopidine is administered to the patient per day. In another embodiment, a dose of 180 mg of pridopidine is administered to the patient per day, or a dose of 225 mg of pridopidine is administered to the patient per day. In another embodiment, a dose of 90 mg of pridopidine is administered to the patient per day, a dose of 135 mg of pridopidine is administered to the patient per day, or a dose of 180 mg of pridopidine is administered to the patient per day. In another embodiment, a dose of 90 mg of pridopidine is administered to the patient per day. In another embodiment, a dose of 90 mg of pridopidine is administered to the patient per day in unit doses of 45 mg twice per day. In another embodiment, a dose of 135 mg of pridopidine is administered to the patient per day. In another embodiment, a dose of 135 mg of pridopidine is administered to the patient per day in unit doses of 67.5 mg twice per day. In another embodiment, a dose of 180 mg of pridopidine is administered to the patient per day. In another embodiment, a dose of 180 mg of pridopidine is administered to the patient per day in unit doses of 90 mg twice per day. In another embodiment, a dose of 225 mg of pridopidine is administered to the patient per day. In another embodiment, a dose of 225 mg of pridopidine is administered to the patient per day in unit doses of 112.5 mg twice per day.

The invention further provides a method of reducing dystonia or maintaining a level of dystonia in a human patient in need thereof comprising periodically orally administering to the patient a pharmaceutical composition comprising pridopidine such that a dose of 90-225 mg of pridopidine is administered to the patient per day, so as to thereby reduce dystonia or maintain a level of dystonia in the human patient.

In one embodiment, dystonia is measured by the UHDRS TMS Dystonia score. In another embodiment, the level of dystonia in the human patient is reduced or maintained for at least 12 weeks, at least 20 weeks, at least 26 weeks, at least 52 weeks, or at least 78 weeks.

In some embodiment the dystonia is limb dystonia.

The invention also provides a method of treating limb dystonia in a human patient in need thereof comprising periodically orally administering to the patient a pharmaceutical composition comprising pridopidine such that a dose of 90-225 mg of pridopidine is administered to the patient per day, so as to thereby treat the limb dystonia in the human patient. In many embodiments, (a) the pharmaceutical composition is administered for more than 26 weeks or (b) a titration dose of an amount different from the intended dose is administered for a period of time at the start of the periodic administration or (c) the human patient is afflicted with early stage HD In an embodiment, a dose of 135-225 mg of pridopidine is administered to the patient per day. In another embodiment, a dose of 135 mg of pridopidine is administered to the patient per day, a dose of 135 mg of pridopidine is administered to the patient per day, a dose of 180 mg of pridopidine is administered to the patient per day, or a dose of 225 mg of pridopidine is administered to the patient per day. In another embodiment, a dose of 135 mg of pridopidine is administered to the patient per day, a dose of 180 mg of pridopidine is administered to the patient per day, or a dose of 225 mg of pridopidine is administered to the patient per day. In another embodiment, a dose of 180 mg of pridopidine is administered to the patient per day, or a dose of 225 mg of pridopidine is administered to the patient per day. In another embodiment, a dose of 180 mg of pridopidine is administered to the patient per day. In another embodiment, a dose of 90 mg of pridopidine is administered to the patient per day.

In another embodiment, the pharmaceutical composition is administered for at least 12 weeks, at least 20 weeks, at least 26 weeks, more than 26 weeks, at least 52 weeks, at least 54 weeks, at least 78 weeks, at least 104 weeks or more. In another embodiment, the treating limb dystonia comprises preventing the slowing, the reduction in amplitude, or the impairment of the human patient's finger tapping ability and/or preventing the slowing or the irregular performance of the Pronate-Supinate Hands test in the human patient.

This invention also provides a method of preventing the slowing, the reduction in amplitude, or the impairment of the human patient's finger tapping ability and/or preventing the slowing or the irregular performance of the Pronate-Supinate Hands test in a human HD patient comprising periodically orally administering to the patient a pharmaceutical composition comprising pridopidine such that a dose of 90-225 mg of pridopidine is administered to the patient per day so as to thereby prevent the slowing, the reduction in amplitude, or the impairment of the human patient's finger tapping ability and/or prevent the slowing or the irregular performance of the Pronate-Supinate Hands test in the human patient.

In another embodiment, the treating limb dystonia comprises preventing the impairment of the human patient's finger tapping ability and/or preventing the slowing or the irregular performance of the Q-Motor: Pro-Sup-Frequency-MN-Hand (Hz) test. In another embodiment, the treating comprises improving the human patient's Q-Motor tap speed frequency. In another embodiment, the treating comprises improving the human patient's Q-Motor tap speed inter onset interval (IOI).

The invention further provides a method of improving or maintaining, a human patient's gait and balance comprising periodically orally administering to the human patient in need thereof a pharmaceutical composition comprising pridopidine such that a dose of 90-225 mg of pridopidine is administered to the patient per day, so as to thereby improve or maintain, a human patient's gait and balance.

In one embodiment, a dose of 90 mg, 135 mg, 180 mg, or 225 mg of pridopidine is administered to the patient per day. In another embodiment, a dose of 90 mg of pridopidine is administered to the patient per day. In another embodiment, a dose of 180 mg of pridopidine is administered to the patient per day. In another embodiment, a dose of 135 mg or 180 mg of pridopidine is administered to the patient per day.

Additionally provided is a method of improving, maintaining, or lessening the decline of, a human patient's gait and balance comprising periodically orally administering to the human patient in need thereof a pharmaceutical composition comprising pridopidine such that a dose of 90 mg of pridopidine is administered to the patient per day, so as to thereby improve, maintain, or lessen the decline of, a human patient's gait and balance.

Also provided is a method of improving, maintaining, or slowing the decline of, a human patient's gait and balance comprising periodically orally administering to the human patient in need thereof a pharmaceutical composition comprising pridopidine such that a dose of 90 mg of pridopidine is administered to the patient per day, so as to thereby improve, maintain, or slow the decline of, a human patient's gait and balance.

In an embodiment, the human patient's gait and balance is measured by the UHDRS gait and balance score. In some embodiments, the human patient's gait and balance is improved or maintained or the decline is lessened for at least 12 weeks, at least 20 weeks, at least 26 weeks, at least 52 weeks, or at least 78 weeks.

In an embodiment, the human patient's gait and balance is measured by the UHDRS gait and balance score. In some embodiments, the human patient's gait and balance is improved or maintained or the decline is slowed for at least 12 weeks, at least 20 weeks, at least 26 weeks, at least 52 weeks, or at least 78 weeks.

The invention also provides a method of improving or maintaining, a human patient's independence comprising periodically orally administering to the human patient in need thereof a pharmaceutical composition comprising pridopidine such that a dose of 90-225 mg of pridopidine is administered to the patient per day, so as to thereby improve or maintain a human patient's independence.

In one embodiment, a dose of 90 mg, 135 mg, 180 mg, or 225 mg of pridopidine is administered to the patient per day. In another embodiment, a dose of 90 mg of pridopidine is administered to the patient per day. In another embodiment, a dose of 225 mg of pridopidine is administered to the patient per day.

The invention also provides a method of improving, maintaining, or lessening the decline of, a human patient's independence comprising periodically orally administering to the human patient in need thereof a pharmaceutical composition comprising pridopidine such that a dose of 90 mg of pridopidine is administered to the patient per day, so as to thereby improve, maintain, or lessen the decline of, a human patient's independence.

The invention also provides a method of improving, maintaining, or slowing the decline of, a human patient's independence comprising periodically orally administering to the human patient in need thereof a pharmaceutical composition comprising pridopidine such that a dose of 90 mg of pridopidine is administered to the patient per day, so as to thereby improve, maintain, or slow the decline of, a human patient's independence.

In an embodiment, the human patient's independence is measured by the UHDRS Independence score. In some embodiments, the human patient's independence is improved or maintained, or the decline is slowed for at least 12 weeks, at least 20 weeks, at least 26 weeks, at least 52 weeks, or at least 78 weeks. In one embodiment, the human patient's independence is improved or maintained, or the decline is lessened for at least 12 weeks, at least 20 weeks, at least 26 weeks, at least 52 weeks, or at least 78 weeks.

The invention also provides a method of improving or maintaining a human patient's cognitive domains comprising periodically orally administering to the human patient in need thereof a pharmaceutical composition comprising pridopidine such that a dose of 90-225 mg of pridopidine is administered to the patient per day, so as to thereby improve or maintain the human patient's cognitive domains. A patient's cognitive domains may also be the patient's cognitive performance across a variety of domains In one embodiment, a dose of 90-180 mg of pridopidine is administered to the patient per day. In another embodiment, a dose of 90 mg, 135 mg, or 180 mg of pridopidine is administered to the patient per day. In another embodiment, a dose of 90 mg, or 180 mg of pridopidine is administered to the patient per day.

Further provided is a method of improving, maintaining, or lessening the decline of, a human patient's cognitive domains comprising periodically orally administering to the human patient in need thereof a pharmaceutical composition comprising pridopidine such that a dose of 90 mg of pridopidine is administered to the patient per day, so as to thereby improve, maintain, or lessen the decline of, a human patient's cognitive domains. Cognitive domains may be understood as cognitive performance across a variety of domains.

Further provided is a method of improving, maintaining, or slowing the decline of, a human patient's cognitive domains comprising periodically orally administering to the human patient in need thereof a pharmaceutical composition comprising pridopidine such that a dose of 90 mg of pridopidine is administered to the patient per day, so as to thereby improve, maintain, or slow the decline of, a human patient's cognitive domains. Cognitive domains may be understood as cognitive performance across a variety of domains.

The human patient's cognitive domains may be measured, for example, by the cognitive assessment battery (CAB). The human patient's cognitive domains may also be measured by the Hopkins Verbal Learning Test—Revised (HVLT-R). The human patient's cognitive domains may additionally be measured by the Paced Tapping test, the Montreal Cognitive Assessment (MoCA) scale or the Symbol Digit Modalities Test (SDMT). The human patient's cognitive domains may additionally be measured by trail making test B (TMT-B). In one embodiment, the human patient's cognitive domains is maintained or improved, or the decline is slowed for at least 12 weeks, at least 20 weeks, at least 26 weeks, at least 52 weeks, or at least 78 weeks. In some embodiments, slowing the decline of a human patient's cognitive domains comprises slowing the rate of cognitive decline. In an embodiment, the human patient's cognitive domains is maintained or improved, or the decline is lessened for at least 12 weeks, at least 20 weeks, at least 26 weeks, at least 52 weeks, or at least 78 weeks.

The invention also provides a method of reducing the severity of the sustained or intermittent muscle contractions associated with dystonia in a human patient in need thereof comprising periodically orally administering to the patient a pharmaceutical composition comprising pridopidine such that a dose of 90-225 mg of pridopidine is administered to the patient per day, so as to thereby reduce the severity of the sustained or intermittent muscle contractions associated with dystonia in the human patient. In many embodiments, (a) the pharmaceutical composition is administered for more than 26 weeks or (b) a titration dose of an amount different from the intended dose is administered for a period of time at the start of the periodic administration and/or (c) the human patient is afflicted with early stage HD.

The severity of the sustained or intermittent muscle contractions associated with dystonia in a human patient may be measured by, for example, the UHDRS TMS Dystonia score.

Further provided is a method of improving or maintaining motor ability in a human patient in need thereof comprising periodically orally administering to the patient a pharmaceutical composition comprising pridopidine such that a dose of 90-225 mg of pridopidine is administered to the patient per day, so as to thereby maintain or improve motor ability in the human patient.

The motor ability may be measured, for example, by the UHDRS TMS score, the UHDRS TMS score excluding chorea or UHDRS TMS score excluding dystonia.

In an embodiment, a dose of 90 mg, 135 mg, 180 mg, or 225 mg of pridopidine is administered to the patient per day. In another embodiment, a dose of 90 mg of pridopidine is administered to the patient per day. In another embodiment, a dose of 180 mg of pridopidine is administered to the patient per day. In another embodiment, the motor ability is maintained or improved for at least 12 weeks, at least 20 weeks, at least 26 weeks, at least 52 weeks, at least 78 weeks.

The invention also provides a method of reducing or maintaining the level of chorea in a human patient in need thereof comprising periodically orally administering to the patient a pharmaceutical composition comprising pridopidine such that a dose of 90-225 mg of pridopidine is administered to the patient per day, so as to thereby reduce or maintain the level of chorea in a human patient.

In one embodiment, a dose of 90 mg, 135 mg, 180 mg, or 225 mg of pridopidine is administered to the patient per day. In another embodiment, a dose of 90 mg of pridopidine is administered to the patient per day. In another embodiment, a dose of 135 mg or 180 mg of pridopidine is administered to the patient per day. The level of chorea may also be reduced.

The invention also provides a method of reducing, maintaining, or lessening the increase of, chorea in a human patient in need thereof comprising periodically orally administering to the patient a pharmaceutical composition comprising pridopidine such that a dose of 90 mg of pridopidine is administered to the patient per day, so as to thereby reduce, maintain, or lessen the increase of, chorea in a human patient.

The invention also provides a method of reducing, maintaining, or slowing the increase of, chorea in a human patient in need thereof comprising periodically orally administering to the patient a pharmaceutical composition comprising pridopidine such that a dose of 90 mg of pridopidine is administered to the patient per day, so as to thereby reduce, maintain, or slow the increase of, chorea in a human patient.

In one embodiment, the chorea in the human patient is improved, or maintained, or the increase is slowed for at least 12 weeks, at least 20 weeks, at least 26 weeks, at least 52 weeks, or at least 78 weeks. In an embodiment, the chorea in the human patient is improved, or maintained, or the increase is lessened for at least 12 weeks, at least 20 weeks, at least 26 weeks, at least 52 weeks, or at least 78 weeks. The human patient's chorea may be measured by the UHDRS TMS chorea score.

The invention further provides a method of improving, maintaining, reducing or lessening the decline of a human patient's behavior and/or psychiatric state comprising periodically orally administering to the human patient in need thereof a pharmaceutical composition comprising pridopidine such that a dose of 90-225 mg of pridopidine is administered to the patient per day, so as to thereby improve, maintain, reduce, or lessen the decline of the human patient's behavior and/or psychiatric state.

In one embodiment, the method comprises maintaining a human patient's behavior and/or psychiatric state. In another embodiment, the method comprises improving the human patient's behavior and/or psychiatric state. In another embodiment, the human patient's behavior and/or psychiatric state is improved, maintained or the decline is reduced or lessened for at least 12 weeks, at least 20 weeks, at least 26 weeks, at least 52 weeks, or at least 78 weeks.

The human patient's behavior and/or psychiatric state may be measured by the Problem Behaviors Assessment (PBA) total score. The human patient's behavior and/or psychiatric state may also be measured by the Problem Behaviors Assessment-short form (PBA-s). The human patient's behavior and/or psychiatric state may also be measured by the Problem Behaviors Assessment for depressed mood. The human patient's behavior and/or psychiatric state may also be measured by the Problem Behaviors Assessment for irritability. The human patient's behavior and/or psychiatric state may also be measured by the Problem Behaviors Assessment for lack of initiative or apathy. The human patient's behavior and/or psychiatric state may also be measured by the Problem Behaviors Assessment short form apathy sub-item. The human patient's behavior and/or psychiatric state may also be measured by the Apathy Evaluation Scale (AES). The human patient's behavior and/or psychiatric state may be measured by the Problem Behaviors Assessment for obsessive-compulsiveness. The human patient's behavior and/or psychiatric state may also be measured by the Problem Behaviors Assessment for disoriented behavior. In some embodiments, the human patient's behavior and/or psychiatric state is measured by the Problem Behaviors Assessment short form apathy sub-item or the Problem Behaviors Assessment-short form (PBA-s).

The invention also provides a method of reducing or maintaining a human patient's involuntary movements comprising periodically orally administering to the human patient in need thereof a pharmaceutical composition comprising pridopidine such that a dose of 90-225 mg of pridopidine is administered to the patient per day, so as to thereby reduce or maintain a human patient's involuntary movements.

In one embodiment, the human patient's involuntary movements are reduced or maintained for at least 12 weeks, at least 20 weeks, at least 26 weeks, at least 52 weeks, or at least 78 weeks. The patient's involuntary movements may be measured by UHDRS TMS Involuntary Movements score.

The invention further provides method of improving or maintaining a human patient's mobility comprising periodically orally administering to the human patient in need thereof a pharmaceutical composition comprising pridopidine such that a dose of 90-225 mg of pridopidine is administered to the patient per day, so as to thereby improve or maintain the human patient's mobility.

In one embodiment, the human patient's mobility is improved, or maintained for at least 12 weeks, at least 20 weeks, at least 26 weeks, at least 52 weeks, or at least 78 weeks. The human patient's mobility may be measured by the Timed Up and Go Test. The human patient's mobility may also be measured by the Walk-12 Total Score. The human patient's mobility may further be measured by the patient's walking ability.

This invention also provides a method of improving or maintaining a human patient's ability to perform physical tasks comprising periodically orally administering to the human patient in need thereof a pharmaceutical composition comprising pridopidine such that a dose of 90-225 mg of pridopidine is administered to the patient per day, so as to thereby improve or maintain the human patient's ability to perform physical tasks.

In one embodiment, the human patient's ability to perform physical tasks is improved, or maintained for at least 12 weeks, at least 20 weeks, at least 26 weeks, at least 52 weeks or at least 78 weeks. In one embodiment, the human patient's ability to perform physical tasks is measured by the modified physical performance test (mPPT).

In another embodiment, the human patient's ability to perform physical tasks is measured by the mPPT stairs climbing test. In another embodiment, the human patient's ability to perform physical tasks is measured by the mPPT total score. In another embodiment, the human patient's ability to perform physical tasks is measured by the mPPT standing static balance test. In another embodiment, the human patient's ability to perform physical tasks is measured by the mPPT chair rise test. In another embodiment, the human patient's ability to perform physical tasks is measured by the mPPT lift a book and put it on a shelf test. In another embodiment, the human patient's ability to perform physical tasks is measured by the mPPT put on and remove a jacket test. In another embodiment, the human patient's ability to perform physical tasks is measured by the mPPT pick up a penny from floor test. In another embodiment, the human patient's ability to perform physical tasks is measured by the mPPT turn 360 degrees test. In another embodiment, the human patient's ability to perform physical tasks is measured by the mPPT 50 feet walk test. In another embodiment, the human patient's ability to perform physical tasks is measured by the mPPT climb one flight of stairs test. In another embodiment, the human patient's ability to perform physical tasks is measured by the mPPT climb stairs test (flights up and down).

The invention also provides, a method of improving or maintaining a human patient's quality of life comprising periodically orally administering to the patient a pharmaceutical composition comprising pridopidine such that a dose of 90-225 mg of pridopidine is administered to the patient per day, so as to thereby improve or maintain the human patient's quality of life.

In one embodiment, the human patient's quality of life is improved, or maintained for at least 12 weeks, at least 20 weeks, at least 26 weeks, at least 52 weeks, or at least 78 weeks. In another embodiment, the human patient's quality of life is maintained. In another embodiment, the human patient's quality of life is measured by the Huntington's Disease Quality of Life (HD-QoL) score.

The invention further provides a method of reducing the natural decline in the total functional capacity of a HD patient, comprising periodically orally administering to the patient a pharmaceutical composition comprising pridopidine such that a dose of 90-225 mg of pridopidine is administered to the patient per day, so as to thereby reduce the natural decline in the total functional capacity in the human patient. In one embodiment, the natural decline is reduced by 20-70%, 30%-60%, or 35%-45%. In another embodiment, the natural decline is reduced by 20%, 30%, 40%, 50%, 60% or 70%. In an embodiment, the natural decline is lessened by 0.16-0.56, 0.24-0.48, 0.28-0.36 points per year as measured by the UHDRS-TFC. In another embodiment, the natural decline is lessened by 0.16, 0.24, 0.32, 0.4, 0.48 or 0.56 points per year as measured by UHDRS-TFC.

Neurofilament light proteins (NfL) may be used as a biomarker of neurodegeneration in HD patients (Byrne 2017). NfL concentrations in plasma were found to increase with advancing HD disease. Thus, NfL concentrations in plasma of HD patients may provide a means for assessing and predicting neural damage in patients with HD (Byrne 2017). Additionally, results suggest that NfL in the blood could provide a reliable estimate of the concentration of NfL in the CSF (Byrne 2017).

The invention further provides a method of maintaining, reducing, or lessening the increase of, the concentration of neurofilament light protein in a HD patient, comprising periodically orally administering to the patient a pharmaceutical composition comprising pridopidine such that a dose of 90-225 mg of pridopidine is administered to the patient per day, so as to thereby maintain, decrease, or lessen the increase of, the concentration of neurofilament light protein in the human patient. In one embodiment, the increase of the concentration of neurofilament light protein is lessened in the human patient. In another embodiment, the concentration of neurofilament light protein is maintained or decreased in the human patient.

The invention further provides a method of predicting clinical responsiveness to pridopidine therapy in a subject afflicted with HD, the method comprising administering an amount of pridopidine and evaluating the amount of a neurofilament light protein in the subject, so as to thereby predict clinical responsiveness to pridopidine.

In one embodiment, the method further comprising predicting positive clinical responsiveness to pridopidine if the amount of the neurofilament light protein is decreased in the subject after administration of pridopidine compared to baseline. In one embodiment, the method further comprising predicting positive clinical responsiveness to pridopidine if the amount of the neurofilament light protein is maintained in the subject after administration of pridopidine relative to baseline. In another embodiment, the method further comprising predicting positive clinical responsiveness to pridopidine if the amount of the neurofilament light protein is increased in the subject after administration of pridopidine. Baseline, in this paragraph, is the amount of the neurofilament light protein prior to administration of pridopidine.

In one embodiment, the subject is identified as a pridopidine responder if amount of the biomarker is higher than a reference value. In another embodiment, the subject is identified as a pridopidine responder if amount of the biomarker is lower than a reference value.

In another embodiment, if the subject is identified as a pridopidine responder, the subject is thereafter administered a pharmaceutical composition comprising pridopidine.

In one embodiment, a dose of 90 mg, 135 mg, 180 mg or 225 mg of pridopidine is administered to the patient per day. In another embodiment, a dose of 90 mg, 135 mg, or 225 mg of pridopidine is administered to the patient per day. In another embodiment, a dose of 90 mg of pridopidine is administered to the patient per day. In another embodiment, a dose of 135 mg of pridopidine is administered to the patient per day. In another embodiment, a dose of 180 mg of pridopidine is administered to the patient per day. In another embodiment, a dose of 225 mg of pridopidine is administered to the patient per day.

In an embodiment, the human patient is afflicted with HD.

In some embodiments, a unit dose of the pharmaceutical composition contains 45 mg, 67.5 mg, 90 mg, or 112.5 mg of pridopidine.

In an embodiment, the pharmaceutical composition is administered twice per day. In another embodiment, an equal amount of the pharmaceutical composition is administered at each administration. In an embodiment, the two doses are administered at least 6 hours apart, at least 7 hours, at least 8 hours, at least 9 hours, at least 10 hours, at least 11 hours apart. In some embodiments, the pharmaceutical composition is administered for at least 12 weeks, at least 20 weeks, at least 26 weeks, more than 26 weeks, at least 52 weeks, or at least 78 weeks.

In one embodiment, the patient has a UHDRS-TMS score ≥25 before beginning treatment. In another embodiment, the patient has a UHDRS-IS (UHDRS-Independence Scale) score below 90% before beginning treatment. In another embodiment, the patient has greater than or equal to 36 CAG repeats in the huntingtin gene. In another embodiment, the human patient has greater than 44 CAG repeats in the huntingtin gene. In another embodiment, the human patient has less than 44 CAG repeats in the huntingtin gene. In another embodiment, the human patient is afflicted with early stage HD. In another embodiment, the human patient has a baseline TFC score which is greater than or equal to 9. In another embodiment, the human patient has a baseline TFC score which is greater than or equal to 7. In another embodiment, the human patient has a baseline TFC score of 11-13. In another embodiment, the human patient has a baseline TFC score of 7-10. In another embodiment, the human patient has a baseline TFC score of 0-6. In another embodiment, the human patient is afflicted with HD and has a baseline TMS score which is in the least severe quarter of the overall population of patients afflicted with HD. In another embodiment, the human patient is afflicted with HD and has a baseline TMS score which is in the two least severe quarters of the overall population of patients afflicted with HD. In another embodiment, the human patient is afflicted with HD and has a baseline TMS score which is in the three least severe quarters of the overall population of patients afflicted with HD. In another embodiment, the human patient is afflicted with HD and has a baseline TMS score which is in the three least severe quarters of the overall population of patients afflicted with HD or a baseline TFC score which is greater than or equal to 9. In another embodiment, the human patient is afflicted with HD and has a baseline TMS score which is in the three least severe quarters of the overall population of patients afflicted with HD or a baseline TFC score which is greater than or equal to 9 or less than 44 CAG repeats in the huntingtin gene. In another embodiment, the human patient is afflicted with HD and has a baseline TMS score which is in the two least severe quarters of the overall population of patients afflicted with Huntington's disease. In another embodiment, the human patient is afflicted with HD and has a baseline TFC score which is greater than or equal to 9 or greater than 44 CAG repeats in the huntingtin gene. In another embodiment, the human patient is afflicted with HD and has a baseline TMS score which is in the three least severe quarters of the overall population of patients afflicted with HD or less than 44 CAG repeats in the huntingtin gene. In another embodiment, the human patient is afflicted with HD and has a baseline TFC score which is greater than or equal to 9 or a baseline TMS score which is in the three least severe quarters of the overall population of patients afflicted with HD.

In one embodiment, the pridopidine is pridopidine hydrochloride.

In an embodiment, a titration dose of an amount different from the intended dose is administered for a period of time at the start of the periodic administration. In some embodiments, the titration dose is half the amount of the intended dose. In another embodiment, the titration dose is administered in one administration per day and the intended dose is administered in two administrations per day. In one embodiment, the titration dose is administered for 7-21 or 7-14 days prior to the administration of the intended dose. In another embodiment, the titration dose is administered for 7 days, 14 days, or 21 days prior to the administration of the intended dose. The titration dose is preferably administered for fourteen days prior to the administration of the intended dose.

In an embodiment, the method further comprises no worsening of the human patient's other HD symptoms compared to baseline. In an embodiment, the method further comprises no worsening of another symptom of HD in comparison to a human patient not administered pridopidine. In another embodiment, the symptoms are not worsened for at least 12 weeks, at least 20 weeks, at least 26 weeks, at least 52 weeks or at least 78 weeks.

Provided herein is a pharmaceutical composition comprising pridopidine for use in maintaining functional capacity in a human patient wherein the pharmaceutical composition is to be periodically orally administered to the patient such that a dose of 90-225 mg of pridopidine is to be administered to the patient per day. In some embodiments functional capacity includes ADL.

Provided herein is use of an amount of pridopidine in the manufacture of a medicament maintaining functional capacity in a human patient wherein the medicament is formulated for periodic oral administration to the patient such that a dose of 90-225 mg of pridopidine is to be administered to the patient per day. In some embodiments functional capacity includes ADL.

Provided herein is a pharmaceutical composition comprising pridopidine for use in slowing the clinical progression of HD as measured by total functional capacity in a human patient wherein the pharmaceutical composition is to be periodically orally administered to the patient such that a dose of 90-225 mg of pridopidine is to be administered to the patient per day.

Provided herein is a use of an amount of pridopidine in the manufacture of a medicament for slowing the clinical progression of HD as measured by total functional capacity in a human patient wherein the medicament is formulated for periodic oral administration to the patient such that a dose of 90-225 mg of pridopidine is to be administered to the patient per day.

Provided herein is a pharmaceutical composition comprising pridopidine for use in maintaining a human patient's ability to perform activities of daily living in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in maintaining a human patient's ability to perform activities of daily living in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing dystonia or maintaining a level of dystonia in a human patient wherein the pharmaceutical composition is to be periodically orally administered to the patient such that a dose of 90-225 mg of pridopidine is to be administered to the patient per day. In some embodiments dystonia includes limb dystonia.

Provided herein is use of an amount of pridopidine in the manufacture of a medicament for use in reducing dystonia or maintaining a level of dystonia in a human patient wherein the medicament is formulated for periodic oral administration to the patient such that a dose of 90-225 mg of pridopidine is to be administered to the patient per day. In some embodiments dystonia includes limb dystonia.

Provided herein is a pharmaceutical composition comprising pridopidine for use in treating limb dystonia in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in treating limb dystonia in a human patient wherein the medicament is formulated for periodic oral administration to the patient such that a dose of 90-225 mg of pridopidine is to be administered to the patient per day.

Provided herein is a pharmaceutical composition comprising pridopidine for use in improving or maintaining gait and balance in a human patient wherein the pharmaceutical composition is to be periodically orally administered to the patient such that a dose of 90-225 mg of pridopidine is to be administered to the patient per day. In some embodiments the administration slows the decline of a patients gait and balance.

Provided herein is use of an amount of pridopidine in the manufacture of a medicament for use in improving or maintaining, a human patient's gait and balance in a human patient wherein the medicament is formulated for periodic oral administration to the patient such that a dose of 90-225 mg of pridopidine is to be administered to the patient per day. In some embodiments the administration slows the decline of a patients gait and balance.

Provided herein is a pharmaceutical composition comprising pridopidine for use in improving, maintaining, or slowing the decline of gait and balance in a human patient wherein the pharmaceutical composition is to be periodically orally administered to the patient such that a dose of 90 mg of pridopidine is to be administered to the patient per day. In some embodiments the administration slows the decline of a patients gait and balance.

Provided herein is use of an amount of pridopidine in the manufacture of a medicament for use in improving, maintaining, or slowing the decline of, a human patient's gait and balance in a human patient wherein the medicament is formulated for periodic oral administration to the patient such that a dose of 90 mg of pridopidine is to be administered to the patient per day. In some embodiments the administration slows the decline of a patients gait and balance.

Provided herein is a pharmaceutical composition comprising pridopidine for use in improving or maintaining independence in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining, a human patient's independence wherein the medicament is formulated for periodic oral administration to the patient such that a dose of 90-225 mg of pridopidine is to be administered to the patient per day.

Provided herein is a pharmaceutical composition comprising pridopidine for use in improving or maintaining or slowing the decline of a human patient's independence wherein the pharmaceutical composition is to be periodically orally administered to the patient such that a dose of 90 mg of pridopidine is to be administered to the patient per day.

Provided herein is use of an amount of pridopidine in the manufacture of a medicament for use in improving or maintaining, or slowing the decline of a human patient's independence wherein the medicament is formulated for periodic oral administration to the patient such that a dose of 90 mg of pridopidine is to be administered to the patient per day.

Provided herein is a pharmaceutical composition comprising pridopidine for use in improving or maintaining a human patient's cognitive domains wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's cognitive domains wherein the medicament is formulated for periodic oral administration to the patient such that a dose of 90 mg of pridopidine is to be administered to the patient per day.

Provided herein is a pharmaceutical composition comprising pridopidine for use in improving or maintaining or slowing the decline of a human patient's cognitive domains wherein the pharmaceutical composition is to be periodically orally administered to the patient such that a dose of 90 mg of pridopidine is to be administered to the patient per day.

Provided herein is use of an amount of pridopidine in the manufacture of a medicament for use in improving or maintaining or slowing the decline of a human patient's cognitive domains wherein the medicament is formulated for periodic oral administration to the patient such that a dose of 90-225 mg of pridopidine is to be administered to the patient per day.

Provided herein is a pharmaceutical composition comprising pridopidine for use in reducing the severity of the sustained or intermittent muscle contractions associated with dystonia in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing the severity of the sustained or intermittent muscle contractions associated with dystonia in a human patient wherein the medicament is formulated for periodic oral administration to the patient such that a dose of 90-225 mg of pridopidine is to be administered to the patient per day.

Provided herein is a pharmaceutical composition comprising pridopidine for use in improving or maintaining motor ability in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining motor ability in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining the level of chorea in a human patient wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing or maintaining the level of chorea in a human patient wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining or slowing the increase of chorea in a human patient wherein the pharmaceutical composition is to be periodically orally administered to the patient such that a dose of 90 mg of pridopidine is to be administered to the patient per day.

Provided herein is use of an amount of pridopidine in the manufacture of a medicament for use in reducing or maintaining or slowing the increase of chorea in a human patient wherein the medicament is formulated for periodic oral administration to the patient such that a dose of 90 mg of pridopidine is to be administered to the patient per day.

Provided herein is a pharmaceutical composition comprising pridopidine for use in improving or maintaining a human patient's behavior and/or psychiatric state wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's behavior and/or psychiatric state wherein the medicament is formulated for periodic oral administration to the patient such that a dose of 90-225 mg of pridopidine is to be administered to the patient per day.

Provided herein is a pharmaceutical composition comprising pridopidine for use in reducing or maintaining a human patient's involuntary movements wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in reducing or maintaining a human patient's involuntary movements wherein the medicament is formulated for periodic oral administration to the patient such that a dose of 90-225 mg of pridopidine is to be administered to the patient per day.

Provided herein is a pharmaceutical composition comprising pridopidine for use in improving or maintaining a human patient's mobility wherein the pharmaceutical composition is to be periodically orally administered to the patient such that a dose of 90-225 mg of pridopidine is to be administered to the patient per day.

Provided herein is use of an amount of pridopidine in the manufacture of a medicament for use in improving or maintaining a human patient's mobility wherein the medicament is formulated for periodic oral administration to the patient such that a dose of 90-225 mg of pridopidine is to be administered to the patient per day.

The subject invention also provides a package comprising:
a) a pharmaceutical composition comprising pridopidine; and
b) instructions for use of the pharmaceutical composition according to the methods of the present invention.

Provided herein is a pharmaceutical composition comprising pridopidine for use in improving or maintaining a human patient's ability to perform physical tasks wherein the pharmaceutical composition is to be periodically orally administered to the patient such that a dose of 90-225 mg of pridopidine is to be administered to the patient per day.

Provided herein is a use of an amount of pridopidine in the manufacture of a medicament for use in improving or maintaining a human patient's ability to perform physical tasks wherein the medicament is formulated for periodic oral administration to the patient such that a dose of 90-225 mg of pridopidine is to be administered to the patient per day.

The invention also provides, a method of maintaining or improving total functional capacity, in a human patient afflicted with HD comprising periodically orally administering to the patient a pharmaceutical composition comprising pridopidine such that a dose of 90 or 180 mg of pridopidine is administered to the patient per day, so as to thereby maintain functional capacity, or improve total functional capacity, in the human patient as measured by the UHDRS-TFC for at least 26 or 52 weeks.

In one embodiment, a dose of 90 mg of pridopidine is administered to the patient per day. In another embodiment, the human patient has a baseline TFC score of 11-13. In another embodiment, the human patient has a baseline TFC score of 7-10. In another embodiment, the human patient has a baseline TMS score which is in the two least severe quarters of the overall population of patients afflicted with HD. In another embodiment, the human patient has a baseline TMS score which is in the three least severe quarters of the overall population of patients afflicted with HD. In another embodiment, the human patient has less than 44 CAG repeats in the Huntingtin gene.

The invention also provides, a method of maintaining, or improving a human patient's ability to perform activities of daily living, comprising periodically orally administering to the patient a pharmaceutical composition comprising pridopidine such that a dose of 90 or 180 mg of pridopidine is administered to the patient per day, so as to thereby maintain, or improve the human patient's ability to perform activities of daily living as measured by Activities of Daily Living domain of the UHDRS-TFC for at least 26 or 52 weeks, wherein the human patient is afflicted with HD.

In one embodiment, administering further maintains or improves the human patient's ability to manage finances as measured by measured by the Managing Finances domain of the UHDRS-TFC for at least 26 or 52 weeks.

The invention also provides, a method of maintaining, or improving a human patient's ability to manage finances, comprising periodically orally administering to the patient a pharmaceutical composition comprising pridopidine such that a dose of 90 or 180 mg of pridopidine is administered to the patient per day, so as to thereby maintain, or improve the human patient's ability to manage finances as measured by Managing Finances domain of the UHDRS-TFC for at least 26 or 52 weeks, wherein the human patient is afflicted with HD.

In one embodiment, a dose of 90 mg of pridopidine is administered to the patient per day. In another embodiment, the human patient has a baseline UHDRS-TFC score of 11-13. In another embodiment, the human patient has a baseline UHDRS-TFC score of 7-10. In another embodiment, the human patient has a baseline TMS score which is in the two least severe quarters of the overall population of patients afflicted with HD. In another embodiment, the human patient has a baseline TMS score which is in the three least severe quarters of the overall population of patients afflicted with HD.

The invention also provides, a method of maintaining, improving, or the rate of decline of, a human patient's ability to perform domestic chores as measured by the Domestic Chores domain of the UHDRS-TFC, comprising periodically orally administering to the patient a pharmaceutical composition comprising pridopidine such that a dose of 90 mg of pridopidine is administered to the patient per day, so as to thereby maintain, improve, or reduce the rate of decline of the human patient's ability to perform domestic chores, wherein the human patient is afflicted with HD and has a baseline TFC score of 11-13.

The invention also provides, a method of maintaining, improving, or lessening the decline of, a human patient's ability to perform domestic chores as measured by the Domestic Chores domain of the UHDRS TFC, comprising periodically orally administering to the patient a pharmaceutical composition comprising pridopidine such that a dose of 90 mg of pridopidine is administered to the patient per day, so as to thereby maintain, improve, or lessen the decline of the human patient's ability to perform domestic chores, wherein the human patient is afflicted with HD and has a baseline TFC score of 11-13.

The invention also provides, a method of maintaining, improving, or reducing the rate of decline of, a human patient's care level as measured by the Care Level of the UHDRS TFC, comprising periodically orally administering to the patient a pharmaceutical composition comprising pridopidine such that a dose of 90 mg of pridopidine is administered to the patient per day, so as to thereby maintain, improve, or reduce the rate of decline of the human patient's care level, wherein the human patient is afflicted with HD and has a baseline TFC score of 11-13.

The invention also provides, a method of maintaining, improving, or lessening the decline of, a human patient's care level as measured by the Care Level of the UHDRS TFC, comprising periodically orally administering to the patient a pharmaceutical composition comprising pridopidine such that a dose of 90 mg of pridopidine is administered to the patient per day, so as to thereby maintain, improve, or lessen the decline of, the human patient's care level, wherein the human patient is afflicted with HD and has a baseline TFC score of 11-13.

The invention also provides, a method of improving or maintaining, a human patient's gait and balance comprising periodically orally administering to the patient a pharmaceutical composition comprising pridopidine such that a dose of 90 mg of pridopidine is administered to the patient per day, so as to thereby improve, or maintain, a human patient's gait and balance as measured by the UHDRS gait and balance score for at least 52 weeks, wherein the human patient is afflicted with HD and has a baseline TFC score of 11-13.

The invention also provides, a method of reducing dystonia or maintaining a level of dystonia in a human patient afflicted with HD comprising periodically orally administering to the patient a pharmaceutical composition comprising pridopidine such that a dose of 90 or 180 mg of pridopidine is administered to the patient per day, so as to thereby reduce or maintain a level of dystonia as measured by the UHDRS TMS Dystonia score and the human patient has a baseline TFC score of 11-13.

The invention also provides, a method of improving, maintaining, or slowing the decline of, a human patient's independence comprising periodically orally administering to the patient a pharmaceutical composition comprising pridopidine such that a dose of 90 mg of pridopidine is administered to the patient per day, so as to thereby improve, maintain, or slow the decline of, a human patient's independence as measured by the UHDRS Independence Score for at least 26 weeks, wherein the human patient is afflicted with HD.

The invention also provides, a method of improving, maintaining, or lessening the decline of, a human patient's independence comprising periodically orally administering to the patient a pharmaceutical composition comprising pridopidine such that a dose of 90 mg of pridopidine is administered to the patient per day, so as to thereby improve, maintain, or lessen the decline of, a human patient's independence as measured by the UHDRS Independence Score for at least 26 weeks, wherein the human patient is afflicted with HD.

In one embodiment, the human patient has a baseline TFC score of 11-13. In another embodiment, the human patient has a baseline TFC score of greater than or equal to 7.

The invention also provides, a method of preventing the slowing, the reduction in amplitude, or the impairment of the human patient's finger tapping ability in a human patient afflicted with HD comprising periodically orally administering to the patient a pharmaceutical composition comprising pridopidine such that a dose of 90 mg of pridopidine is administered to the patient per day, so as to thereby prevent the slowing, the reduction in amplitude, or the impairment of the human patient's finger tapping ability.

In one embodiment, the method further comprises preventing the slowing or the irregular performance of the Pronate-Supinate Hands test in the human patient.

The invention also provides, a method of improving or maintaining a human patient's behavior and/or psychiatric state comprising periodically orally administering to the human patient afflicted with HD a pharmaceutical composition comprising pridopidine such that a dose of 90 or 180 mg of pridopidine is administered to the patient per day, so as to thereby improve or maintain the human patient's behavior and/or psychiatric state for at least 26 weeks or at least 52 weeks as measured by the Problem Behaviors Assessment for irritability or for disoriented behavior.

In one embodiment, the human patient has a baseline TFC score of 0-6, the human patient's behavior and/or psychiatric state is measured by the Problem Behaviors Assessment for irritability and the human patient's behavior and/or psychiatric state is improved or maintained for at least 52 weeks. In another embodiment, the human patient has a baseline TFC score of 11-13, the human patient's behavior and/or psychiatric state is measured by the Problem Behaviors Assessment for disoriented behavior and the human patient's behavior and/or psychiatric state is improved or maintained for at least 26 weeks.

The invention also provides, a method of maintaining:
a) functional capacity in a human patient;
b) a human patient's ability to perform activities of daily living;
c) a human patient's ability to manage finances;
d) a human patient's ability to perform domestic chores;
e) the human patient's care level;
f) Dystonia in a human patient;
g) a human patient's Gait and balance;
h) a human patient's independence;
i) a human patient's cognitive domains;
j) chorea in a human patient;
k) a human patient's behavior and/or psychiatric state;
l) motor ability in a human patient;
m) a human patient's mobility; or
n) a human patient's ability to perform physical tasks;
comprising periodically orally administering to the patient a pharmaceutical composition comprising pridopidine such that a dose of 90-225 mg of pridopidine is administered to the patient per day.

The invention also provides, a method of improving:
a) functional capacity;
b) a human patient's ability to perform activities of daily living;
c) a human patient's ability to manage finances;
d) a human patient's ability to perform domestic chores;
e) a human patient's care level;
f) a human patient's gait and balance;
g) a human patient's independence;
h) a human patient's cognitive domains;
i) motor ability in a human patient;
j) chorea in a human patient;
k) a human patient's behavior and/or psychiatric state;
l) a human patient's mobility; or
m) a human patient's ability to perform physical tasks;
comprising periodically orally administering to the patient a pharmaceutical composition comprising pridopidine such that a dose of 90-225 mg of pridopidine is administered to the patient per day.

The invention also provides, a method of reducing:
a) dystonia in a human patient;
b) a human patient's involuntary movements; or
c) the severity of the sustained or intermittent muscle contractions associated with dystonia in a human patient,
comprising periodically orally administering to the patient a pharmaceutical composition comprising pridopidine such that a dose of 90-225 mg of pridopidine is administered to the patient per day.

The invention also provides a method of reducing:
a) the decline of functional capacity in a human patient;
b) the rate of decline of a human patient's ability to perform activities of daily living;
c) the rate of decline of a human patient's ability to manage finances;
d) the rate of decline of a human patient's ability to perform domestic chores;
e) the rate of decline of a human patient's care level; or
f) the decline of a human patient's behavior and/or psychiatric state;
comprising periodically orally administering to the patient a pharmaceutical composition comprising pridopidine such that a dose of 90-225 mg of pridopidine is administered to the patient per day.

The invention also provides a method of lessening:
a) the decline of functional capacity in a human patient;
b) the decline of a human patient's ability to perform activities of daily living;
c) the decline of a human patient's ability to manage finances;
d) the decline of a human patient's ability to perform domestic chores;
e) the decline of a human patient's care level; or
f) the decline of a human patient's behavior and/or psychiatric state;
comprising periodically orally administering to the patient a pharmaceutical composition comprising pridopidine such that a dose of 90-225 mg of pridopidine is administered to the patient per day.

The invention also provides a method of:
a) slowing the decline of, a human patient's gait and balance;
b) slowing the decline of, a human patient's independence; or
c) slowing the decline of, a human patient's cognitive domains;
comprising periodically orally administering to the patient a pharmaceutical composition comprising pridopidine such that a dose of 90 mg of pridopidine is administered to the patient per day.

The invention also provides a method of:
a) lessening the decline of, a human patient's gait and balance;
b) lessening the decline of, a human patient's independence; or
c) lessening the decline of, a human patient's cognitive domains;
comprising periodically orally administering to the patient a pharmaceutical composition comprising pridopidine such that a dose of 90 mg of pridopidine is administered to the patient per day.

The invention also provides a method of:
a) slowing the clinical progression of HD as measured by total functional capacity in a human patient; or
b) treating limb dystonia, preferably, wherein treating comprises
  i. preventing the slowing, the reduction in amplitude, or the impairment of the human patient's finger tapping ability and preventing the slowing or irregular performance of the Pronate-Supinate Hands test in the human patient;
  ii. preventing the slowing or the irregular performance of the Pronate-Supinate Hands test in the human patient;
  iii. improving the human patient's Q-motor tap speed frequency; or
  iv. improving the human patient's Q-motor tap speed inter onset interval (IOD;
comprising periodically orally administering to the patient a pharmaceutical composition comprising pridopidine such that a dose of 90-225 mg of pridopidine is administered to the patient per day.

The invention further provides a pharmaceutical composition comprising pridopidine for use in (1) (a) maintaining functional capacity, improving functional capacity, or lessening functional decline in a human patient in need thereof, (b) slowing the clinical progression of HD, (c) reducing dystonia or maintaining a level of dystonia in a human patient in need thereof, (d) treating limb dystonia in a human patient in need thereof, (e) preventing the slowing, the reduction in amplitude, or the impairment of the human patient's finger tapping ability and/or preventing the slowing or the irregular performance of the Pronate-Supinate Hands test, (f) improving or maintaining, a human patient's gait and balance in a human patient in need thereof, (g) improving or maintaining, a human patient's independence in a human patient in need thereof, (h) improving or maintaining a human patient's cognitive performance across a variety of domains in a human patient in need thereof, (i) lessening the severity of the sustained or intermittent muscle contractions associated with dystonia in a human patient in need thereof, (j) improving or maintaining motor ability in a human patient in need thereof, (k) reducing or maintaining the level of chorea in a human patient in need thereof, (l) improving, maintaining, or lessening the decline of a human patient's behavior and/or psychiatric state in a human patient in need thereof, (m) reducing or maintaining a human patient's involuntary movements in a human patient in need thereof, (n) improving or maintaining a human patient's mobility in a human patient in need thereof, (o) improving or maintaining a human patient's ability to perform physical tasks, (p) improving or maintaining a human patient's quality of life wherein the pharmaceutical composition is to be periodically orally administered to the patient such that a dose of 90-225 mg of pridopidine is to be administered to the patient per day, or (2) (a) improving, maintaining, or lessening the decline of gait and balance in a human patient in need thereof (b) improving, maintaining, or lessening the decline of, a human patient's independence in a human patient in need thereof, (c) improving, maintaining, or lessening the decline of, a human patient's cognitive performance across a variety of domains in a human patient in need thereof, (d) reducing, maintaining, or lessening the increase of, chorea, in a human patient in need thereof, wherein the pharmaceutical composition is to be periodically orally administered to the patient such that a dose of 90 mg of pridopidine is to be administered to the patient per day.

The invention also provides the use of an amount of pridopidine in the manufacture of a medicament for (1) (a) maintaining functional capacity, improving functional capacity, or lessening functional decline in a human patient in need thereof, (b) slowing the clinical progression of HD, (c) reducing dystonia or maintaining a level of dystonia in a human patient in need thereof, (d) treating limb dystonia in a human patient in need thereof, (e) preventing the slowing, the reduction in amplitude, or the impairment of the human patient's finger tapping ability and/or preventing the slowing or the irregular performance of the Pronate-Supinate Hands test, (f) improving or maintaining, a human patient's gait and balance in a human patient in need thereof, (g) improving or maintaining, a human patient's independence in a human patient in need thereof, (h) improving or maintaining a human patient's cognitive performance across a variety of domains in a human patient in need thereof, (i) lessening the severity of the sustained or intermittent muscle contractions associated with dystonia in a human patient in need thereof, (j) improving or maintaining motor ability in a human patient in need thereof, (k) reducing or maintaining the level of chorea in a human patient in need thereof, (l) improving, maintaining, or lessening the decline of a human patient's behavior and/or psychiatric state in a human patient in need thereof, (m) reducing or maintaining a human patient's involuntary movements in a human patient in need thereof, (n) improving or maintaining a human patient's mobility in a human patient in need thereof, (o) improving or maintaining a human patient's ability to perform physical tasks, (p) improving or maintaining a human patient's quality of life wherein the pharmaceutical composition is to be periodically orally administered to the patient such that a dose of 90-225 mg of pridopidine is to be administered to the patient per day, or (2) (a) improving, maintaining, or lessening the decline of gait and balance in a human patient in need thereof (b) improving, maintaining, or lessening the decline of, a human patient's independence in a human patient in need thereof, (c) improving, maintaining, or lessening the decline of, a human patient's cognitive performance across a variety of domains in a human patient in need thereof, (d) reducing, maintaining, or lessening the increase of, chorea, in a human patient in need thereof wherein the medicament is formulated for periodic oral administration to the patient such that a dose of 90 mg of pridopidine is to be administered to the patient per day.

The invention additionally provides the use of an amount of pridopidine for (1) (a) maintaining functional capacity, improving functional capacity, or lessening functional decline in a human patient in need thereof, (b) slowing the clinical progression of HD, (c) reducing dystonia or maintaining a level of dystonia in a human patient in need thereof, (d) treating limb dystonia in a human patient in need thereof, (e) preventing the slowing, the reduction in amplitude, or the impairment of the human patient's finger tapping ability and/or preventing the slowing or the irregular performance of the Pronate-Supinate Hands test, (f) improving or maintaining, a human patient's gait and balance in a human patient in need thereof, (g) improving or maintaining, a human patient's independence in a human patient in need thereof, (h) improving or maintaining a human patient's cognitive performance across a variety of domains in a human patient in need thereof, (i) lessening the severity of the sustained or intermittent muscle contractions associated with dystonia in a human patient in need thereof, (j) improving or maintaining motor ability in a human patient in need thereof, (k) reducing or maintaining the level of chorea in a human patient in need thereof, (l) improving, maintaining, or lessening the decline of a human patient's behavior and/or psychiatric state in a human patient in need thereof, (m) reducing or maintaining a human patient's involuntary movements in a human patient in need thereof, (n) improving or maintaining a human patient's mobility in a human patient in need thereof, (o) improving or maintaining a human patient's ability to perform physical tasks, (p) improving or maintaining a human patient's quality of life wherein the pharmaceutical composition is to be periodically orally administered to the patient such that a dose of 90-225 mg of pridopidine is to be administered to the patient per day, or (2) (a) improving, maintaining, or lessening the decline of gait and balance in a human patient in need thereof (b) improving, maintaining, or lessening the decline of, a human patient's independence in a human patient in need thereof, (c) improving, maintaining, or lessening the decline of, a human patient's cognitive performance across a variety of domains in a human patient in need thereof, (d) reducing, maintaining, or lessening the increase of, chorea, in a human patient in need thereof wherein the medicament is formulated for periodic oral administration to the patient such that a dose of 90 mg of pridopidine is to be administered to the patient per day.

Each embodiment disclosed herein is contemplated as being applicable to each of the other disclosed embodiments. For instance, all combinations of the various elements described herein are within the scope of the invention. Additionally, the elements recited in the packaging and pharmaceutical composition embodiments can be used in the method and use embodiments described herein.

Terms

As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to maintain functional capacity or lessen decline in functional capacity. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., reducing a symptom, inducing inhibition, regression, or stasis of the disorder and/or disease. As used herein, "inhibition" of disease progression or disease complication in a subject means preventing or reducing the disease progression and/or disease complication in the subject.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. The administration can be periodic administration.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

As used herein, "maintaining functional capacity in a human patient" means that the functional capacity score after a period of administration of pridopidine ("the after administration score") is unchanged compared to the human patient's functional capacity score immediately prior to the period of administration ("the baseline score"). The after administration score is considered to be unchanged if the difference between the baseline score and the after administration score is not statistically significant. The functional capacity score can be measured as described herein and includes subsets of the functional capacity score.

As used herein, "improving functional capacity in a human patient" means that the functional capacity score after a period of administration of pridopidine ("the after administration score") is improved compared to the human patient's functional capacity score immediately prior to the period of administration ("the baseline score").

The functional capacity score of a human patient afflicted with HD can decrease over time. The rate of such decrease can be referred to as a rate of decline of the functional capacity score or a rate of decline of functional capacity or a rate of functional decline. For example, on average the rate of functional decline or the reduction in TFC score is faster for early stage HD patients (TFC score 7-13) than for advanced stage patients (TFC score of <7). On average the decline is about 0.8-1.2 points per year in early stage HD patients, less than ½ (about 0.2-0.3) point per year for patients with TFC 3-6; and less than 0.1 for patients with TFC 0-2 (Marder 2000). Therefore, TFC is most sensitive to change in the earlier stages of disease. The total functional capacity score can be measured as described herein and includes subsets of the functional capacity score. This decline may also be referred to as the natural decline or the untreated decline in functional capacity.

Accordingly, as used herein, "reducing the rate of decline of functional capacity", "slowing the rate of functional decline", "reducing the rate of functional decline", "decreased functional decline", or 'slowing functional decline" means that the rate of decline of the functional capacity score after a period of administration of pridopidine ("the after administration score") is slowed, reduced or decreased compared to the functional capacity score of a patient who has not received the same treatment with pridopidine.

As used herein, "lessening the decline of functional capacity" or "reducing the decline of functional capacity" means that the decrease in a functional capacity score in a patient after a period of administration of pridopidine is less than the decrease in the functional capacity score of a patient who has not received the same treatment with pridopidine over the same period.

As used herein, "maintaining a human patient's ability to perform activities of daily living" means that the activities of daily living (ADL) score after a period of administration of pridopidine ("the after administration score") is unchanged compared to the human patient's activities of daily living score immediately prior to the period of administration ("the baseline score"). The after administration score is considered to be unchanged if the difference between the baseline score and the after administration score is not statistically significant. The activities of daily living score is a subset of the total functional capacity score and can be measured as described herein.

There are six basic ADLs: eating, bathing, dressing, toileting, transferring (functional mobility) and continence. ADL is scored as follows: a patient requiring total care=0, a patient able to carry out gross tasks only=1, a patient having minimal impairment=2, a patient with no impairment (normal)=3.

As used herein, "maintaining a human patient's ability to manage finances" means that the finances score after a period of administration of pridopidine ("the after administration score") is unchanged compared to the human patient's finances score immediately prior to the period of administration ("the baseline score"). The after administration score is considered to be unchanged if the difference between the baseline score and the after administration score is not statistically significant. The finances score is a subset of the total functional capacity score and can be measured as described herein.

Finance is scored as follows: a patient unable to manage finances=0, a patient requiring major assistance=1, a patient requiring minor assistance=2, a patient a patient requiring no assistance (normal)=3.

As used herein, "no worsening of other HD symptoms compared to baseline" means that the severity of each of the human patient's HD symptoms after a period of administration of pridopidine is equal to or less than the severity of the symptom immediately prior to the start of the period of administration (baseline).

For each baseline score discussed above, in one embodiment, there is no administration of pridopidine to the patient prior to attainment of the baseline score. In another embodiment, an amount of pridopidine is administered to the patient prior to attainment of the baseline score. In a further embodiment, the amount of pridopidine administered to the patient prior to attainment of the baseline score is less than or more than the amount of pridopidine administered to the patient after the attainment of the baseline score.

As used herein, an "amount" or "dose" of pridopidine as measured in milligrams refers to the milligrams of pridopidine present in a preparation, regardless of the form of the preparation. A "dose of 90 mg pridopidine" means the amount of pridopidine acid in a preparation is 90 mg, regardless of the form of the preparation. Thus, when in the form of a salt, e.g. a pridopidine hydrochloride, the weight of the salt form necessary to provide a dose of 90 mg pridopidine would be greater than 90 mg due to the presence of the additional salt ion.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1; 0.2 . . . 0.9; and 1, 2 . . . 49 mg unit amounts are included as embodiments of this invention.

As used herein, "pridopidine" means pridopidine base or a pharmaceutically acceptable salt thereof, as well as derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. In certain embodiments, pridopidine is a pharmaceutically acceptable salt, such as the HCl salt or tartrate salt. Preferably, in any embodiments of the invention as described herein, the pridopidine is in the form of its hydrochloride salt.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials Pharmaceutically Acceptable Salts The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the L-tartrate, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of Remington's Pharmaceutical Sciences (Mack Publishing Co., Easton, Pa.).

Listing of Abbreviations

The following abbreviations are used throughout this application: ALT: alanine aminotransferase; ADL: Activities of Daily Living; AR: Autoregressive; AUC: area under the concentration-time curve; bid or b.i.d.: twice daily; BL=Baseline; CAB: cognitive assessment battery; CAB HVLT-R: Cognitive Assessment Battery Hopkins Verbal Learning Test, revised; CGI-C: Clinical Global Impression of Change; CGI-S: Clinical Global Impression of Severity; CI: confidence interval; CIBIC-Plus: Clinician's Interview-based Impression of Change plus Caregiver Input; CIBIS: Clinician's Interview-based Impression of Severity; CIOMS: Council for International Organizations of Medical Sciences; Cmax: maximum observed plasma drug concentration; CNS: central nervous system; CRF: case report form; CRO: contract research organization; CS: Compound Symmetry; C-SSRS: Columbia-Suicide Severity Rating Scale; CYP: cytochrome P450; DSM-IV TR: Diagnostic and Statistical Manual—Fourth Edition Text Revision; EM: extensive metabolizers; EU: European Union; FA: Functional Assessment; FAS: full analysis set; Freq: tapping frequency; GCP: Good Clinical Practice; GFV-C: grip force variability in the static phase; GGT: gamma-glutamyl transpeptidase; HART: Huntington's disease ACR16 Randomized Trial; HCG: human chorionic gonadotropin; HD: Huntington's disease; HD-QoL=Huntington's disease Quality of Life; HVLT-R: HAD-CAB Hopkins Verbal Learning Test-Revised; ICH: International Conference on Harmonisation; IEC: Independent Ethics Committee; IOI: inter onset interval; IPI: inter peak interval; IRB: Institutional Review Board; IRT: interactive response technology; IS: Independence Score; ITI: inter tap interval; ITT: intent-to-treat; LSO: local safety officer; MAD: multiple ascending dose; MedDRA: Medical Dictionary for Regulatory Activities; MermaiHD: Multinational European Multicentre ACR16 study in HD; ML: Maximum-Likelihood; mMS: Modified Motor Score; MoCA: Montreal cognitive assessment; MS: Multiple sclerosis; MTD: maximum tolerated dose; NMDA:

N-methyl-D-aspartate; NOAEL: no observed adverse effect level; PBA-s: Problem Behaviors Assessment-Short form; PD: pharmacodynamic(s); PDS: Physical disability scale; PK: pharmacokinetic(s); PM: poor metabolizer; PPT: physical performance test; Qd: once daily; Q-Motor: Quantitative motor; QoL: Quality of life; QTcF: Fridericia-corrected QT interval; RBC: red blood cell; REML: Restricted Maximum-Likelihood; SAE: serious adverse event; SD: standard deviation; SDMT: symbol digit modalities test; SOC: system organ class; SOP: standard operating procedure; SUSAR: suspected unexpected serious adverse reaction; t½: half life; TC=telephone call; TD: tap duration; TF: tapping force; TFC: Total Functional Capacity; TMS: Total Motor Score; TMS Involuntary Movements=TMS for performance of Domestic Chores and Dystonia scores combined. TUG: timed up and go; UHDRS: Unified Huntington's Disease Rating Scale; ULN: upper limit of the normal range; US: United States; WBC: white blood cell; WHO: World Health Organization; WHO: Drug World Health Organization (WHO) drug dictionary; ΔHR: change from baseline in heart rate; ΔQTcF: change from baseline in QTcF; ΔΔHR: placebo-corrected change from baseline in heart rate; Placebo-Controlled Study-Huntington's Disease; ΔΔQTcF: placebo-corrected change from baseline in QTcF, wk: week; EQ5D-5L European Quality of Life-5 Dimensions (5 levels).

Clinical Studies

Sixteen (16) clinical studies have been completed with pridopidine, including 8 studies in healthy subjects (of which 1 study also included patients with schizophrenia), 1 study in patients with Parkinson's disease, 2 studies in patients with schizophrenia (including the study mentioned above), and 6 studies in patients with HD (including 1 open-label extension study). In addition, a compassionate use program for pridopidine in patients with HD is ongoing in Europe, and an open-label, long term safety study is ongoing in the United States (US) and Canada. An overview of these studies are presented in International Publication No. WO 2014/205229, the content of which is hereby incorporated by reference.

This invention will be better understood by reference to the Experimental Details which follow, but those skilled in the art will readily appreciate that the specific experiments detailed are only illustrative of the invention as described more fully in the claims which follow thereafter.

EXAMPLES

Example 1

A Phase II, Dose-finding, Randomized, Parallel-Group, Double-Blind, Placebo-Controlled Study, Evaluating the Safety and Efficacy of Pridopidine 45 mg, 67.5 mg, 90 mg, and 112.5 mg Twice-Daily versus Placebo for Symptomatic Treatment in Patients with HD ("PRIDE-HD")

The present study assessed the efficacy of pridopidine 45 mg to 112.5 mg twice daily (bid) on motor impairment in patients with HD over at least 52 weeks of treatment using the UHDRS TMS. The study also assessed the effect of at least 52 weeks of treatment with pridopidine 45 mg bid to 112.5 mg bid on the Modified Physical Performance Test (mPPT). The study also assessed the effect of at least 52 weeks of treatment with pridopidine 45 mg bid to 112.5 mg bid on UHDRS measures for total function capacity (TFC) and cognitive assessment battery (CAB). The study also compared data from all patients to those obtained in HD subpopulations. The study also (i) evaluated the safety and tolerability of a range of pridopidine doses in patients with HD during at least 52 weeks of treatment, (ii) explored the pharmacokinetics (PK) of pridopidine in the study population and (iii) investigated the relationship between exposure to pridopidine and outcome measures (e.g., clinical efficacy and toxicity parameters).

Study Design

General Design and Study Schema

This was a randomized, parallel-group, double blind, placebo controlled study that compared the efficacy and safety of pridopidine 45 mg, 67.5 mg, 90 mg, and 112.5 mg bid versus placebo in the treatment of motor impairment in HD. The administration of pridopidine to patients is summarized in Table 2. The study procedures and assessments are summarized in Table 3. A detailed clinical procedure, including screening procedures and other procedures, is listed as Example 3 in U.S. Patent Application Publication No. US 2014/0378508 and International Publication No. WO 2014/205229, the content of which are hereby incorporated by reference.

Primary and Secondary Variables and Endpoints

The primary efficacy variable and endpoint for this study was change from baseline in the UHDRS TMS (defined as the sum of all UHDRS motor domains ratings) at Week 26 or Week 52. The primary measure of motor impairment is the UHDRS motor assessment section, which was administered by a trained examiner. The first part of the motor assessment consisted of five TMS subscores, provided below. The sum total of all the 31 items is referred to as the Total Motor Score (TMS). The secondary efficacy variable and endpoint was change from baseline in the mPPT at Week 26 or Week 52.

The mPPT quantifies the patient's performance in physical tasks (Brown 2000). It is a standardized 9-item test (standing static balance, chair rise, lift a book and put it on a shelf, put on and remove a jacket, pick up a penny from floor, turn 360 degrees, 50 feet walk, climb one flight of stairs, climb stairs test (flights up and down)), that measures the patient's performance on functional tasks. Both the speed and accuracy at which the patients complete the items are taken into account during scoring. The maximum score of the test is 36, with higher scores indicating better performance. The Multiple Sclerosis Walking Scale (MSWS-12) was adapted to become a generic measure of walking and mobility and renamed the Walk-12.

Other Efficacy Variables and Endpoints: Other efficacy variables and endpoints for this study are as follows:

Global Functional Scales: CIBIC-Plus global score as compared to baseline; Change from baseline in the PDS score; Change from baseline in UHDRS FA; CGIC as compared to baseline; Change from baseline in UHDRS TFC; and Change from baseline in UHDRS IS.

Global/Functional Scales:

Change from baseline in HD QoL; and Change from baseline in Walk-12 scale.

TMS Subscores:

Change from baseline in hand movement score (defined as the sum of UHDRS domains finger taps, pronate-supinate hands and luria [fist-hand-palm test]); Change from baseline in Gait and balance score (defined as the sum of UHDRS domains gait, tandem walking and retropulsion pull test); Change from baseline in UHDRS mMS (defined as the sum of UHDRS domains dysarthria, tongue protrusion, finger taps, pronate-supinate hands, luria, rigidity, bradykinesia, gait, tandem walking, retropulsion pull test); Change from baseline in UHDRS Chorea; Change from baseline in UHDRS Dystonia; and Responders, defined as patients with UHDRS TMS change from baseline ≤0.

Other Motor Assessments:

Change from baseline in Q Motor measurements including digitomography (speeded index finger tapping), dysdiadochomotography (pronation/supination hand tapping), manumotography and choreomotography (grip force and chorea analysis) and pedomotography (speeded foot tapping); and Change from baseline in the TUG test.

Cognitive/Psychiatric Assessments:

Change from baseline in HD-CAB brief: SDMT, Emotion Recognition, Trail Making Test, HVLT-R, Paced Tapping at 3 Hz, OTS; and Change from baseline in PBA-s.

Safety Variables and Endpoints

Safety variables and endpoints include the following: AEs throughout the study; Changes from baseline in QTcF and other ECG parameters throughout the study; Clinical safety laboratory (clinical chemistry, hematology, and urinalysis) throughout study; Changes from baseline C-SSRS throughout the study; Vital signs throughout the study.

Tolerability Variables and Endpoints

Tolerability variables and endpoints include the following: the number (%) of patients who failed to complete the study; and the number (%) of patients who failed to complete the study due to AEs.

Pharmacokinetic Variables and Endpoints

The primary PK measure was determination of plasma concentration of pridopidine. Concentrations were also incorporated into a pridopidine population PK model and individual exposure for the study patients (Cmax and AUC) was calculated.

Study Drugs and Dosage: Pridopidine (as pridopidine hydrochloride) was provided as a white hard gelatin capsule, size 2 containing 45 mg pridopidine and a white hard gelatin capsule, size 4 containing 22.5 mg pridopidine. Placebo was presented as white hard gelatin capsules matching the 22.5 mg or 45 mg pridopidine capsules but containing no active ingredient, only the excipients (silicified microcrystalline cellulose and magnesium stearate).

TABLE 2

Dose Administration (Capsules were Administered Twice Daily to Give the Total Daily Dose)

| Treatment | Titration Period | | | | Full Dose Period |
|---|---|---|---|---|---|
| | Week 1 | Week 2 | Week 3 | Week 4[a] | Weeks 4[b] to 52 |
| Pridopidine 45 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 45 mg Pridopidine<br>1 × 22.5 mg Placebo<br>1 × 45 mg Placebo<br>(TDD = 90 mg) |
| Pridopidine 67.5 mg bid | 1 × 22.5 mg Pridopidine<br>1 × 22.5 mg Placebo<br>1 × 45 mg Placebo<br>(TDD = 45 mg) | 1 × 22.5 mg Pridopidine<br>1 × 22.5 mg Placebo<br>1 × 45 mg Placebo<br>(TDD = 45 mg) | 1 × 22.5 mg Pridopidine<br>2 × 22.5 mg Placebo<br>(TDD = 90 mg) | 1 × 45 mg Pridopidine<br>2 × 22.5 mg Placebo<br>(TDD = 90 mg) | 1 × 22.5 mg Pridopidine<br>1 × 45 mg Pridopidine<br>1 × 45 mg Placebo<br>(TDD = 135 mg) |
| Pridopidine 90 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>1 × 22.5 mg Pridopidine<br>1 × 22.5 mg Placebo<br>(TDD = 135 mg) | 2 × 45 mg Pridopidine<br>1 × 22.5 mg Placebo<br>(TDD = 180 mg) |
| Pridopidine 112.5 mg bid | 1 × 22.5 mg Pridopidine<br>1 × 22.5 mg Placebo<br>1 × 45 mg Placebo<br>(TDD = 45 mg) | 1 × 45 mg Pridopidine<br>2 × 22.5 mg Placebo<br>(TDD = 90 mg) | 1 × 45 mg Pridopidine<br>1 × 22.5 mg Pridopidine<br>1 × 22.5 mg Placebo<br>(TDD = 135 mg) | 1 × 45 mg Pridopidine<br>2 × 22.5 mg Pridopidine<br>(TDD = 180 mg) | 1 × 22.5 mg Pridopidine<br>2 × 45 mg Pridopidine<br>(TDD = 225 mg) |
| Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 2 × 22.5 mg Placebo<br>1 × 45 mg Placebo | 1 × 22.5 mg Placebo<br>2 × 45 mg Placebo |

TDD = total daily dose;
[a]Excluding Day 28;
[b]Day 28 only

TABLE 3

Study Procedures and Assessments

| TV7820-CNS-20002:<br>Procedures and Assessments | Screening | Titration Period | | | Full Dose Treatment Period | | | |
|---|---|---|---|---|---|---|---|---|
| | | First 26-Week Study Period | | | | | | |
| Visit | V0[a]<br>Maximum | V1 | TC<br>6 ± 3 | V2<br>14 ± 3 | TC<br>20 ± 3 | V3<br>28 ± 4 | TC<br>35 ± 3 | V4[a]<br>42 ± 5 | V5[a]<br>56 ± 5 | V6[a]<br>84 ± 7 |
| Day<br>Procedures and assessments | 12 weeks<br>Screening | 0<br>BL | week<br>1 | week<br>2 | week<br>3 | week<br>4 | week<br>5 | week<br>6 | week<br>8 | week<br>12 |
| On-site visit | X | X | | X | | X | | X | X | X |
| Telephone call | | | X | | X | | | | | |
| Informed consent | X | | | | | | | | | |
| Demography | X | | | | | | | | | |
| Medical and psychiatric history | X | | | | | | | | | |
| Prior medication history | X | | | | | | | | | |
| Inclusion and exclusion criteria[b] | X | X | | | | | | | | |
| Randomization | | X | | | | | | | | |

TABLE 3-continued

| Procedures and Assessments | | | | | | | | | |
|---|---|---|---|---|---|---|---|---|---|
| Clinical laboratory tests (hematology and biochemistry) | X | X | X[c] | X | | X | X | X | |
| Urinalysis | X | X | | X | | X | X | X | |
| Pregnancy test (women of childbearing potential)[d] | X | X | | X | | | X | X | |
| Full physical and neurological examination, including weight (height at screening only) | X | X | | X | | | | X | |
| ECG | X[e] | X[f] | X[g] | X[a] | | X[a] | X[h] | X[a] | |
| Vital signs measurement | X | X | X | X | | X | X | X | |
| C-SSRS (Baseline version) | X | | | | | | | | |
| C-SSRS (Since Last Visit version) | | X | | X | | X | X | X | |
| Blood sample for genetic analyses[k] | X | | | | | | | | |
| UHDRS-TMS | X | X[l] | | X[a] | | | X[a] | X[a] | |
| mPPT | | X[a] | | X[a] | | | X[a] | X[a] | |
| UHDRS-FA | | X | | X | | | | X | |
| UHDRS-TFC | | X | | X | | | | X | |
| UHDRS-IS | X | X | | X | | | | X | |
| PBA-s | | X | | X | | | | X | |
| Abbreviated PBA-s | | | | | | | | | |
| CIBIS | | X | | | | | | | |
| CIBIC-Plus | | | | X | | | | X | |
| PDS | | X | | X | | | | X | |
| CGI-S | | X | | | | | | | |
| CGI-C | | | | X | | | | X | |
| HD-QoL | | X | | | | | | | |
| EQ5D-5L | | X | | | | | | | |
| Walk-12 | | X | | X | | | | X | |
| Q-Motor assessments[n] | X | X | | X | | | | X | |
| TUG Test | | X | | X | | | | X | |
| Cognitive assessment battery[o] | X | X | | | | | | X | |
| Blood samples for drug concentration | | X[a] | X[p] | X[q] | | X[a] | | X[a] | |
| Adverse event inquiry | X | X | X | X | X | X | X | X | X |
| Concomitant medication inquiry | X | X | X | X | X | X | X | X | X |
| Benzodiazepines and antidepressants inquiry[t] | | | | | | | | | |
| Alcohol/Illicit drug use inquiry | | | | | | | | | |
| Review of tolerability to study drug prior to dose escalation (if applicable) | | X | X | X | | | | | |
| Dispense/collect study drug | | X | | X | X | | X | X | |
| Review study compliance & adherence | | X | | X | X | X | X | X | |
| Study drug administrations[w,x] | — | — | — | — | — | — | — | — | — |

Study Procedures and Assessments

| TV7820-CNS-20002: Procedures and Assessments | Full Dose Treatment Period | | | | | | | | Follow Up | |
|---|---|---|---|---|---|---|---|---|---|---|
| | First 26-Week Study Period | | | | | Second 26-week Study Period | | | | |
| Visit | V7[a] | V8[a] | V9[a] | TC | V10[a] | TC | TC | TC | V11[a] | V12[a] |
| | 112 ± 7 | 140 ± 7 | 182 ± 7 | 224 ± 10 | 273 ± 7 | 280-308 ± 10 | 315 ± 10 | 322-357 ± 10 | 364 ± 7 | 378 ± 7 |
| Day | week | week | week | week | week | week | week | week | week | week |
| Procedures and assessments | 16 | 20 | 26 | 32 | 39 | 40-44 | 45 | 46-51 | 52 | 54 |
| On-site visit | X | X | X | | X | | | | X | X |
| Telephone call | | | | X | | X | X | X | | |
| Informed consent | | | | | | | | | | |
| Demography | | | | | | | | | | |
| Medical and psychiatric history | | | | | | | | | | |
| Prior medication history | | | | | | | | | | |
| Inclusion and exclusion criteria[b] | | | | | | | | | | |
| Randomization | | | | | | | | | | |
| Clinical laboratory tests (hematology and biochemistry) | X | X | X | | X | | | | X | X |
| Urinalysis | X | X | X | | X | | | | X | X |
| Pregnancy test (women of childbearing potential)[d] | X | X | X | | X | | | | X | X |
| Full physical and neurological examination, including weight (height at screening only) | | | X | | X | | | | X | X |

TABLE 3-continued

| | 1 | 2 | 3 | 4 | 5 | 6 | 7 | 8 | 9 | 10 |
|---|---|---|---|---|---|---|---|---|---|---|
| ECG | $X^a$ | $X^a$ | X | | X | | | | $X^i$ | $X^j$ |
| Vital signs measurement | X | X | X | | X | | | | X | X |
| C-SSRS (Baseline version) | | | | | | | | | | |
| C-SSRS (Since Last Visit version) | X | X | X | | X | X | X | X | X | |
| Blood sample for genetic analyses[k] | | | | | | | | | | |
| UHDRS-TMS | $X^a$ | $X^a$ | $X^a$ | | | | | | $X^a$ | X |
| mPPT | $X^a$ | $X^a$ | $X^a$ | | | | | | $X^a$ | |
| UHDRS-FA | | | X | X | | | | | X | |
| UHDRS-TFC | | | X | X | | | | | X | |
| UHDRS-IS | | | X | X | | | | | X | |
| PBA-s | | | | X | X | | | | X | |
| Abbreviated PBA-s | | | | | | $X^m$ | $X^a$ | $X^a$ | | |
| CIBIS | | | | | | | | | | |
| CIBIC-Plus | | | | X | | | | | X | |
| PDS | | | | X | | | | | X | |
| CGI-S | | | | | | | | | | |
| CGI-C | | | | X | | | | | X | |
| HD-QoL | | | | X | | | | | X | |
| EQ5D-5L | | | | X | | | | | X | |
| Walk-12 | | | | X | | | | | X | |
| Q-Motor assessments[n] | | | | X | | | | | X | X |
| TUG Test | | | | X | | | | | X | |
| Cognitive assessment battery[o] | | | | X | | | | | X | |
| Blood samples for drug concentration | $X^a$ | $X^a$ | X | | | | | | $X^r$ (trough) | $X^s$ |
| Adverse event inquiry | X | X | X | X | X | X | X | X | X | X |
| Concomitant medication inquiry | X | X | X | X | X | X | X | X | X | X |
| Benzodiazepines and antidepressants inquiry[t] | | | | | X | X | X | X | X | |
| Alcohol/Illicit drug use inquiry | | | | | X | X | X | X | X | |
| Review of tolerability to study drug prior to dose escalation (if applicable) | | | | | | | | | | |
| Dispense/collect study drug | X | X | X | | X | | | | $X^u$ | |
| Review study compliance & adherence | X | X | X | | X | $X^v$ | $X^a$ | $X^a$ | X | |
| Study drug administrations[w,x] | — | — | — | — | — | — | — | — | → | |

Primary Efficacy Variable and Endpoint

The UHDRS comprises a broad assessment of features associated with HD (Huntington Study Group 1996). It is a research tool which has been developed to provide a uniform assessment of the clinical features and course of HD. The TMS component of UHDRS comprises 31 assessments from the 15 items of the UHDRS, with each assessment rated on a 5-point scale from 0 (normal) to 4 (maximally abnormal).

Secondary Efficacy Variable and Endpoint

The secondary efficacy variable and endpoint, the Modified Physical Performance Test (mPPT), quantifies the patient's performance in physical tasks (Brown 2000). It is a standardized 9-item test that measures the patient's performance on functional tasks. Assistive devices are permitted for the tasks that require a standing position (items 6 to 9). Both the speed and accuracy at which the patients complete the items were taken into account during scoring. The maximum score of the test is 36, with higher scores indicating better performance.

Other Efficacy Variables and Endpoints

Clinician Interview Based Impression of Change Plus Caregiver Input

The CIBIC-Plus (version ADCS-CGIC) was developed, validated, and is commonly used in studies of anti-dementia drugs in Alzheimer's disease (Joffres 2000). An independent rater evaluated the patient's overall disease severity prior to the initiation of pridopidine or placebo. This assessment, known as the CIBIS, rates the patient on a 7-point Likert scale from extremely severe HD to no symptoms of HD. At each subsequent visit in which the evaluation is performed, the CIBIC-Plus was administered by the same independent rater, but without knowledge of other endpoint assessments or the AEs experienced by the patient during the study (so as not to confound the rating of CIBIC as an efficacy measure or to unblind the study). The independent rater exclusively considers observations of the patient's cognitive, functional, and behavioral performance obtained through interviewing the patient and the caregiver. The rater then compared those findings to the baseline assessment. The overall impression of change from baseline (CIBIC-Plus) is rated on a 7-point scale: 1=marked improvement; 2=moderate improvement; 3=minimal improvement; 4=no change; 5=minimal worsening; 6=moderate worsening; 7=marked worsening; all assessments were relative to baseline. A higher score indicates a worsening of global function. In HD, the inclusion of caregiver input is particularly critical for a global assessment as previous studies have demonstrated that patients have limited awareness and recognition of their deficits.

Physical Disability Scale

The PDS was used during the study as a measure of disability. Patients were scored on a scale from 10 ("Fixed posture requiring total care—gastrotomy, catheterization") to 100 ("Normal; no disease evident") (Myers 1991).

UHDRS Functional Assessments or UHDRS Total Functional Assessment

The TFA scale of the UHDRS assessed functionality in 25 tasks of daily living (e.g., "Could patient engage in gainful employment in his/her accustomed work?"). Each question was answered with 'yes' or 'no.

Clinical Global Impression of Severity and Change

CGI-S was assessed at baseline and CGI-C is used at all subsequent time points to assess changes from baseline. The CGI-S scale was initially designed to assess treatment response in patients with mental disorders (Guy 1976) but is now used widely in a range of illnesses. Illness severity is rated by the investigator on a 7-point scale (1=normal, not at all ill to 7=among the most extremely ill patients). The assessment is based on investigator judgment, supported by a comprehensive, semi-structured, patient/caregiver interview. The CGI-C scale measures the change in the patient's clinical status from a specific point in time, using a 7-point scale, ranging from 1 (very much improved) to 7 (very much worse), with a score of 4 indicating no change.

UHDRS Total Functional Capacity (TFC)

The TFC scale of the UHDRS is a standardized scale used to assess 5 functional domains associated with disability shown below (occupation, finances, domestic chores (e.g. laundry, washing dishes), activities of daily living, and care level). The TFC score has a range of 0-13 and is a well-established endpoint for trials aiming disease progression. The TFC score has been developed and deployed by the Huntington Study Group (HSG, 1996) in multiple trials over 2 decades. The TFC score is accepted by regulators and often considered the most widely accepted tool for disease procession in HD patients. Additionally, TFC is considered the gold standard for measuring HD rate of functional decline. Currently, no drug has been shown to slow the decline of TFC despite many attempts. The floor and ceiling effects make TFC scores more sensitive to change in early stage HD than in late stage HD.

Functional Capacity:—

Occupation: 0=unable, 1=marginal work only, 2=reduced capacity for usual job, 3=normal.

Finances: 0=unable, 1=major assistance, 2=slight assistance, 3=normal.

Domestic Chores: 0=unable, 1=impaired, 2=normal.

Activities of Daily Living (ADL): 0=total care, 1=gross tasks only, 2=minimal impairment, 3=normal.

Care level: 0=fill time skill nursing, 1=home or chronic care, 2=home.

UHDRS Independence Scale

The independence scale of the UHDRS is a rating scale where the patient's degree of independence was given in percentage, from 10% (tube fed, total bed care) to 100% (no special care needed). Scores must end in 0 or 5 (e.g., 10%, 15%, 20% etc.). Patients with a UHDRS-IS score >90% at the screening visit were not eligible for the study.

Global/Functional Scales

Huntington's Disease Quality of Life

The HD-QoL is a standardized instrument for measuring health-related quality of life. (Hocaoglu 2012). It is a validated disease-specific measure designed for HD, and can provide a summary score of overall health-related quality of life, as well as scores on several discrete scales. HD-QoL is for people who are living with HD; this includes people who are at risk for HD, people who have tested positive for the huntingtin gene but do not have symptoms, and also for people at early through to late stages of disease. HD-QoL can be used across the full spectrum of HD.

The change from baseline in HD-QoL and in EQSD-5L was analyzed using an Analysis of Covariance (ANCOVA) Model. The model includes the following fixed effects: treatment, center, neuroleptic use or no use, and baseline HD-QoL or EQSD-5L score. The last observation carried forward (LOCF) was applied for these endpoints for early terminated subjects.

Total Motor Score Subscores

UHDRS Hand Movement Score or UHDRS TMS Hand Movement Score

The hand movement score is defined as the sum of UHDRS domains finger taps, pronate-supinate hands and luria (fist-hand-palm test).

UHDRS Gait and Balance Score or UHDRS TMS Gait and Balance Score

The gait and balance score is defined as the sum of UHDRS domains gait, tandem walking and retropulsion pull test.

UHDRS Modified Motor Scale or UHDRS TMS Modified Motor Scale

The UHDRS-mMS is defined as the sum of following domains from UHDRS-TMS: dysarthria, tongue protrusion, finger taps, pronate-supinate hands, luria, rigidity, bradykinesia, gait, tandem walking, and retropulsion pull test.

UHDRS Chorea or UHDRS TMS Chorea

In the UHDRS, maximal chorea was scored from 0 (absent) to 4 (marked/prolonged) on each of the following items: face, mouth, trunk, right upper extremity, left upper extremity, right lower extremity, and left lower extremity. Maximal chorea is the sum of all scores.

UHDRS Dystonia or UHDRS TMS Dystonia

In the UHDRS, maximal dystonia was scored from 0 (absent) to 4 (marked/prolonged) on each of the following items: trunk, right upper extremity, left upper extremity, right lower extremity, and left lower extremity. Maximal dystonia is the sum of all scores.

TMS Proportion of Responders

The percentage of responders, defined as patients with UHDRS-TMS change from baseline ≤0 at Week 26.

Other Motor Assessments

Multiple Sclerosis Walking Scale

The Multiple Sclerosis Walking Scale (MSWS-12) was adapted to become a generic measure of walking and mobility and renamed the Walk-12.

European Quality of Life-3 Dimensions (3 Levels)

The EQ5D 3 level version (EQ5D-3L) was introduced in 1990 (EuroQol Group 1990). It essentially consists of the EQ5D descriptive system and the EQ visual analogue scale (EQ VAS). The EQ5D-3L descriptive system comprises the following 5 dimensions: mobility, self-care, usual activities, pain/discomfort and anxiety/depression. In developing the 5L, the 5-dimensional structure of the original EQ5D-3L was retained but the levels on each dimension were expanded to 5-levels based on qualitative and quantitative studies conducted by the EuroQol Group. The labels for each of the dimensions are: no problems, slight problems, moderate problems, severe problems, and unable to/extreme problems. The EQ-VAS is still an integral part of the EQ5D-5L but has been adapted to make it more user-friendly. The respondent is asked to indicate his/her health state choosing the most appropriate statement in each of the 5 dimensions. The EQ VAS records the respondent's self-rated health on a vertical, visual analogue scale where the endpoints are labeled 'Best imaginable health state' and 'Worst imaginable health state'. This information can be used as a quantitative measure of health outcome as judged by the individual respondents. It should be noted that the numerals 1-3 have no arithmetic properties and should not be used as a cardinal score. The EQ5D can be completed by the patients with caregiver/informant assistance if needed.

Quantitative Motor (Q-Motor) Assessments

Motor deficits can be objectively assessed using different Q-Motor assessments. All Q-Motor assessments are based on the application of precalibrated and temperature controlled force transducers and 3-dimensional position sensors with very high sensitivity and test-retest reliability across sessions and sites in a multicenter clinical study. Q-Motor measures thus aim to reduce the limited sensitivity of categorical clinical rating scales, the intra- and inter-rater variability, and placebo effects observed in scales such as UHDRS-TMS. In addition, Q-Motor assessments allow for the objective monitoring of unintended motor side-effects in clinical studies. Thus, Q-Motor is an objective, reliable, and sensitive measure of motor function that is free of rater bias and limits placebo effect influence. FIG. 36 shows the Q-motor tap measurements for a normal patient, a patient with mild defects and a patient with severe defects. In Track-HD, the largest natural history study of pre-manifest and early stage HD Q-motor tapping deficits correlated with clinical scores as well as regional brain atrophy (FIGS. 36 and 37 and Bechtel 2010).

Digitomotography (Speeded Index Finger Tapping)

The patient placed their hand on a hand rest with their index finger positioned above a force-transducer. Recordings start after practice runs. The patient is instructed to finger tap as fast as possible between 2 auditory cues. The beginning of a tap is defined as a rise of the force by 0.05 N above maximal baseline level. The tap ends when it drops to 0.05 N before the maximal baseline level is reached again. The duration and variability of tap durations (TD), inter onset intervals (IOI), inter peak intervals (IPI), and inter tap intervals (ITI) are the exploratory outcome measures for speeded tapping. In addition, variability of peak tapping forces (TF) is calculated as coefficient of variation, and the tapping frequency (Freq), i.e., the number of taps between the onsets of the first and the last tap divided by the time in between, is determined. Five trials of 10 seconds duration are performed with each hand.

Dysdiadochomotography (Pronation/Supination Hand Tapping)

This task assesses the regularity of hand taps performed when alternating between the palm and dorsal surface of the hand performing a repetitive pronation/supination movement. The force and duration of the hand taps are recorded similarly to the speeded tapping task. A tone cues the start and end of an assessment. Five trials of 10 seconds duration are performed with each hand.

UHDRS Pronation/Supination Assessment

An assessment of the ability to rotate the forearm and hand such that the palm is down (pronation) and to rotate the forearm and hand such that the palm is up (supination) on both sides of the body.

Manumotography and Choreomotography (Grip Force and Chorea Analysis)

This task assessed the coordination of isometric grip forces in the precision grip between the thumb and index finger. Grip forces are assessed during grip initiation, object transport, and in a static holding phase. Patients are instructed to grasp and lift a device equipped with a force transducer and 3-dimensional position sensor in the precision grip between thumb and index finger and hold it stable adjacent to a marker 10-cm high. Grip forces and 3-dimensional position and orientation of the object are recorded. Mean isometric grip forces and grip force variability in the static phase (expressed as coefficient of variation=standard deviation [SD]/mean×100) (GFV-C) are calculated during a 15-second period starting 8 seconds after the first cueing tone. Five trials of 20 seconds duration are performed with each hand. Chorea is assessed calculating a "position-index" and "orientation-index". Start and end of assessment are signaled by a cueing tone.

Pedomotography (Speeded Foot Tapping)

The patient placed a foot on the foot device such that the ball of the foot is positioned above a force-transducer. Recordings started after practice runs. The patient is instructed to tap with the foot as fast as possible between 2 auditory cues. The beginning of a tap is defined as a rise of the force by 0.05 N above maximal baseline level. The tap ends when it dropped to 0.05 N before the maximal baseline level is reached again. The duration and variability of TD, IOI, IPI, and ITI are the exploratory outcome measures for speeded tapping. In addition, variability of peak TF is calculated as coefficient of variation, and the tapping Freq, i.e., the number of taps between the onsets of the first and the last tap divided by the time in between, is determined. Five trials of 10 seconds duration are performed with each foot.

Timed Up and Go Test

The TUG is a simple test used to assess a person's mobility and requires both static and dynamic balance. It uses the time that a person takes to rise from a chair, walk 3 meters, turn around, walk back to the chair, and sit down. During the test, the person is expected to wear their regular footwear and use any mobility aids that they would normally require. The TUG is used frequently in the elderly population, as it is easy to administer and can generally be completed by the majority of older adults. The test is quick, requires no special equipment or training, and is easily included as part of the routine medical examination (Podsiadlo 1991). The use of the TUG test in conjunction with UHDRS has been recommended for clinical studies of HD (Rao 1991).

HD-Cognitive Assessment Battery (CAB)

The CAB may be used to detect symptomatic, "pro-cognitive" effects (6 months-1 year) and slowing rate of cognitive decline (>1 year). It in 6-12 months after beginning treatment, the CAB is especially useful to measure "pro-cognitive" effects and in more than 1 year the CAB is especially useful to detect the slowing rate of cognitive decline. The CAB covers domains most impacted in HD, using tests with good psychometric properties. The following six sections describe the tests that are part of the CAB brief.

1. Symbol Digit Modalities Test

The SDMT is a paper-and-pencil test of psychomotor speed and working memory. Participants view a 'key' at the top of the page containing symbols paired with numbers. The remainder of the page displays rows of symbols, and the participant has 90 seconds to write the corresponding number that matches each symbol.

2. Emotion Recognition

Emotion recognition of facial expressions of emotions is examined using computerized presentations of photographs depicting 6 basic emotions or a neutral expression. Participants are asked to indicate the emotion expressed in each photograph by selecting from the words fear, disgust, happy, sad, surprise, angry, and neutral (10 stimuli per emotion).

3. Trail Making Tests A and B

Visual attention and task switching are assessed using the Trail Making test, which consists of 25 circles on a standard sheet of paper. For Trail A, participants are required to connect, as quickly as possible, circles containing numbers in ascending numerical order. For Trail B, participants are to connect, as quickly as possible, circles containing numbers and letters, alternating between numbers and letters in ascending order (e.g., 1, A, 2, B, 3, C, etc.). Trail A is used only as part of the training (Bowie 2006). Trail A is used only as part of the training.

4. Hopkins Verbal Learning Test, revised

The HVLT-R offers a brief assessment of verbal learning and memory (recognition and recall). It is easy to administer and score and is well tolerated even by significantly impaired individuals. Its use has been validated with brain-disordered populations (e.g., Alzheimer's disease, HD, amnestic disorders) as a measure of verbal learning and memory. Each form consists of a list of 12 nouns (targets) with 4 words drawn from each of 3 semantic categories. The semantic categories differ across the 6 forms, but the forms are very similar in their psychometric properties. Raw scores are derived for Total Recall, Delayed Recall, Retention (% retained), and a Recognition Discrimination Index. The HVLT-R has high test-retest reliability, and its construct, concurrent, and discriminant validity have been well established. Raw scores are derived for Learning Trials 1-3 (i.e., Total Recall) and Trial 4 (e.g., Delayed Recall Trial).

5. Paced Tapping test

Psychomotor function is assessed in a Paced Tapping test (also known as PTAP). Participants tap on left and right mouse buttons, alternating between thumbs, at 3.0 Hz. They first listen to a tone presented at the desired tapping rate, and then begin tapping to the tone. After 11 taps with the tone, the repetition of the tone is discontinued, and participants attempt to continue tapping at the same rate until the end of the trial (31 taps later).

6. One Touch Stockings of Cambridge (OTS)

OTS is a spatial planning task which gives a measure of frontal lobe function. OTS is a variant of the Stockings of Cambridge task, and places greater demands on working memory as the participant has to visualize the solution. As with Stockings of Cambridge, the participant was shown 2 displays containing 3 colored balls. The displays are presented in such a way that they can easily be perceived as stacks of colored balls held in stockings or socks suspended from a beam. This arrangement makes the 3 dimensional concepts involved apparent to the participant, and fits with the verbal instructions. There is a row of numbered boxes along the bottom of the screen. The test administrator first demonstrates to the participant how to use the balls in the lower display to copy the pattern in the upper display, and completes 1 demonstration problem, where the solution requires 1 move. The participant must then complete 3 further problems, 1 each of 2 moves, 3 moves, and 4 moves. Next, the participant is shown further problems, and must work out in their head how many moves the solutions to these problems require, then touch the appropriate box at the bottom of the screen to indicate their response.

Problem Behaviors Assessment-Short Form (PBA-s)

Because of the prominence of psychiatric symptoms in HD, it was recommended that the PBA-s form be used in all HD studies with any need for behavioral assessment as a comprehensive screen for the most common psychiatric symptoms in HD. (Craufurd 2001, Kingma 2008) The PBA-s also includes questions concerning suicidal behavior, a particular concern in HD. The PBA-s is based on the same set of core behavioral symptoms as the UHDRS Behavioral questions, which were used previously as the global psychiatric measure in most HD studies. The PBA-s has more detailed questions and more specific guidance on administration and scoring The PBA-s is a brief semi-structured interview covering the most common behavioral and psychiatric manifestations of HD. The interview is not restricted to a single construct, but rather covers several broad symptom domains relevant to HD, comprising 11 items: low mood, suicidal ideation, anxiety, irritability, anger/aggressive behavior, loss of motivation, perseverative thinking or behavior, obsessive-compulsive behaviors, paranoid thinking, hallucinations, behavior suggestive of disorientation. Each symptom is rated for severity on a 5-point scale according to detailed scoring criteria which roughly correspond to the following: 0="not at all"; 1=trivial; 2=mild; 3=moderate (disrupting everyday activities) and 4=severe or intolerable. Each symptom is also scored for frequency on a 5-point scale as follows: 0=symptom absent; 1=less than once weekly; 2=at least once a week; 3=most days (up to and including some part of everyday); and 4=all day, every day. Severity and frequency scores are multiplied to produce an overall 'PBA score' for each symptom.

Assessment of Safety

In this Example, safety was assessed by qualified study staff by evaluating the following: reported AEs, clinical laboratory test results, vital signs measurements, ECG findings, physical and neurological examination findings (including body weight), and concomitant medication usage.

Clinical Laboratory Tests

Clinical laboratory tests (serum chemistry including electrolytes, hematology and urinalysis) were performed as listed below.

The following serum chemistry tests were performed: calcium; phosphorus; sodium; magnesium; potassium; chloride; bicarbonate or carbon dioxide; glucose; blood urea nitrogen; creatinine; cholesterol; uric acid; ALT; AST (aspartate aminotransferase); lactate dehydrogenase; gamma-glutamyl transpeptidase (GGT); alkaline phosphatase; creatine phosphokinase (in case of elevated creatine phosphokinase, the MB fraction should be measured); total protein, albumin; total bilirubin; direct bilirubin; indirect bilirubin; and prolactin. The following hematology tests were performed: Hemoglobin; hematocrit; red blood cell (RBC) count; platelet count; white blood cell (WBC) count and differential count; absolute neutrophil count; absolute lymphocyte count; absolute eosinophil count; absolute monocytes count; absolute basophil count; and absolute atypical lymphocyte count. Urinalysis includes testing for the following: Protein; glucose; ketones; blood (hemoglobin); pH; specific gravity; leukocyte esterase; microscopic; bacteria; RBCs; WBCs; casts; and crystals.

Vital Signs

Vital signs, including pulse, blood pressure, and body temperature were measured.

Assessment of Pharmacokinetics and Pharmacogenomics

The primary PK measure is a determination of plasma concentration of pridopidine. Concentrations were also incorporated into a pridopidine population PK model and individual exposure for the study patients (Cmax and AUC) was calculated.

Blood Sampling and Handling

Blood samples (4 mL each) were collected for the determination of plasma concentrations via venipuncture or indwelling catheter in the morning before study drug administration at the following visits:

Titration Period: day 0 (baseline)—prior and 1 to 2 hours post first dose and day 14—1 to 2 hours post afternoon dose. Full Treatment Dose Period: day 28—pre afternoon dose and 1 to 2 hours post afternoon dose, day 42—pre afternoon dose and 1 to 2 hours post afternoon dose, day 84—1 to 2 hours post afternoon dose, day 112—pre afternoon dose and 1 to 2 hours post afternoon dose, day 140—1 to 2 hours post afternoon dose, day 182—prior to morning dose, and follow-up visit.

Analysis of Samples

Samples were analyzed using an appropriate validated method for pridopidine and its main metabolite TV-45065 (previously called ACR30). The lower limits of quantification for pridopidine and TV-45065 in plasma are approximately 1.6 to 1.8 ng/mL and 1.5 to 1.9 ng/mL, respectively.

Pharmacogenomic Variables

A blood sample (10 mL) was collected in 2 dipotassium ethylenediaminetetraacetic acid (K2EDTA) plastic tubes at the screening visit for genetic analyses. Analyses include CAG repeats, CYP2D6 status, and genetic long QT syndrome, or any other genetic analyses related to pridopidine response or HD.

Primary Efficacy Analysis

The change from baseline in UHDRS-TMS was analyzed using a Repeated Measures model (SAS® MIXED procedure with REPEATED sub-command). The model includes the following fixed effects: categorical week in study by treatment interaction, center, neuroleptic use or no use, and baseline UHDRS-TMS score. The unstructured covariance matrix for repeated observations within patients was used. In case that the model does not converge, the Maximum-Likelihood (ML) estimation method is used instead of the default Restricted ML (REML). If the model still does not converge then a simpler covariance structures with less parameters is used, according to the following order: Heterogeneous Autoregressive(1) [ARH(1)], Heterogeneous Compound Symmetry (CSH), Autoregressive(1) [AR(1)], and Compound Symmetry (CS). The estimated means at the Week 26 visit of the change from baseline in UHDRS-TMS was compared between the active treatment arms) and the placebo arm.

Sensitivity Analysis

A sensitivity analysis to evaluate if the observed effect in UHDRS-TMS is driven by the Chorea UHDRS-TMS sub-score, the Dystonia UHDRS-TMS sub-score, or the Involuntary Movements (Chorea+Dystonia) UHDRS-TMS sub-score was performed as follows:

Three variables were calculated: (1) The change from baseline to Week 26 and Week 52 in the sum of the UHDRS-TMS items except the Chorea items, (2) The change from baseline to Week 26 and Week 52 in the sum of the UHDRS-TMS items except the Dystonia items, and (3) The change from baseline to Week 26 and Week 52 in the sum of the UHDRS-TMS items except the Chorea and Dystonia items. These variables were analyzed in the same way as the primary efficacy endpoint except that the variable evaluation at baseline were included in the model instead of baseline UHDRS-TMS.

Pharmacokinetic Analysis

Plasma concentration data on pridopidine and the main metabolite TV-45065 are presented by descriptive statistics by dose of pridopidine and also by CYP2D6 metabolizer status. Concentrations are also incorporated into a pridopidine population PK model and individual exposure for the study patients ($C_{max}$ and AUC) are calculated.

| Analysis group, n (%) | Placebo | Pridopidine | | | | | Total |
| --- | --- | --- | --- | --- | --- | --- | --- |
| | | 45 mg bid | 67.5 mg bid | 90 mg bid | 112.5 mg bid | All | |
| Screened | | | | | | | 492 |
| Screened, not in ITT population | | | | | | | 84 |
| Death | | | | | | | 0 |
| Adverse event | | | | | | | 0 |
| Withdrawal by subject | | | | | | | 11 |
| Inclusion criteria not met | | | | | | | 20 |
| Exclusion criteria met | | | | | | | 46 |
| Lost to follow-up | | | | | | | 0 |
| Other | | | | | | | 7 |
| ITT population | 82 (100) | 81 (100) | 82 (100) | 81 (100) | 82 (100) | 326 (100) | 408 (100) |
| ITT population, not treated | 0 | 0 | 0 | 0 | 0 | 0 | 0 |
| Safety population (SP) | 82 (100) | 81 (100) | 82 (100) | 81 (100) | 82 (100) | 326 (100) | 408 (100) |
| PK population (PK) | 0 | 0 | 0 | 0 | 0 | 0 | 0 |
| Full analysis set (FAS) | 81 (99) | 75 (93) | 79 (96) | 81 (100) | 81 (99) | 316 (97) | 397 (97) |
| Full analysis set on study drug (FASOD) | 81 (99) | 75 (93) | 79 (96) | 81 (100) | 81 (99) | 316 (97) | 397 (97) |
| Complete 26 weeks of treatment (CO) | 70 (85) | 59 (73) | 65 (79) | 67 (83) | 62 (76) | 253 (78) | 323* (79) |
| Discontinued treatment during 1st period | 12 (15) | 22 (27) | 17 (21) | 14 (17) | 20 (24) | 73 (22) | 85* (21) |
| Death | 0 | 0 | 0 | 0 | 0 | 0 | 0 |
| Adverse event | 5 (6) | 6 (7) | 11 (13) | 11 (14) | 14 (17) | 42 (13) | 47 (12) |
| Withdrawal by subject | 3 (4) | 9 (11) | 3 (4) | 0 | 3 (4) | 15 (5) | 18 (4) |
| Non-compliance | 2 (2) | 1 (1) | 1 (1) | 0 | 0 | 2 (<1) | 4 (<1) |
| Protocol violation | 1 (1) | 1 (1) | 1 (1) | 1 (1) | 0 | 3 (<1) | 4 (<1) |
| Pregnancy | 0 | 0 | 0 | 0 | 0 | 0 | 0 |
| Lost to follow-up | 0 | 0 | 0 | 0 | 0 | 0 | 0 |
| Lack of efficacy | 0 | 0 | 1 (1) | 0 | 0 | 1 (<1) | 1 (<1) |
| Other | 1 (1) | 5 (6) | 0 | 2 (2) | 3 (4) | 10 (3) | 11 (3) |
| Discontinued treatment during 1st period but continue to FU | 1 (1) | 0 | 2 (2) | 2 (2) | 2 (2) | 6 (2) | 7 (2) |
| Complete 26 weeks of study | 70 (85) | 61 (75) | 66 (80) | 67 (83) | 66 (80) | 260 (80) | 330 (81) |
| Signed protocol amendment 4 | 59 (72) | 55 (68) | 60 (73) | 62 (77) | 57 (70) | 234 (72) | 293 (72) |
| Entered 2nd period | 57 (70) | 49 (60) | 54 (66) | 56 (69) | 46 (56) | 205 (63) | 262 (64) |
| Started treatment for 2nd period | 57 (70) | 49 (60) | 52 (63) | 56 (69) | 46 (56) | 203 (62) | 260 (64) |
| ITT population for the 52 Weeks Analysis (ITT2) | 82 (100) | 81 (100) | 82 (100) | 81 (100) | 82 (100) | 326 (100) | 408 (100) |
| Safety population for the 52 Weeks Analysis (SP2) | 82 (100) | 81 (100) | 82 (100) | 81 (100) | 82 (100) | 326 (100) | 408 (100) |
| PK population for the 52 Weeks Analysis (PK2) | 0 | 0 | 0 | 0 | 0 | 0 | 0 |
| Full analysis set for the 52 Weeks Analysis (FAS2) | 81 (99) | 75 (93) | 79 (96) | 81 (100) | 81 (99) | 316 (97) | 397 (97) |
| Complete 52 weeks of treatment | 52 (63) | 43 (53) | 44 (54) | 53 (65) | 44 (54) | 184 (56) | 236 (58) |
| Discontinued treatment during 2nd period | 5 (6) | 6 (7) | 8 (10) | 3 (4) | 2 (2) | 19 (6) | 24 (6) |
| Death | 0 | 0 | 0 | 1 (1) | 0 | 1 (<1) | 1 (<1) |
| Adverse event | 1 (1) | 4 (5) | 5 (6) | 0 | 1 (1) | 10 (3) | 11 (3) |
| Withdrawal by subject | 2 (2) | 1 (1) | 2 (2) | 0 | 0 | 3 (<1) | 5 (1) |

-continued

| Analysis group, n (%) | Placebo | Pridopidine | | | | | Total |
| --- | --- | --- | --- | --- | --- | --- | --- |
| | | 45 mg bid | 67.5 mg bid | 90 mg bid | 112.5 mg bid | All | |
| Non-compliance | 1 (1) | 0 | 0 | 0 | 0 | 0 | 1 (<1) |
| Protocol violation | 0 | 0 | 0 | 0 | 0 | 0 | 0 |
| Pregnancy | 0 | 0 | 0 | 0 | 0 | 0 | 0 |
| Lost to follow-up | 0 | 0 | 0 | 0 | 0 | 0 | 0 |
| Lack of efficacy | 1 (1) | 0 | 0 | 1 (1) | 1 (1) | 2 (<1) | 3 (<1) |
| Other | 0 | 1 (1) | 1 (1) | 1 (1) | 0 | 3 (<1) | 3 (<1) |
| Discontinued treatment during 2nd period but continue to FU | 0 | 1 (1) | 2 (2) | 0 | 1 (1) | 4 (1) | 4 (<1) |
| Complete 52 weeks of study | 52 (63) | 43 (53) | 46 (56) | 52 (64) | 44 (54) | 185 (57) | 237 (58) |

Stages of Huntington's Disease

Many clinicians and diagnosticians adopt the Shoulson and Fahn rating scale, based on TFC scores, to follow progression of HD. This rating scale groups total TFC scores into five stages of disease, with lower stages indicating more intact functioning. Table 4, below, provides the TFC scores, average years from diagnosis and broad guidelines for typical care level for each stage of disease. (Johnson 2014.) Table 5 below shows the number of patients at each TFC stage participating the study.

TABLE 4

| Stage | TFC score | Years since motor diagnosis | Typical abilities and care level |
| --- | --- | --- | --- |
| 1 | 11-13 | 0-8 | Able to work at least part time, may require slight assistance in one of finances, domestic chores or ADL basic functions |
| 2 | 7-10 | 3-13 | Unable to work, requires some assistance in some basic functions |
| 3 | 3-6 | 5-16 | Unable to work, requires major assistance in most basic functions |
| 4 | 1-2 | 9-21 | Requires major assistance in all basic functions and although comprehension may be intact requires assistance to act. |
| 5 | 0 | 11-26 | Requires major assistance in all basic functions and full time nursing care |

Patients with stage 1 or 2 have the steepest rate of natural decline and are the most sensitive to the clinical measure described in this application. TFC and HD-CAB assessments are designed specifically for patients with stage 1 or 2 and earlier. Patients with stage 3, 4 or 5 often have difficult completing assessments, the floor and ceiling limit the ability to track change and have very significant brain tissue loss.

Early stage HD, as used herein, means stage 1 or stage 2 HD (BL TFC≥7) as defined by Table 4 above.

TABLE 5

HD stages of patients in study

| | N | % | years since HD diagnosis |
| --- | --- | --- | --- |
| Stage 1 (TFC = 11-13) | 78 | 19 | 3 |
| Stage 2 (TFC = 7-10) | 218 | 53 | 5 |
| Stage 3 (TFC = 3-6) | 101 | 25 | 5-8 |
| Stage 4 (TFC = 1-2) | 10 | 2 | >8 |
| Stage 5 (TFC = 0) | 1 | <1 | |

Results

The results of this example are shown in FIGS. 1-47 and Table 6 below.

TABLE 6

| | Observed Data Analysis | |
| --- | --- | --- |
| Responder Analysis Questions | 45 mg bid N = 37 | Placebo N = 41 |
| What proportion of early stage subjects had no deterioration on TFC (score ≥0) at 52 weeks? | 30 (81%) | 20 (49%) |
| p value (Chi-Square) | 0.003 | |
| What proportion of early stage subjects had an improvement of ≥1 points on TFC at 52 weeks? | 10 (27%) | 5 (12%) |
| p value (Chi-Square) | 0.099 | |

A significant difference in the proportion of subjects that showed no decline in TFC over 52 weeks was observed between patients treated with 45 mg bid and patients receiving placebo.

Overview of preliminary analysis of functional, exploratory endpoints and safety:

Endpoints not dependent on rater bias were less prone to placebo effect, such as the Q-motor assessment. The signals detected suggest biological effects of pridopidine. Total Functional Capacity (TFC) showed trends favoring pridopidine after 26 weeks of treatment. There was no major safety findings despite high doses.

Preliminary Results on TFC Scores—Considerations

Expected deterioration of about 0.5 points were seen in the placebo group at 6 months. Historical data indicates that TFC deteriorates about 1 point per year in patients with HD. TFC starts showing separation from placebo at week 12 to 20 and separation becomes a strong trend at week 26. The TFC data supports a finding that pridopidine causes a delay of progression of functional decline. FIG. 42 shows a graphical representation of TFC deterioration at the different stages of disease.

Without wishing to be bound to this theory, the treatment effects shown in the figures were more pronounced when treating early stage patients (including stages 1 and 2), especially early stages with baseline TFC greater than or equal to 7, and even more so in stage 1 (BL TFC=11-13). Without wishing to be bound to this theory this is particularly true for TFC finances and ADL, TFC domestic chores, dystonia, involuntary movements (dystonia and chorea), gait and balances. A patient affected with HD with a baseline TFC score of 11-13 is considered to be a stage 1 HD patient.

Potential Placebo Effect Contributors in this Example

The following items may account for the placebo effect seen in this example: Rater bias, a lack of hope in HD, together with a high expectation for an effective treatment and a desire to get better from patients, overall positive data with pridopidine treatment causes high expectations, patients have an 80% chance to receive active treatment, a high number of pills may cause expectancy, protocol changes during the study, and the number of assessments per visit.

Dystonia

The total Dystonia treatment exemplified in this application is representative of treatment of the following types of Dystonia: early onset generalized dystonia (DYT1 and non-DYT1), Focal dystonia, Musicians' dystonias, Dopa-responsive dystonia, Myoclonus dystonia, Paroxysmal dystonias and dyskinesias, X-linked dystonia-parkinsonism, Rapid-onset dystonia-parkinsonism, Secondary dystonias, dystonia in HD patients and Psychogenic dystonia. In particular, the present invention relates to treating dystonia in a HD patient, for example an early stage (stage 1 or stage 2) HD patient.

Discussion

Pridopidine Efficacy

Pridopidine has previously demonstrated motor function benefit in 2 large, double-blind, placebo-controlled studies in patients with HD (HART and MermaiHD). The primary endpoint for both studies was the mMS. Both studies provided evidence of a beneficial effect on the UHDRS—Total Motor Score (TMS), demonstrating differences favoring pridopidine 45 mg twice daily (bid) compared with placebo. In a pooled analysis of the 2 studies, pridopidine 45 mg bid significantly improved TMS compared with placebo at weeks 12 and 26 (Landwehrmeyer 2011). The PRIDE-HD study used change in TMS from baseline to week 26 as the primary endpoint to further evaluate the effects of pridopidine at doses ranging from 45 mg to 112.5 mg bid.

The PRIDE-HD study recruited patients in all disease stages (i.e. early and advanced), and 72% of the patient population treated with pridopidine were in the early stages of the disease (Stage 1 and 2 HD; baseline TFC scores of 7 to 13 (HD1 and HD2)). During the early stages of HD many of the HD clinical scales and assessment tools are the most sensitive to change over time. PRIDE-HD did not meet the primary endpoint compared with placebo due to a large placebo effect. However, analysis of data from the PRIDE-HD study demonstrated less decline in the UHDRS-TFC score in patients receiving pridopidine 45 mg bid compared with those receiving placebo (no correction for type I error for multiple comparisons was applied). This effect was most evident in patients with early-stage HD.

FIGS. 1 and 2 are graphs showing pridopidine concentration (ng/ml) measures in patients' blood through week 20 of treatment.

FIGS. 3-5 are graphs showing change in UHDRS TMS over time. A lower number represents improvement. FIG. 3 shows a comparison between doses in the PRIDE-HD study. FIG. 4 shows the placebo effect in the UHDRS TMS, which was greater in the PRIDE-HD study than in the MermaiHD or HART studies. FIG. 5a shows an improvement in UHDRS TMS for both 45 mg pridopidine bid and 90 mg pridopidine bid in the PRIDE-HD study compared to the placebo in MermaiHD and HART studies. FIG. 5b shows an overall improvement in UHDRS-TMS for 45 mg pridopidine bid over 52 weeks.

UHDRS Total Functional Capacity (UHDRS TFC)

The data in this application demonstrates that pridopidine shows an effect on progression of HD as measured by total functional capacity (TFC). This effect on TFC was statistically significant in the full analysis set and even more pronounced in early stage HD patients. Early stage HD patients are defined as those with a baseline (BL) TFC score of greater than or equal to 7 (Stage 1 and Stage 2).

There was a significant lessening in UHDRS TFC between patients administered pridopidine at some doses compared to patients administered the placebo at 52 weeks in both the Full Analysis Set (FAS) and the early stage HD sub-population. Patients with early stage HD (baseline 7-13) receiving pridopidine have more positive TFC results than patients with late stage HD (baseline 0-6) receiving pridopidine. The effect on TFC observed at 26 weeks reached significance in the early stage subpopulation (FIGS. 10b and 20b). The effect on TFC observed at 52 weeks reached significance in the early stage subpopulation (FIGS. 10d, 11d, 21j, 31b).

The TFC annual decline of the placebo group shown in, for example, FIGS. 10c, 21j, and 31a, was comparable to the TFC annual decline reported in the literature and observed in historical placebo arms. As shown by, for example, FIGS. 10b, 10d, 21b, 21j, 21n, and 31b, the TFC deterioration in patients given placebo was higher in patients with early stage HD. This data shows a slowing of clinical progression in HD as measured by TFC and is the first clinical trial to do so among eleven (11) other clinical trials. Significance was observed in the UHDRS TFC at week 26 (FIG. 21b) TFC finance at week 26 (FIGS. 12b, 21d, 21f), TFC finance and ADL at week 26 (FIG. 11b, 21d), TFC ADL at week 26 (FIG. 21h) and UHDRS TFC at week 52 (FIG. 21j) TFC finance at week 52 (FIG. 21n), TFC finance and ADL at week 52 (FIG. 11e, 21l), TFC ADL at week 52 (FIG. 21p).

UHDRS Independence Scale (UHDRS IS)

The UHDRS-IS comprises part of the UHDRS functional assessments (Huntington Study Group 1996). It is a rating scale where the patient's degree of independence is given in percentage, from 10% (tube fed, total bed care) to 100% (no special care needed). Scores must end in 0 or 5 (eg, 10%, 15%, 20% etc). The scale was assessed at screening, baseline, weeks 4, 12, 20, 26/Early Termination, 28 and 52/Early Termination.

The change from baseline in the UHDRS-IS week 52 is shown in FIG. 9e. The change from baseline in the UHDRS-IS assessed at week 52 decreased across treatment groups, but was not statistically significant in any treatment group. For the placebo group, there was a decrease (indicating a trend toward decline) in IS at Week 52. Positive trends in the desired direction were observed in early-stage HD patients (baseline TFC score ≥7) at week 52 (see FIG. 20d). No clinically meaningful changes were noted for patients with a baseline TFC<7. The Independence scale supports the TFC effect, which provides a convergence of endpoints.

UHDRS TMS and Motor Endpoints

Motor effects were statistically significant in stage 1 subpopulations. For example, statistically significant changes are seen in the HD Stage 1 patient subgroups for Total TMS, Involuntary movements (Dystonia, Chorea), Ambulation (TMS Gait and Balance, Time Up an Go, Walk 12). The improvement in ambulation may be contributing to TFC data.

A large placebo response masked motor effects in the full analysis set. However, in early HD there was a statistically significant effect on TMS at weeks 26 (FIG. 8b) and 52 (FIG. 8d) driven by a lower placebo effect. Involuntary Movements (chorea and dystonia) as measured by TMS improved in HD stage 1 patients at 26 weeks (FIG. 8n). The effect persisted at 52 weeks as well (FIG. 8p).

Effects were observed primarily with 45 mg bid and 90 mg bid, suggesting a non-linear dose response.

In addition, positive effects on ambulation (such as gait, timed up and go, and stair climbing) were observed in early stage patients administered 45 mg pridopidine bid (see for example FIGS. 18b, 18d, 19b, 19d).

PBA-s

The PBA-s is a brief semi-structured interview covering the most common behavioral and psychiatric manifestations of HD. The interview is not restricted to a single construct, but rather covers several broad symptom domains relevant to HD, comprising 11 items: low mood (depression), suicidal ideation, anxiety, irritability, anger/aggressive behavior, loss of motivation (apathy), perseverative thinking or behavior, obsessive-compulsive behaviors, paranoid thinking, hallucinations, and behavior suggestive of disorientation. Each symptom is rated for severity on a 5-point scale according to detailed scoring criteria, which roughly correspond to the following: 0="not at all"; 1=trivial; 2=mild; 3=moderate (disrupting everyday activities) and 4=severe or intolerable. Each symptom is also scored for frequency on a 5-point scale as follows: 0=symptom absent; 1=less than once weekly; 2=at least once a week; 3=most days (up to and including some part of every day); and 4=all day, every day.

Severity and frequency scores are multiplied (after setting all values outside the range of 0-4 to missing) to produce an overall "PBA-s score" for each symptom. The total PBA score is calculated by the sum of all PBA-s scores across symptoms/domains.

The PBA-s assessments were collected at baseline, weeks 4, 12, 26, and 52.

The change from baseline to week 26 in the PBA-s domains and total scores did not show meaningful results (FIGS. 17a-d, 17i). However, the change from baseline to week 52 in the PBA-s total score as well as several of the PBA-s domains showed a trend to improvement or significant improvement (FIGS. 17d-17h). In the full analysis set, the pridopidine 45 mg bid group showed a trend toward improvement in the PBA-s total score at 52 weeks compared with the placebo group (Δ3.98 points to placebo, p=0.0603, n=75) (see FIGS. 17e-17f)). FIGS. 17j and 17l show a trend to improvement in PBA apathy in early stage patients at 26 weeks and 52 weeks, respectively. FIG. 17r shows a significant improvement in PBA disorientation in early stage patients at 26 weeks for 45 mg bid., respectively.

HD-Cognitive Assessment Battery

The PRIDE-HD study was the first large study to include the HD-Cognitive Assessment Battery (HD-CAB) assessments (Stout et al 2014). The HD-CAB was designed to detect symptomatic, "pro-cognitive" effects (6 months-1 year) and slowing rate of cognitive decline (>1 year) in late pre-manifest, HD1 and HD2 patients. It covers cognitive domains most impacted in HD, using tests with good psychometric properties. The battery includes the following tests: Symbol Digit Modalities Test, Emotion Recognition, Trail Making Test B, Hopkins Verbal Learning Test (revised), Paced Tapping at 3 Hz, and One Touch Stockings of Cambridge.

For the 6 domains of the HD-CAB, there was no consistent pattern of improvement or decline as demonstrated by the mean changes from baseline for the pridopidine or placebo treatment groups.

Positive findings indicating potential improvement from baseline in the Paced Tapping at 3 Hz assessment (a measure of psychomotor function) were observed in the full analysis set at week 52 for the 45 mg bid treatment group (see FIG. 41d).

Example 2

Effect of Pridopidine on Functional Capacity of Patients with Huntington Disease Objective To explore functional decline measured by the Total Functional Capacity (TFC) scale in patients treated with open-label pridopidine 90 mg/day for 36 months (OPEN-HART) and compare results to historical cohorts of placebo patients enrolled in HSG-sponsored trials (CARE-HD and 2CARE).

Background

Patients with HD experience motor, cognitive and behavioral symptoms that lead to serious, long-term disability. TFC (range 0-13, high scores indicate greater capacity) evaluates patients' capacity to work, handle finances and domestic chores, perform activities of daily living and live independently, and is most sensitive to early changes in disability. TFC was utilized in OPEN-HART and the Coenzyme Q10 studies, CARE-HD and 2CARE.

Methods

This analysis compared the OPEN-HART cohort (n=50) that received pridopidine 90 mg/day and the placebo arms of CARE-HD (n=80) and 2CARE (n=213) without matching on baseline characteristics. For this analysis, TFC scores at baseline, 12, 24, and 36 months from OPEN-HART and 2CARE, and TFC scores at baseline, 12, 25, and 30 months from CARE were utilized.

Results

At baseline, the OPEN-HART cohort had the lowest absolute mean (SD) TFC score compared with the CARE-HD and 2CARE cohorts [9.14(2.78), 10.3(1.7) and 11.05 (1.47), respectively].

The mean change from baseline in TFC at 12 months was OPEN-HART: −0.49 (1.60), CARE: −1.00 (1.48) and 2CARE: −1.11 (1.62); at 24 months (OPEN-HART and 2CARE) and 25 months (CARE) was: −1.00 (1.92), −1.80 (2.06) and −2.24 (1.91), respectively; at 36 months (OPEN-HART and 2CARE) was: −1.68 (2.22) and −2.54 (2.53), respectively; and at 30 months (CARE) was: −2.80(2.27).

The results show that the TFC decline over time was slower in patients who received pridopidine in OPEN-HART compared to those who received placebo in CARE-HD and 2CARE. A slowdown in TFC decline was observed, which suggests that pridopidine has neuroprotective and/or disease-modifying properties.

Example 3

Phase 3 Study

The proposed Phase 3 study is a 78-week, multicenter, randomized, double-blind, placebo controlled, parallel group study to evaluate the efficacy and safety of pridopidine administered at a dose of 45 mg bid in adult patients with early stage HD.

The study consists of a screening period (up to 8 weeks); a 2-week titration period; a 76-week, double-blind, full-dose treatment period; and a follow-up period (consisting of an end of study visit at 3 to 4 weeks after the end of treatment visit).

During the screening period, patients provide informed consent and subsequently undergo assessments to determine eligibility for participation in the study. The stage of HD is established by the UHDRS TFC scale. The TMS and UHDRS-IS is assessed. The TMS assessment is rated by trained raters at the site and also videotaped for central rating by an independent blinded third party (Independent Adjudication Committee (IAC)). An IAC minimizes rater bias and error during screening by reviewing all information collected at screening, including patient medical history, prior to approving any patient for randomization.

Eligible patients are invited to return for a baseline visit and baseline assessments. Those patients who remain eligible for study participation will be randomly assigned (1:1 ratio) to 1 of the 2 treatment groups: 45 mg bid pridopidine or placebo bid. For patients assigned to receive pridopidine, the dose is titrated during the first 2 weeks from 45 mg qd to the final dose of 45 mg bid pridopidine.

During titration (days 0 to 14), patients receive 1 scheduled telephone call (TC) during the second week. Patients attend on-site clinic visits at weeks 26, 52, and 78 for safety and efficacy measures and blood sampling for pharmacokinetic assessments. At weeks 3, 6, 12, 39 and 65, safety visits will be conducted either by a visiting nurse at home or at the clinic for safety assessments. Patients will receive 1 scheduled TC approximately 6 to 7 weeks following each at home or on-site clinic visit.

During these TCs, patients are asked about the following: adverse events, concomitant medications, alcohol/drug use, tolerability of study drug, use of benzodiazepines and antidepressants, and compliance. The C-SSRS (since last visit version) and abbreviated PBA-s (a subset of PBA-s questions on depressed mood, suicidal ideation, anxiety, irritability, loss of motivation, and obsessive-compulsive behaviors) are assessed.

Patients who complete all scheduled visits have final procedures and assessments performed at the end of treatment visit (week 78). Patients who withdraw from the study before completing the evaluation period will have the week 78 procedures and assessments performed at their final visit, which is considered their early termination visit.

There is an on-site end of study visit approximately 3 to 4 weeks after the last dose of study drug to evaluate efficacy, safety (including a single ECG), pharmacokinetics, rebound, and dependence.

Primary Endpoint:

The primary efficacy endpoint to be evaluated is the change from baseline in TFC at week 78 in patients treated with pridopidine 45 mg bid compared to patients receiving placebo. The primary efficacy analysis is carried out using a linear mixed model for repeated measures with change from baseline in the primary endpoint (TFC) as the dependent variable in the modified intent-to-treat population (randomized patients with at least 1 post-baseline TFC assessment). The model includes visit (4 levels: weeks 12, 26, 52, and 78), treatment group, visit by treatment group interaction, country, HD stage (HD1 or HD2), and neuroleptic use (yes or no) as fixed factors, and includes the corresponding baseline score as a covariate. The unstructured covariance matrix for repeated observations within patients is used and the Kenward-Rodger method is used to calculate the denominator degrees of freedom. The primary analysis for TFC will compare the change from baseline to week 78 between the 45 mg bid pridopidine and placebo groups. Lower scores indicate more severe functional impairment than higher scores.

Secondary Endpoints:

Two secondary endpoints are selected based on the evidence-based trends observed in PRIDE-HD.

1. Change from baseline to week 78 in UHDRS TMS in patients receiving pridopidine 45 mg bid compared with patients receiving placebo.

The TMS is the standard and well-accepted clinical tool for tracking the progression of motor symptoms in patients with HD (Huntington Study Group 1996). The motor section of the UHDRS assesses motor features of HD with standardized ratings of oculomotor function, dysarthria, chorea, dystonia, gait, and postural stability. The TMS is the sum of 31 individual motor ratings, with each assessment rated on a 5 point scale from 0 (normal) to 4 (maximally abnormal). Higher scores indicate more severe motor impairment than lower scores.

Results from the HART and MermaiHD studies suggested a potential benefit for pridopidine in improving motor symptoms in HD (de Yebenes 2011; Huntington Study Group HART Investigators 2013). In the PRIDE-HD study, TMS showed improvement at all doses at week 26, but did not reach statistical significance, likely due to the high and sustained placebo effect, thus obscuring the ability to assess the potential motor function benefit of pridopidine. The current proposed study incorporates several measures to minimize the placebo effect and to allow an accurate assessment of the potential for pridopidine to provide a motor function benefit.

2. Change from baseline to week 78 in the Apathy Evaluation Scale (AES) in patients receiving pridopidine 45 mg bid, compared with patients receiving placebo. Apathy is one of the most prevalent neurobehavioral symptoms in HD, occurring in approximately 50-70% of the symptomatic HD population, and increases as the disease progresses. Symptoms include lack of interest and motivation, inability to start activities, social withdrawal, and emotional flatness. Apathy scores in patients with HD are highly correlated with duration of illness, suggesting that apathy is an inevitable consequence of advanced disease. Although less distressing than symptoms like depression and less disruptive than irritability or aggression, apathy has a considerable adverse impact on those affected with HD because it leads to a decrease of the goal-directed behaviors that contribute much to the day-to-day quality of life (Krishnamoorthy 2011; Martinez-Horta 1 2016).

Exploratory analysis in the PRIDE-HD study revealed that Problems Behavioral Assessment apathy sub-score was improved in early HD patients receiving 45 mg bid pridopidine compared with placebo at week 52. An improvement in apathy will provide convergent evidence for clinical utility with the primary endpoint, TFC. The AES was developed to measure abnormalities in goal-directed behavior, goal related thought content, and emotional indifference (Marin et al 1991). This more comprehensive scale was selected as a secondary endpoint, while the PBA will remain as an exploratory endpoint.

The Bonferroni-Holms method to control type 1 error will be used in the following fashion: If the primary endpoint is achieved, both secondary endpoints will be tested simultaneously at $\alpha=0.025$. If one of these secondary endpoints is achieved, the other can subsequently be tested at $\alpha=0.05$.

REFERENCES CITED

Alexander G E, DeLong M R, Strick P L. Parallel organization of functionally segregated circuits linking basal ganglia and cortex. Annu Rev Neurosci. 1986; 9: 357-81.

Bechtel, N. et al., Tapping linked to function and structure in premanifest and symptomatic Huntington disease. Neurology. 2010 Dec. 14; 75(24): 2150-60.

Bezdicek O, Majerova V, Novak M, Nikolai T, Ruzicka E, Roth J. Validity of the Montreal Cognitive Assessment in the detection of cognitive dysfunction in Huntington's disease. Appl Neuropsychol Adult. 2013; 20(1): 33-40.

Bowie C R, Harvey P D. Administration and interpretation of the Trail Making Test. Nat Protoc. 2006; 1(5): 2277-81.

Brown M, Sinacore D R, Binder E F, Kohrt W M. Physical and performance measures for the identification of mild to moderate frailty. J Gerontol A Biol Sci Med Sci. 2000 June; 55A(6): M350-5.

Byrne, L M et al., Neurofilament light protein in blood as a potential biomarker of neurodegeneration in Huntington's disease: a retrospective cohort analysis, Lancet Neurol published Jun. 7, 2017, Carlsson A, Lindqvist M. Effect of chlorpromazine or haloperidol on formation of 3-methoxytyramine and normetanephrine in mouse brain. Acta Pharmacol Toxicol (Copenh). 1963; 20: 140-4.

Cepeda C, Cummings D M, AndréV M, Holley S M, Levine M S. Genetic mouse models of Huntington's disease: focus on electrophysiological mechanisms. ASN Neuro. 2010 Apr. 7; 2(2): e00033.

Coenzyme Q10 in Huntington's Disease (HD) (2CARE), ClinicalTrials.gov Identifier: NCT00608881, clinicaltrials.gov/ct2/show/NCT00608881?term=2CARE%20+Huntington&rank=1, accessed Sep. 13, 2016.

Craufurd D, Thompson J C, Snowden J S. Behavioral changes in Huntington Disease. Neuropsychiatry Neuropsychol Behav Neurol. 2001 October-December; 14(4): 219-26.

Dunlop B W, Nemeroff C B. The role of dopamine in the pathophysiology of depression. Arch Gen Psychiatry. 2007 March; 64(3): 327-37.

Dyhring T, Nielsen E O, Sonesson C, Pettersson F, Karlsson J, Svensson P, Christophersen P, Waters N. The dopaminergic stabilizers pridopidine (ACR16) and (−)-OSU6162 display dopamine D(2) receptor antagonism and fast receptor dissociation properties. Eur J Pharmacol. 2010 Feb. 25; 628(1-3): 19-26.

Exploratory Population Pharmacokinetic Modeling and Simulations With Pridopidine (Report Number: CP-13-013). Pharsight Consulting Services, 10 Jul. 2013.

Guy W. Clinical Global Impression: ECDEU assessment manual for psychopharmacology. Publication ADM-76-338, US Department of Health, Education, and Welfare Washington D.C.: US Government Printing Office. 1976: 217-22.

Hobart J C, Riazi A, Lamping D L, Fitzpatrick R, Thompson A J. Measuring the impact of MS on walking ability: the 12-Item MS Walking Scale (MSWS-12). Neurology. 2003 Jan. 14; 60(1): 31-6.

Hocaoglu M B, Gaffan E A, Ho A K. The Huntington's Disease health-related Quality of Life questionnaire (HDQoL): a disease-specific measure of health-related quality of life. Clin Genet. 2012 February; 81(2): 117-22.

Huntington Study Group TREND-HD Investigators. Randomized controlled trial of ethyleicosapentaenoic acid in Huntington disease: the TREND-HD study. Arch Neurol. 2008 December; 65(12): 1582-9.

Huntington Study Group. Unified Huntington's Disease Rating Scale: Reliablility and Consistency, Movement Disorders, 1996, 11(2): 136-142.

Huntington Study Group. Dosage effects of riluzole in Huntington's disease: a multicenter placebo-controlled study. Neurology. 2003 Dec. 9; 61(11): 1551-6.

Huntington Study Group. Tetrabenazine as antichorea therapy in Huntington disease: a randomized controlled trial. Neurology. 2006 Feb. 14; 66(3): 366-72.

Huot P, Levesque M, Parent A. The fate of striatal dopaminergic neurons in Parkinson's disease and Huntington's chorea. Brain. 2007 January; 130 (Pt 1): 222-32.

Joffres C, Graham J, Rockwood K. Qualitative analysis of the clinician interview-based impression of change (Plus): methodological issues and implications for clinical research. Int Psychogeriatr. 2000 September; 12(3): 403-13.

Johnson A C and Paulsen J S. Huntington's Disease: A Guide for Professionals. D. Lovecky and K. Tarapata eds. 2014. Huntington's Disease Society of Americas (HDSA)

Kieburtz K, Koroshetz W, McDermott M, et al. A randomized, placebo-controlled trial of coenzyme Q10 and remacemide in Huntington's disease. Neurol. 2001 Aug. 14; 57(3): 397-404.

Kingma E M, van Duijn E, Timman R, van der Mast R C, Roos R A. Behavioural problems in Huntington's disease using the Problem Behaviours Assessment. Gen Hosp Psychiatry. 2008 March-April; 30(2): 155-6

Krishnamoorthy, A. and Craufurd, D. Treatment of Apathy in Huntington's Disease and Other Movement Disorders. Current Treatment Options in Neurology, 2011, 13(5): 508-19

Kung V W, Hassam R, Morton A J, Jones S. Dopamine-dependent long term potentiation in the dorsal striatum is reduced in the R6/2 mouse model of Huntington's disease. Neuroscience. 2007 Jun. 8; 146(4): 1571-80.

Landwehrmeyer B, Marder K, Biilmann Ronn B, Haglund M on behalf of the MermaiHD and HART study investigators. Effects of the dopaminergic stabilizer pridopidine on motor symptoms in Huntington's disease: a meta-analysis. Presented at the World Congress on Huntington's Disease, 11-14 Sep. 2011, Melbourne (Australia).

Mahant N, McCusker E A, Byth K, Graham S; Huntington Study Group. Huntington's disease: clinical correlates of disability and progression. Neurology. 2003 Oct. 28; 61(8):1085-92.

Marder K, Zhao H, Myers R H, Cudkowicz M, Kayson E, Kieburtz K, Orme C, Paulsen J, Penney J B Jr,Siemers E, Shoulson I. Rate of functional decline in Huntington's disease. Huntington Study Group. Neurology 2000; 54: 452-58

Marin R S, Biedrzycki R C, Firinciogullari S. Reliability and validity of the Apathy Evaluation Scale. Psychiatry Res 1991; 38(2): 143-62.

Martinez-Horta S, Perez-Perez J, van Duijn E, Fernandez-Bobadilla R, Carceller M, Pagonabarraga J, et al. Neuropsychiatric symptoms are very common in premanifest and early stage Huntington's Disease. Parkinsonism Relat Disord 2016; 25: 58-64.

Mestre T, Ferreira J, Coelho M M, Rosa M, Sampaio C. Therapeutic interventions for disease progression in Huntington's disease. Cochrane Database Syst Rev. 2009 Jul. 8; (3).

Mestre T, Ferreira J, Coelho M M, Rosa M, Sampaio C. Therapeutic interventions for symptomatic treatment in Huntington's disease. Cochrane Database Syst Rev. 2009 Jul. 8; (3).

Myers R H, Sax D S, Koroshetz W J, Mastromauro C, Cupples L A, Kiely D K, Pettengill F K, Bird E D. Factors associated with slow progression in Huntington's disease. Arch Neurol. 1991 August 48(8): 800-4.

Natesan S, Svensson K A, Reckless G E, Nobrega J N, Barlow K B, Johansson A M, Kapur S. The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. J Pharmacol Exp Ther. 2006 August; 318(2): 810-8.

Nieoullon A, Coquerel A. Dopamine: a key regulator to adapt action, emotion, motivation and cognition. Curr Opin Neurol. 2003 December; 16 Suppl 2: S3-9.

Open-label Extension Study of Pridopidine (ACR16) in the Symptomatic Treatment of Huntington Disease (OPEN-HART), ClinicalTrials.gov Identifier: NCT01306929, clinicaltrials.gov/ct2/show/NCT01306929, accessed Sep. 13, 2016.

Podsiadlo D, Richardson S. The timed "Up & Go": a test of basic functional mobility for frail elderly persons. J Am Geriatr Soc. 1991 Febuary; 39(2): 142-8.

Ponten H, Kullingsjo J, Lagerkvist S, Martin P, Pettersson F, Sonesson C, Waters S, Waters N. In vivo pharmacology of the dopaminergic stabilizer pridopidine. Eur J Pharmacol. 2010 Oct. 10; 644(1-3): 88-95.

Posner K, Brown G K, Stanley B, Brent D A, Yershova K V, Oquendo M A, Currier G W, Melvin G A, Greenhill L, Shen S, Mann J J. The Columbia-Suicide Severity Rating Scale: initial validity and internal consistency findings from three multisite studies with adolescents and adults. Am J Psychiatry. 2011 December; 168(12): 1266-77.

Rao A K, Muratori L, Louis E D, Moskowitz C B, Marder K S. Clinical measurement of mobility and balance impairments in Huntington's disease: validity and responsiveness. Gait Posture. 2009 April; 29(3): 433-6.

Reuben D B, Siu A L. An objective measure of physical function of elderly outpatients. The Physical Performance Test. J Am Geriatr Soc. 1990 October; 38(10): 1105-12.

Stout J C, Queller S, Baker K N, Cowlishaw S, Sampaio C, Fitzer-Attas C, Borowsky B; HD-CAB Investigators. HD-CAB: a cognitive assessment battery for clinical trials in Huntington's disease. Mov Disord 2014; 29(10): 1281-8.

Stroop J R. Studies of interference in serial verbal reactions. J Exp Psychol 1935; 18: 643-62.

The EuroQol Group. EuroQol-a new facility for the measurement of health-related quality of life. Health Policy 1990; 16: 199-208.

Waters S, Pettersson F, Dyhring T, Sonesson C, Tedroff J, Waters N et al. Pharmacology of the dopaminergic stabilizer pridopidine (ACR16). Clin Genet 2009; 76(S1): 74 (Abstract D10).

Zhan L, Kerr J R, Lafuente M J, Maclean A, Chibalina M V, Liu B, Burke B, Bevan S, Nasir J. Altered expression and coregulation of dopamine signalling genes in schizophrenia and bipolar disorder. Neuropathol Appl Neurobiol. 2011 Febuary; 37(2): 206-19.

The invention claimed is:

1. A method of (a) maintaining functional capacity, or (b) improving functional capacity, in a human patient afflicted with early stage Huntington disease (HD1 and HD2, TFC 7-13) comprising periodically orally administering to the patient a pharmaceutical composition comprising pridopidine or a pharmaceutically acceptable salt thereof such that a dose of 90-225 mg of pridopidine is administered to the patient per day, wherein the pharmaceutical composition is administered for at least 26 weeks, so as to thereby maintain functional capacity, or improve functional capacity in the human patient.

2. The method of claim 1, wherein the functional capacity is total functional capacity (TFC) and optionally the total functional capacity is measured by the Total Functional Capacity (TFC) scale of the UHDRS.

3. The method of claim 1, wherein the functional capacity is total functional capacity (TFC) measured by the Total Functional Capacity (TFC) scale of the UHDRS and the human patient has an improvement of 1 or more points or maintaining the same score on the UHDRS-TFC.

4. The method of claim 1, wherein the functional capacity is total functional capacity, wherein a dose of 90 or 180 mg of pridopidine is administered to the human patient per day, and wherein the pharmaceutical composition is administered for at least 26 weeks.

5. The method of claim 1, wherein the functional capacity is
   (a) ability to perform activities of daily living,
   (b) ability to manage finances,
   (c) ability to maintain occupation,
   (d) ability to perform domestic chores, and/or
   (e) the care level of the human patient.

6. The method of claim 5, wherein the functional capacity is the ability to perform activities of daily living as measured by Activities of Daily Living domain of the UHDRS-TFC which is maintained or improved, wherein a dose of 90-225 mg of pridopidine is administered to the human patient per day.

7. The method of claim 5, wherein the method comprises improving or maintaining ability to manage finances as measured by the Managing Finances domain of the UHDRS-TFC.

8. The method of claim 1, wherein a dose of 90 mg of pridopidine is administered to the human patient per day.

9. The method of claim 5, wherein the functional capacity is the continued ability to perform domestic chores as measured by the Domestic Chores domain of the UHDRS TFC which is maintained, or improved, wherein a dose of 90 mg of pridopidine is administered to the human patient per day.

10. The method of claim 5, wherein the functional capacity is care level as measured by the Care level of the UHDRS TFC which is maintained or improved.

11. The method of claim 1, wherein a dose of 90 mg, 135 mg, 180 mg or 225 mg of pridopidine is administered to the patient per day.

12. The method of claim 1, wherein the pharmaceutical composition is administered for at least 26 weeks, optionally, wherein (A) a unit dose of the pharmaceutical composition contains 45 mg, 67.5 mug, 90 mg, or 112.5 mg of pridopidine, (B) the pharmaceutical composition is administered twice per day, (C) an equal amount of the pharmaceutical composition is administered at each administration, (D) the patient has greater than or equal to 36 CAG repeats in the huntingtin gene, (E) the human patient has a baseline TFC score which is greater than or equal to 7, (F) the pridopidine is pridopidine or salt thereof, or (G) the method further comprises no worsening of another symptom of Huntington disease in comparison to a human patient not treated with pridopidine.

13. A method of maintaining functional capacity or improving functional capacity in a human patient afflicted with early stage Huntington disease (HD1 and HD2, TFC 7-13), comprising periodically orally administering to the patient a pharmaceutical composition comprising pridopidine such that a dose of 90 mg of pridopidine is administered to the patient per day, so as to thereby maintain functional capacity or improve functional capacity, wherein the functional capacity is total functional capacity and wherein the pharmaceutical composition is administered for at least 26 weeks.

14. The method of claim 3, wherein the human patient has an improvement of one (1) or more points in the UHDRS-TFC after at least 26 weeks of administration of the pharmaceutical composition.

15. The method of claim 13, wherein a unit dose of the pharmaceutical composition contains 45 mg of pridopidine and the unit dose is administered twice per day.

16. The method of claim 5, wherein the functional capacity is maintaining occupation as measured by occupation of the UHDRS TFC which is maintained, or improved.

* * * * *